(12) United States Patent
Karsten et al.

(10) Patent No.: US 11,243,218 B2
(45) Date of Patent: Feb. 8, 2022

(54) BLOOD PREPARATION AND PROFILING

(71) Applicant: Sangui Bio Pty Ltd, Manly (AU)

(72) Inventors: Elisabeth Karsten, Northmead (AU); Ben Herbert, North Epping (AU); Alan Liddle, Manly (AU); Cameron Hill, St. Leonards (AU)

(73) Assignee: SANGUI BIO PTY LTD., Manly (AU)

( * ) Notice: Subject to any disclaimer, the term of this patent is extended or adjusted under 35 U.S.C. 154(b) by 0 days.

(21) Appl. No.: 15/765,963

(22) PCT Filed: Oct. 6, 2016

(86) PCT No.: PCT/AU2016/000341
§ 371 (c)(1),
(2) Date: Apr. 4, 2018

(87) PCT Pub. No.: WO2017/059477
PCT Pub. Date: Apr. 13, 2017

(65) Prior Publication Data
US 2018/0306817 A1    Oct. 25, 2018

(30) Foreign Application Priority Data
Oct. 7, 2015   (AU) ................................ 2015904075

(51) Int. Cl.
*G01N 33/80* (2006.01)
*G01N 33/574* (2006.01)
*G01N 33/49* (2006.01)
*G01N 33/569* (2006.01)

(52) U.S. Cl.
CPC ............ *G01N 33/80* (2013.01); *G01N 33/49* (2013.01); *G01N 33/57484* (2013.01); *G01N 33/56972* (2013.01); *G01N 33/57488* (2013.01); *G01N 2800/368* (2013.01)

(58) Field of Classification Search
None
See application file for complete search history.

(56) References Cited

U.S. PATENT DOCUMENTS

| | | | |
|---|---|---|---|
| 4,931,276 A | 6/1990 | Franco et al. | |
| 5,858,358 A | 1/1999 | June et al. | |
| 10,273,455 B2 | 4/2019 | Baek et al. | |
| 2008/0095749 A1 | 4/2008 | Aggarwal et al. | |
| 2009/0054741 A1 | 2/2009 | Mcaleer | |
| 2012/0195869 A1 | 8/2012 | Terman et al. | |
| 2019/0000884 A1 | 1/2019 | Karsten et al. | |
| 2020/0096512 A1 | 3/2020 | Herbert et al. | |

FOREIGN PATENT DOCUMENTS

| CN | 1662817 A | 8/2005 |
|---|---|---|
| CN | 1969184 A | 5/2007 |
| CN | 101248187 A | 8/2008 |
| FR | 2778851 B1 | 7/2002 |
| JP | 2007510149 A | 4/2007 |
| JP | 2012530133 A | 11/2012 |
| JP | 2013501926 A | 1/2013 |
| JP | 2015055620 A | 3/2015 |
| JP | 2015523384 A | 8/2015 |
| WO | WO 1992005801 A1 | 4/1992 |
| WO | WO 2002007752 A2 | 1/2002 |
| WO | WO 2002007752 A3 | 1/2002 |
| WO | WO 2003087833 A2 | 10/2003 |
| WO | WO 2003087833 A3 | 10/2003 |
| WO | WO 2005045441 A1 | 5/2005 |
| WO | WO 2005103678 A2 | 11/2005 |
| WO | WO 2005103678 A3 | 11/2005 |
| WO | WO 2006081324 A2 | 8/2006 |
| WO | WO 2006081324 A3 | 8/2006 |
| WO | WO 2008134526 A3 | 11/2006 |
| WO | WO 2008134526 A2 | 11/2008 |
| WO | WO 2009019317 A1 | 2/2009 |
| WO | WO 2009111595 A2 | 9/2009 |
| WO | WO 2009137629 A2 | 11/2009 |
| WO | WO 2009137629 A3 | 11/2009 |
| WO | WO 2010147621 A1 | 12/2010 |
| WO | WO 2011018288 A1 | 2/2011 |
| WO | WO 2011091154 A2 | 7/2011 |
| WO | WO 2011091154 A3 | 7/2011 |
| WO | WO 2011127056 A2 | 10/2011 |
| WO | WO 2011127056 A3 | 10/2011 |
| WO | WO 2012166055 A1 | 12/2012 |
| WO | WO 2013045885 A1 | 4/2013 |
| WO | WO 2013139906 A1 | 9/2013 |
| WO | WO 2013/156806 | 10/2013 |
| WO | WO 2014011901 A2 | 1/2014 |
| WO | WO 2014181309 A1 | 11/2014 |
| WO | WO 2015156586 A1 | 10/2015 |

(Continued)

OTHER PUBLICATIONS

Haudek et al (J. Proteome Res. (2009) 8, 8, 3834-3843) (Year: 2009).*
Anniss (Transfusion. Sep. 2005;45(9):1426-33). (Year: 2005).*
Mayeux (NeuroRx. Apr. 2004;1(2):182-8) (Year: 2004).*
Waiker et al (J Am Soc Nephrol. Jan. 2012; 23(1): 13-21) (Year: 2012).*
Dalton (Chemical & Engineering News Jan. 2, 2017; 95(1): 16-19) (Year: 2017).*
Dzieciatkowska et al (Vox Sang. Oct. 2013 ; 105(3): 210-218). (Year: 2013).*
Darbonne, et al (Clin Invest. Oct. 1991;88(4):1362-9. doi: 10.1172/JCI115442.) (Year: 1991).*
Sparrow et al (Transfusion 2004;44:722-730). (Year: 2004).*
Hanahan,D., and J.E. Ekholm. (1974.The preparation of red cell ghosts. MethodsEnzymol.31:168-172.) (Year: 1974).*
Kumar et al (Am. J. Hematol. 90:31-36, 2015) (Year: 2015).*

(Continued)

*Primary Examiner* — Brian Gangle
*Assistant Examiner* — Andrea K McCollum
(74) *Attorney, Agent, or Firm* — Jones Day

(57) ABSTRACT

The present disclosure relates to methods for generating blood protein profiles in red blood cell-enriched blood samples. The disclosed methods represent a new and improved laboratory technique for producing a protein profile from blood, increasing protein detection.

18 Claims, 81 Drawing Sheets

(56) References Cited

FOREIGN PATENT DOCUMENTS

| WO | WO 2016187353 A1 | 11/2016 |
|---|---|---|
| WO | WO 2017106899 A2 | 6/2017 |
| WO | WO 2017106899 A3 | 6/2017 |
| WO | WO 2018112500 A1 | 6/2018 |

OTHER PUBLICATIONS

International Search Report dated Dec. 20, 2016 for PCT/AU2016/000341.
Anniss, A.M. et al., "Proteomic analysis of supernatants of stored red blood cell products," *Transfusion*, 45 (2005) 1426-1433.
Ferru, E. et al., "A new method for the capture of surface proteins in Plasmodium falciparum parasitized erythrocyte," *Journal of Infection in Developing Countries*, 6 (2012) 536-541.
Haudek, V. et al., "Proteome Maps of the Main Human Peripheral Blood Constituents," *Journal of Proteome Research*, 8 (2009) 3834-3843.
Pasini, E.M. et al., "In-depth analysis of the membrane and cytosolic proteome of red blood cells," *Blood*, 108 (2006) 791-801.
Pasini, E.M. et al., "Red blood cell (RBC) membrane proteomics—Part I: Proteomics and RBC physiology," *Journal of Proteomics*, 73 (2010) 403-420.
Villanueva, V.R. et al., "Chromatography, flow injection analysis and electrophoresis in computer-assisted comparative biochemistry: its application and possibilities in clinical research," *Journal of Chromatography*, 440 (1988) 261-273.
Zaccaria, A. et al., "Accessing to the minor proteome of red blood cells through the influence of the nanoparticle surface properties on the corona composition," *International Journal of Nanomedicine*, 10 (2015) 1869-1883.
Ayache et al, 2006, "Effects of storage time and exogenous protease inhibitors on plasma protein levels", Am J Clin Pathol., 126(2):174-184.
Baruchel et al., 2015, "Updated Clinical Activity of Graspa Versus Native 1-Asparaginase in Combination with Cooprall Regimen in Phase 3 Randomized Trial in Patients with Relapsed Acute Lymphoblastic Leukemia (NCT01518517)", Blood, 126(23):3723.
Bjork et al., 1996, "A new enzyme activity in human blood cells and isolation of the responsible protein (D-dopachrome tautomerase) from erythrocytes", Eur J Haematol, 57(3):254-256.
Bowyer et al, 2011, "Global profiling of proteolysis during rupture of Plasmodium falciparum from the host erythrocyte", Mol Cell Proteomics, 10(5):M110.001636 (14 pages).
Bruil et al., 1995, "The mechanisms of leukocyte removal by filtration", Transfus Med Rev., 9(2):145-166.
Cassell et al., 1962, "Transfusion of buffy coat-poor red cell suspensions prepared by dextran sedimentation: description of newly designed equipment and evaluation of its use",Transfusion, 2:216-220.
D'Amici et al, 2007, "Proteomic analysis of RBC membrane protein degradation during blood storage", J Proteome Res., 6(8):3242-3255.
Danesh et al., 2014, "Exosomes from red blood cell units bind to monocytes and induce proinflammatory cytokines, boosting T-cell responses in vitro", Blood, 123(5):687-696 (Epub 2013).
Day et al., 1989, "Expression and regulation of erythrocyte auto-antibodies in mice following immunization with rat erythrocytes", Eur J Immunol., 19(5):795-801.
Hansell et al., 2011, "DARC and D6: silent partners in chemokine regulation?", Immunol Cell Biol., 89(2):197-206 (Epub 2010).
International Search Report and Written Opinion of International Patent Application No. PCT/AU2016/000341 (published as WO 2017059477) dated Dec. 20, 2016 (13 pages).
International Search Report and Written Opinion of International Patent Application No. PCT/AU2016/000404 (published as WO 2017106899) dated Aug. 17, 2017 (17 pages).
International Search Report and Written Opinion of International Patent Application No. PCT/AU2017/000282 (published as WO 2018112500) dated Feb. 28, 2018 (22 pages).
Karsten et al., 2018, "Red blood cells are dynamic reservoirs of cytokines", Sci Rep., 8(1):3101 (12 pages).
Li et al 2006, "Development and characterization of dried blood spot materials for the measurement of immunoreactive trypsinogen", J Med Screen, 13(2):79-84.
Makinen et al., 1977, "Migration inhibition factor and the blood clotting system: effects of defibrination, heparin and thrombin", Clin Exp Immunol., 29(1):181-186.
Mayr et al., 2008, "Duffy antigen modifies the chemokine response in human endotoxemia", Crit Care Med., 36(1):159-165.
McDade et al., 2007, "What a drop can do: dried blood spots as a minimally invasive method for integrating biomarkers into population-based research", Demography, 44(4):899-925.
Oliveri et al, 2001, "The effect of protease inhibitors on the two-dimensional electrophoresis pattern of red blood cell membranes", Electrophoresis, 22(3):560-565.
Rubin et al., 2012, "Red blood cell microparticles: clinical relevance", Transfus Med Hemother, 39(5):342-347.
Schnabel et al., 2010, "Duffy antigen receptor for chemokines (Darc) polymorphism regulates circulating concentrations of monocyte chemoattractant protein-1 and other inflammatory mediators", Blood, 115(26):5289-5299 (Epub 2009).
Sirchia et al., 1980, "Evaluation of three procedures for the preparation of leukocyte-poor and leukocyte-free red blood cells for transfusion", Vox Sang, 38(4):197-204.
Tenczar, 1973, "Comparison of inverted centrifugation, saline washing, and dextran sedimentation in the preparation of leukocyte-poor red cells", Transfusion, 13(4):183-188.
Zecher et al., 2014, "Erythrocyte-derived microvesicles amplify systemic inflammation by thrombin-dependent activation of complement", Arterioscler Thromb Vasc Biol., 34(2):313-320 (Epub 2013).
Zeng et al., 2014, "Mechanical response of red blood cells entering a constriction", Biomicrofluidics, 8(6):064123.
Zhou et al., 2012, "Opsonization of malaria-infected erythrocytes activates the inflammasome and enhances inflammatory cytokine secretion by human macrophages", Malar J., 11:343 (13 pages).
Autunes et al., 2011, "Red blood cells release factors with growth and survival bioactivities for normal and leukemic T cells," Immunol Cell Biol., 89(1): 111-121.
Fonseca et al., 2001, "Red blood cells inhibit activation-induced cell death and oxidative stress in human peripheral blood T lymphocytes," Blood, 97(10):3152-3160.
Fredriksson et al., 2003, "Red blood cells stimulate human lung fibroblasts to secrete interleukin-8," Inflammation, 27(2):71-78.

\* cited by examiner

Figure 21A

| Protein | Plasma* | | | RBCs* | | | | |
|---|---|---|---|---|---|---|---|---|
| | No. of subjects | pg/mL of whole blood | | No. of subjects | pg/mL of whole blood | | Corrected for WBC contamination (pg/mL) | | Fold change |
| | | Conc. | SD | | Conc. | SD | Conc. | SD | |
| Anti-inflammatory | | | | | | | | | |
| IL-1ra | 5 | 20.8 | 6.6 | 1 | 299.6 | - | - | - | - |
| IL2-ra | 6 | 29.3 | 5.3 | 3 | 282.6 | 31.7 | 280.9 | 28.8 | 10 |
| IL-4 | 4 | 0.4 | 0.2 | 2 | 4.6 | 0.8 | 3.3 | 0.9 | 8 |
| IL-10 | 1 | 1.4 | - | 0 | - | - | - | - | - |
| IL-13 | 5 | 2.0 | 1.0 | 3 | 2.3 | 2.3 | 1.4 | 2.3 | 1 |
| Chemokines | | | | | | | | | |
| CTACK | 6 | 36.3 | 9.3 | 5 | 222.2 | 85.7 | 131.4 | 100.5 | 4 |
| Eotaxin | 5 | 6.4 | 2.2 | 6 | 79.3 | 38.4 | 74.6 | 38.4 | 12 |
| GRO-α | 3 | 6.0 | 1.7 | 4 | 187.3 | 47.8 | 184.0 | 54.3 | 31 |
| IL-16 | 6 | 46.6 | 11.2 | 5 | 2904.9 | 3231.7 | 2904.9 | 3231.7 | 62 |
| MCP-1 | 0 | - | - | 2 | 55.0 | 6.8 | 36.1 | 7.7 | - |
| MCP-3 | 4 | 23.4 | 5.5 | 0 | - | - | - | - | - |
| MIG | 6 | 70.2 | 34.5 | 0 | - | - | - | - | - |
| MIP-1α | 6 | 0.5 | 0.3 | 4 | 5.2 | 2.3 | 3.9 | 2.1 | 8 |
| MIP-1β | 6 | 6.3 | 3.5 | 2 | 42.7 | 56.3 | 25.7 | 48.9 | 4 |
| RANTES | 6 | 510.7 | 268.5 | 6 | 8744 | 11,785 | 5618 | 10,489 | 11 |
| SDF-1α | 6 | 121.9 | 11.3 | 6 | 872.4 | 206.2 | 811.8 | 193.4 | 7 |

Figure 21B

| Protein | Plasma* | | | RBCs* | | | | | |
|---|---|---|---|---|---|---|---|---|---|
| | No. of subjects | pg/mL of whole blood | | No. of subjects | pg/mL of whole blood | | Corrected for WBC contamination (pg/mL) | | Fold change |
| | | Conc. | SD | | Conc. | SD | Conc. | SD | |
| Growth Factors | | | | | | | | | |
| bFGF | 6 | 4.8 | 2.0 | 6 | 197.1 | 72.4 | 147.2 | 87.3 | 31 |
| G-CSF | 6 | 5.3 | 3.6 | 3 | 148.8 | 79.0 | 131.1 | 79.1 | 25 |
| GM-CSF | 0 | - | - | 5 | 939.7 | 460.2 | 772.3 | 538.5 | - |
| HGF | 6 | 39.8 | 7.8 | 6 | 800.3 | 490.5 | 691.2 | 500.3 | 17 |
| IL-3 | 6 | 18.1 | 2.0 | 6 | 345.8 | 209.7 | 334.2 | 217.6 | 18 |
| IL-7 | 5 | 1.7 | 0.9 | 2 | 34.6 | 5.2 | 34.0 | 6.2 | 20 |
| IP-10 | 6 | 132.5 | 142.7 | 4 | 147.8 | 87.1 | 134.0 | 83.3 | 1 |
| M-CSF | 6 | 4.3 | 3.2 | 3 | 115.6 | 7.9 | 99.5 | 13.2 | 23 |
| β-NGF | 5 | 1.2 | 0.2 | 0 | - | - | - | - | - |
| PDGF-bb | 6 | 20.3 | 17.4 | 5 | 1073.5 | 2004.9 | 115.4 | 2095.6 | 6 |
| SCF | 6 | 6.5 | 1.5 | 1 | 54.1 | - | 51.9 | - | 8 |
| SCGF-β | 3 | 944.3 | 563.9 | 0 | - | - | - | - | - |
| VEGF | 5 | 2.1 | 0.8 | 6 | 113.9 | 50.3 | 82.8 | 53.7 | 39 |
| Analytes with multiple functions | | | | | | | | | |
| IL-2 | 0 | - | - | 0 | - | - | - | - | - |
| IL-6 | 2 | 0.5 | 0.1 | 0 | - | - | - | - | - |
| IL-12p40 | 1 | 44.5 | - | 3 | 1914.7 | 357.9 | 1693.7 | 254.7 | 38 |
| LIF | 6 | 5.7 | 3.2 | 3 | 119.5 | 27.5 | 119.5 | 27.5 | 21 |

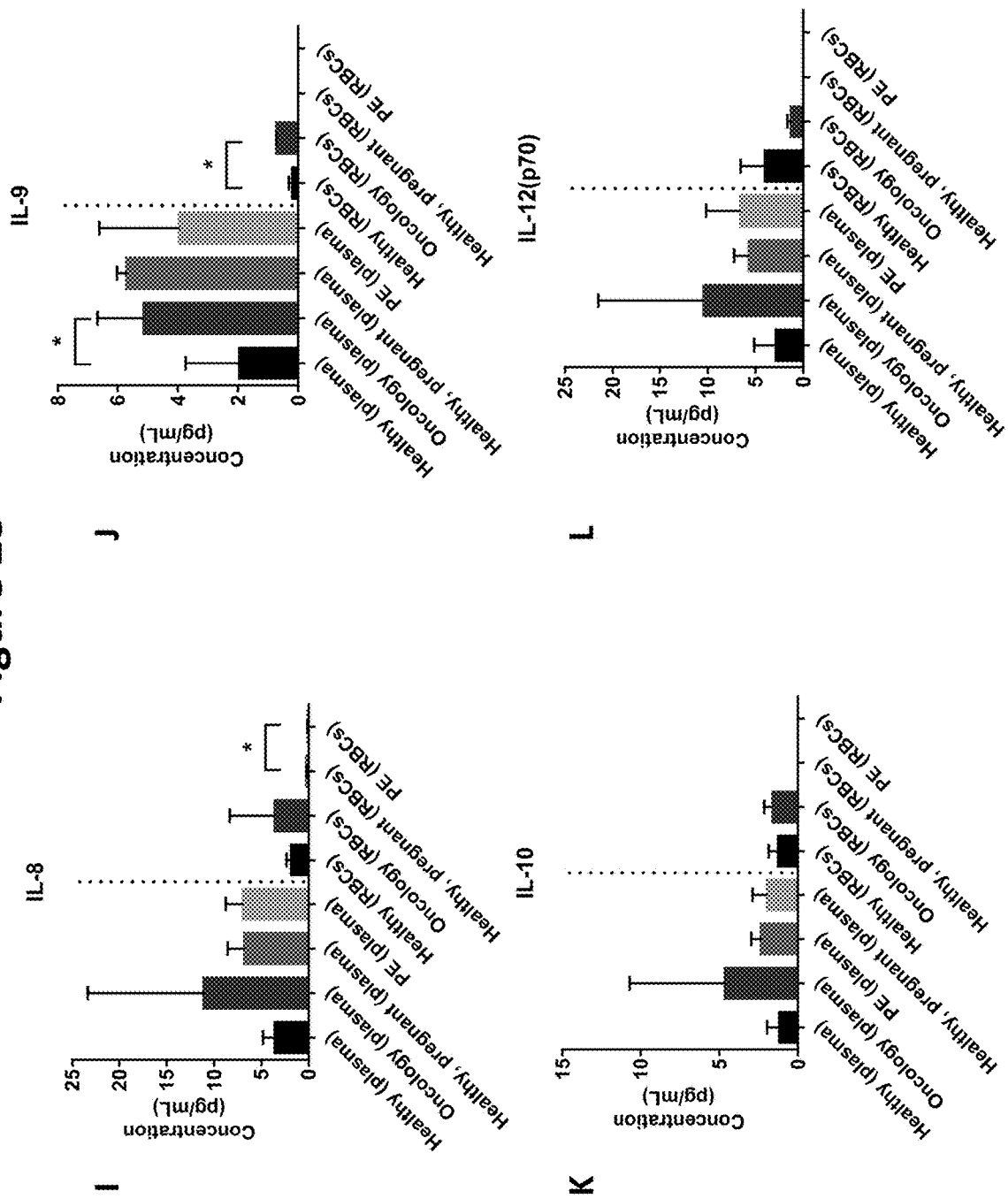

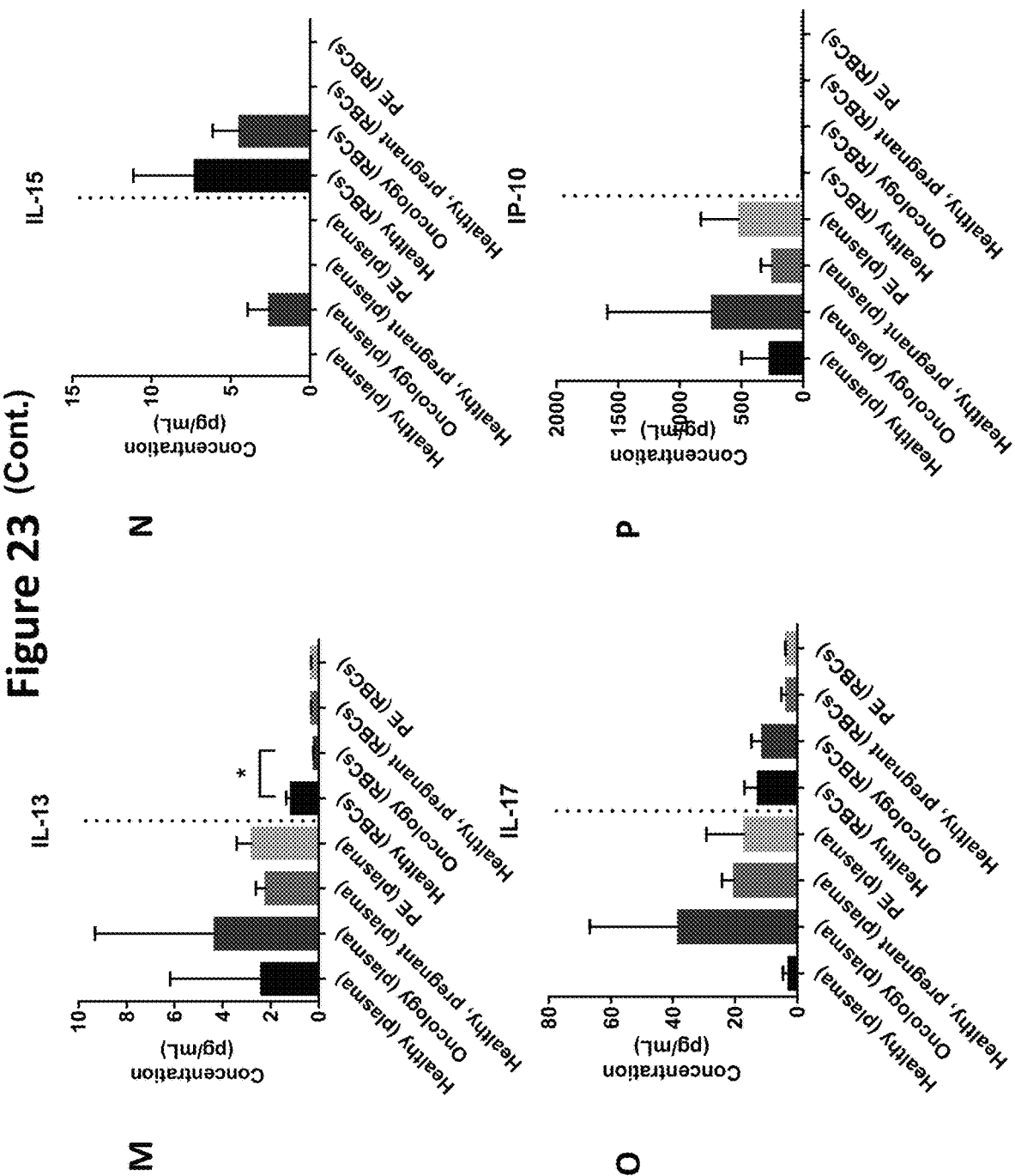

Figure 24A

| Analyte | Plasma* | | | RBCs* | | | Fold change |
|---|---|---|---|---|---|---|---|
| | No. of subjects | pg/mL of whole blood | | No. of subjects | pg/mL of whole blood | | |
| | | Conc. | SD | | Conc. | SD | |
| | | | Pro-inflammatory | | | | |
| IFN-α2 | 3 | 24.4 | 18.9 | 3 | 251.5 | 32.4 | 14.97 |
| IFN-γ | 3 | 18.6 | 1.9 | 3 | 18.3 | 12.2 | 0.96 |
| IL-1α | 3 | 3.6 | 6.2 | 3 | 35.9 | 44.3 | 156.39 |
| IL-1β | 3 | 0.3 | 0.1 | 3 | 1.9 | 1.5 | 7.28 |
| IL-5 | 3 | 2.7 | 0.4 | 0 | - | - | - |
| IL-8 | 3 | 5.5 | 6.2 | 2 | 31.9 | 41.8 | 1.93 |
| IL-9 | 3 | 2.6 | 0.8 | 2 | 7.8 | 2.5 | 2.10 |
| IL-12(p70) | 3 | 5.2 | 5.6 | 3 | 15.3 | 5.6 | 6.11 |
| IL-15 | 3 | 1.3 | 0.7 | 3 | 53.6 | 20.3 | 62.29 |
| IL-17 | 3 | 19.1 | 14.4 | 3 | 132.8 | 26.2 | 9.75 |
| IL-18 | 3 | 67.0 | 91.9 | 3 | 1209.7 | 535.3 | 79.51 |
| MIF | 3 | 45.5 | 47.2 | 3 | 8348.1 | 4259.3 | 280.31 |
| TNF-α | 3 | 7.0 | 1.3 | 2 | 8.5 | 6.0 | 0.83 |
| TNF-β | 1 | 77.24 | - | 0 | - | - | - |
| TRAIL | 3 | 29.9 | 31.2 | 0 | - | - | - |

Figure 24B

| Analyte | Plasma* | | | RBCs* | | | Fold change |
|---|---|---|---|---|---|---|---|
| | No. of subjects | pg/mL of whole blood | | No. of subjects | pg/mL of whole blood | | |
| | | Conc. | SD | | Conc. | SD | |
| Anti-inflammatory | | | | | | | |
| IL-1ra | 3 | 13.1 | 0.9 | 3 | 1182.4 | 970.5 | 87.35 |
| IL2-ra | 3 | 87.3 | 93.7 | 3 | 108.5 | 73.6 | 2.63 |
| IL-4 | 3 | 0.3 | 0.1 | - | - | - | - |
| IL-10 | 3 | 2.3 | 3.0 | 3 | 19.0 | 6.0 | 118.47 |
| IL-13 | 3 | 2.2 | 2.5 | 3 | 2.4 | 1.4 | 3.42 |
| Chemokines | | | | | | | |
| CTACK | 3 | 65.9 | 76.9 | 1 | 64.9 | - | 1.81 |
| Eotaxin | 3 | 20.9 | 26.3 | 3 | 38.6 | 23.1 | 3.67 |
| GRO-α | 3 | 32.9 | 33.7 | 3 | 217.6 | 98.0 | 10.11 |
| IL-16 | 3 | 361.8 | 461.0 | 3 | 3563.4 | 3915.3 | 12.29 |
| MCP-1 | 3 | 7.0 | 7.8 | 3 | 285.2 | 63.1 | 95.56 |
| MCP-3 | 2 | 6.3 | 6.5 | 0 | - | - | - |
| MIG | 3 | 249.7 | 285.1 | 0 | - | - | - |
| MIP-1α | 3 | 1.8 | 1.8 | 3 | 3.0 | 2.4 | 3.76 |
| MIP-1β | 3 | 10.4 | 8.2 | 3 | 4.6 | 1.8 | 0.87 |
| RANTES | 3 | 415.3 | 58.0 | 3 | 1717.1 | 398.8 | 4.10 |
| SDF-1α | 3 | 65.7 | 25.0 | 2 | 246.5 | 231.5 | 2.82 |

Figure 24C

| Analyte | Plasma* | | | RBCs* | | Fold change |
|---|---|---|---|---|---|---|
| | No. of subjects | pg/mL of whole blood | | No. of subjects | pg/mL of whole blood | |
| | | Conc. | SD | | Conc. | SD | |
| *Anti-inflammatory* | | | | | | | |
| IL-1ra | 3 | 13.1 | 0.9 | 3 | 1182.4 | 970.5 | 87.35 |
| IL2-ra | 3 | 87.3 | 93.7 | 3 | 108.5 | 73.6 | 2.63 |
| IL-4 | 3 | 0.3 | 0.1 | - | - | - | - |
| IL-10 | 3 | 2.3 | 3.0 | 3 | 19.0 | 6.0 | 118.47 |
| IL-13 | 3 | 2.2 | 2.5 | 3 | 2.4 | 1.4 | 3.42 |
| *Chemokines* | | | | | | | |
| CTACK | 3 | 65.9 | 76.9 | 1 | 64.9 | - | 1.81 |
| Eotaxin | 3 | 20.9 | 26.3 | 3 | 38.6 | 23.1 | 3.67 |
| GRO-α | 3 | 32.9 | 33.7 | 3 | 217.6 | 98.0 | 10.11 |
| IL-16 | 3 | 361.8 | 461.0 | 3 | 3563.4 | 3915.3 | 12.29 |
| MCP-1 | 3 | 7.0 | 7.8 | 3 | 285.2 | 63.1 | 95.56 |
| MCP-3 | 2 | 6.3 | 6.5 | 0 | - | - | - |
| MIG | 3 | 249.7 | 285.1 | 0 | - | - | - |
| MIP-1α | 3 | 1.8 | 1.8 | 3 | 3.0 | 2.4 | 3.76 |
| MIP-1β | 3 | 10.4 | 8.2 | 3 | 4.6 | 1.8 | 0.87 |
| RANTES | 3 | 415.3 | 58.0 | 3 | 1717.1 | 398.8 | 4.10 |
| SDF-1α | 3 | 65.7 | 25.0 | 2 | 246.5 | 231.5 | 2.82 |

BLOOD PREPARATION AND PROFILING

CROSS REFERENCE TO RELATED APPLICATION

This application is the National Phase application of International Application No. PCT/AU2016/000341, filed 6 Oct. 2016, which designates the United States and was published in English, which claims priority to and is related to Australian Application No. 2015904075 entitled "Blood Preparation and Profiling" filed on 7 Oct. 2015. These applications are incorporated herein by reference in their entirety. In addition, the other references or publications referred to in the present disclosure are also hereby incorporated by reference in their entirety.

TECHNICAL FIELD

The present disclosure relates generally to the field of haematology. The present disclosure also relates to protein profiling in the blood and, in particular, methods for producing or generating blood protein profiles, including cytokine and/or chemokine profiles, in red blood cell-enriched blood samples.

BACKGROUND

Protein profiling of blood is used for a variety of purposes. For example, the profiling of indicative proteins in peripheral blood mononuclear cells (PBMC) and serum/plasma is commonly used in disease diagnosis. Additionally, monitoring protein profiles within the blood may assist in directing more effective therapeutic interventions by providing a means of monitoring responsiveness to treatment and an indication of remission or regression.

Biological markers in blood compartments such as cytokines, chemokines and growth factors may provide insight into inflammation, immune responses, and repair. In particular, the detection and quantification of pro- and/or anti-inflammatory cytokine and chemokine levels in blood is widely employed to gauge immune status. These cytokines and chemokines are commonly used to diagnose certain disease states, determine a predisposition to developing disease, and/or to predict prognostic outcomes.

Typically, the detection and quantification of various proteins in the blood compartment is assessed using isolated serum/plasma, and/or PBMC. This effectively neglects erythrocytes/red blood cells (RBCs) which are the most abundant cellular component of blood and account for 40%-50% of its volume. RBCs are routinely removed prior to conducting protein analyses on plasma/serum and/or white blood cells (leukocytes) because they may complicate processing/assaying and/or are not considered to provide a significant contribution to the overall protein profile of the blood. Accordingly, current analyses are inadequate in the case where RBCs make a substantial contribution and/or otherwise influence the protein profile of blood.

It has also become evident that inconsistencies in blood collection techniques and/or the way in which blood is processed may adversely affect the accuracy of known protein profiling.

A need therefore exists for more comprehensive, and/or consistent methods for determining protein profiles in blood. Accordingly, systems, methods and/or kits for addressing these and other problems disclosed herein are desirable. The present disclosure is directed to overcoming and/or ameliorating at least one of the disadvantages of the prior art as will become apparent from the discussion herein.

SUMMARY OF THE DISCLOSURE

The present inventors have surprisingly identified that RBCs, a major component of the blood that is routinely excluded from blood protein profile analyses seeking to determine blood protein profiles, are nonetheless a source of a number of different proteins (e.g., cytokines, chemokines, growth factors) at substantial levels. Moreover, the present inventors have found that the levels of various proteins detected within individual blood compartments (e.g., red blood cells, plasma, leukocytes) may differ significantly depending on the manner in which the blood and/or the components are collected and processed. Thus, the present inventors have created a new and useful laboratory technique for producing a protein profile of an enriched red blood cell sample by evaluating the presence or level of proteins newly-identified in RBCs. The new and useful laboratory technique is a significant improvement over current techniques for producing a protein profile from blood, increasing the ability to detect proteins (e.g., increasing the level of detection). Proteins are more easily detected in an enriched RBC sample due to their higher concentration in RBCs, a unique process to further increase their detectable levels in RBCs, and RBC isolation methods requiring less cell processing. Moreover, the high concentration of proteins in RBCs allows them to be detected in a small volume of blood. Without being bound to theory, it is postulated that RBCs may act as a reservoir for various proteins (e.g., cytokines, chemokines, and growth factors), and the manner in which blood is processed may influence the release and/or sequestration of these proteins by RBCs. This in turn may alter and/or enhance the protein profile of blood and/or other blood compartment(s).

Accordingly, the present disclosure provides improved methods, kits, and/or systems for producing or generating protein profiles in a small volume red blood cell-enriched sample or fraction, thereby reducing or eliminating blood processing effects on protein profiles.

Certain non-limiting embodiments of the present disclosure are listed below:

In one aspect of the disclosure, provide herein are methods for producing a protein profile in a red blood cell-enriched blood sample comprising obtaining a blood sample; leukodepleting at least a portion of the blood sample to produce a red blood cell-enriched sample; and detecting the presence of one or more proteins in a small volume of the red blood cell-enriched sample, wherein the small volume is 5 µL to 100 µL, and wherein the protein profile produced comprises one or more proteins detected in the red blood cell-enriched sample. In one embodiment, the method further comprises measuring the level of the one or more proteins detected in the red blood cell-enriched sample, wherein the protein profile produced comprises one or more proteins measured in the red blood cell-enriched sample. In another embodiment, the method further comprises contacting the red blood cell-enriched sample with at least one cationic salt prior to detecting the presence or measuring the level of the one or more proteins, wherein the cationic salt increases the detectable level of one or more proteins in the red blood cell-enriched sample.

In other aspects of the disclosure, provided herein are methods of producing a protein profile comprising obtaining a blood sample; leukodepleting at least a portion of the blood sample to produce a red blood cell-enriched sample; contacting the red blood cell-enriched sample with at least one cationic salt, wherein the at least one cationic salt increases the detectable level of one or more proteins in the red blood cell-enriched sample; and detecting the presence of one or more proteins in a small volume of the red blood cell-enriched sample, wherein the small volume is 5 µL to 100 µL, wherein the protein profile produced comprises one or more proteins detected in the red blood cell-enriched sample. In one embodiment, the method further comprises measuring the level of the one or more proteins detected in the red blood cell-enriched sample, wherein the protein profile produced comprises one or more proteins measured in the red blood cell-enriched sample. In another embodiment, a cation of the at least one cationic salt is a metal ion or an ammonium ion. In other embodiments, the at least one cationic salt is selected from the group consisting of a sodium salt, a potassium salt, a magnesium salt, a lithium salt, a rubidium salt, a cesium salt, an iron salt, a francium salt, a pyridinium salt, and combinations thereof. In still other embodiments, the at least one cationic salt is a chloride salt selected from the group consisting of sodium chloride, potassium chloride, rubidium chloride, cesium chloride, lithium chloride, and combinations thereof. In another embodiment, the at least one cationic salt is a carbonate salt selected from the group consisting of sodium carbonate, potassium carbonate, rubidium carbonate, cesium carbonate, lithium carbonate, and combinations thereof. In yet another embodiment, the at least one cationic salt is an ammonium salt. In still other embodiments, the ammonium salt is selected from the group consisting of ammonium carbonate, ammonium chloride, ammonium nitrate, and combinations thereof.

In another aspect of the disclosure, provided herein are methods of producing a protein profile in a red blood cell-enriched blood sample comprising obtaining a blood sample; leukodepleting at least a portion of the blood sample to produce a red blood cell-enriched sample; isolating the red blood cells and the plasma in the red blood cell-enriched sample; measuring the level of one or more proteins in the red blood cells and the level of the one or more proteins in the plasma; and calculating a protein ratio comprising the level of the one or more proteins in red blood cells to the level of the one or more proteins in the plasma, wherein the protein profile produced comprises one or more proteins that have a protein ratio of at least 2:1.

In another aspect of the disclosure, provided herein are methods of producing a protein profile in a red blood cell-enriched blood sample comprising obtaining a blood sample; leukodepleting at least a portion of the blood sample to produce a red blood cell-enriched sample; incubating the red blood cells in the red blood cell-enriched sample in a medium; and detecting one or more proteins in the medium, wherein the protein profile produced comprises one or more proteins detected in the medium. In one embodiment, the method further comprises measuring the level of the one or more proteins detected in the medium, wherein the protein profile produced comprises one or more proteins measured in the red blood cell-enriched sample. In another embodiment, the medium is one or more selected from the group consisting of isotonic salt solution, balanced salt solution, saline, phosphate buffered saline (PBS), hank's balanced salt solution (HBSS), and/or Earles' balanced salt solution (EBSS), Roswell Park Memorial Institute medium (RPMI), minimum essential medium (MEM), Improved Minimum Essential Medium (IMEM), Eagle's minimal essential medium (EMEM), Dubelco's modified Eagle's medium (DMEM), and/or Iscove's Modified Dulbecco's Media (IMDM).

In yet another aspect of the disclosure, provided herein are methods of producing a protein profile in a red blood cell-enriched blood sample comprising: obtaining a small volume blood sample; leukodepleting at least a portion of the small volume blood sample to produce a red blood cell-enriched sample; and detecting one or more proteins in the red blood cell-enriched sample, wherein the protein profile produced comprises one or more proteins detected in the red blood cell-enriched sample. In one embodiment, the method further comprises measuring the level of the one or more proteins detected in the red blood cell-enriched sample, wherein the protein profile produced comprises one or more proteins measured in the red blood cell-enriched sample. In another embodiment, the small volume blood sample is obtained from a subject. In another embodiment, the small volume blood sample is between 5 µL and 100 µL. In another embodiment, the small volume blood sample is between 5 µL and 20 µL. In other embodiments, the small volume blood sample is obtained from a finger, heel, ear, or tail. In further embodiments, the small volume blood sample is obtained by finger prick, heel prick, ear prick, or tail prick. In certain embodiments, the small volume blood sample is obtained a number of times selected from the group consisting of one or more times per day, two or more times per day, three or more times per day, four or more times per day, and five or more times per day. In another embodiment, the small volume blood sample is obtained a number of times selected from the group consisting of one or more times per week, two or more times per week, three or more times per week, four or more times per week, five or more times per week, six or more times per week, and seven or more times per week. In yet another embodiment, the small volume blood sample is obtained daily. In another embodiment, the small volume blood sample is obtained a number of times selected from the group consisting of once a week, once every two weeks, once every three weeks, and once every four weeks. In other embodiments, the small volume blood sample is obtained once a month.

In certain embodiments of the methods provided herein, the blood sample is obtained from a subject. In another embodiment, the blood sample is obtained from the capillary of the subject or the vein of the subject. In yet another embodiment, the subject is a human or a non-human animal. In certain embodiments, the subject is a human. In certain other embodiments, the subject is a non-human animal selected from the group consisting of a mouse, rat, hamster, ferret, gerbil, rabbit, monkey, chimpanzee, horse, pony, donkey, sheep, pig, chicken, goat, cat, and dog. In yet another embodiment, the subject has a disease or disorder.

In other embodiments of the methods of the disclosure, the blood sample is leukodepleted by one or more methods selected from the group consisting of flow cytometry, magnetic bead separation, centrifugation, cellulose column, and dextran sedimentation. In certain embodiments, the red blood cells are leukodepleted by dextran sedimentation.

In certain embodiments of the methods of the disclosure, the small volume of the red blood cell-enriched sample is between 5 µL and 20 µL. In yet another embodiment, the small volume of the red blood cell-enriched sample is 5 µL.

In another embodiment of the methods provided herein, the one or more proteins are detected or measured from one or more places selected from the group consisting of the one of more proteins are detected or measured from one or more places selected from the group consisting of the surface of the red blood cells, the interior of red blood cells, the lysate of red blood cells, the supernatant of the red blood cells, medium containing the red blood cells, and medium that previously contained the red blood cells.

In other embodiments of the methods provided herein, the presence of two or more proteins is detected or the level of two or more proteins is measured in the red blood cell-enriched sample. In another embodiment, the presence of three or more proteins is detected or the level of three or more proteins is measured in the red blood cell-enriched sample. In yet another embodiment, the presence of four or more proteins is detected or the level of four or more proteins is measured in the red blood cell-enriched sample. In still another embodiment, the presence of five or more proteins is detected or the level of five or more proteins is measured in the red blood cell-enriched sample. In another embodiment, the presence of ten or more proteins is detected or the level of ten or more proteins is measured in the red blood cell-enriched sample. In still other embodiments, the presence of thirty or more proteins is detected or the level of thirty or more proteins is measured in the red blood cell-enriched sample. In certain embodiments, the presence of one or more proteins is detected or the level of one or more proteins is measured using one or more antibodies. In some embodiments, the one or more proteins are selected from the group consisting of chemokines, cytokines, growth factors, receptors, intracellular signal transmitters, hormones, nuclear transcription factors, neurotransmitters, and extracellular matrix components, and enzymes. In yet another embodiment, the one or more proteins are selected from the group consisting of the proteins listed in Table 1 or a combination of proteins listed in Table 2. In still other embodiments, the one or more proteins are selected from the group consisting of basic FGF, CTACK, Eotaxin, G-CSF, GM-CSF, HGF, IFN-α2, IFN-γ, IL-10, IL-12p70, IL-13, IL-12p40, IL-15, IL-16, IL-17A, IL-18, IL-1α, IL-1β, IL-2, IL-2ra, IL-3, IL-4, IL-5, IL-6, IL-7, IL-9, IP-10, LIF, M-CSF, MIG, MIP-1α, MIP-1β, PDGF-BB, SDF-1α, TNF-α, TNF-β, TRAIL, VEGF, CRP, and DDT.

In one aspect of the disclosure, provided herein are methods for producing a disease protein profile in a red blood cell-enriched blood sample comprising obtaining at least one protein profile produced according to the methods provided herein from a subject having a disease or disorder, and a subject not having the disease or disorder; and comparing the protein profile of the subject having the disease or disorder to the protein profile of the subject not having the disease or disorder, wherein the disease protein profile produced comprises one or more proteins that have a different presence or level in the protein profile from a subject having the disease or disorder compared to the protein profile of the subject not having the disease or disorder. In one embodiment, the disease or disorder is cancer. In a further embodiment, the disease protein profile is a cancer protein profile comprising one or more proteins selected from the group consisting of IL-1, IL-2, IL-4, IL-5, IL-6, IL-8, IL-10, IL-12, IL-15, IL-17, TNF-α, TGF-β, and IFN-γ. In another embodiment, the disease or disorder is preeclampsia. In yet another embodiment, the disease profile is a preeclampsia protein profile comprising one or more proteins selected from the group consisting of TNF-α, IFN-γ, IL-4, IL-5, IL-10, IL-1β, IL-6, IL-8, and IL-12. In a further embodiment, the preeclampsia protein profile comprises one or more proteins selected from the group consisting of IL-6, IL-8, and IFN-γ.

In another aspect of the disclosure, provided herein are methods for determining whether a subject has a disease or disorder comprising obtaining a protein profile of the subject produced according to the methods provided herein; and comparing the protein profile of the subject to a disease protein profile, wherein similarities in the presence or level of one or more proteins in the protein profile of the subject compared to the presence or level of the one or more proteins in the disease protein profile indicate the subject has the disease or disorder. In one embodiment, the disease or disorder is selected from the group consisting of cancer, preeclampsia, autoimmune disease, cardiovascular disease, neurodegenerative disease, diabetes, metabolic disorders, musculoskeletal disease, infectious disease, genetic disorders, renal disorders, and gastrointestinal disorders.

In yet another aspect of the disclosure, provided herein are methods of monitoring treatment in a subject comprising obtaining a protein profile produced according the methods provided herein from a subject before treatment and after treatment; and comparing the protein profile of the subject before treatment to the protein profile of the subject after treatment, wherein a difference in the presence or level of one or more proteins in the protein profile of the subject before treatment compared to the protein profile of the subject after treatment indicates an effect of the treatment on the subject. In one embodiment, the protein profile of a subject who has received no treatment is compared to the protein profile of the subject after receiving treatment. In another embodiment, at least one protein profile of a subject after treatment at one point in time is compared to at least one protein profile of the subject after treatment at a different point in time. In further embodiments, the subject has received the same treatment. In still other embodiments, the subject has received a different treatment. In certain embodiments, the blood sample is a small volume blood sample. In certain other embodiments, the subject is monitored a number of times selected from the group consisting of one or more times per day, two or more times per day, three or more times per day, four or more times per day, and five or more times per day. In further embodiments, the subject is monitored a number of times selected from the group consisting of one or more times per week, two or more times per week, three or more times per week, four or more times per week, five or more times per week, six or more times per week, and seven or more times per week. In another embodiment, the subject is monitored daily. In yet another embodiment, the subject is monitored a number of times selected from the group consisting of once a week, once every two weeks, once every three weeks, and once every four weeks. In yet another embodiment, the subject is monitored once a month.

In other aspects of the disclosure, provided herein are methods of determining the effectiveness of a treatment comprising obtaining at least one protein profile produced according to the methods provided herein from a subject that has undergone the treatment, and a subject that has not undergone the treatment; and comparing the protein profile of the subject who has undergone the treatment to the protein profile of the subject who has not undergone the treatment, wherein similarities in the presence or level of one or more proteins in the protein profile of the subject that has undergone the treatment compared to the protein profile of the subject that has not undergone the treatment indicate the effectiveness of the treatment.

In another aspect of the disclosure, provided herein are methods for increasing the accuracy of the detection or measurement of one or more proteins in a blood sample comprising contacting the blood sample with dextran; allowing the blood sample to form a leukocyte-containing layer and a red blood cell dense layer; isolating the red blood cells in the red blood cell dense layer to create a red blood cell-enriched blood sample; and detecting the presence or measuring the level of one or more proteins in the red blood cell-enriched blood sample. In one embodiment, the blood sample is a small volume blood sample. In a further embodiment, the small volume blood sample is between 5 µL and 100 µL. In another embodiment, the ratio of blood to dextran in the blood sample is selected from the group consisting of 1:1, 2:1, 3:1, 4:1, 5:1, 6:1, 7:1, 8:1, 9:1, and 10:1. In other embodiments, the average depletion of white blood cells and platelets from the blood sample is 85% to 99%.

In another aspects of the disclosure, provided herein are kits for measuring the protein profile of a blood sample comprising at least one reagent to leukodeplete a blood sample and produce a red blood cell-enriched sample; and at least one reagent to detect the presence or measure the level of one or more proteins in a small volume red blood cell-enriched sample. In one embodiment, the kit further comprises at least one reagent to obtain a blood sample from a subject. In another embodiment, the reagent to detect the presence or measure the level of one or more proteins is one or more antibodies. In certain embodiments, the reagent to detect the presence or measure the level of one or more proteins is an enzyme-linked immunosorbent assay (ELISA) apparatus.

In one aspect of the disclosure, provided herein is a method for generating a protein profile from a blood sample obtained from a subject or a component of the blood sample, the method comprising: determining levels of one or more proteins in the blood sample or the blood sample component, wherein the blood sample and the blood sample component each comprise red blood cells (RBCs).

In one embodiment of the method, the protein profile is generated from the blood sample component. In another embodiment of the method the number of RBCs constitute more than: 0.5%, 1%, 5%, 10%, 20%, 30%, 40%, 50%, 60%, 70%, 80%, 90%, 95%, 97.5%, 98%, 99%, 99.5%, 99.75%, 99.9%, or 99.95%; of total blood cells present in the blood sample component. In yet another embodiment of the methods, the blood sample component is a RBCs-enriched fraction produced by leukodepletion of the blood sample. In other embodiments of the method, the leukodepletion removes more than: 90%, 92.5%, 95%, 97.5%, 99%, 99.5%, 99.75%, 99.9%, or 99.95% of the original number of leukocytes from the blood sample or portion thereof. In still other embodiments, the leukodepletion provides a RBCs-enriched fraction in which more than: 99%, 99.5%, 99.75%, 99.9%, or 99.95% of the total number of blood cells in the fraction are RBCs. In further embodiments, the blood sample or portion thereof is subjected to platelet depletion. In another embodiment, the platelet depletion removes more than: 90%, 92.5%, 95%, 97.5%, 99%, 99.5%, 99.75%, 99.9%, or 99.95% of the original number of platelets from the blood sample or portion thereof.

In certain embodiments of the methods, the one or more proteins are selected from the group consisting of: basic FGF, CTACK, Eotaxin, G-CSF, GM-CSF, HGF, IFN-α2, IFN-γ, IL-10, IL-12p70, IL-13, IL-12p40, IL-15, IL-16, IL-17A, IL-18, IL-1α, IL-10, IL-2, IL-2ra, IL-3, IL-4, IL-5, IL-6, IL-7, IL-9, IP-10, LIF, M-CSF, MIG, MIP-1α, MIP-1β, PDGF-BB, SDF-1α, TNF-α, TNF-β, TRAIL, VEGF, CRP, DDT, and combinations thereof. In other embodiments, the one or more proteins comprise or consist of a protein listed in Table 1 or a combination of proteins listed in Table 2.

In some embodiments of the methods, the levels of one or more proteins on the surface of the RBCs are determined. In still other embodiments, the levels of one or more proteins within the RBCs are determined. In another embodiment, the levels of one or more proteins released by the RBCs are determined. In yet another embodiment, the blood sample is a dried blood spot sample (DBS).

In one aspect of the disclosure, generation the protein profile comprises: producing a cell lysate, a cell wash, or a cell supernatant from a cell population comprising the RBCs; and determining levels of one or more proteins in the cell lysate, the cell wash, or the cell supernatant. In one embodiment, determination of the levels of one or more proteins is conducted using the cell lysate. In other embodiments of the methods, determination of the levels of one or more proteins is conducted by snap freezing the RBCs; thawing the RBCs to produce the cell lysate; and determining levels of the one or more proteins in the cell lysate. In yet another embodiment, determination of the levels of one or more proteins is conducted using a cell wash. In a further embodiment, the cell wash is produced by combining two or more cell washes. In yet another embodiment, the cell wash is produced using wash liquid comprising one or more of: isotonic salt solution, balanced salt solution, saline, phosphate buffered saline (PBS), hank's balanced salt solution (HBSS), and/or Earles' balanced salt solution (EBSS).

In some embodiments, determination of the levels of one or more proteins is conducted using the cell supernatant. In another embodiment, the cell supernatant is produced by culturing cells used to produce the cell supernatant in cell culture media comprising one or more of: Roswell Park Memorial Institute medium (RPMI), minimum essential medium (MEM), Improved Minimum Essential Medium (IMEM), Eagle's minimal essential medium (EMEM), Dubelco's modified Eagle's medium (DMEM), and/or Iscove's Modified Dulbecco's Media (IMDM). In other embodiments, the step of determining levels of one or more proteins is conducted using multiple samples of the cell supernatant, and the samples of the cell supernatant are extracted at different time points from a culture of the cells used to produce the cell supernatant.

In certain embodiments, methods comprise: contacting the blood sample with an anticoagulant; and determining levels of one or more proteins in leukocytes separated from the RBCs. In one embodiment, the method comprises: snap freezing the leukocytes; thawing the leukocytes to produce a leukocyte lysate; and determining levels of one or more proteins in the thawed leukocytes. In another embodiment, the method comprises: determining levels of one or more proteins in a cell wash and/or a cell supernatant generated by washing and/or culturing the leukocytes. In further embodiments, the methods comprise: contacting the blood sample with an anticoagulant; and determining levels of one or more proteins in platelets separated from the RBCs. In still other embodiments, the method comprises snap freezing the platelets; thawing the platelets to produce a platelet lysate; and determining levels of one or more proteins in the thawed platelets. In another embodiment, the method comprises determining levels of one or more proteins in a cell wash and/or a cell supernatant generated by washing and/or culturing the platelets.

In some embodiments, the methods comprise contacting the blood sample with an anticoagulant; and determining levels of one or more proteins in plasma separated from the RBCs.

In other embodiments of the methods, snap freezing is at a temperature of below or at: −5° C., −10° C., −20° C., −30° C., −40° C., −50° C., −60° C., −70° C., −75° C., −80° C., 100° C., −120° C., −140° C., −160° C., −180° C., −190° C., −195° C., or −196° C. In other embodiments of the methods, the snap freezing and thawing comprises multiple freeze-thaw cycles.

In another embodiment of the methods, leukocytes are separated from the RBCs by flow cytometry and/or dextran sedimentation. In other embodiments, platelets are separated from the RBCs by centrifugation.

In still other embodiments of the methods, the blood sample has been mixed with a blood stabilising agent during collection. In another embodiment, the blood sample obtained from the subject is contacted with a blood stabilising agent prior to determining the levels of one or more proteins. In yet another embodiment of the methods, the blood stabilising agent is one or more of: a protease inhibitor, a surfactant, a protein denaturation agent, an RNA stabiliser, an anticoagulant, and/or an anticoagulant in combination with another stabilising agent that is not an anticoagulant. In some embodiments of the methods, the blood stabilising agent is not an anticoagulant. In another embodiment, the blood stabilising agent is a protease inhibitor selected from the group consisting of: aprotinin, leupeptin, α2-macroglobulin, antipain dihydrochloride, calpain inhibitor I, calpain inhibitor II, chymostatin, TLCK (CAS 131918-97-3), trypsin-inhibitor, Pefabloc SC (Roche), PMSF (C6H5CH2SO2F—Thermo Fisher Scientific), complete protease inhibitor cocktail (Roche), and combinations thereof. In still other embodiments, the anticoagulant is selected from the group consisting of: heparin, heparin sulfate, perlecan, agrin, syndecan, betaglycan, glypican, serglycin, citrate, acid citrate dextrose, EDTA, and combinations thereof.

In certain embodiments of the methods, the step of contacting the blood sample with the blood stabilising agent is performed within: 5 seconds, 10 seconds, 20 seconds, 30 seconds, 1 minute, 2 minutes, 3 minutes, 4 minutes, 5 minutes, 10 minutes, 15 minutes, 30 minutes, 45 minutes, 1 hour, 2 hours, 3 hours, 4 hours, 5 hours, 7.5 hours or 10 hours of the blood sample being obtained from the subject.

In one embodiment of the methods, the blood sample is obtained from a capillary of the subject. In other embodiments of the methods, the blood sample is obtained from a vein of the subject.

In some embodiments of the methods, the step of determining the levels of one or more proteins is conducted within: 2 minutes, 5 minutes, 10 minutes, 15 minutes, 20 minutes, 25 minutes, 30 minutes, 40 minutes, 50 minutes, 1 hour, 1.5 hours, 2 hours, 3 hours, 4 hours, 5 hours, 6 hours, 7 hours, 8 hours, 9 hours, 10 hours, 11 hours, 12 hours, 18, hours, 24 hours, 36 hours, or 48 hours of when the blood sample is obtained.

In certain aspects, the methods further comprise a first step of obtaining the blood sample from the subject.

Further non-limiting embodiments of the present disclosure are listed below:

In certain aspects of the disclosure, provided herein is a method for generating a protein profile from a blood sample obtained from a subject, the method comprising the steps of: producing a cell lysate, a cell wash, or a cell supernatant from the blood sample or a component of the blood sample; and determining levels of one or more proteins in the cell lysate, the cell wash, or the cell supernatant, wherein the blood sample or the blood sample component comprises red blood cells. In one embodiment of the method, the red blood cells constitute more than: 0.5%, 1%, 5%, 10%, 20%, 30%, 40%, 50%, 60%, 70%, 80%, 90%, 95%, 97.5%, 98%, 99%, 99.5%, 99.75%, 99.9%, or 99.95% of total number of blood cells present in the blood sample or the blood sample component. In another embodiment, the methods comprise leukodepletion of the blood sample and/or the blood sample component prior to producing the cell lysate, the cell wash, or the cell supernatant. Still other embodiments of the method comprise a step of: contacting the blood sample or the blood sample component with a blood stabilising agent; and/or snap freezing the blood sample or the blood sample component.

In one aspect of the disclosure, provided herein is a method comprises generating a protein profile from a blood sample obtained from a subject, the method comprising the steps of: producing a red blood cell (RBCs)-enriched fraction by leukodepletion of the blood sample or a component of the blood sample; producing a cell lysate, a cell wash, or a cell supernatant from the RBCs-enriched fraction; and determining levels of one or more proteins in the cell lysate, the cell wash, or the cell supernatant. In one embodiment, the leukodepletion provides an RBCs-enriched fraction in which more than: 90%, 92.5%, 95%, 97.5%, 99%, 99.5%, 99.75%, 99.9%, or 99.95% of the number of leukocytes present in the blood sample are removed. In another embodiment of the methods, the leukodepletion provides an RBC-enriched fraction comprising more than: 99%, 99.5%, 99.75%, 99.9%, or 99.95% of the number of RBCs in total blood cells.

In other embodiments, the methods comprise: contacting the RBCs-enriched fraction with a blood stabilising agent; and/or snap freezing the blood sample or the blood sample component prior to producing the cell lysate, the cell wash, or the cell supernatant. In yet another embodiment, the step of producing the RBC-enriched fraction is performed prior to said snap freezing. In yet another embodiment, the step of producing the RBC-enriched fraction is performed after said snap freezing.

In some embodiments of the methods, said one or more proteins in the cell lysate, the cell wash, or the cell supernatant are selected from the group consisting of: basic FGF, CTACK, Eotaxin, G-CSF, GM-CSF, HGF, IFN-α2, IFN-γ, IL-10, IL-12p70, IL-13, IL-12p40, IL-15, IL-16, IL-17A, IL-18, IL-1α, IL-1β, IL-2, IL-2ra, IL-3, IL-4, IL-5, IL-6, IL-7, IL-9, IP-10, LIF, M-CSF, MIG, MIP-1α, MIP-1β, PDGF-BB, SDF-1α, TNF-α, TNF-β, TRAIL, VEGF, and combinations thereof. In another embodiment, said one or more proteins in the cell lysate, the cell wash, or the cell supernatant comprise or consist of: a protein listed in Table 1; or a combination of proteins listed in Table 2.

In still other embodiments, the methods comprise platelet depletion of: the blood sample, or the blood sample component. In one embodiment, the platelet depletion removes more than: 90%, 92.5%, 95%, 97.5%, 99%, 99.5%, 99.75%, 99.9%, or 99.95% of the total number of platelets present in the blood sample or the blood sample component.

In another embodiment, the step of contacting the blood with a blood stabilising agent and/or snap freezing is performed within: 5 seconds, 10 seconds, 20 seconds, 30 seconds, 1 minute, 2 minutes, 3 minutes, 4 minutes, 5 minutes, 10 minutes, 15 minutes, 30 minutes, 45 minutes, 1 hour, 2 hours, 3 hours, 4 hours, 5 hours, 7; 5 hours or 10 hours of conducting the step of the blood sample being obtained from the subject. In other embodiments, the step of producing the cell lysate comprises: one or more cycles of snap freezing and thawing cells.

In other embodiments, the methods comprise: contacting a blood sample with an anticoagulant; and determining levels of one or more proteins in leukocytes obtained from said leukodepletion of the blood sample or the blood sample component. In certain embodiments, the methods comprise:

snap freezing leukocytes obtained from said leukodepletion of the blood sample or the blood sample component; thawing the leukocytes; and determining levels of one or more proteins in the thawed leukocytes. In further embodiments, the methods comprise contacting the blood sample with an anticoagulant; and determining levels of one or more proteins in platelets obtained from said platelet depletion of the blood sample or the blood sample component. In still other embodiments, the methods comprise: snap freezing platelets obtained from said platelet depletion of the blood sample or the blood sample component; thawing the platelets; and determining levels of one or more proteins in the thawed platelets.

In still other embodiments, the methods comprise: contacting the blood sample with an anticoagulant; separating plasma from the blood sample or the blood sample component; and determining levels of the one or more proteins in the plasma. In a further embodiment, the method further comprises: snap freezing the plasma; thawing the plasma; and determining levels of one or more proteins in the thawed plasma.

In some embodiments, the platelet depletion of the blood sample or the blood sample component is by centrifugation. In other embodiments, leukodepletion of the blood sample or the component of the blood sample is by flow cytometry and/or dextran sedimentation. In still other embodiments, the step of snap freezing is at a temperature of below: $-5°$ C., $-10°$ C., $-20°$ C., $-30°$ C., $-40°$ C., $-50°$ C., $-60°$ C., $-70°$ C., $-75°$ C., or $-80°$ C. In further embodiments, the step of thawing to generate the cellular lysate comprises: one freeze-thaw cycle, two freeze-thaw cycles, three freeze-thaw cycles, four freeze-thaw cycles, five free-thaw cycles, or more than two freeze-thaw cycles, more than three freeze-thaw cycles, more than four freeze-thaw cycles, or more than five freeze-thaw cycles.

In other embodiments of the methods, the blood sample or the blood sample component comprises heparin and/or EDTA.

In still other embodiments of the methods, the step of determining levels of one or more proteins is conducted using the cell wash. In another embodiment, the cell wash is produced by combining two or more cell washes. In yet another embodiment, the cell wash is produced using wash fluid comprising one or more of: isotonic salt solution, balanced salt solution, saline, phosphate buffered saline (PBS), Hank's balanced salt solution (HBSS), and Earles' balanced salt solution (EBSS).

In certain embodiments of the methods, the step of determining the levels of one or more proteins is conducted using the cell supernatant. In another embodiment, the cell supernatant is produced by culturing the cells used to produce the cell supernatant in cell culture media comprising one or more of: Roswell Park Memorial Institute medium (RPMI), minimum essential medium (MEM), Improved Minimum Essential Medium (IMEM), Eagle's minimal essential medium (EMEM), Dubelco's modified Eagle's medium (DMEM), and Iscove's Modified Dulbecco's Media (IMDM).

In other embodiments of the methods, the step of determining levels of one or more proteins is conducted using multiple samples of the cell supernatant, and the samples of the cell supernatant are extracted at different time points from a culture of the cells used to produce the supernatant.

In another embodiment, the methods comprise: contacting the blood sample with an anticoagulant; and determining levels of one or more proteins in leukocytes obtained from leukodepletion of the blood sample or the blood sample component. In other embodiments, the methods comprise contacting the blood sample with an anticoagulant; and determining levels of one or more proteins in a cell wash and/or a cell supernatant generated by washing and/or culturing leukocytes obtained from leukodepletion of the blood sample or the blood sample component. In yet other embodiments, the methods comprise contacting the blood sample with an anticoagulant; and determining levels of one or more proteins in platelets obtained from platelet depletion of the blood sample or the blood sample component. In still other embodiments, the methods comprise contacting the blood sample with an anticoagulant; and determining levels of one or more proteins in a platelet wash and/or a platelet supernatant generated by washing and/or culturing platelets obtained from platelet depletion of the blood sample or the blood sample component. In another embodiment, the methods comprise contacting the blood sample with an anticoagulant; separating plasma from the blood sample; and determining the levels of the one or more proteins in the plasma.

In other embodiments, the platelet depletion comprises centrifugation. In another embodiment, the leukodepletion comprises flow cytometry and/or dextran sedimentation.

In other embodiments, the blood sample or the blood sample component comprises heparin and/or EDTA. In further embodiments, the methods comprise a step of: contacting the blood sample or the blood sample component with a blood stabilising agent prior to the step of producing the cell wash or the cell supernatant. In another embodiment, the step of contacting with the blood stabilising agent is performed within: 5 seconds, 10 seconds, 20 seconds, 30 seconds, 1 minute, 2 minutes, 3 minutes, 4 minutes, 5 minutes, 10 minutes, 15 minutes, 30 minutes, 45 minutes, 1 hour, 2 hours, 3 hours, 4 hours, 5 hours, 7.5 hours or 10 hours of the blood sample being obtained from the subject.

In some embodiments, the blood stabilising agent is: a protease inhibitor, a protein denaturation agent, an RNA stabiliser, an anticoagulant, and/or an anticoagulant in combination with another stabilising agent that is not an anticoagulant; is not an anticoagulant; an anticoagulant in combination with another stabilising agent that is not an anticoagulant, and/or is not heparin, EDTA, EGTA, a citrate (e.g., sodium citrate), or a fluoride (e.g., sodium fluoride).

In certain embodiments, the blood sample is obtained from a capillary of the subject. In other embodiments, the blood sample is obtained from a vein of the subject.

In other embodiments of the methods, the step of determining levels of one or more proteins is conducted within: 2 minutes, 5 minutes, 10 minutes, 15 minutes, 20 minutes, 25 minutes, 30 minutes, 40 minutes, 50 minutes, 1 hour, 1.5 hours, 2 hours, 3 hours, 4 hours, 5 hours, 6 hours, 7 hours, 8 hours, 9 hours, 10 hours, 11 hours, 12 hours, 18, hours, 24 hours, 36 hours, or 48 hours of when the blood sample is obtained.

In one aspect of the disclosure, provided herein are methods for generating a protein profile from a blood sample of a subject, the method comprising the steps of: producing a cell lysate from a whole blood sample obtained from a subject; and determining levels of one or more proteins in the cell lysate. In one embodiment, the method comprises: snap-freezing the whole blood sample; thawing the whole blood sample to produce the cell lysate; and determining levels of one or more proteins in the cell lysate. In another embodiment, said step of thawing the whole blood sample to generate the cell lysate comprises more than: one freeze-thaw cycle, two freeze-thaw cycles, or three freeze-thaw cycles. In still other embodiments, snap freezing is at a temperature of below: −5° C., −10° C., −20° C., −30° C., −40° C., −50° C., −60° C., −70° C., −75° C., −80° C., −90, −100° C., −120° C., −104° C., −160° C., −180° C., −190° C., −200° C.

In certain embodiments of the methods, the one or more proteins in the cell lysate is/are selected from the group consisting of: basic FGF, CTACK, Eotaxin, G-CSF, GM-CSF, HGF, IFN-α2, IFN-γ, IL-10, IL-12p70, IL-13, IL-12p40, IL-15, IL-16, IL-17A, IL-18, IL-1α, IL-1β, IL-2, IL-2ra, IL-3, IL-4, IL-5, IL-6, IL-7, IL-9, IP-10, LIF, M-CSF, MIG, MIP-1α, MIP-1β, PDGF-BB, SDF-1α, TNF-α, TNF-β, TRAIL, VEGF, and combinations thereof. In some embodiments, the one or more proteins in the cell lysate comprise or consist of: a protein listed in Table 1; or a combination of proteins listed in Table 2.

In other embodiments, the methods comprise: contacting the whole blood sample with a blood stabilising agent prior to the step of producing the cell lysate. In another embodiment, the blood stabilising agent: is a protease inhibitor, a protein denaturation agent, an RNA stabiliser, an anticoagulant, and/or an anticoagulant in combination with another stabilising agent that is not an anticoagulant; is not an anticoagulant; is an anticoagulant in combination with another stabilising agent that is not an anticoagulant, and/or is not heparin, EDTA, EGTA, a citrate (e.g., sodium citrate), or a fluoride (e.g., sodium fluoride). In still another embodiment, contacting of the whole blood sample with the blood stabilising agent occurs when the whole blood sample is obtained, or, within: 5 seconds, 10 seconds, 20 seconds, 30 seconds, 45 seconds, 1 minute, 2 minutes, 3 minutes, 4 minutes, 5 minutes, 10 minutes, 15 minutes, 30 minutes, 45 minutes, 1 hour, 2 hours, 3 hours, 4 hours, 5 hours, 7.5 hours or 10 hours of when the whole blood sample is obtained. In yet other embodiments, the methods comprise: contacting the whole blood sample with an anticoagulant. In another embodiment, the anticoagulant is heparin and/or EDTA. In further embodiments of the methods, the whole blood sample is obtained from a capillary of the subject. In another embodiment, the whole blood sample is obtained from a vein of the subject.

In still other embodiments of the methods, the step of determining levels of one or more proteins is conducted within: 2 minutes, 5 minutes, 10 minutes, 15 minutes, 20 minutes, 25 minutes, 30 minutes, 40 minutes, 50 minutes, 1 hour, 1; 5 hours, 2 hours, 3 hours, 4 hours, 5 hours, 6 hours, 7 hours, 8 hours, 9 hours, 10 hours, 11 hours, 12 hours, 18, hours, 24 hours, 36 hours, or 48 hours of the step of the whole blood sample being obtained from the subject.

As well as the embodiments discussed in the summary, other embodiments are disclosed in the specification, drawings, and claims. The summary is not meant to cover each and every embodiment; combination or variations are contemplated with the present disclosure.

BRIEF DESCRIPTION OF THE DRAWINGS

Embodiments of the present disclosure are described, by way of example only, with reference to the accompanying figures.

FIG. 21A-21B is a chart indicating the ratio of the levels of various proteins in red blood cells to the levels in plasma.

FIG. 24A-24C is a chart indicating the ratio of the levels of various proteins in red blood cells to the levels in plasma isolated from oncology patients.

DEFINITIONS

Figure 1:
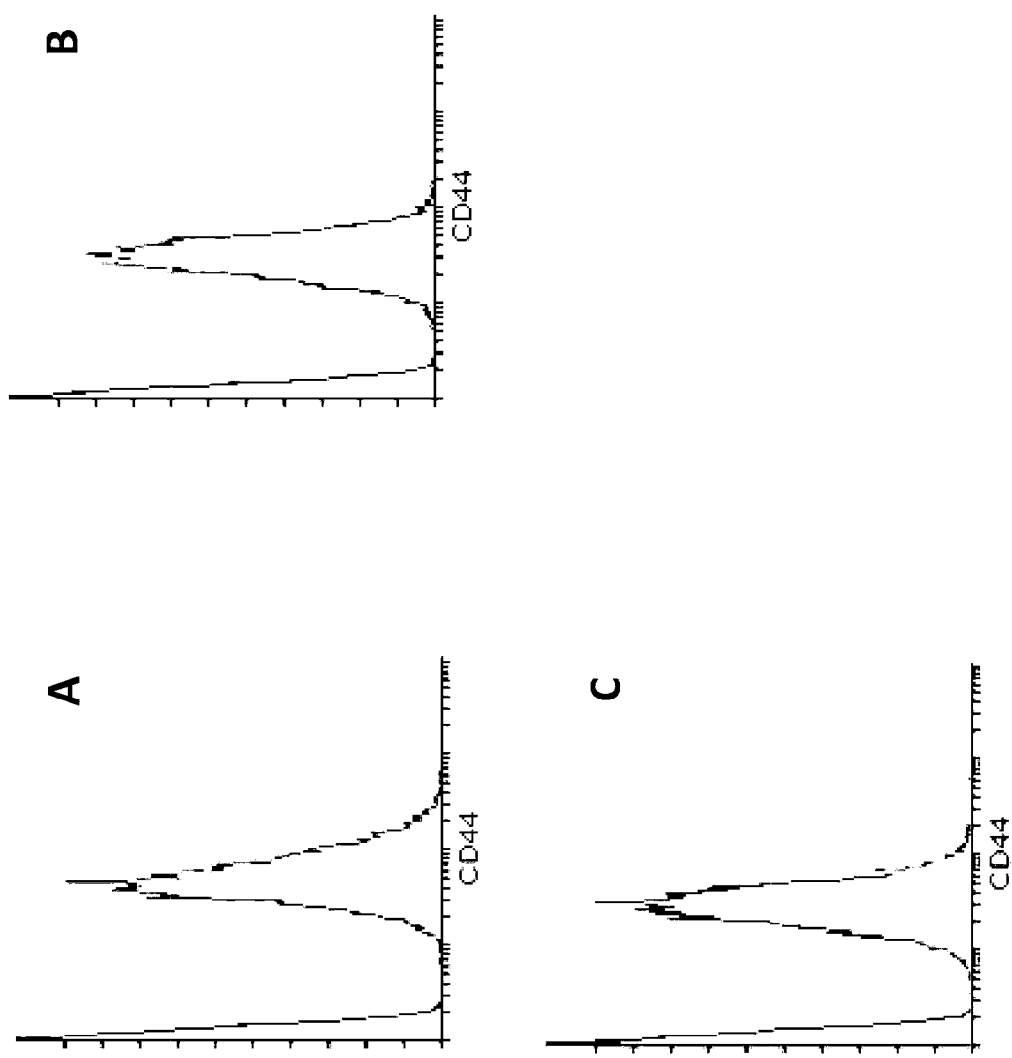
FIG. 1A-1C shows the results of RBC immunophenotyping for CD44 against IgG controls. Cells (filled with grey histogram) are positive for CD44 (n=3).

As used in this application, the singular form "a", "an" and "the" include plural references unless the context clearly dictates otherwise. For example, the term "a cell lysate" includes multiple cell lysates.

As used herein, the term "comprising" means "including." Variations of the word "comprising", such as "comprise" and "comprises," have correspondingly varied meanings. Thus, for example, a method "comprising" steps 'A' and 'B' may consist exclusively of steps 'A' and 'B' or may include one or more additional steps (e.g., steps 'A', 'B', and 'C').

The subject headings used in the detailed description are included for the ease of reference or the reader and should not be used to limit the subject matter found throughout the disclosure or the claims. The subject headings should not be used in construing the scope of the claims or the claim limitations.

As used herein, the term "subject" includes any animal of economic, social or research importance including bovine, equine, ovine, primate, avian and rodent species. Hence, a "subject" may be a mammal such as, for example, a human or a non-human mammal.

As used herein, the terms "antibody" and "antibodies" include IgG (including IgG1, IgG2, IgG3, and IgG4), IgA (including IgA1 and IgA2), IgD, IgE, or IgM, and IgY, whole antibodies, including single-chain whole antibodies, and antigen-binding fragments thereof. Antigen-binding antibody fragments include, but are not limited to, Fab, Fab' and F(ab')2, Fd, single-chain Fvs (scFv), single-chain antibodies, disulfide-linked Fvs (sdFv) and fragments comprising either a VL or VH domain. The antibodies may be from any animal origin. Antigen-binding antibody fragments, including single-chain antibodies, may comprise the variable region(s) alone or in combination with the entire or partial of the following: hinge region, CH1, CH2, and CH3 domains. Also included are combinations of variable region(s) and hinge region, CH1, CH2, and CH3 domains. Antibodies may be monoclonal, polyclonal, chimeric, multispecific, humanized, and human monoclonal and polyclonal antibodies which specifically bind the biological molecule.

As used herein, the term "protein" refers to a polymer made up of amino acids linked together by peptide bonds.

As used herein, the term "protein profile" refers to protein(s) and/or protein fragment(s) present in a sample. The sample may or may not comprise cells. If the sample comprises cells, the proteins or protein fragments may exist intracellularly and/or partially or completely at the cell surface. Although not a requirement, the protein profile may also provide quantitative information for protein(s) and/or protein fragment(s) in the sample.

As used herein, the term "blood sample" refers to a sample comprising at least in part blood and/or blood components. The blood sample can be obtained directly from one or more subjects or from a pre-existing collection of blood from one or more subjects. The blood sample can be obtained from a human subject by a number of methods known in the art e.g., venipuncture (e.g., butterfly needle and VACUTAINER, straight needle and VACUTAINER, and butterfly needle and syringe) of a body part (e.g., arm, leg, ear) or by stick (e.g., finger, heel, or ear prick). The blood sample can be obtained from a non-human mammal subject by a number of methods known in the art e.g., venipuncture (e.g., needle and syringe) of any body part (e.g., tail, arm, leg (e.g., thigh), nose, face, ear, thorax, neck/throat, tongue, heart) or by stick (e.g., finger, heel, ear, or tail prick). The blood sample can be obtained from other non-human animals (e.g., chicken, birds) by a number of methods known in the art e.g., venipuncture (e.g., needle and syringe) of a body part (e.g., wing, throat, heart).

As used herein, the term "blood cells" or "cell present in the blood sample" refers to cells in the sample, including red blood cells and white blood cells, but excludes platelets.

As used herein, the term "red blood cell-enriched blood sample" or "RBC-enriched fraction" refers to a sample or component of a sample in which the proportion of RBCs is increased compared to that of the blood sample prior to enriching. The proportion of RBCs may be increased, for example, by removing cell type(s) from the sample that are not RBCs (e.g., removal of leukocytes (leukodepletion) and/or removal of platelets), and/or by removing RBCs from other cell type(s) in the sample to provide a separate sample. The RBC-enriched fraction may comprise more than 99.5%, more than 99.6%, more than 99.7%, more than 99.75%, more than 99.8%, more than 99.85%, more than 99.9%, more than 99.5%, approximately 100% red blood cells, or 100% red blood cells of the total blood cell number.

As used herein, the term "snap freezing" refers to freezing blood cells (e.g., RBCs) and/or plasma/serum to a temperature below their freezing point generally within a rapid time period (for example, in a period of a few milliseconds, 1-2 seconds, 1-5 seconds, 1-10 seconds, 1-15 seconds, 1-20 seconds, 10-20 seconds, 10-30 seconds, 30-60 seconds, less than one minute, or less than two minutes).

As used herein, "leukodepletion" refers to reducing the proportion of leukocytes in a blood sample or a blood sample component, for example, by removing leukocytes from the blood sample or blood sample component, or alternatively by removing other blood constituent(s) from the blood sample or blood sample component to provide a separate leukodepleted sample. In some embodiments, leukodepletion includes platelet depletion.

As used herein, "platelet depletion" refers to reducing the proportion of platelets in a blood sample or a blood sample component, for example, by removing platelets from the blood sample or blood sample component, or alternatively by isolating other blood constituent(s) from the blood sample or blood sample component to provide a separate platelet depleted sample.

As used herein, a "cell supernatant" will be understood to mean a cell culture medium used to culture a population cells at a given temperature or a given range of temperatures for a given time period, for example, more than: 30 minutes, 1 hour, 2 hours, 3 hours, 6 hours, 12 hours, 24 hours, 48 hours, 72 hours, 96 hours, or 120 hours.

As used herein, a "cell wash" will be understood to mean a liquid that has been used to rinse a population of cells, and differs from a cell supernatant as defined above insofar as the cell wash is not used as a medium for cell culture. Accordingly, a fluid used as to generate a "cell wash" may be mixed with the cell population for a period of less than: 30 minutes, 20 minutes, 15 minutes, 10 minutes, 5 minutes, 4, minutes, 3 minutes, 2 minutes, 1 minute, or 30 seconds.

As used herein, a "medium" refers to a composition having the ability to maintain the viability of cells within a blood sample, cells isolated from a blood sample, or cell components produced from cells isolated from a blood sample. The medium can stimulate cell growth and proliferation or maintain cells at a particular and/or existing state. Non-limiting examples of media include isotonic salt solution, balanced salt solution, saline, phosphate buffered saline (PBS), hank's balanced salt solution (HBSS), Earles' balanced salt solution (EBSS), Roswell Park Memorial Institute medium (RPMI), minimum essential medium (MEM), Improved Minimum Essential Medium (IMEM), Eagle's minimal essential medium (EMEM), Dubelco's modified Eagle's medium (DMEM), and Iscove's Modified Dulbecco's Media (IMDM)

As used herein, the term "small volume" refers to a volume of blood that is one millilitre or less. A small volume can be 1 μL to 100 μL, 100 μL to 200 μL, 200 μL to 300 μL, 300 μL to 400 μL, 400 μL to 500 μL, 500 μL to 600 μL, 600 μL to 700 μL, 700 μL to 800 μL, 800 μL to 900 μL and 900 μL to 1000 μL. In some embodiments, a small volume is 50 μL to 100 μL, 100 μL to 150 μL, 150 μL to 200 μL, 200 μL to 250 μL, 250 μL to 300 μL, 300 μL to 350 μL, 350 μL to 400 μL, 400 μL to 450 μL, 450 μL to 500 μL, 500 μL to 550 μL, 550 μL to 600 μL, 600 μL to 650 μL, 650 μL to 700 μL, 700 μL 750 μL, 750 μL to 800 μL, 800 μL, to 850 μL, 850 μL to 900 μL, 900 μL to 950 μL, 950 μL to 1000 μL. In some embodiments, a small volume is 1 μL to 10 μL, 10 μL to 20 μL, 20 μL to 30 μL, 30 μL to 40 μL, 40 μL to 50 μL, 50 μL to 60 μL, 60 μL to 70 μL, 70 μL to 80 μL, 80 μL to 90 μL, or 90 μL to 100 μL. In other embodiments, a small volume is 1 μL to 5 μL, 5 μL to 10 μL, 10 μL to 15 μL, 15 μL to 20 μL, 20 μL to 25 μL, 25 μL to 30 μL, 30 μL to 35 μL, 35 μL to 40 μL, 40 μL to 45 μL, 45 μL to 50 μL, 50 μL to 55 μL, 55 μL to 60 μL, 50 μL to 65 μL, 65 μL to 70 μL, 70 μL to 75 μL, 75 μL to 80 μL, 80 μL to 85 μL, 85 μL to 90 μL, 90 μL to 95 μL, or 95 μL to 100 μL. In some embodiments, a small volume is 5 μL to 10 μL, 5 μL to 15 μL, 5 μL to 20 μL, 5 μL to 25 μL, 5 μL to 30 μL, 5 μL to 35 μL, 5 μL to 40 μL, 5 μL to 45 μL, 5 μL to 50 μL, 5 μL to 55 μL, 5 μL to 60 μL, 5 μL to 65 μL, 5 μL to 70 μL, 5 μL to 75 μL, 5 μL to 80 μL, 5 μL to 85 μL, 5 μL to 90 μL, 5 μL to 95 μL, or 5 μL to 100 μL. In other embodiments, a small volume is 1 μL, 2 μL, 3 μL, 4 μL, 5 μL, 6 μL, 7 μL, 8 μL, 9 μL, 10 μL, 11 μL, 12 μL, 13 μL, 14 μL, 15 μL, 16 μL, 17 μL, 18 μL, 19 μL, 20 μL, 21 μL, 22 μL, 23 μL, 24 μL, 25 μL, 26 μL, 27 μL, 28 μL, 29 μL, 30 μL, 31 μL, 32 μL, 33 μL, 34 μL, 35 μL, 36 μL, 37 μL, 38 μL, 39 μL, 40 μL, 41 μL, 42 μL, 43 μL, 44 μL, 45 μL, 46 μL, 47 μL, 48 μL, 49 μL, or 50 μL.

As used herein, the term "detectable level" or "level of detection" refers to the ability of a composition or agent to indicate and/or signal the presence of a desired molecule, such as a protein, in a sample (e.g., a blood sample). In a red blood cell-enriched sample described in the methods disclosed herein, for example, the detectable level of a protein may increase due to an increase in the protein available for detection. This increase may be due to one or more reasons, for example, through a disruption of protein-molecule interactions (e.g., protein-protein, protein-membrane, protein-nucleic acid) that prevent and/or decrease the detection of the protein.

As used herein, protein "release" from RBCs refers to proteins that have moved by active or inactive mechanisms from (i) the intracellular region or interior of a RBC to the surface and/or extracellular or exterior region of the RBC (e.g., plasma, serum, or medium) or (ii) moved from the extracellular or exterior region of the RBC (from, e.g., the plasma, serum or medium) to the surface and/or extracellular region or the exterior of the RBC. In some embodiment, the proteins are bound to the surface of the RBCs by cell surface-protein binding interactions known in the art (e.g., receptors, covalent attachment, noncovalent attachment, adhesion). In a further embodiment, the surface bound proteins may be released back into the extracellular or exterior region of the RBC (e.g., into the plasma, serum, or medium).

As used herein, "treatment" refers to one or more therapies, protocols, methods and/or agents that can be used in preventing, managing, alleviating, or ameliorating a disease, disorder, or condition, including in the prevention, alleviation, or amelioration of one or more symptoms of a disease, disorder, or condition and/or a symptom related thereto. In certain embodiments, the terms "treatment" and "treatments" refer to a biological therapy, supportive therapy, and/or other therapies useful in the prevention, management, alleviation, and/or amelioration of a disease, disorder, or condition known to one of skill in the art, such as medical personnel.

As used herein, the phrase "substantially similar" or "substantially the same" denotes a sufficiently high degree of similarity between two numeric values such that one of skill in the art would consider the difference between the two values (e.g., protein concentration/level) to be of little or no biological and/or statistical significance within the context of the biological characteristic measured by the values. For example, the difference between the two values may be less than about 50%, less than about 40%, less than about 30%, less than about 20%, less than about 10%, or less than about 5%.

As used herein, the term "kit" refers to a delivery system having all the components necessary to carry out the methods described herein. By way of non-limiting example, the kits may comprise means for: collecting blood, anticoagulant/s, blood stabilizing agent/s, enrichment of RBC, removal/separation of non-RBC blood components, snap-freezing blood or component/s thereof, lysing cells, washing cells, culturing cells, detecting specific target protein/s intracellularly and/or extracellularly, or combinations thereof. In some embodiments, kits may comprise one or more of the following: device/s for obtaining a blood sample from a subject (e.g. a syringe, needle, butterfly needle, tube, needle holder, blood collection set, transfer device, VACUTAINER, HEMAPEN™); device/s for obtaining a dried blood sample from a subject (e.g. filter paper, cards, HEMASPOT™); device/s for obtaining a red blood cell fraction, a leukocyte fraction, and/or a platelet fraction from a liquid blood sample (e.g. antibody coated magnetic beads); anticoagulants; protease inhibitors; protein denaturation agents; and the like. Such delivery systems include systems that allow for the storage, transport, or delivery of reaction reagents (for example labels, reference samples, supporting material, etc. in the appropriate containers) and/or supporting materials (for example, buffers, written instructions for performing an assay etc.) from one location to another. For example, kits may include one or more enclosures, such as boxes, containing the relevant reaction reagents and/or supporting materials. The term "kit" includes both fragmented and combined kits.

As used herein, the term "fragmented kit" refers to a delivery system comprising two or more separate containers that contain a subportion of the total kit components. The containers may be delivered to the intended recipient together or separately. A delivery system comprising two or more separate containers that each contains a subportion of the total kit components are included within the meaning of the term "fragmented kit".

As used herein, a "combined kit" refers to a delivery system containing all of the components of a reaction assay in a single container (e.g., in a single box housing each of the desired components).

Any description of prior art documents herein, or statements herein derived from or based on those documents, is not an admission that the documents or derived statements are part of the common general knowledge of the relevant art.

DETAILED DESCRIPTION

Currently used techniques for profiling protein levels in blood typically restrict the analysis to serum/plasma and/or PBMC. RBCs are routinely removed during blood processing prior to generating protein profiles.

The present inventors have made the unexpected determination that RBCs provide a significant source of protein markers including various cytokines and chemokines. Accordingly, a deficiency in current technologies has been identified in that RBCs were not previously recognised to provide a source of various protein markers described herein, and their exclusion from protein profiling thus provides an inadequate and/or inaccurate assessment. The present disclosure remedies this deficiency by providing methods for generating protein profiles from blood that incorporate analyses of RBCs. In particular, the present disclosure provides a new and useful laboratory technique for producing a protein profile of an enriched red blood cell sample by evaluating the presence or level of proteins newly-identified in RBCs.

Additionally, it has been determined by the present inventors that protein profiling in blood may vary depending on a number of factors including, for example, the source of the blood (e.g., venous, capillary etc.), whether an anticoagulant is used, the type of anticoagulant used, the timeframe within which protein content is measured after collection, whether blood is initially stabilised upon collection, and the particular blood compartment(s) analysed. Without limitation to a particular mode of action, variations in blood protein profiles arising from factors including those mentioned above are hypothesised to arise at least in part from the previously unknown capacity of RBCs to sequester and release numerous different proteins (e.g., cytokines and chemokines). The degree of protein release (or alternatively sequestration) by RBCs is thought to be influenced by various factors arising during blood collection and processing. Accordingly, a further deficiency in current technologies has been identified in that the protein profile of specific blood compartments (e.g., plasma/serum) was not known to be significantly affected by factors such as blood source (e.g., venous, capillary etc.), anticoagulants, timeframe before measurement post-collection, and/or the presence/absence of stabilising agents. The present disclosure remedies this deficiency by providing methods for generating protein profiles from blood in a manner that minimises changes in RBCs protein profiles during the collection and processing of blood, while also taking into account the protein profile of the RBCs compartment.

The following description conveys exemplary embodiments of the present disclosure in sufficient detail to enable those of ordinary skill in the art to practice it. Features or limitations of the various embodiments described do not necessarily limit other embodiments of the present disclosure or the present disclosure as a whole. Hence, the following detailed description does not limit the scope of the present disclosure, which is defined only by the claims.

Protein Profiling in Red Blood Cells (RBCs)

Blood protein analyses are typically performed using separated serum/plasma and/or PBMC. Despite representing a major component of blood and by far the most abundant cell type (usually >99% of total blood cells), RBCs are routinely excluded from protein profiling assays.

The present disclosure arises at least in part from the unexpected observation that RBCs contain a number of different protein markers relevant to, for example, diagnostic and prognostic outcomes in subjects. Given that RBCs represent a significant portion of the blood and almost its entire cellular component, it is useful to assess the protein profile of RBCs to gain a fuller picture of the overall protein marker content of blood.

The present disclosure also provides methods for generating a protein profile from a blood sample, red blood cell-enriched sample, and/or blood sample component comprising RBCs. In some embodiments, the number of RBCs constitute more than: 0.5%, 1%, 5%, 10%, 20%, 30%, 40%, 50%, 60%, 70%, 80%, 90%, 95%, 97.5%, 98%, 99%, 99.5%, 99.75%, 99.9%, or 99.95%, of total number of blood cells present in the blood sample or the blood sample component.

Blood Samples

The blood sample obtained in the methods is as defined herein (see, e.g., "blood sample") and may be obtained from a subject or an existing collection of blood (e.g., blood previously obtained from one or more subjects). The blood sample may be obtained from a subject using exemplary means known to those of ordinary skill in the art (see, for example, World Health Organisation, "*Requirements for the collection, processing and quality control of blood, blood components and plasma derivatives*", World Health Organisation Technical report Series, No. 840, 1994, Annex 2). By way of non-limiting example, the blood sample may be obtained from a subject using venous blood, capillary blood, arterial blood or combinations thereof.

In some embodiments, a small volume blood sample is obtained from a subject or an existing collection of blood. The small volume can be obtained from a subject by methodologies known to those of ordinary skill in the art, including, for example, by stick (e.g., finger prick, heel prick, ear prick, tail prick). In one embodiment, the small volume blood sample is obtained by finger prick, heel prick, or ear prick (from, e.g., a human). In another embodiment, the small volume blood sample is obtained by tail prick (from, e.g., a mouse or rat). In other embodiments, the small volume blood sample is obtained by finger prick. In other embodiments, the small volume blood sample is obtained by heel prick (from, e.g., an infant). In still other embodiments, the small volume blood sample is obtained by ear prick. In further embodiment, the small volume blood sample is obtained by tail prick.

In some embodiments, the small volume is as defined herein (see, e.g., "small volume"). In other embodiments, the small volume is 5 µL to 100 µL. In another embodiment, the small volume is 5 µL to 50 µL. In other embodiments, the small volume is 5 µL to 20 µL. In yet other embodiments, the small volume is 5 µL to 10 µL. In still other embodiments, the small volume is 5 µL.

Obtaining a small volume blood sample allows for the more frequent sampling of, for example, a subject compared to a larger volume blood sample because taking a small volume blood sample decreases the harm to the subject (e.g., pain, blood loss, slow recovery of blood levels). For instance, using current methods, frequent blood sampling from small animals (e.g., rats, mice) is not achievable because a comprehensive blood analysis requires so much blood that the animal must be sacrificed. Similarly, to prevent harm from blood loss, infants can only be safely sampled frequently by stick (e.g., heel prick). According in the methods provided herein, a small volume blood sample can be obtained, in certain embodiments, with a frequency of one or more times per day, two or more times per day, three or more times per day, four or more times per day, and five or more times per day. In other embodiments, a small volume blood sample is obtained one or more times per week, two or more times per week, three or more times per week, four or more times per week, five or more times per week, six or more times per week, and seven or more times per week. In other embodiments, a small volume blood sample is obtained daily. In still other embodiments, a small volume blood sample is obtained once a week, once every two weeks, once every three weeks, and once every four weeks. In certain embodiments, a small volume blood sample is obtained once a month.

Enriched Red Blood Cell Samples or Fractions

In some embodiments, the methods involve producing or generating a protein profile from a red blood cell-enriched blood sample or a red blood cell-enriched fraction and determining the levels of one or more proteins in the red blood cell-enriched sample or fraction. The red blood cell-enriched sample and red blood cell-enriched fraction may be produced from a blood sample taken from a subject, for example, by leukodepletion and/or platelet depletion. Additionally or alternatively, RBCs may be removed from a sample to produce the red blood cell-enriched sample or fraction.

Methodologies for leukodepletion and platelet depletion are well known to those of ordinary skill in the art (see, for example Wenz, B., "Methods for leukodepletion" in "Clinical Benefits of Leukodepleted Blood Products", pp 5-16, 1995, Springer Berlin Heidelberg; Novotny V., and Brand, A., "Leukocyte-Poor Blood and Platelet Transfusions" in "Modern Transfusion Medicine", pp 117-121, 1995, CRC Press, Inc.; White and Jennings, "Platelet Protocols: Research and Clinical Laboratory Procedures", 1999, Academic Press). Non-limiting examples of suitable techniques for leukodepletion include flow cytometry, dextran sedimentation, ficol/percol density gradient centrifugation, and the like.

The present disclosure also provides methods for increasing the sensitivity of the detection or measurement of one or more proteins in a blood sample by producing a red blood cell-enriched sample and detecting the presence or measuring the level of one or more proteins in the red blood cell-enriched sample, In certain embodiments, the ratio of blood to dextran is between 1:1 and 2:1, 1:1 and 3:1, 1:1 and 4:1, 1:1 and 5:1, 1:1 and 6:1, 1:1 and 7:1, 1:1 and 8:1, 1:1 and 9:1, 1:1 and 10:1. In other embodiments, the ratio of blood to dextran is 1:1, 2:1, 3:1, 4:1, 5:1, 6:1, 7:1, 8:1, 9:1, 10:1. In still other embodiments, the ratio of blood to dextran is 2:1. In further embodiments, the ratio of blood to dextran is 4:1.

By way of non-limiting example, the red blood cell-enriched sample or fraction may be generated by leukodepletion of more than 90%, 92.5%, 95%, 97.5%, 99%, 99.5%, 99.75%, or 99.9% of the number of leukocytes that were present in the blood sample. 'Leukodepletion' in this context may be achieved by depleting leukocytes from the blood sample directly, and/or by removing RBCs from the sample to provide a separate leukodepleted (RBCs-enriched) fraction. In some embodiments, leukodepletion includes platelet depletion.

Additionally or alternatively, the red blood cell-enriched sample or fraction may be generated by platelet depletion of more than 90%, 92.5%, 95%, 97.5%, 99%, 99.5%, 99.75%, or 99.9% of the number of platelets that were present in the blood sample. 'Platelet depletion' in this context may be achieved by depleting platelets from the blood sample directly, and/or by removing RBCs from the sample to provide a separate platelet depleted (RBCs-enriched) fraction.

In some embodiments the red blood cell-enriched sample or fraction may comprise more than 99.75%, more than 99.8%, more than 99.9%, more than 99.95%, approximately 100%, or 100% red blood cells (as a component of the total number of blood cells present within the RBCs-enriched fraction).

The percentage of RBCs in a given enriched sample or fraction may be assessed using routine methodologies known to those of ordinary skill in the art including, for example, flow cytometry, fluorescence microscopy, other antibody-based techniques, and the like.

Small Volume Red Blood Cell-Enriched Samples

The present disclosure also provides methods of producing a protein profile from a small volume of a red blood cell-enriched blood sample. A small volume can be obtained from a red blood cell-enriched blood sample by methods known in the art and as deemed appropriate by one of ordinary skill in the art for subsequent methods of protein detection or protein measurement in the red blood cell-enriched sample (see, e.g., protein profiling below). A small volume is a volume as defined herein (see, e.g., "small volume"). By way of non-limiting example, in other embodiments, the small volume can be 5 µL to 10 µL, 5 µL to 20 µL, 5 µL to 30 µL, 5 µL to 40 µL, 5 µL to 50 µL, 5 µL to 60 µL, 5 µL to 70 µL, 5 µL to 80 µL, 5 µL to 90 µL, or 5 µL to 100 µL. In one embodiment, the small volume is 5 µL to 100 µL. In another embodiment, the small volume is 5 µL to 50 µL. In yet other embodiments, the small volume is 5 µL to 20 µL. In still other embodiments, the small volume is 5 µL to 10 µL. In certain embodiments, the small volume is 5 µL.

Whole Blood Comprising RBCs

In other embodiments, the methods of the present disclosure involve the analysis of a whole blood sample comprising RBCs. In these embodiments, the whole blood sample is analysed for a protein profile without or substantially without altering the relative proportions of blood cell types within the sample and without separating plasma/serum.

The whole blood sample may be obtained using exemplary means known to those of ordinary skill in the art (see, for example, World Health Organisation, "*Requirements for the collection, processing and quality control of blood, blood components and plasma derivatives*", World Health Organisation Technical report Series, No. 840, 1994, Annex 2). Methodology is also presented in the Examples of the present specification.

By way of non-limiting example, the whole blood sample may be obtained using venous blood, capillary blood, arterial blood or combinations thereof.

In some embodiments, methods of the present disclosure involving the analysis of whole blood may be carried out using dried blood spot (DBS) sampling. Non-limiting advantages of DBS sampling include one or more of the following: sample stability, minimal volume requirements (e.g., 30-100 µL per spot), ease of sample collection (e.g., finger, toe or heel prick) and transport. A DBS sample obtained for use in the present disclosure may, for example, maintain stability for months to years under refrigeration and/or at ambient temperature.

Suitable methodologies for DBS are well known to those of ordinary skill in the art (see for example, McDade, et al; Demography 2007, 44: 899-925; De Jesus et al. Clin Chem 2009, 55:1; 158-164; Sharma et al. Drug Testing and Analysis, 2014, 6(5), 399-414).

Briefly, and again by way of non-limiting example only, whole blood may be obtained from a subject of interest (e.g., finger, heel or toe prick) using an appropriate instrument (e.g., a sterile surgical blade or disposable lancet) and spotted onto, for example, a membrane or paper (e.g., filter paper cards). For quantitative analyses a measured volume of blood may be applied. The blood may then be allowed to dry for example, at room temperature and/or under nitrogen flow and/or controlled humidity. Drying time will generally depend at least in part on sample volume. DBS membranes or paper may be stored at ambient temperature or refrigerated, and may be appropriately packaged to avoid humidity. The DBS may then be extracted for analysis at a suitable time (e.g., using an extraction solvent or similar).

Analyses of Additional Blood Compartments

In addition to protein profiling of enriched RBCs fractions or whole blood samples comprising RBCs, the methods of the present disclosure may further comprise conducting protein profile analyses of one or more additional blood compartment(s).

For example, protein profile analyses may be conducted on one or more additional blood compartment(s) selected from plasma, serum, platelets, leukocytes, an enriched platelet fraction, an enriched leukocyte fraction, platelet-rich plasma, leukocyte-rich plasma, a mixture of platelets and leukocytes, specific leukocyte(s) (e.g., one or more of T lymphocytes (e.g., CD4+ T lymphocytes, CD8+ T lymphocytes), B lymphocytes, NK cells, monocytes, neutrophils, eosinophils, basophils, and the like), and combinations thereof.

The additional blood compartment(s) for analysis may be prepared using known techniques. For example, cellular components may be isolated by flow cytometry, magnetic bead separation, centrifugation, and the like. Plasma/serum separation techniques are also well known in the art. Many standard texts and protocols are available and widely used for these purposes, and by way of non-limiting example reference is made to: World Health Organisation, "Requirements for the collection, processing and quality control of blood, blood components and plasma derivatives", World Health Organisation Technical report Series, No. 840, 1994, Annex 2; Wenz, B., "Methods for leukodepletion" in "Clinical Benefits of Leukodepleted Blood Products", pp 5-16, 1995, Springer Berlin Heidelberg; Novotny V., and Brand, A. "Leukocyte-Poor Blood and Platelet Transfusions" in "Modern Transfusion Medicine", pp 117-121, 1995, CRC Press, Inc.; White and Jennings, "Platelet Protocols: Research and Clinical Laboratory Procedures", 1999, Academic Press).

Blood Stabilising Agents and Anticoagulants

As noted above and again without limitation to specific mechanistic features, it is hypothesised that RBCs may have a capacity to sequester and release different proteins (e.g., cytokines and chemokines), and the degree of protein release (or alternatively sequestration) by RBCs is thought to be influenced by various factors arising during blood collection and processing.

In some embodiments a blood sample or a component thereof used in the methods of the present disclosure may be mixed with a blood stabilising agent. Agents having a capacity to stabilise RBCs are useful so as to reduce or prevent the sequestration and/or release of proteins from RBCs during processing.

The blood cell stabilising agent may be mixed with the blood sample at the time of collecting the blood sample from the subject and/or during subsequent processing of the blood sample or component(s) thereof. By way of non-limiting example, the blood stabilising agent may be mixed with the blood sample or a component thereof within 1 second, 2 seconds, 3 seconds, 4 seconds, 5 seconds, 10 seconds, 20 seconds, 30 seconds, 1 minute, 2 minutes, 3 minutes, 4 minutes, 5 minutes, 10 minutes, 15 minutes, 30 minutes, 45 minutes, 1 hour, 2 hours, 3 hours, 4 hours, 5 hours, 7.5 hours or 10 hours of the blood sample being obtained from the subject.

Non-limiting examples of suitable blood stabilising agents include protease inhibitors (e.g., aprotinin, leupeptin, $\alpha_2$-macroglobulin, antipain dihydrochloride, calpain inhibitor I, calpain inhibitor II, chymostatin, TLCK (CAS 131918-97-3), trypsin-inhibitor, Pefabloc SC (Roche), PMSF ($C_6H_5CH_2SO_2F$—Thermo Fisher Scientific), complete protease inhibitor cocktail (Roche), and the like), anticoagulants, RNA stabilisers (e.g., RNALater—Thermo Fisher Scientific), protein denaturation agents, or combinations thereof.

In exemplary embodiments, the blood stabilising agent is an anticoagulant. The anticoagulant may be mixed with the anticoagulant at time of collecting the blood sample from the subject (e.g., a vessel or container into which the blood sample is collected may contain the anticoagulant), and/or during subsequent processing of the blood sample or component(s) thereof.

Non-limiting examples of suitable anticoagulants include heparin, ethylenediaminetetraacetic acid (EDTA), EDTA disodium salt, EDTA tetrasodium salt, EDTA dipotassium salt, EDTA diammonium salt, ethylenebis(oxyethylenenitrilo)tetraacetic acid (EGTA), EDTA trisodium salt, EDTA tripotassium salt, ethylene glycol-O,O-bis(2-aminoethyl)-N,N,N,N-tetraacetic acid, N-(2-hydroxyethyl)ethylenediamine-N,N,N-triacetic acid trisodium salt, citrate, acid-citrate-dextrose, di-ammonium hydrogen citrate, di-ammonium tartrate, warfarin, N-(2-bis(carboxymethyl) aminoethyl)-N-(2-hydroxyethyl)glycin salt dihydrate, citric acid, citric acid monosodium salt, citric acid disodium salt, citric acid trisodium salt, citric acid monopotassium salt, citric acid tripotassium salt, protein C/protein S, nitrilotriacetic acid, potassium sodium tartrate, potassium hydrogen D-tartrate, L-tartaric acid monosodium salt, L-tartaric acid disodium salt, L-tartaric acid dipotassium salt, streptokinase, protamine sulfate, tris(carboxymethyl)amine, anti-thrombin III, phenprocoumon, hirudin, nicoumalone, Coumadin, glycosaminoglymays, ibuprofen, acetylsalicylic acid, indomethacin, prostaglandins, sulfinpyrazone, urokinase, hirulog, tissue plasminogen activator, coumarin, or combinations thereof.

An anticoagulant may be beneficial to use, for example, when, in addition to the analysis of a RBC-enriched fraction, protein profiling of one or more of leukocytes (white blood cells), platelets and/or plasma is desirable. An anticoagulant may also be beneficial to use if it is desirable to conduct protein profiling of the full cellular component of blood (i.e., mixed population of blood cells minus the plasma component).

In other embodiments, a blood sample used in the methods of the present disclosure may not be mixed with an anticoagulant. This may be the case where protein profiling is to be conducted on RBCs, enriched RBCs, or a whole blood sample. In such cases, other stabilising agents without anti-coagulant activity or with only a nominal amount of anticoagulant activity may be mixed with the blood sample or a component thereof.

In other embodiments, a blood sample or a component thereof used in the methods of the present disclosure may be stabilised by freezing (e.g., snap freezing) or by drying (e.g., dried blood spot).

Lysate Analyses

In some embodiments, the methods of the present disclosure comprise generating a protein profile from a cellular lysate.

By way of non-limiting example only, an enriched RBCs fraction prepared in accordance with the methods of the present disclosure may be treated to provide a lysate in which the levels of one or more proteins are determined. For example, the lysate may be produced from one or more other blood compartment(s) selected from whole blood, plasma, serum, platelets, leukocytes, an enriched platelet fraction, an enriched leukocyte fraction, platelet-rich plasma, leukocyte-rich plasma, a mixture of platelets and leukocytes, specific leukocyte(s) (e.g., one or more of T lymphocytes (e.g., CD4+ T lymphocytes, CD8+ T lymphocytes), B lymphocytes, NK cells, monocytes, neutrophils, eosinophils, basophils, and the like), and combinations thereof.

Additionally or alternatively, other cellular components of blood that are not RBCs, or that contain minimal amounts of RBCs (e.g., less than: 10%, 5%, 4%, 3%, 2%, 1%, or 0.5% RBCs) may be treated to provide a lysate in which the levels of one or more proteins are determined.

Cell lysates for use in the methods of the disclosure may be produced using suitable means including, for example, liquid homogenization, mechanical disruption, freeze/thaw cycles, high frequency sound waves, manual grinding, chemical permeabilisation, enzymatic permeabilisation, permeabilisation using streptolysin, and the like.

In some embodiments, cell lysates are prepared by one, two, three, four, five, or more than five cycles of freeze/thawing. This technique offers the potential benefit of providing a means of stabilising a blood sample or component(s) thereof at the point of freezing and allowing storage prior to lysing and analysis of protein content. Typically, the snap freezing may be performed at a temperature of at or below: −10° C., −20° C., −30° C., −40° C., −50° C., −60° C., −70° C., −75° C., −80° C., −90° C., −100° C., −120° C., −140° C., −160° C., −180° C., −190° C., −195° C., or −196° C. In still another embodiment, snap freezing is performed at a temperature of below: −5° C., −10° C., −20° C., −30° C., −40° C., −50° C., −60° C., −70° C., −75° C., −80° C., −90, −100° C., −120° C., −104° C., −160° C., −180° C., −190° C., −200° C. In still another embodiment, snap-freezing is performed at a temperature below: −190° C., −191° C., −192° C., −193° C., −194° C., −195° C., −196° C., −197° C., −198° C., or −199° C. A whole blood sample, a RBC-enriched sample or fraction, and/or another different cellular components may be snap frozen to stabilise the cells. This may reduce or prevent, for example, the sequestration and/or release of proteins from RBCs and/or other cell types present during processing.

Analyses of Cell Washes and Supernatants

In some embodiments, the methods of the present disclosure comprise generating a protein profile from a cell wash and/or a cell supernatant.

The cell wash and/or cell supernatant may be produced from a blood sample or blood sample component comprising RBCs. In some embodiments, the number of RBCs constitute more than: 0.5%, 1%, 5%, 10%, 20%, 30%, 40%, 50%, 60%, 70%, 80%, 90%, 95%, 97.5%, 98%, 99%, 99.5%, 99.75%, 99.9%, or 99.95%, of total number of blood cells present in the blood sample or the blood sample component.

In some embodiments, the cell wash may be produced by washing RBCs-enriched cells and/or by separately washing one or more cellular blood compartment(s) selected from whole blood, platelets, leukocytes, an enriched platelet fraction, an enriched leukocyte fraction, platelet-rich plasma, leukocyte-rich plasma, mixtures of platelets and leukocytes, specific leukocyte(s) (e.g., one or more of T lymphocytes (e.g., CD4+ T lymphocytes, CD8+ T lymphocytes), B lymphocytes, NK cells, monocytes, neutrophils, eosinophils, basophils, and the like), or combinations thereof.

In some embodiments, the cell supernatant may be produced by incubating or culturing RBCs-enriched cells and/or by separately incubating or culturing one or more cellular blood compartment(s) selected from platelets, leukocytes, an enriched platelet fraction, an enriched leukocyte fraction, platelet-rich plasma, leukocyte-rich plasma, mixtures of platelets and leukocytes, specific leukocyte(s) (e.g., one or more of T lymphocytes (e.g., CD4+ T lymphocytes, CD8+ T lymphocytes), B lymphocytes, NK cells, monocytes, neutrophils, eosinophils, basophils, and the like), or combinations thereof. Cell supernatant may then be separated from the cells and analysed for proteins released (intracellularly and/or from the cell surface) by the incubated or cultured cells. Optionally, cells remaining after removal of the supernatant may be washed and used to generate a protein profile. The cell wash may be combined with the cell supernatant to generate the protein profile, or alternatively individual protein profiles may be generated from the cell wash and the cell supernatant separately. This will allow comparison of the two individual profiles if desired.

A series of cell supernatants may be produced by culturing cells as above for a time period and collecting a series of supernatants at different time points. Each supernatant may be analysed for protein content to provide a protein profile analysis over multiple time points. Optionally, the incubation or culture conditions (e.g., content of media, temperature, etc.) may be varied between time point sampling of supernatants. Optionally, cells remaining after removal of the supernatant at one or more time points may be washed and used to generate a protein profile. The cell wash may be combined with the cell supernatant of a given time point (e.g., the same time point) to generate the protein profile. Alternatively, individual protein profiles may be generated from individual cell washes and individual cell supernatants. Alternatively, cell washes from multiple time points may be pooled and analysed to generate the protein profile. Likewise, cell supernatants from multiple time points may be pooled and analysed to generate the protein profile.

Suitable exemplary protocols and/or media for incubating or culturing the RBCs-enriched cells and/or separately incubating or culturing the other cellular blood compartment(s) are known to those of ordinary skill in the art (see, for example, Koller, Palsson, Masters, (Eds) "Human Cell Culture: Vol IV. Primary Hematopoietic cells", 2006, Springer Science and Business Media; Mirty and Hughes (Eds) 2001, "Human Cell Culture Protocols, Third edition", 2011, Humana Press). Methodology is also presented in the Examples of the present specification.

Cell washes may be performed using suitable media such as, for example, phosphate buffered saline (PBS), an isotonic salt solution, a growth medium, a culture medium, or combinations thereof.

Non-limiting examples of suitable media for use as cell wash liquid, cell culture media, or cell incubation media in the methods of the present disclosure include isotonic salt solution, balanced salt solution, saline, phosphate buffered saline (PBS), hank's balanced salt solution (HBSS), Earles' balanced salt solution (EBSS), Roswell Park Memorial Institute medium (RPMI), minimum essential medium (MEM), Improved Minimum Essential Medium (IMEM), Eagle's minimal essential medium (EMEM), Dubelco's modified Eagle's medium (DMEM), and Iscove's Modified Dulbecco's Media (IMDM), or combinations thereof. In some embodiments, the media is PBS or HBSS to maintain the RBCs in a non-growth or proliferation state. In other embodiments, the media is RPMI to stimulate the growth or proliferation is RBCs.

Use of Cationic Salts

In some embodiments, the methods of the present disclosure comprise contacting a red blood cell-enriched sample with at least one cationic salt that increases and/or enhances the detectable level of one or more proteins in the sample. The cationic salt may be one or more that are suitable for use in the methods, as determined by one of ordinary skill in the art. The cationic salt, in one embodiment, is a monovalent or multivalent (e.g., divalent, trivalent) metal ion salt. In other embodiments, the cationic salt is an ammonium salt.

Monovalent metal cationic salts suitable for use in the methods may include, for example, a sodium salt, a potassium salt, a lithium salt, and the like, or combinations thereof. Suitable sodium salts may include, for example, sodium chloride, sodium citrate, sodium sulfate, sodium lactate, sodium acetate, sodium bicarbonate, sodium carbonate, sodium stearate, sodium ascorbate, sodium benzoate, sodium biphosphate, dibasic sodium phosphate, sodium phosphate, sodium bisulfite, sodium borate, sodium gluconate, sodium metasilicate, sodium propionate and the like, or combinations thereof. Suitable potassium salts may include, for example, potassium chloride, potassium citrate, potassium bromide, potassium iodide, potassium bicarbonate, potassium nitrite, potassium persulfate, potassium sulfite, potassium sulfate, potassium bisulfite, potassium phosphate, potassium acetate, potassium citrate, potassium glutamate, dipotassium guanylate, potassium gluconate, potassium malate, potassium ascorbate, potassium sorbate, potassium succinate, potassium tartrate and combinations thereof. Suitable lithium salts include, for example, lithium chloride, lithium bromide, lithium carbonate, lithium nitrate, lithium sulfate, lithium acetate, lithium lactate, lithium citrate, lithium aspartate, lithium gluconate, lithium malate, lithium ascorbate, lithium orotate, lithium succinate or combinations thereof.

Divalent metal cation salts suitable for use in the methods may include, for example, a calcium salt, a potassium salt, a beryllium salt, a strontium salt, a barium salt, a radium salt, an a iron (ferrous) salt, and the like, or combinations thereof. Suitable calcium salts include, for example, calcium chloride, calcium sulfate, calcium lactate, calcium citrate, calcium carbonate, calcium acetate, calcium phosphate, calcium alginite, calcium stearate, calcium sorbate, calcium gluconate and the like, or combinations thereof. Suitable magnesium salts may include, for example, magnesium fluoride, magnesium chloride, magnesium bromide, magnesium iodide, magnesium lactate, magnesium phosphate, magnesium sulfate, magnesium sulfite, magnesium carbonate, magnesium oxide, magnesium nitrate, magnesium borate, magnesium acetate, magnesium citrate, magnesium gluconate, magnesium maleate, magnesium succinate, magnesium malate, magnesium taurate, magnesium orotate, magnesium glycinate, magnesium naphthenate, magnesium acetylacetonate, magnesium formate, magnesium hydroxide, magnesium stearate, magnesium hexafluorsilicate, magnesium salicylate or combinations thereof. Suitable beryllium salts may include, for example, beryllium phosphate, beryllium acetate, beryllium tartrate, beryllium citrate, beryllium gluconate, beryllium maleate, beryllium succinate, sodium beryllium malate, beryllium alpha brom camphor sulfonate, beryllium acetylacetonate, beryllium formate or combinations thereof. Suitable strontium salts may include, for example, strontium chloride, strontium phosphate, strontium sulfate, strontium carbonate, strontium oxide, strontium nitrate, strontium acetate, strontium tartrate, strontium citrate, strontium gluconate, strontium maleate, strontium succinate, strontium malate, strontium aspartate in either L and/or D-form, strontium fumarate, strontium glutamate in either L- and/or D-form, strontium glutarate, strontium lactate, strontium L-threonate, strontium malonate, strontium ranelate (organic metal chelate), strontium ascorbate, strontium butyrate, strontium clodronate, strontium ibandronate, strontium salicylate, strontium acetyl salicylate or combinations thereof. Suitable barium salts may include, for example, barium hydroxide, barium fluoride, barium chloride, barium bromide, barium iodide, barium sulfate, barium sulfide (S), barium carbonate, barium peroxide, barium oxide, barium nitrate, barium acetate, barium tartrate, barium citrate, barium gluconate, barium maleate, barium succinate, barium malate, barium glutamate, barium oxalate, barium malonate, barium naphthenate, barium acetylacetonate, barium formate, barium benzoate, barium p-t-butylbenzoate, barium adipate, barium pimelate, barium suberate, barium azelate, barium sebacate, barium phthalate, barium isophthalate, barium terephthalate, barium anthranilate, barium mandelate, barium salicylate, barium titanate or combinations thereof. Suitable radium salts may include, for example, radium fluoride, radium chloride, radium bromide, radium iodide, radium oxide, radium nitride or combinations thereof. Suitable radium salts included, for example, radium fluoride, radium chloride, radium bromide, radium iodide, radium oxide, radium nitride, and the like. Suitable iron (ferrous) salts may include, for example, ferrous sulfate, ferrous oxides, ferrous acetate, ferrous citrate, ferrous ammonium citrate, ferrous gluconate, ferrous oxalate, ferrous fumarate, ferrous maleate, ferrous malate, ferrous lactate, ferrous ascorbate, ferrous erythrobate, ferrous glycerate, ferrous pyruvate, and the like, or combinations thereof.

In certain embodiments, the cationic salt is one that may prevent and/or minimize pH change in the red blood cell-enriched sample (e.g., a chloride or carbonate salt). Thus, in certain embodiments, the cationic salt is a carbonate salt. In further embodiments, the cationic salt may also prevent or minimize damage to cell membranes (e.g., RBC membranes). In certain embodiments, the cationic salt is a chloride salt. In other embodiments, the cationic salt is calcium chloride, potassium chloride, strontium chloride, barium chloride, radium chloride, or combinations thereof. In still other embodiments, the cationic salt is sodium chloride, potassium chloride, rubidium chloride, cesium chloride, lithium chloride, or combinations thereof. In yet another embodiment, the cationic salt is lithium chloride. In another embodiment, the cationic salt may be sodium chloride. In certain embodiments, the cationic salt may be calcium carbonate, potassium carbonate, strontium carbonate, barium carbonate, or radium carbonate. In still other embodiments, the cationic salt is sodium carbonate, potassium carbonate, rubidium carbonate, cesium carbonate, lithium carbonate, or combinations thereof. In yet other embodiments, the cationic salt is lithium carbonate. In other embodiments, the cationic salt is sodium carbonate.

Salts other than monovalent or divalent metal cation salts may be used in the methods, including, for example, a trivalent or other multivalent salt, such as aluminum, silicon, scandium, titanium, vanadium, chromium, cobalt, nickel, copper, manganese, zinc, tin, silver and the like, or combinations thereof.

Ammonium salts may also be used in the methods with suitable ammonium salts including ammonium carbonate, ammonium chloride, ammonium nitrate, ammonium acetate, ammonium biorate, ammonium bromide, ammonium carbamate, ammonium cerium (IV) sulphate, ammonium chromate, ammonium dichromate, ammonium dihydrogen phosphate, ammonium fluoride, ammonium formate, ammonium phosphate, ammonium sodium phosphate dibasic tetrahydrate, ammonium thiosulfate, ammonium zirconium, and the like, or combinations thereof.

In certain embodiments, the cationic salt is ammonium chloride. In other embodiments, the cationic salt is ammonium carbonate.

In certain embodiments, the red blood cell-enriched sample is contacted with one or more combinations of the foregoing cationic salts to increase and/or enhance the detectable level of one or more protein levels in the sample. In some embodiments, the red blood cell-enriched sample is contacted with at least one cationic salt. In other embodiments, the red blood cell-enriched sample is contacted with at least two cationic salts. In still other embodiments, the red blood cell-enriched sample is contacted with at least three cationic salts.

In certain embodiments, the blood sample is contacted with one or more combinations of the foregoing cationic salts to increase and/or enhance the detectable level of one or more protein levels in the sample prior to the red blood cell enriching of the blood sample. In some embodiments, the blood sample is contacted with at least one cationic salt. In other embodiments, the blood sample is contacted with at least two cationic salts. In still other embodiments, the blood sample is contacted with at least three cationic salts.

The references to salts (e.g., sodium containing salts) herein include anhydrous forms and hydrated forms of the salt.

In certain embodiments, a whole blood sample is contacted with at least one of the foregoing cationic salts to produce a protein profile. The whole blood sample may be obtained from venous blood, capillary blood, arterial blood or combinations thereof, using methods known to one of ordinary skill in the art.

In other embodiments, one or more additional blood compartment(s) selected from plasma, serum, platelets, leukocytes, an enriched platelet fraction, an enriched leukocyte fraction, platelet-rich plasma, leukocyte-rich plasma, a mixture of platelets and leukocytes, specific leukocyte(s) (e.g., one or more of T lymphocytes (e.g., CD4+ T lymphocytes, CD8+ T lymphocytes), B lymphocytes, NK cells, monocytes, neutrophils, eosinophils, basophils, and the like), and combinations thereof, are contacted by at least one for the foregoing cationic salts to produce a protein profile. The additional blood compartment(s) for analysis may be prepared using known techniques (e.g., flow cytometry, magnetic bead separation, centrifugation, and the like).

Protein Profiling

The present disclosure provides methods for producing a protein profile from a blood sample comprising RBCs (e.g., an RBCs-enriched fraction or a whole blood sample). The production of such profiles may provide insight into important biological processes including, but not limited to inflammation, immune responses, and/or cellular repair, or disease state.

While not imparting particular limitations to the type(s) of proteins that may be detected in generating a protein profile by the methods of the present disclosure, non-limiting examples include signalling molecules, e.g., chemokines, cytokines, growth factors, receptors, intracellular signal transmitters, hormones, nuclear transcription factors, neurotransmitters, and extracellular matrix components, and enzymes. For instance, growth factors can include those that stimulate the growth, proliferation, healing, or differentiation of, for example, skin cells (e.g., epidermal growth factor (EGF), keratinocyte growth factor (KGF), migration stimulating factor (MSF)), nerve cells/nervous system (e.g., neuregulins (e.g., neuregulin 1-4) and neurotrophins (e.g., nerve growth factor (NGF), brain-derived neurotrophic factor (BDNF), neurotrophin-3 (NT-3), neurotrophin-4 (NT-4))), connective tissue and mesenchymal cells (e.g., fibroblast growth factor (FGF)), blood vessel cells (e.g., platelet-derived growth factor (PDGF), placental growth factor (PGF), vascular endothelial growth factor (VEGF)), blood cells (e.g., erythropoietin, granulocyte colony stimulating factor (G-CSF), granulocyte macrophage colony-stimulating factor (GM-CSF)), and cell proliferation (e.g., insulin-like growth factor (IGF-1), insulin-like growth factor-2 (IGF-2)) along with pleitropic growth factors (e.g, transforming growth factor-beta (TGF-β), transforming growth factor-beta (TGF-α), tumor necrosis factor (TNF)).

Receptors can include intracellular receptors (e.g., nuclear (e.g., transcription factors), cytoplasmic (e.g., steroid), and endoplasmic recticulum (e.g., $IP_3$) receptors) or cell surface receptors (e.g., ion channel-linked, G-protein-linked, enzyme-linked, toll gate, and ligand gated receptors, integrins). Hormones can include lipid-derived (e.g., prostaglandins, leukotrienes, prostacylins, thromboxane); amino acid-derived (e.g., epinephrine, melatonin, thyroxine); peptide (e.g., amylin, adiponenctin, angiotensinogen, calcitonin, brain natriuretic peptide (BNP), erythropoietin, follicle-stimulating hormone (FSH), ghrelin, glucagon-like peptide-1 (GLP-1), human chorionic gonadotropin (hCG), insulin, insulin-like growth factor (IGF), and the like); and steroids (e.g., androgen, estrogen, glucocorticoid, progestogen, secosteroid, and the like). Intracellular signal transmitters or transducers can include families of proteins and protein kinases (e.g., Ras and Src families), and Wnt signalling family proteins. Neurotransmitters can include amino acids, peptides (e.g., β-endorphin, opioid), monoamines, trace amines, purines, and gasotransmitters. Nuclear transcription factors can include modulators of DNA transcription (e.g., fos, myc, N-myc), and modulators of mRNA transcription, and suppressors of cell division (e.g., p53, pRb). Enzymes can include oxidoreductases (e.g., alcohol, aldehyde, amino acid, sulphur, diphenol, peroxidises, and the like) NADH, NADPH, nucleases, proteases, kinases, transferases, hydrolases, lyases, isomerases, and ligases. Chemokines and cytokines are numerous can include, for example, those listed in Table 1 and Table 2 below.

In certain embodiments, the methods comprise producing a protein profile consisting of, or comprising, a single protein or combinations of proteins as set out in Tables 1 and 2 below. The profile may be generated from a blood sample comprising RBCs (e.g., a red blood cell-enriched sample, RBC-enriched fraction, or a whole blood sample). Additional profile(s) may be generated from other cellular compartment(s) including, but not limited to, plasma, serum, platelets, leukocytes, an enriched platelet fraction, an enriched leukocyte fraction, platelet-rich plasma, leukocyte-rich plasma, a mixture of platelets and leukocytes, specific leukocyte(s) (e.g., one or more of T lymphocytes (e.g., CD4+ T lymphocytes, CD8+ T lymphocytes), B lymphocytes, NK cells, monocytes, neutrophils, eosinophils, basophils, and the like), or combinations thereof.

TABLE 1

Non-limiting examples of individual proteins that may be included in a protein profile generated by the methods of the present disclosure. The protein profile may comprise or consist of one or more of the proteins listed.

| Single Protein (acronym) | Single Protein (full name) |
|---|---|
| basic FGF | basic fibroblast growth factor |
| CTACK (CCL27) | cutaneous T cell-attracting chemokine |
| Eotaxin 1 | CCL11 #1 |
| G-CSF (GCSF) | granulocyte-colony stimulating factor |
| GM-CSF (CSF2) | granulocyte-macrophage colony-stimulating factor |
| HGF | hepatocyte growth factor |
| IFN-α2 | interferon alpha subtype α2 |
| IFN-γ | interferon gamma |
| IL-10 | interleukin 10 |
| IL-12 (IL-12p70) | interleukin 12 p35 and p40 heterodimer |
| IL-13 | interleukin 13 |
| IL-12p40 | interleukin 12 p40 subunit |
| IL-15 | interleukin 15 |
| IL-16 | interleukin 16 |
| IL-17A | interleukin 17A |
| IL-18 | interleukin 18 |
| IL-1α | interleukin 1 alpha |
| IL-1β | interleukin 1 beta |
| IL-2 | interleukin 2 |
| IL-2ra | interleukin 2 receptor alpha chain |
| IL-3 | interleukin 3 |
| IL-5 | interleukin 5 |
| IL-6 | interleukin 6 |
| IL-7 | interleukin 7 |
| IL-9 | interleukin 9 |
| IP-10 (CXCL10) | interferon gamma-induced protein 10 |
| LIF | leukaemia inhibitory factor |
| M-CSF (CSF1) | macrophage colony-stimulating factor |
| MIG (CXCL9) | monokine induced by IFNγ, Chemokine (C—X—C motif) ligand 9 |
| MIP-1α (CCL3) | macrophage inflammatory protein-1 alpha |
| MIP-1β (CCL4) | macrophage inflammatory protein-1 alpha |
| PDGF-BB | platelet-derived growth factor B chain homodimer |
| SDF-1α (CXCL12) | stromal cell-derived factor 1 |
| TNF-α (cachexin) | tumour necrosis factor alpha |
| TNF-β (lymphotoxin) | tumour necrosis factor-beta |
| TRAIL | TNF-related apoptosis-inducing ligand |
| VEGF | vascular endothelial growth factor |
| IL-8 | interleukin 8 |
| MCP-1 (CCL2) | monocyte chemoattractant protein-1 |
| MGSA | maintenance of genome stability protein A |
| PGE-2 | prostaglandin E2 |
| RANTES (CCL5) | regulated on activation, normal T cell expressed and secreted |
| MIF (MMIF) | macrophage migration inhibitory factor |
| GRO-α (CXCL1) | Growth-regulated oncogene α |
| CRP | C-reactive protein |
| DDT (MIF-2) | D-dopachrome tautomerase |
| IGF-1 | insulin like growth factor 1 |

TABLE 2

Non-limiting examples of protein pairs that may be included in a protein profile generated by the methods of the present disclosure. The protein profile may comprise or consist of one or more protein pairs listed.

| Protein #1 | Protein #2 | Protein #1 | Protein #2 | Protein #1 | Protein #2 | Protein #1 | Protein #2 |
|---|---|---|---|---|---|---|---|
| basic FGF | CTACK | CTACK | Eotaxin 1 | Eotaxin 1 | G-CSF | G-CSF | GM-CSF |
| basic FGF | Eotaxin 1 | CTACK | G-CSF | Eotaxin 1 | GM-CSF | G-CSF | HGF |
| basic FGF | G-CSF | CTACK | GM-CSF | Eotaxin 1 | HGF | G-CSF | IFN-α2 |
| basic FGF | GM-CSF | CTACK | HGF | Eotaxin 1 | IFN-α2 | G-CSF | IFN-γ |
| basic FGF | HGF | CTACK | IFN-α2 | Eotaxin 1 | IFN-γ | G-CSF | IL-10 |
| basic FGF | IFN-α2 | CTACK | IFN-γ | Eotaxin 1 | IL-10 | G-CSF | IL-12 |
| basic FGF | IFN-γ | CTACK | IL-10 | Eotaxin 1 | IL-12 | G-CSF | IL-13 |
| basic FGF | IL-10 | CTACK | IL-12 | Eotaxin I | IL-13 | G-CSF | IL-12p40 |
| basic FGF | IL-12 | CTACK | IL-13 | Eotaxin 1 | IL-12p40 | G-CSF | IL-15 |
| basic FGF | IL-13 | CTACK | IL-12p40 | Eotaxin 1 | IL-15 | G-CSF | IL-16 |
| basic FGF | IL-12p40 | CTACK | IL-15 | Eotaxin 1 | IL-16 | G-CSF | IL-17A |
| basic FGF | IL-15 | CTACK | IL-16 | Eotaxin 1 | IL-17A | G-CSF | IL-18 |
| basic FGF | IL-16 | CTACK | IL-17A | Eotaxin 1 | IL-18 | G-CSF | IL-1α |
| basic FGF | IL-17A | CTACK | IL-18 | Eotaxin 1 | IL-1α | G-CSF | IL-1β |
| basic FGF | IL-18 | CTACK | IL-1α | Eotaxin 1 | IL-1β | G-CSF | IL-2 |
| basic FGF | IL-1α | CTACK | IL-1β | Eotaxin I | IL-2 | G-CSF | IL-2ra |
| basic FGF | IL-1β | CTACK | IL-2 | Eotaxin 1 | IL-2ra | G-CSF | IL-3 |
| basic FGF | IL-2 | CTACK | IL-2ra | Eotaxin 1 | IL-3 | G-CSF | IL-5 |
| basic FGF | IL-2ra | CTACK | IL-3 | Eotaxin 1 | IL-5 | G-CSF | IL-6 |
| basic FGF | IL-3 | CTACK | IL-5 | Eotaxin 1 | IL-6 | G-CSF | IL-7 |
| basic FGF | IL-5 | CTACK | IL-6 | Eotaxin 1 | IL-7 | G-CSF | IL-9 |
| basic FGF | IL-6 | CTACK | IL-7 | Eotaxin 1 | IL-9 | G-CSF | IP-10 |
| basic FGF | IL-7 | CTACK | IL-9 | Eotaxin 1 | IP-10 | G-CSF | LIF |
| basic FGF | IL-9 | CTACK | IP-10 | Eotaxin 1 | LIF | G-CSF | M-CSF |
| basic FGF | IP-10 | CTACK | LIF | Eotaxin 1 | M-CSF | G-CSF | MIG |
| basic FGF | LIF | CTACK | M-CSF | Eotaxin 1 | MIG | G-CSF | MIP-1α |
| basic FGF | M-CSF | CTACK | MIG | Eotaxin 1 | MIP-1α | G-CSF | MIP-1β |
| basic FGF | MIG | CTACK | MIP-1α | Eotaxin I | MIP-1β | G-CSF | PDGF-BB |
| basic FGF | MIP-1α | CTACK | MIP-1β | Eotaxin 1 | PDGF-BB | G-CSF | SDF-1α |

TABLE 2-continued

Non-limiting examples of protein pairs that may be included in a protein profile generated by the methods of the present disclosure. The protein profile may comprise or consist of one or more protein pairs listed.

| Protein #1 | Protein #2 | Protein #1 | Protein #2 | Protein #1 | Protein #2 | Protein #1 | Protein #2 |
|---|---|---|---|---|---|---|---|
| basic FGF | MIP-1β | CTACK | PDGF-BB | Eotaxin 1 | SDF-1α | G-CSF | TNF-α |
| basic FGF | PDGF-BB | CTACK | SDF-1α | Eotaxin 1 | TNF-α | G-CSF | TNF-β |
| basic FGF | SDF-1α | CTACK | TNF-α | Eotaxin 1 | TNF-β | G-CSF | TRAIL |
| basic FGF | TNF-α | CTACK | TNF-β | Eotaxin 1 | TRAIL | G-CSF | VEGF |
| basic FGF | INF-β | CTACK | TRAIL | Eotaxin 1 | VEGF | G-CSF | IL-8 |
| basic FGF | TRAIL | CTACK | VEGF | Eotaxin 1 | IL-8 | G-CSF | MCP-1 |
| basic FGF | VEGF | CTACK | IL-8 | Eotaxin 1 | MCP-1 | G-CSF | MGSA |
| basic FGF | IL-8 | CTACK | MCP-1 | Eotaxin 1 | MGSA | G-CSF | PGE-2 |
| basic FGF | MCP-1 | CTACK | MGSA | Eotaxin 1 | PGE-2 | G-CSF | RANTES |
| basic FGF | MGSA | CLACK | PGE-2 | Eotaxin 1 | RANTES | G-CSF | MIF |
| basic FGF | PGE-2 | CTACK | RANTES | Eotaxin 1 | MIF | G-CSF | GRO-α |
| basic FGF | RANTES | CTACK | MIF | Eotaxin 1 | GRO-α | G-CSF | CRP |
| basic FGF | MIF | CTACK | GRO-α | Eotaxin 1 | CRP | G-CSF | DDL |
| basic FGF | GRO-α | CTACK | CRP | Eotaxin 1 | DDT | | |
| basic FGF | CRP | CTACK | DDT | | | | |
| basic FGF | DDT | | | | | | |
| GM-CSF | HGF | HGF | IFN-α2 | IFN-α2 | IFN-γ | IFN-γ | IL-10 |
| GM-CSF | IFN-α2 | HGF | IFN-γ | IFN-α2 | IL-10 | IFN-γ | IL-12 |
| GM-CSF | IFN-γ | HGF | IL-10 | IFN-α2 | IL-12 | IFN-γ | IL-13 |
| GM-CSF | IL-10 | HGF | IL-12 | IFN-α2 | IL-13 | IFN-γ | IL-12p40 |
| GM-CSF | IL-12 | HGF | IL-13 | IFN-α2 | IL-12p40 | IFN-γ | IL-15 |
| GM-CSF | IL-13 | HGF | IL-12p40 | IFN-α2 | IL-15 | IFN-γ | IL-16 |
| GM-CSF | IL-12p40 | HGF | IL-15 | IFN-α2 | IL-16 | IFN-γ | IL-17A |
| GM-CSF | IL-15 | HGF | IL-16 | IFN-α2 | IL-17A | IFN-γ | IL-18 |
| GM-CSF | IL-16 | HGF | IL-17A | IFN-α2 | IL-18 | IFN-γ | IL-1α |
| GM-CSF | IL-17A | HGF | IL-18 | IFN-α2 | IL-1α | IFN-γ | IL-1β |
| GM-CSF | IL-18 | HGF | IL-1α | IFN-α2 | IL-1β | IFN-γ | IL-2 |
| GM-CSF | IL-1α | HGF | IL-1β | IFN-α2 | IL-2 | IFN-γ | IL-2ra |
| GM-CSF | IL-1β | HGF | IL-2 | IFN-α2 | IL-2ra | IFN-γ | IL-3 |
| GM-CSF | IL-2 | HGF | IL-2ra | IFN-α2 | IL-3 | IFN-γ | IL-5 |
| GM-CSF | IL-2ra | HGF | IL-3 | IFN-α2 | IL-5 | IFN-γ | IL-6 |
| GM-CSF | IL-3 | HGF | IL-5 | IFN-α2 | IL-6 | IFN-γ | IL-7 |
| GM-CSF | IL-5 | HGF | IL-6 | IFN-α2 | IL-7 | IFN-γ | IL-9 |
| GM-CSF | IL-6 | HGF | IL-7 | IFN-α2 | IL-9 | IFN-γ | IP-10 |
| GM-CSF | IL-7 | HGF | IL-9 | IFN-α2 | IP-10 | IFN-γ | LIF |
| GM-CSF | IL-9 | HGF | IP-10 | IFN-α2 | LIF | IFN-γ | M-CSF |
| GM-CSF | IP-10 | HGF | LIF | IFN-α2 | M-CSF | IFN-γ | MIG |
| GM-CSF | LIF | HGF | M-CSF | IFN-α2 | MIG | IFN-γ | MIP-1α |
| GM-CSF | M-CSF | HGF | MIG | IFN-α2 | MIP-1α | IFN-γ | MIP-1β |
| GM-CSF | MIG | HGF | MIP-1α | IFN-α2 | MIP-1β | IFN-γ | PDGF-BB |
| GM-CSF | MIP-1α | HGF | MIP-1β | IFN-α2 | PDGF-BB | IFN-γ | SDF-1α |
| GM-CSF | MIP-1β | HGF | PDGF-BB | IFN-α2 | SDF-1α | IFN-γ | TNF-α |
| GM-CSF | PDGF-BB | HGF | SDF-1α | IFN-α2 | TNF-α | IFN-γ | TNF-β |
| GM-CSF | SDF-1α | HGF | TNF-α | IFN-α2 | TNF-β | IFN-γ | TRAIL |
| GM-CSF | TNF-α | HGF | TNF-β | IFN-α2 | TRAIL | IFN-γ | VEGF |
| GM-CSF | TNF-β | HGF | TRAIL | IFN-α2 | VEGF | IFN-γ | IL-8 |
| GM-CSF | TRAIL | HGF | VEGF | IFN-α2 | IL-8 | IFN-γ | MCP-1 |
| GM-CSF | VEGF | HGF | IL-8 | IFN-α2 | MCP-1 | IFN-γ | MGSA |
| GM-CSF | IL-8 | HGF | MCP-1 | IFN-α2 | MGSA | IFN-γ | PGE-2 |
| GM-CSF | MCP-1 | HGF | MGSA | IFN-α2 | PGE-2 | IFN-γ | RANTES |
| GM-CSF | MGSA | HGF | PGE-2 | IFN-α2 | RANTES | IFN-γ | MIF |
| GM-CSF | PGE-2 | HGF | RANTES | IFN-α2 | MIF | IFN-γ | GRO-α |
| GM-CSF | RANTES | HGF | MIF | IFN-α2 | GRO-α | IFN-γ | CRP |
| GM-CSF | MIF | HGF | GRO-α | IFN-α2 | CRP | IFN-γ | DDT |
| GM-CSF | GRO-α | HGF | CRP | IFN-α2 | DDT | | |
| GM-CSF | CRP | HGF | DDT | | | | |
| GM-CSF | DDT | | | | | | |
| IL-10 | IL-12 | IL-12 | IL-13 | IL-13 | IL-12p40 | IL-12p40 | IL-15 |
| IL-10 | IL-13 | IL-12 | IL-12p40 | IL-13 | IL-15 | IL-12p40 | IL-16 |
| IL-10 | IL-12p40 | IL-12 | IL-15 | IL-13 | IL-16 | IL-12p40 | IL-17A |
| IL-10 | IL-15 | IL-12 | IL-16 | IL-13 | IL-17A | IL-12p40 | IL-18 |
| IL-10 | IL-16 | IL-12 | IL-17A | IL-13 | IL-18 | IL-12p40 | IL-1α |
| IL-10 | IL-17A | IL-12 | IL-18 | IL-13 | IL-1α | IL-12p40 | IL-1β |
| IL-10 | IL-18 | IL-12 | IL-1α | IL-13 | IL-1β | IL-12p40 | IL-2 |
| IL-10 | IL-1α | IL-12 | IL-1β | IL-13 | IL-2 | IL-12p40 | IL-2ra |
| IL-10 | IL-1β | IL-12 | IL-2 | IL-13 | IL-2ra | IL-12p40 | IL-3 |
| IL-10 | IL-2 | IL-12 | IL-2ra | IL-13 | IL-3 | IL-12p40 | IL-5 |
| IL-10 | IL-2ra | IL-12 | IL-3 | IL-13 | IL-5 | IL-12p40 | IL-6 |
| IL-10 | IL-3 | IL-12 | IL-5 | IL-13 | IL-6 | IL-12p40 | IL-7 |
| IL-10 | IL-5 | IL-12 | IL-6 | IL-13 | IL-7 | IL-12p40 | IL-9 |
| IL-10 | IL-6 | IL-12 | IL-7 | IL-13 | IL-9 | IL-12p40 | IP-10 |
| IL-10 | IL-7 | IL-12 | IL-9 | IL-13 | IP-10 | IL-12p40 | LIF |
| IL-10 | IL-9 | IL-12 | IP-10 | IL-13 | LIF | IL-12p40 | M-CSF |
| IL-10 | IP-10 | IL-12 | LIF | IL-13 | M-CSF | IL-12p40 | MIG |

TABLE 2-continued

Non-limiting examples of protein pairs that may be included in a protein profile generated by the methods of the present disclosure. The protein profile may comprise or consist of one or more protein pairs listed.

| Protein #1 | Protein #2 | Protein #1 | Protein #2 | Protein #1 | Protein #2 | Protein #1 | Protein #2 |
|---|---|---|---|---|---|---|---|
| IL-10 | LIF | IL-12 | M-CSF | IL-13 | MIG | IL-12p40 | MIP-1α |
| IL-10 | M-CSF | IL-12 | MIG | IL-13 | MIP-1α | IL-12p40 | MIP-1β |
| IL-10 | MIG | IL-12 | MIP-1α | IL-13 | MIP-1β | IL-12p40 | PDGF-BB |
| IL-10 | MIP-1α | IL-12 | MIP-1β | IL-13 | PDGF-BB | IL-12p40 | SDF-1α |
| IL-10 | MIP-1β | IL-12 | PDGF-BB | IL-13 | SDF-1α | IL-12p40 | TNF-α |
| IL-10 | PDGF-BB | IL-12 | SDF-1α | IL-13 | TNF-α | IL-12p40 | TNF-β |
| IL-10 | SDF-1α | IL-12 | TNF-α | IL-13 | TNF-β | IL-12p40 | TRAIL |
| IL-10 | TNF-α | IL-12 | TNF-β | IL-13 | TRAIL | IL-12p40 | VEGF |
| IL-10 | TNF-β | IL-12 | TRAIL | IL-13 | VEGF | IL-12p40 | IL-8 |
| IL-10 | TRAIL | IL-12 | VEGF | IL-13 | IL-8 | IL-12p40 | MCP-1 |
| IL-10 | VEGF | IL-12 | IL-8 | IL-13 | MCP-1 | IL-12p40 | MGSA |
| IL-10 | IL-8 | IL-12 | MCP-1 | IL-13 | MGSA | IL-12p40 | PGE-2 |
| IL-10 | MCP-1 | IL-12 | MGSA | IL-13 | PGE-2 | IL-12p40 | RANTES |
| IL-10 | MGSA | IL-12 | PGE-2 | IL-13 | RANTES | IL-12p40 | MIF |
| IL-10 | PGE-2 | IL-12 | RANTES | IL-13 | MIF | IL-12p40 | GRO-α |
| IL-10 | RANTES | IL-12 | MIF | IL-13 | GRO-α | IL-12p40 | CRP |
| IL-10 | MIF | IL-12 | GRO-α | IL-13 | CRP | IL-12p40 | DDT |
| IL-10 | GRO-α | IL-12 | CRP | IL-13 | DDT | | |
| IL-10 | CRP | IL-12 | DDT | | | | |
| IL-10 | DDT | | | | | | |
| IL-15 | IL-16 | IL-16 | IL-17A | IL-17A | IL-18 | IL-18 | IL-1α |
| IL-15 | IL-17A | IL-16 | IL-18 | IL-17A | IL-1α | IL-18 | IL-1β |
| IL-15 | IL-18 | IL-16 | IL-1α | IL-17A | IL-1β | IL-18 | IL-2 |
| IL-15 | IL-1α | IL-16 | IL-1β | IL-17A | IL-2 | IL-18 | IL-2ra |
| IL-15 | IL-1β | IL-16 | IL-2 | IL-17A | IL-2ra | IL-18 | IL-3 |
| IL-15 | IL-2 | IL-16 | IL-2ra | IL-17A | IL-3 | IL-18 | IL-5 |
| IL-15 | IL-2ra | IL-16 | IL-3 | IL-17A | IL-5 | IL-18 | IL-6 |
| IL-15 | IL-3 | IL-16 | IL-5 | IL-17A | IL-6 | IL-18 | IL-7 |
| IL-15 | IL-5 | IL-16 | IL-6 | IL-17A | IL-7 | IL-18 | IL-9 |
| IL-15 | IL-6 | IL-16 | IL-7 | IL-17A | IL-9 | IL-18 | IP-10 |
| IL-15 | IL-7 | IL-16 | IL-9 | IL-17A | IP-10 | IL-18 | LIF |
| IL-15 | IL-9 | IL-16 | IP-10 | IL-17A | LIF | IL-18 | M-CSF |
| IL-15 | IP-10 | IL-16 | LIF | IL-17A | M-CSF | IL-18 | MIG |
| IL-15 | LIF | IL-16 | M-CSF | IL-17A | MIG | IL-18 | MIP-1α |
| IL-15 | M-CSF | IL-16 | MIG | IL-17A | MIP-1α | IL-18 | MIP-1β |
| IL-15 | MIG | IL-16 | MIP-1α | IL-17A | MIP-1β | IL-18 | PDGF-BB |
| IL-15 | MIP-1α | IL-16 | MIP-1β | IL-17A | PDGF-BB | IL-18 | SDF-1α |
| IL-15 | MIP-1β | IL-16 | PDGF-BB | IL-17A | SDF-1α | IL-18 | TNF-α |
| IL-15 | PDGF-BB | IL-16 | SDF-1α | IL-17A | TNF-α | IL-18 | TNF-β |
| IL-15 | SDF-1α | IL-16 | TNF-α | IL-17A | TNF-β | IL-18 | TRAIL |
| IL-15 | TNF-α | IL-16 | TNF-β | IL-17A | TRAIL | IL-18 | VEGF |
| IL-15 | TNF-β | IL-16 | TRAIL | IL-17A | VEGF | IL-18 | IL-8 |
| IL-15 | TRAIL | IL-16 | VEGF | IL-17A | IL-8 | IL-18 | MCP-1 |
| IL-15 | VEGF | IL-16 | IL-8 | IL-17A | MCP-1 | IL-18 | MGSA |
| IL-15 | IL-8 | IL-16 | MCP-1 | IL-17A | MGSA | IL-18 | PGE-2 |
| IL-15 | MCP-1 | IL-16 | MGSA | IL-17A | PGE-2 | IL-18 | RANTES |
| IL-15 | MGSA | IL-16 | PGE-2 | IL-17A | RANTES | IL-18 | MIF |
| IL-15 | PGE-2 | IL-16 | RANTES | IL-17A | MIF | IL-18 | GRO-α |
| IL-15 | RANTES | IL-16 | MIF | IL-17A | GRO-α | IL-18 | CRP |
| IL-15 | MIF | IL-16 | GRO-α | IL-17A | CRP | IL-18 | DDT |
| IL-15 | GRO-α | IL-16 | CRP | IL-17A | DDT | | |
| IL-15 | CRP | IL-16 | DDT | | | | |
| IL-15 | DDT | | | | | | |
| IL-1α | IL-1β | IL-1β | IL-2 | IL-2 | IL-2ra | IL-2ra | IL-3 |
| IL-1α | IL-2 | IL-1β | IL-2ra | IL-2 | IL-3 | IL-2ra | IL-5 |
| IL-1α | IL-2ra | IL-1β | IL-3 | IL-2 | IL-5 | IL-2ra | IL-6 |
| IL-1α | IL-3 | IL-1β | IL-5 | IL-2 | IL-6 | IL-2ra | IL-7 |
| IL-1α | IL-5 | IL-1β | IL-6 | IL-2 | IL-7 | IL-2ra | IL-9 |
| IL-1α | IL-6 | IL-1β | IL-7 | IL-2 | IL-9 | IL-2ra | IP-10 |
| IL-1α | IL-7 | IL-1β | IL-9 | IL-2 | IP-10 | IL-2ra | LIF |
| IL-1α | IL-9 | IL-1β | IP-10 | IL-2 | LIF | IL-2ra | M-CSF |
| IL-1α | IP-10 | IL-1β | LIF | IL-2 | M-CSF | IL-2ra | MIG |
| IL-1α | LIF | IL-1β | M-CSF | IL-2 | MIG | IL-2ra | MIP-1α |
| IL-1α | M-CSF | IL-1β | MIG | IL-2 | MIP-1α | IL-2ra | MIP-1β |
| IL-1α | MIG | IL-1β | MIP-1α | IL-2 | MIP-1β | IL-2ra | PDGF-BB |
| IL-1α | MIP-1α | IL-1β | MIP-1β | IL-2 | PDGF-BB | IL-2ra | SDF-1α |
| IL-1α | MIP-1β | IL-1β | PDGF-BB | IL-2 | SDF-1α | IL-2ra | TNF-α |
| IL-1α | PDGF-BB | IL-1β | SDF-1α | IL-2 | TNF-α | IL-2ra | TNF-β |
| IL-1α | SDF-1α | IL-1β | TNF-α | IL-2 | TNF-β | IL-2ra | TRAIL |
| IL-1α | TNF-α | IL-1β | TNF-β | IL-2 | TRAIL | IL-2ra | VEGF |
| IL-1α | TNF-β | IL-1β | TRAIL | IL-2 | VEGF | IL-2ra | IL-8 |
| IL-1α | TRAIL | IL-1β | VEGF | IL-2 | IL-8 | IL-2ra | MCP-1 |
| IL-1α | VEGF | IL-1β | IL-8 | IL-2 | MCP-1 | IL-2ra | MGSA |
| IL-1α | IL-8 | IL-1β | MCP-1 | IL-2 | MGSA | IL-2ra | PGE-2 |

TABLE 2-continued

Non-limiting examples of protein pairs that may be included in a protein profile generated by the methods of the present disclosure. The protein profile may comprise or consist of one or more protein pairs listed.

| Protein #1 | Protein #2 | Protein #1 | Protein #2 | Protein #1 | Protein #2 | Protein #1 | Protein #2 |
|---|---|---|---|---|---|---|---|
| IL-1α | MCP-1 | IL-1β | MGSA | IL-2 | PGE-2 | IL-2ra | RANTES |
| IL-1α | MGSA | IL-1β | PGE-2 | IL-2 | RANTES | IL-2ra | MIF |
| IL-1α | PGE-2 | IL-1β | RANTES | IL-2 | MIF | IL-2ra | GRO-α |
| IL-1α | RANTES | IL-1β | MIF | IL-2 | GRO-α | IL-2ra | CRP |
| IL-1α | MIF | IL-1β | GRO-α | IL-2 | CRP | IL-2ra | DDT |
| IL-1α | GRO-α | IL-1β | CRP | IL-2 | DDT | | |
| IL-1α | CRP | IL-1β | DDT | | | | |
| IL-1α | DDT | | | | | | |
| IL-3 | IL-5 | IL-5 | IL-6 | IL-6 | IL-7 | IL-7 | IL-9 |
| IL-3 | IL-6 | IL-5 | IL-7 | IL-6 | IL-9 | IL-7 | IP-10 |
| IL-3 | IL-7 | IL-5 | IL-9 | IL-6 | IP-10 | IL-7 | LIF |
| IL-3 | IL-9 | IL-5 | IP-10 | IL-6 | LIF | IL-7 | M-CSF |
| IL-3 | IP-10 | IL-5 | LIF | IL-6 | M-CSF | IL-7 | MIG |
| IL-3 | LIF | IL-5 | M-CSF | IL-6 | MIG | IL-7 | MIP-1α |
| IL-3 | M-CSF | IL-5 | MIG | IL-6 | MIP-1α | IL-7 | MIP-1β |
| IL-3 | MIG | IL-5 | MIP-1α | IL-6 | MIP-1β | IL-7 | PDGF-BB |
| IL-3 | MIP-1α | IL-5 | MIP-1β | IL-6 | PDGF-BB | IL-7 | SDF-α1 |
| IL-3 | MIP-1β | IL-5 | PDGF-BB | IL-6 | SDF-1α | IL-7 | TNF-α |
| IL-3 | PDGF-BB | IL-5 | SDF-1α | IL-6 | TNF-α | IL-7 | TNF-β |
| IL-3 | SDF-1α | IL-5 | TNF-α | IL-6 | TNF-β | IL-7 | TRAIL |
| IL-3 | TNF-α | IL-5 | TNF-β | IL-6 | TRAIL | IL-7 | VEGF |
| IL-3 | TNF-β | IL-5 | TRAIL | IL-6 | VEGF | IL-7 | IL-8 |
| IL-3 | TRAIL | IL-5 | VEGF | IL-6 | IL-8 | IL-7 | MCP-1 |
| IL-3 | VEGF | IL-5 | IL-8 | IL-6 | MCP-1 | IL-7 | MGSA |
| IL-3 | IL-8 | IL-5 | MCP-1 | IL-6 | MGSA | IL-7 | PGE-2 |
| IL-3 | MCP-1 | IL-5 | MGSA | IL-6 | PGE-2 | IL-7 | RANTES |
| IL-3 | MGSA | IL-5 | PGE-2 | IL-6 | RANTES | IL-7 | MIF |
| IL-3 | PGE-2 | IL-5 | RANTES | IL-6 | MIF | IL-7 | GRO-α |
| IL-3 | RANTES | IL-5 | MIF | IL-6 | GRO-α | IL-7 | CRP |
| IL-3 | MIF | IL-5 | GRO-α | IL-6 | CRP | IL-7 | DDT |
| IL-3 | GRO-α | IL-5 | CRP | IL-6 | DDT | | |
| IL-3 | CRP | IL-5 | DDT | | | | |
| IL-3 | DDT | | | | | | |
| IL-9 | IP-10 | IP-10 | LIF | LIE | M-CSF | M-CSF | MIG |
| IL-9 | LIF | IP-10 | M-CSF | LIE | MIG | M-CSF | MIP-1α |
| IL-9 | M-CSF | IP-10 | MIG | LIF | MIP-1α | M-CSF | MIP-1β |
| IL-9 | MIG | IP-10 | MIP-1α | LIE | MIP-1β | M-CSF | PDGF-BB |
| IL-9 | MIP-1α | IP-10 | MIP-1β | LIF | PDGF-BB | M-CSF | SDF-1α |
| IL-9 | MIP-1β | IP-10 | PDGF-BB | LIF | SDF-1α | M-CSF | TNF-α |
| IL-9 | PDGF-BB | IP-10 | SDF-1α | LIF | TNF-α | M-CSF | TNF-β |
| IL-9 | SDF-1α | IP-10 | TNF-α | LIF | TNF-β | M-CSF | TRAIL |
| IL-9 | TNF-α | IP-10 | TNF-β | LIF | TRAIL | M-CSF | VEGF |
| IL-9 | TNF-β | IP-10 | TRAIL | LIF | VEGF | M-CSF | IL-8 |
| IL-9 | TRAIL | IP-10 | VEGF | LIE | IL-8 | M-CSF | MCP-1 |
| IL-9 | VEGF | IP-10 | IL-8 | LIF | MCP-1 | M-CSF | MGSA |
| IL-9 | IL-8 | IP-10 | MCP-1 | LIF | MGSA | M-CSF | PGE-2 |
| IL-9 | MCP-1 | IP-10 | MGSA | LIF | PGE-2 | M-CSF | RANTES |
| IL-9 | MGSA | IP-10 | PGE-2 | LIF | RANTES | M-CSF | MIF |
| IL-9 | PGE-2 | IP-10 | RANTES | LIF | MIF | M-CSF | CRP |
| IL-9 | RANTES | IP-10 | MIF | LIF | GRO-α | M-CSF | DDT |
| IL-9 | MIF | IP-10 | GRO-α | LIF | CRP | | |
| IL-9 | GRO-α | IP-10 | CRP | LIF | DDT | | |
| IL-9 | CRP | IP-10 | DDT | | | | |
| IL-9 | DDT | | | | | | |
| MIG | MIP-1α | MIP-1α | MIP-1β | MIP-1β | PDGF-BB | PDGF-BB | SDF-1α |
| MIG | MIP-1β | MIP-1α | PDGF-BB | MIP-1β | SDF-1α | PDGF-BB | TNF-α |
| MIG | PDGF-BB | MIP-1α | SDF-1α | MIP-1β | TNF-α | PDGF-BB | TNF-β |
| MIG | SDF-1α | MIP-1α | TNF-α | MIP-1β | TNF-β | PDGF-BB | TRAIL |
| MIG | TNF-α | MIP-1α | TNF-β | MIP-1β | TRAIL | PDGF-BB | VEGF |
| MIG | TNF-β | MIP-1α | TRAIL | MIP-1β | VEGF | PDGF-BB | IL-8 |
| MIG | TRAIL | MIP-1α | VEGF | MIP-1β | IL-8 | PDGF-BB | MCP-1 |
| MIG | VEGF | MIP-1α | IL-8 | MIP-1β | MCP-1 | PDGF-BB | MGSA |
| MIG | IL-8 | MIP-1α | MCP-1 | MIP-1β | MGSA | PDGF-BB | PGE-2 |
| MIG | MCP-1 | MIP-1α | MGSA | MIP-1β | PGE-2 | PDGF-BB | RANTES |
| MIG | MGSA | MIP-1α | PGE-2 | MIP-1β | RANTES | PDGF-BB | MIF |
| MIG | PGE-2 | MIP-1α | RANTES | MIP-1β | MIF | PDGF-BB | GRO-α |
| MIG | RANTES | MIP-1α | MIF | MIP-1β | GRO-α | PDGF-BB | CRP |
| MIG | MIF | MIP-1α | GRO-α | MIP-1β | CRP | PDGF-BB | DDT |
| MIG | GRO-α | MIP-1α | CRP | MIP-1β | DDT | | |
| MIG | CRP | MIP-1α | DDT | | | | |
| MIG | DDT | | | | | | |
| SDF-1α | TNF-α | TNF-α | TNF-β | TNF-β | TRAIL | TRAIL | VEGF |
| SDF-1α | TNF-β | TNF-α | TRAIL | TNF-β | VEGF | TRAIL | IL-8 |
| SDF-1α | TRAIL | TNF-α | VEGF | TNF-β | IL-8 | FRAIL | MCP-1 |

TABLE 2-continued

Non-limiting examples of protein pairs that may be included in a protein profile generated by the methods of the present disclosure. The protein profile may comprise or consist of one or more protein pairs listed.

| Protein #1 | Protein #2 | Protein #1 | Protein #2 | Protein #1 | Protein #2 | Protein #1 | Protein #2 |
|---|---|---|---|---|---|---|---|
| SDF-1α | VEGF | TNF-α | IL-8 | TNF-β | MCP-1 | TRAIL | MGSA |
| SDF-1α | IL-8 | TNF-α | MCP-1 | TNF-β | MGSA | TRAIL | PGE-2 |
| SDF-1α | MCP-1 | TNF-α | MGSA | TNF-β | PGE-2 | TRAIL | RANTES |
| SDF-1α | MGSA | TNF-α | PGE-2 | TNF-β | RANTES | TRAIL | MIF |
| SDF-1α | PGE-2 | TNF-α | RANTES | TNF-β | MIF | TRAIL | GRO-α |
| SDF-1α | RANTES | TNF-α | MIF | TNF-β | GRO-α | TRAIL | CRP |
| SDF-1α | MIF | TNF-α | GRO-α | TNF-β | CRP | TRAIL | DDT |
| SDF-1α | GRO-α | TNF-α | CRP | TNF-β | DDT | | |
| SDF-1α | CRP | TNF-α | DDT | | | | |
| SDF-1α | DDT | | | | | | |
| VEGF | IL-8 | IL-8 | MCP-1 | MCP-1 | MGSA | MGSA | PGE-2 |
| VEGF | MCP-1 | IL-8 | MGSA | MCP-1 | PGE-2 | MGSA | RANTES |
| VEGF | MGSA | IL-8 | PGE-2 | MCP-1 | RANTES | MGSA | MIF |
| VEGF | PGE-2 | IL-8 | RANTES | MCP-1 | MIF | MGSA | GRO-α |
| VEGF | RANTES | IL-8 | MIF | MCP-1 | GRO-α | MGSA | CRP |
| VEGF | MIF | IL-8 | GRO-α | MCP-1 | CRP | MGSA | DDT |
| VEGF | GRO-α | IL-8 | CRP | MCP-1 | DDT | | |
| VEGF | CRP | IL-8 | DDT | | | | |
| VEGF | DDT | | | | | | |
| PGE-2 | RANTES | RANTES | MIF | MIF | GRO-α | GRO-α | CRP |
| PGE-2 | MIF | RANTES | GRO-α | MIF | CRP | GRO-α | DDT |
| PGE-2 | GRO-α | RANTES | CRP | MIF | DDT | | |
| PGE-2 | CRP | RANTES | DDF | | | | |
| PGE-2 | DDT | | | | | | |
| CRP | DDT | | | | | | |

In certain embodiments, the presence or level of one or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty-one or more, twenty-two or more, twenty-three or more, twenty-four or more, twenty-five or more, twenty-six or more, twenty-seven or more, twenty-eight or more, twenty-nine or more or thirty or more proteins is detected or measured in a red blood cell-enriched sample.

In certain other embodiments, the presence of one or more proteins is detected or the level of one or more proteins is measured in a red blood cell-enriched sample. In another embodiment, the presence of two or more proteins is detected or the level of two or more proteins is measured in a red blood cell-enriched sample. In other embodiments, the presence of three or more proteins is detected or the level of three or more proteins is measured in a red blood cell-enriched sample. In another embodiment, the presence of four or more proteins is detected or the level of four or more proteins is measured in a red blood cell-enriched sample. In yet another embodiment, the presence of five or more proteins is detected or the level of five or more proteins is measured in a red blood cell-enriched sample. In other embodiments, the presence of six or more proteins is detected or the level of six or more proteins is measured in a red blood cell-enriched sample. In another embodiment, the presence of seven or more proteins is detected or the level of seven or more proteins is measured in a red blood cell-enriched sample. In still another embodiment, the presence of eight or more proteins is detected or the level of eight or more proteins is measured in a red blood cell-enriched sample. In yet another embodiment, the presence of eight or more proteins is detected or the level of eight or more proteins is measured in a red blood cell-enriched sample. In other embodiments, the presence of nine or more proteins is detected or the level of nine or more proteins is measured in a red blood cell-enriched sample. In still other embodiments, the presence of ten or more proteins is detected or the level of ten or more proteins is measured in a red blood cell-enriched sample. In yet other embodiments, the presence of eleven or more proteins is detected or the level of eleven or more proteins is measured in a red blood cell-enriched sample. In some embodiments, the presence of twelve or more proteins is detected or the level of twelve or more proteins is measured in a red blood cell-enriched sample. In some other embodiment, the presence of thirteen or more proteins is detected or the level of thirteen or more proteins is measured in a red blood cell-enriched sample. In yet other embodiments, the presence of fourteen or more proteins is detected or the level of fourteen or more proteins is measured in a red blood cell-enriched sample. In further embodiments, the presence of fifteen or more proteins is detected or the level of fifteen or more proteins is measured in a red blood cell-enriched sample. In another embodiment, the presence of sixteen or more proteins is detected or the level of sixteen or more proteins is measured in a red blood cell-enriched sample. In still other embodiments, the presence of seventeen or more proteins is detected or the level of seventeen or more proteins is measured in a red blood cell-enriched sample. In yet other embodiments, the presence of eighteen or more proteins is detected or the level of eighteen or more proteins is measured in a red blood cell-enriched sample. In another embodiment, the presence of nineteen or more proteins is detected or the level of nineteen or more proteins is measured in a red blood cell-enriched sample. In still another embodiment, the presence of twenty or more proteins is detected or the level of twenty or more proteins is measured in a red blood cell-enriched sample. In yet another embodiment, the presence of twenty-one or more proteins is detected or the level of twenty-one or more proteins is measured in a red blood cell-enriched sample. In other embodiments, the presence of twenty-two or more proteins is detected or the level of twenty-two or more proteins is measured in a red blood cell-enriched sample. In another embodiment, the presence of twenty-three or more proteins is detected or the level of twenty-three or more proteins is measured in a red blood cell-enriched sample. In still other embodiments, the presence of twenty-four or more proteins is detected or the level of twenty-four or more proteins is measured in a red blood cell-enriched sample. In yet another embodiment, the presence of twenty-five or more proteins is detected or the level of twenty-five or more proteins is measured in a red blood cell-enriched sample. In still another embodiment, the presence of twenty-six or more proteins is detected or the level of twenty-six or more proteins is measured in a red blood cell-enriched sample. In still other embodiment, the presence of twenty-seven or more proteins is detected or the level of twenty-seven or more proteins is measured in a red blood cell-enriched sample. In another embodiment, the presence of twenty-eight or more proteins is detected or the level of twenty-eight or more proteins is measured in a red blood cell-enriched sample. In another embodiment, the presence of twenty-nine or more proteins is detected or the level of twenty-nine or more proteins is measured in a red blood cell-enriched sample. In still another embodiment, the presence of thirty or more proteins is detected or the level of thirty or more proteins is measured in a red blood cell-enriched sample.

A protein profile may be produced or generated for example, by detecting the presence of one or more proteins in a lysate, cell wash, cell supernatant, or a combination thereof prepared according to the methods of the present disclosure. The protein(s) detected may also be quantified (e.g., measure the levels) to produce or generate the protein profile.

Methods for the detection and/or quantification of proteins in single or mixed blood cell populations and plasma/serum are well known to those of ordinary skill in the art. Non-limiting examples of suitable methods include antibody-based methods generally, flow cytometry, ELISA, lateral flow, immunostaining, immunofluorescence, immunoelectrophoresis (including, e.g., Western blot), and the like. Alternatively, proteins may be detected and/or quantified using mass spectrometry, spectroscopy, chromatography, electrophoresis, bicinchoninic acid assay (BCA), enzyme assay and the like. Again by way of example only, protein quantification methods are described in U.S. Pat. Nos. 7,501,286, 8,530,182, and United States Patent Publication Number 2013028838. Methodology is also presented in the Examples of the present specification.

The present disclosure also provides methods for producing a protein profile from a red blood cell-enriched sample by calculating a protein ratio comprising the level of one or more proteins in red blood cells to the level of those same one or more proteins in plasma. The protein ratio can be calculated by normalizing the measured protein concentration in the RBCs and the plasma and then dividing the concentration of the protein(s) in the RBCs by the concentration of the protein(s) in the plasma. The concentration of the protein(s) in the RBCs and plasma are normalized by calculating their relative concentration per millilitre in whole blood (percent in whole blood).

In certain embodiments, the protein ratio comprising the level of one or more proteins in red blood cells to the level of those one or more proteins in the plasma is at least 2:1, at least 10:1, at least 20:1, at least 30:1, at least 40:1, at least 50:1, at least 60:1, at least 70:1, at least 80:1, at least 90:1, at least 100:1, at least 110:1, at least 120:1, at least 130:1, at least 140:1, at least 150:1, at least 160:1, at least 170:1, at least 180:1, at least 190:1, or at least 200:1. In other embodiments, the protein ratio is at least 3:1, at least 4:1, at least 5:1, at least 6:1, at least 7:1, at least 8:1, at least 9:1, at least 10:1, at least 11:1, at least 12:1, at least 13:1, at least 14:1, at least 15:1, at least 16:1, at least 17:1, at least 18:1, at least 19:1, at least 20:1, at least 21:1, at least 22:1, at least 23:1, at least 24:1, at least 25:1, at least 26:1, at least 27:1, at least 28:1, at least 29:1, at least 30:1, at least 31:1, at least 32:1, at least 33:1, at least 34:1, at least 35:1, at least 36:1, at least 37:1, at least 38:1, at least 39:1 or at least 40:1.

Disease Profiles

The present disclosure provides methods herein for producing a disease protein profile in a red blood cell-enriched blood sample. A disease profile can be produced for any disease or disorder for which there is a difference in the presence or levels of one or more proteins associated with a red blood cell-enriched sample. By way of non-limiting example, a disease profile can be produced for any disease or disorder for which there is a difference in the presence or level of one or more of the proteins set out in Table 1 or one or more combinations of proteins set out in Table 2. For example, in certain embodiments, the disease or disorder profiled is selected from the group consisting of cancer, preeclampsia, autoimmune disease, cardiovascular disease, neurodegenerative disease, diabetes, metabolic disorders, musculoskeletal disease, infectious disease, genetic disorders, renal disorders, and gastrointestinal disorders.

A disease protein profile(s) is produced according to the methods by obtaining a protein profile produced from one or more subjects having a disease or disorder and a protein profile produced from one or more subject not having the disease or disorder. In one embodiment, at least one protein profile is obtained from a subject having a disease or disorder and at least one profile is obtained from a subject not having the disease or disorder. In another embodiment, the blood samples are obtained from one or more subjects having a disease or disorder and pooled. In another embodiment, blood samples are obtained from one or more subjects not having the disease or disorder and pooled. Then, a protein profile is obtained from the pooled blood samples of the one or more subjects having the disease or disorder and/or the one or more subjects not having the disease or disorder. In another embodiment, one or more protein profiles are obtained from subjects having a disease or disorder and one or more protein profiles are obtained from subjects not having the disease or disorder and a statistical analysis is performed to determine the proteins that comprise (by a statistically relevant difference in presence and/or level of the proteins) a protein profile for a subject having a disease or disorder and a protein profile for a subject not having the disease or disorder. The protein profile of a subject having a disease or disorder and the protein profile of a subject not having the disease or disorder can be produced at any time prior to determining a disease protein profile.

In one embodiment, the disease protein profile comprises one or more proteins that are present in a subject having a disease or disorder but not present in a subject not having the disease or disorder. In another embodiment, the disease protein profile comprises one or more proteins that are not present in a subject having a disease or disorder, but are present in a subject not having the disease or disorder. In still other embodiments, the disease protein profile comprises one or more proteins that have a higher level in a subject having a disease or disorder compared to the one or more proteins in a subject not having the disease or disorder. In another embodiment, the disease protein profile comprises one or more proteins that have a lower level in a subject having a disease or disorder compared to the one or more proteins in a subject not having the disease or disorder. In certain embodiments, a disease protein profile comprises proteins that have a different (e.g., higher, lower, or both higher and lower) level of one or more proteins in a subject having a disease or disorder compared to the one or more proteins in a subject not having the disease or disorder.

In certain embodiments, the disease protein profile is a cancer protein profile comprising one or more proteins selected from the group consisting of IL-1, IL-2, IL-4, IL-5, IL-6, IL-8, IL-10, IL-12, IL-15, IL-17, TNF-α, TGF-β, and IFN-γ. In other embodiments, the disease protein profile is a preeclampsia protein profile comprising one or more proteins selected from the group consisting of TNF-α, IFN-γ, IL-4, IL-5, IL-10, IL-1β, IL-6, IL-8, and IL-12. In particular embodiments, the preeclampsia protein profile comprises one or more proteins selected from the group consisting of IL-6, IL-8, and IFN-γ.

The present disclosure also provides methods for determining whether a subject has a disease or disorder using a disease profile produced by the methods provided herein. A protein profile can be obtained from a subject that is/was produced by one of the methods provided herein. The protein profile of the subject can be compared to a disease protein profile for similarities between the two protein profiles (in e.g., protein presence or protein levels). Similarities between a subject's protein profile and a disease protein profile may indicate that the subject has the disease or disorder. In one embodiment, there are similarities between at least one protein, at least two proteins, at least three proteins, at least four proteins, at least five proteins, at least six proteins, at least seven proteins, at least eight proteins, at least nine proteins, at least ten proteins, at least eleven proteins, at least twelve proteins, at least thirteen proteins, at least fourteen proteins, at least fifteen proteins, at least sixteen proteins, at least seventeen proteins, at least eighteen proteins, at least nineteen proteins, at least twenty proteins, at least twenty-one proteins, at least twenty-two proteins, at least twenty-three proteins, at least twenty-four proteins, at least twenty-five proteins, at least twenty-six proteins, at least twenty-seven proteins, at least twenty-eight proteins, at least twenty-nine proteins, or at least thirty proteins. In another embodiment, there are similarities between at least one protein. In yet another embodiment, there are similarities between at least 3 proteins. In still other embodiments, there are similarities between at least 5 proteins. In still other embodiments, there are similarities between at least 10 proteins. In yet other embodiments, there are similarities between at least 15 proteins. In other embodiments, there are similarities between at least 20 proteins. In other embodiments, there are similarities between at least 30 proteins.

In certain embodiments, a subject's protein profile and a disease protein profile have the same one or more proteins present, indicating that the subject may have the disease or disorder. In other embodiments, a subject's protein profile and a disease protein profile have the same or substantially similar level of one or more proteins, indicating that the subject may have the disease or disorder. The same or substantially similar level of one or more proteins can include, for example, protein levels that are the same (e.g., within a relevant statistical analysis as determined by one of skill in the art) to protein levels that are determined to be sufficiently different by a person of ordinary skill in the art by, for example, a statistical analysis or a determined threshold fold difference (e.g., less than a two-fold difference). In some embodiments, the level of one or more proteins of a subject's protein profile and a disease protein profile are the same. In yet another embodiment, the level of one or more proteins of a subject's protein profile and a disease protein profile are substantially similar. In another embodiment, the difference in the level of one or more proteins of a subject's protein profile and a disease protein profile is determined by statistical methods known to one skilled in the art (e.g., a T-test with a p-value of 0.05 or greater). In yet another embodiment, the difference in the level of one or more proteins of a subject's protein profile and a disease protein profile is determined by comparison to a predetermined reference range (e.g., a healthy or normal concentration range) known to those of skill in the art. In other embodiments, the level of one or more proteins of a subject's protein profile and a disease protein profile is less than 0.5 fold different. In certain other embodiments, the level of one or more proteins of a subject's protein profile and a disease protein profile is less than 1-fold different. In still another embodiment, the level of one or more proteins of a subject's protein profile and a disease protein profile is less than 1.5-fold different. In still other embodiments, the level of one or more proteins of a subject's protein profile and a disease protein profile is less than 2-fold different.

Treatment Evaluation

The present disclosure also provides methods for monitoring treatment in a subject using a protein profile produced by the methods provided herein. A protein profile produced according to the methods provided herein is obtained from a subject before treatment and after treatment and the protein profiles compared for differences between the two (in, e.g., protein presence or protein levels). In one embodiment, the subject receiving treatment can be undergoing one or more treatments or a number of treatments. In another embodiment, the subject has received and/or is receiving a particular treatment. In one embodiment, the protein profile obtained before treatment can be obtained from a subject who has had no treatment and is compared to the protein profile of the subject after treatment. In another embodiment, a protein profile is measured during the course of a treatment and at least one protein profile of a subject obtained at one point in time during the treatment is compared to at least one protein profile of the subject obtained at a different point in time during the treatment. In certain embodiments, the protein profiles before treatment and after treatment are obtained from a subject that is undergoing the same treatment during the course of a treatment. In another embodiment, the protein profiles before treatment and after treatment are obtained from a subject that is undergoing a different treatment during the course of a treatment (e.g., a subject that has switched treatments).

Differences between a subject's protein profile (e.g., protein presence or levels) before treatment and after treatment may indicate that the treatment has had an effect on the subject. In one embodiment, there are differences between at least one protein, at least two proteins, at least three proteins, at least four proteins, at least five proteins, at least six proteins, at least seven proteins, at least eight proteins, at least nine proteins, at least ten proteins, at least eleven proteins, at least twelve proteins, at least thirteen proteins, at least fourteen proteins, at least fifteen proteins, at least sixteen proteins, at least seventeen proteins, at least eighteen proteins, at least nineteen proteins, at least twenty proteins, at least twenty-one proteins, at least twenty-two proteins, at least twenty-three proteins, at least twenty-four proteins, at least twenty-five proteins, at least twenty-six proteins, at least twenty-seven proteins, at least twenty-eight proteins, at least twenty-nine proteins, or at least thirty proteins. In another embodiment, there are differences between at least one protein. In yet another embodiment, there are differences between at least 3 proteins. In still other embodiments, there are differences between at least 5 proteins. In still other embodiments, there are differences between at least 10 proteins. In yet other embodiments, there are differences between at least 15 proteins. In other embodiments, there are differences between at least 20 proteins. In other embodiments, there are differences between at least 30 proteins.

In certain embodiments, a subject's protein profile obtained before treatment comprises different protein(s) than the protein profile obtained after treatment, indicating that the treatment may have had an effect on the subject. In other embodiments, a subject's protein profile obtained before treatment has different levels of one or more proteins compared to the protein profile obtained after treatment, indicating that the treatment may have had an effect on the subject. The different levels of one or more proteins can include, for example, levels that are greater than a 1-fold difference. In certain embodiments, the difference in the level of one or more proteins of a subject's protein profile before and after treatment is greater than 1-fold, greater than 1.5 fold, greater than 2-fold, greater than 2.5 fold, greater than 3-fold, greater than 3.5-fold, greater than 4-fold, greater than 4.5 fold, greater than 5-fold, greater than 5.5 fold, greater than 6-fold, greater than 6.5-fold, greater than 7-fold, greater than 7.5-fold, greater than 8-fold, greater than 8.5-fold, greater than 9-fold, greater than 9.5-fold, and greater than 10-fold. In some embodiments, the difference in the level of one or more proteins of a subject's protein profile before and after treatment is greater than 1.5-fold. In other embodiments, the difference in the level of one or more proteins of a subject's protein profile before and after treatment is greater than 2-fold. In other embodiments, the difference in the level of one or more proteins of a subject's protein profile before and after treatment is greater than 2.5-fold. In still other embodiments, the difference in the level of one or more proteins of a subject's protein profile before and after treatment is greater than 3-fold. In still other embodiments, the difference in the level of one or more proteins of a subject's protein profile before and after treatment is greater than 4-fold. In another embodiment, the difference in the level of one or more proteins of a subject's protein profile before and after treatment is greater than 5-fold. In other embodiments, the difference in the level of one or more proteins of a subject's protein profile before and after treatment is greater than 6-fold. In still other embodiment, the difference in the level of one or more proteins of a subject's protein profile before and after treatment is greater than 7-fold. In another embodiment, the difference in the level of one or more proteins of a subject's protein profile before and after treatment is greater than 8-fold. In yet another embodiment, the difference in the level of one or more proteins of a subject's protein profile before and after treatment is greater than 9-fold. In still another embodiment, the difference in the level of one or more proteins of a subject's protein profile before and after treatment is greater than 10-fold.

In certain embodiments, a small volume blood sample is obtained to produce the protein profiles before treatment and after treatment in order to monitor treatment of a subject. A small volume blood sample allows the subject to be sampled frequently and, consequently, allows for treatment monitoring at a frequency not previously achievable. In some embodiments, a small volume blood sample can be obtained at a frequency of one or more times per day, two or more times per day, three or more times per day, four or more times per day, and five or more times per day. In other embodiments, a small volume blood sample is obtained one or more times per week, two or more times per week, three or more times per week, four or more times per week, five or more times per week, six or more times per week, and seven or more times per week. In other embodiments, a small volume blood sample is obtained daily. In still other embodiments, a small volume blood sample is obtained once a week, once every two weeks, once every three weeks, and once every four weeks. In certain embodiments, a small volume blood sample is obtained once a month.

The present disclosure also provides methods for determining the effectiveness of a treatment in a subject using protein profiles produced by the methods provided herein. In one embodiment, at least one protein profile is obtained from a subject that has undergone a treatment. In another embodiment, at least one protein profile is obtained from a subject that has not undergone a treatment and the protein profile of the subject that has undergone treatment is compared to the protein profile of the subject that has not undergone treatment. In another embodiment, the protein profile is produced using blood samples obtained from one or more subjects who have not undergone treatment and the blood samples are pooled. In another embodiment, a protein profile is produced using one or more blood samples obtained from a subject who has undergone treatment and the blood samples are pooled. A protein profile is then obtained from the pooled blood samples of the one or more subjects that have not undergone treatment and/or the one or more blood samples from a subject that has not undergone treatment. In another embodiment, one or more protein profiles are obtained from one or more subjects that have not undergone treatment and/or one or more protein profiles are obtained from a subject that has undergone treatment, and a statistical analysis is performed by means known in the art to determine the proteins that will comprise (by a difference in presence and/or level) the protein profile of a subject that has not undergone treatment and the protein profile of a subject that has undergone treatment. The protein profile of a subject that has undergone a treatment and the protein profile of a subject that has not undergone a treatment can be produced at any time prior to comparison of the two protein profiles.

Similarities in the presence or level of one or more proteins between the protein profile of the subject that has undergone treatment, compared to the protein profile of the subject that has not undergone treatment may indicate the effectiveness of the treatment. In one embodiment, there are similarities between at least one protein, at least two proteins, at least three proteins, at least four proteins, at least five proteins, at least six proteins, at least seven proteins, at least eight proteins, at least nine proteins, at least ten proteins, at least eleven proteins, at least twelve proteins, at least thirteen proteins, at least fourteen proteins, at least fifteen proteins, at least sixteen proteins, at least seventeen proteins, at least eighteen proteins, at least nineteen proteins, at least twenty proteins, at least twenty-one proteins, at least twenty-two proteins, at least twenty-three proteins, at least twenty-four proteins, at least twenty-five proteins, at least twenty-six proteins, at least twenty-seven proteins, at least twenty-eight proteins, at least twenty-nine proteins, or at least thirty proteins. In another embodiment, there are similarities between at least one protein. In yet another embodiment, there are similarities between at least 3 proteins. In still other embodiments, there are similarities between at least 5 proteins. In still other embodiments, there are similarities between at least 10 proteins. In yet other embodiments, there are similarities between at least 15 proteins. In other embodiments, there are similarities between at least 20 proteins. In other embodiments, there are similarities between at least 30 proteins.

In certain embodiments, the protein profile of a subject that has undergone treatment and the protein profile of a subject that has not undergone treatment have the same one or more proteins present, indicating that the treatment may have been effective. In other embodiments, the protein profile of a subject that has undergone treatment and the protein profile of a subject that has not undergone treatment have the same or substantially similar level of one or more proteins, indicating that the treatment may have been effective. The same or substantially similar level of one or more proteins can include, for example, protein levels that are the same (e.g., within a relevant statistical analysis as determined by one of skill in the art) to protein levels that are determined to be sufficiently different by a person of ordinary skill in the art by, for example, a statistical analysis or a determined threshold fold difference (e.g., less than a two-fold difference). In some embodiments, the level of one or more proteins of the protein profile of a subject that has undergone treatment and the protein profile of a subject that has not undergone treatment are the same. In yet another embodiment, the level of one or more proteins of the protein profile of a subject that has undergone treatment and the protein profile of a subject that has not undergone treatment are substantially similar. In another embodiment, the difference in the level of one or more proteins of the protein profile of a subject that has undergone treatment and the protein profile of a subject that has not undergone treatment is determined by statistical methods known to one skilled in the art (e.g., a T-test with a p-value of 0.05 of greater). In yet another embodiment, the difference in the level of one or more proteins of the protein profile of a subject that has undergone treatment and the protein profile of a subject that has not undergone treatment is determined by comparison to a predetermined reference range (e.g., a healthy or normal concentration range) known to those of skill in the art. In another embodiment, the level of one or more proteins of the protein profile of a subject that has undergone treatment and the protein profile of a subject that has not undergone treatment is less than 0.5 fold different. In another embodiment, the level of one or more proteins of the protein profile of a subject that has undergone treatment and the protein profile of a subject that has not undergone treatment is less than 1-fold different. In still another embodiment, the level of one or more proteins of the protein profile of a subject that has undergone treatment and the protein profile of a subject that has not undergone treatment is less than 1.5-fold different. In still other embodiments, the level of one or more proteins of the protein profile of a subject that has undergone treatment and the protein profile of a subject that has not undergone treatment is less than 2-fold different.

Subjects

Certain embodiments relate to determining the protein profile of a blood sample or component thereof from a subject.

The subject may be an animal in which blood comprises red blood cells (e.g., a mammal, bird, fish, reptile, or amphibian). Non-limiting examples of suitable subjects include bovine, equine, ovine, primate, avian and rodent species. Hence, in some embodiments the subject may be a human, a non-human mammal, a mouse, rat, hamster, ferret, gerbil, rabbit, monkey, chimpanzee, horse, pony, donkey, sheep, pig, chicken, goat, cat, or dog.

Kits

The present disclosure also provides kits comprising the components necessary for carrying out the methods described herein.

By way of non-limiting example, the kits may comprise means for: collecting blood, anticoagulant(s), blood stabilising agent(s), enrichment of RBCs, removal/separation of non-RBCs blood components, snap-freezing blood or component(s) thereof, lysing cells, washing cells, culturing cells, detecting specific target protein(s) intracellularly and/or extracellularly, and/or combinations thereof. In certain embodiments, the kits comprise at least one reagent to leukodeplete a blood sample and produce a red blood cell-enriched sample and at least one reagent to detect the presence or measure the level of one or more proteins in a small volume red blood cell-enriched sample. In one embodiment, the regent to detect the presence or measure the level of one or more proteins is an ELISA apparatus. In other embodiments, the kit further comprises at least one reagent to obtain a blood sample from a subject.

In some embodiments, kits according to the present disclosure may comprise one or more of the following: device(s) for obtaining a blood sample from a subject (e.g., a syringe, needle, butterfly needle, tube, needle holder, blood collection set, transfer device, VACUTAINER, HEMAPEN™), device(s) for obtaining a dried blood sample from a subject (e.g., filter paper, cards, HEMASPOT™); device(s) for obtaining a red blood cell fraction, a leukocyte fraction, and/or a platelet fraction from a liquid blood sample (e.g., antibody coated magnetic beads); anticoagulants; protein denaturation agents; and the like.

EXAMPLES

The present disclosure will now be described with reference to specific example(s), which should not be construed as in any way limiting.

Figure 2:
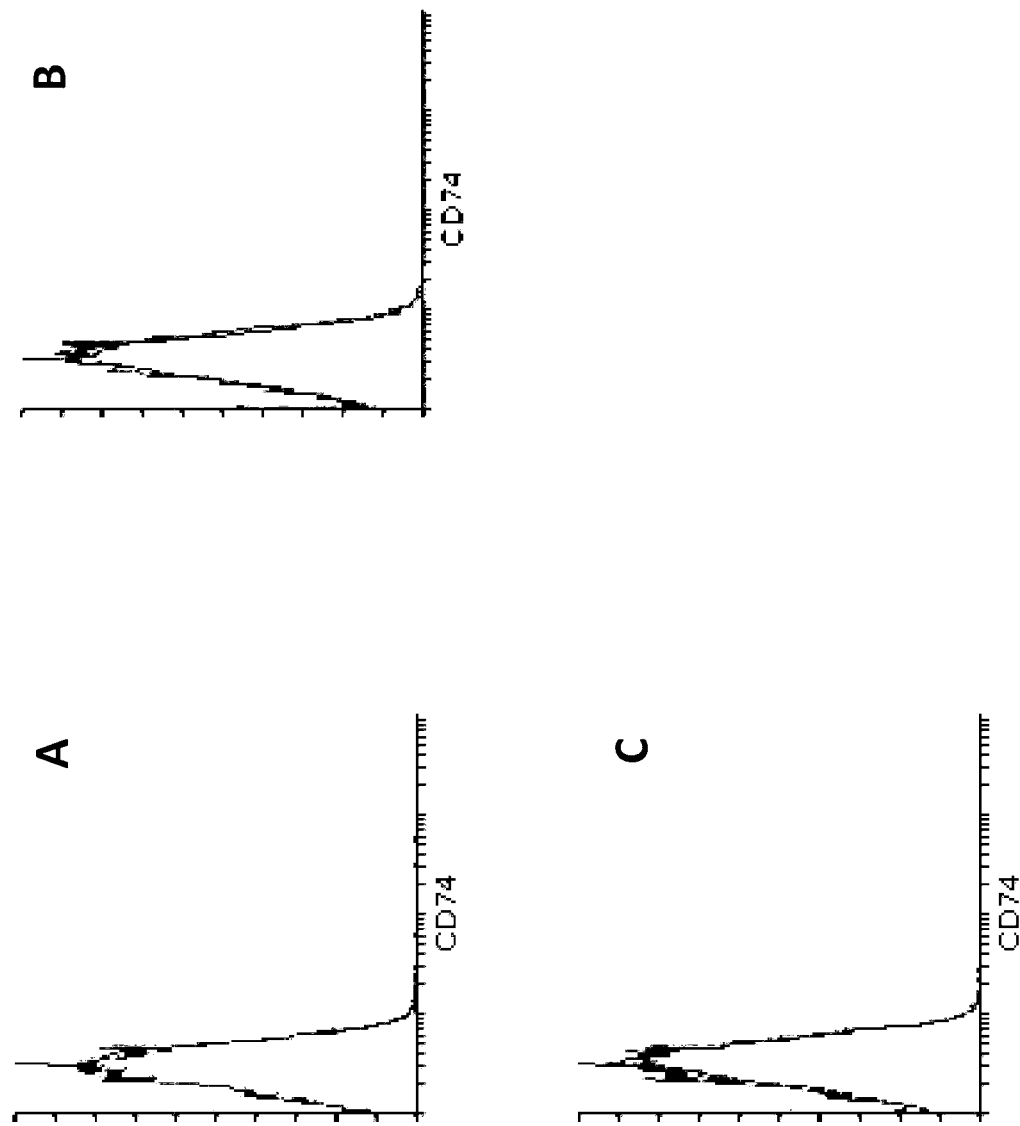
FIG. 2 shows the results of RBC immunophenotyping for CD74 against IgG controls demonstrating that cells (filled with grey histogram) are negative for CD74 (n=3).

Example 1. Investigating the Presence of the MIF Receptor on the Surface of RBCs RBCs contain MIF. To determine whether RBCs have a receptor to bind MIF they were analyzed for the most well-known receptor for MIF, a complex formed between CD44 and CD74 on the cell surface. Immunophenotyping was used to identify the absence or presence of CD44 and CD74 on RBCs. Whole blood (WB) was collected into an EDTA VACUTAINER, washed twice in PBS+FBS (2%) (centrifuged at 500 g, for 5 minutes) and finally resuspended to 1 mL of solution. 5 uL of solution was added to each respective tube. Cells were then stained with 5 μL or 20 μL of each antibody (anti-CD44, anti-CD74, anti-CD45, and an IgG control) and 50 μL of PBS+FBS (2%). Cell solutions were incubated in the dark at room temperature for 15 minutes and after incubation, cells were washed three times in 1×PBS (500 g, 5 minutes). Cells were resuspended in 200 uL of PBS and were analysed by flow cytometry using quadrant statistics and overlay histograms As shown in FIG. 1A-1C, RBCs were positive for the receptor CD44. However, they did not appear to be positive for CD74 (FIG. 2). As expected, RBCs were not positive for the white blood cell (WBC) marker CD45 (data not shown). Because RBCs were positive for CD44, but not positive for CD74, RBCs do not have the primary MIF receptor. Therefore, if MIF is on the surface of RBCs, it must bind by another mechanism.

Example 2. MIF Localization in RBCs

Figure 3:
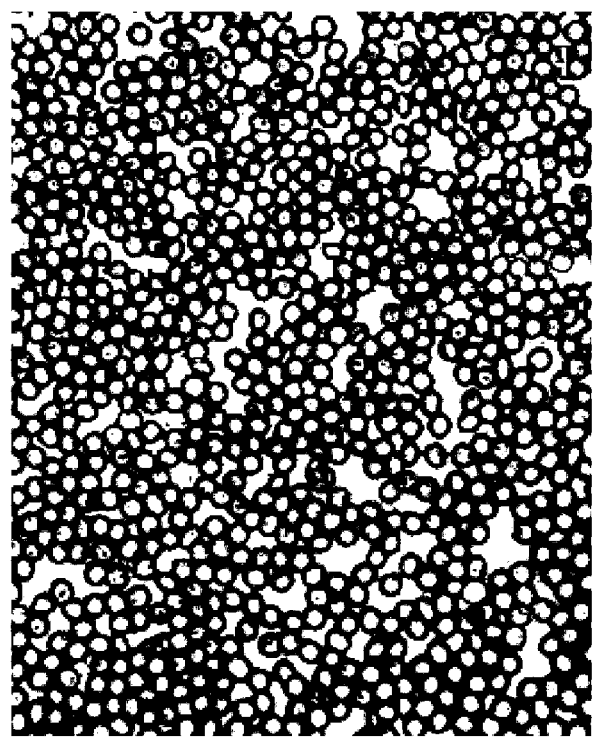
FIG. 3 shows the results of immunocytochemistry for MIF with alkaline phosphate staining of blood slides, positive (stained) sample (n=1).
Figure 4:
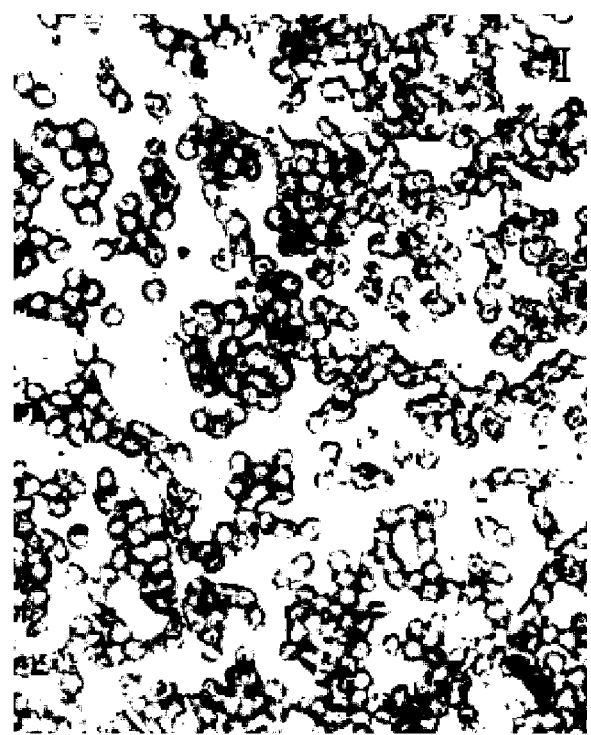
FIG. 4 shows the results of immunocytochemistry for MIF with alkaline phosphate staining of blood slides, negative (unstained) control (n=1).

RBCs were analyzed for the localization of MIF using immunocytochemistry. Whole blood was collected into a syringe and washed twice in 1×PBS (spun in a centrifuge at 500 g, for 5 minutes). The cell pellet was the used to prepare blood smears (10 µL per slide) and the blood slides left to dry at room temperature for at least 2 hours. Once the slides were completely dried, the smears were fixed in 100% methanol for 5 minutes at room temperature. After the slides were fixed, they were removed from the methanol and were left to air dry for ~10 minutes. Slides were washed thoroughly with 1×PBS and blood smears were then blot dried. The smears were blocked with PBS+5% BSA for 1 hour at room temperature. After blocking, the samples were incubated with or without primary MIF antibody (anti-human, rabbit MIF antibody, 1 µg/mL) overnight at 4° C. After incubation, slides were washed well with 1×PBS and then incubated with secondary antibody (anti-rabbit, AP conjugated antibody, 1:50 dilution) for 30 minutes at room temperature. Slides were rinsed well with 1×PBS and excess fluid was removed. Freshly prepared substrate (AP development buffer:substrate A:substrate B=100:1:1) was dropped over the slide, left to incubate for 20 minutes at room temperature, and the reaction terminated with MILLI-Q water. Slides were dried and mounted and images collected using light microscopy Next, paraffin embedded samples of RA synovium (human) were sectioned and applied to glass slides. Paraffin was removed from the samples using washes in xylene (2 times, 5 minutes) and ethanol (100%, 100%, 95%, 70%, 3 minutes each) and finally running tap water. Heat-induced epitope retrieval was then performed using a boiling water bath by the following method: a TISSUE-TEK container was filled with buffer (pH 6) and heated to 95° C. in water bath; slides were placed in container in boiling water bath and incubated for 20 minutes; slides were removed from the water bath and left to cool for 20 minutes at room temperature; and cold water was gradually added and finally slides were washed in cold tap water for 2-3 minutes. Slides were attached to Sequenza trays and were washed for 6 minutes with wash buffer (TBST). Sections were blocked using DAKO Protein Block Serum Free (100 µL, 10 minutes). Primary antibody (or corresponding negative IgG control) was added to slides at prepared concentrations and incubated overnight (100 µL, 4° C.; 0.5 µg/mL, 1 µg/mL, 2 µg/mL, 4 µg/mL). After incubation, slides were washed with TBST (6 minutes, room temperature). Secondary antibody (ENVISION polymer, rabbit, HRP) was added to slides (3 drops) and slides were incubated for 30 minutes at room temperature. Slides were then washed with TBST (6 minutes, room temperature), removed from Sequenza trays, and an HRP substrate reagent (NOVARED) was added to each slide (200 µL) by dropping directly it onto each slide. Slides were incubated for 15 minutes at room temperature. Slides were then washed in running tap water for 5 minutes to stop the reaction and the samples were counterstained with haematoxylin (2 minutes, room temperature) and Scott's Blue (30 seconds, room temperature). Samples were then dehydrated in increasing concentrations of ethanol then xylene, mounted, and observed using light microscopy A clear intracellular staining of white blood cells (FIG. 3) was observed as anticipated (WBCs contain high intracellular pools of MIF). These results also showed that the cell surface of the RBCs were stained (FIG. 3), suggesting that MIF is present on the cell surface. There was no clear intracellular staining on the RBCs (FIG. 3). The negative control is shown in FIG. 4.

Figure 5:
FIG. 5 shows the results of immunohistochemistry for MIF with HRP staining of RA synovium, negative control (n=1).
Figure 6:
FIG. 6 shows the results of immunocytochemistry with HRP staining of RA synovium, positive control (n=1).

Staining synovium sections was also successful. There was little to no staining with the negative controls (FIG. 5) and good staining of the endothelial cells and the inflammatory cells in the positive control (FIG. 6). There appeared to be staining of the RBCs inside the blood vessels; however, the localisation of staining was not determined These results suggested that the MIF is localised on the cell membrane but not within the cell. In contrast, RBCs ghosts and RBCs lysates did not exhibit MIF staining (data not shown). WBCs do contain intracellular MIF.

Example 3. Investigating the Presence of MIF in RBCs

Figure 7:
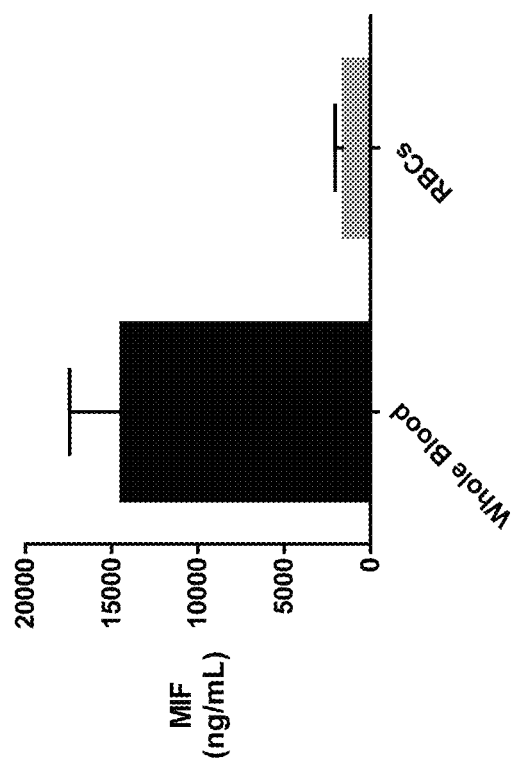
FIG. 7 is a graph showing macrophage migration inhibitory factor (MIF) concentration in RBCs isolated using FACS, with blood collected from fingertip prick (n=4).
Figure 8:
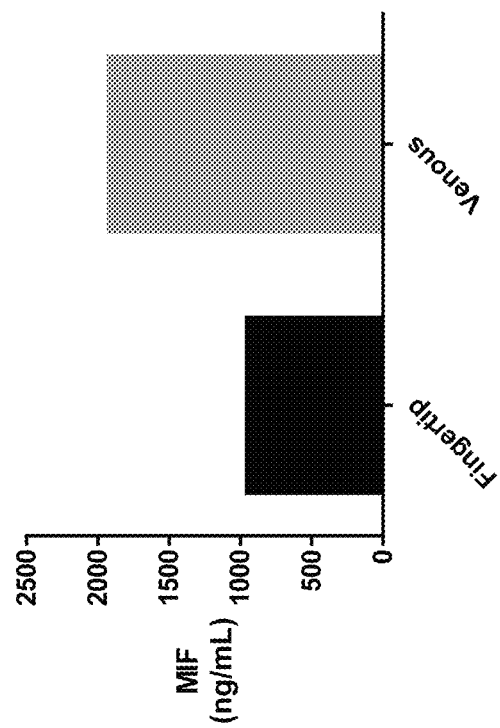
FIG. 8 is a graph showing MIF concentration in RBCs isolated using FACS, with blood collected from fingertip prick and venipuncture (n=1).

Because MIF levels were ~1000 times higher in RBCs than in plasma, RBCs were analyzed for their intracellular levels of MIF. Whole blood was collected from the capillary bed (fingertip collection). Blood was anti-coagulated (1:1) with EDTA (30 mg/mL) solution and washed twice with PBS+FBS (2%). Cells were stained with CD45-FITC (5 µL) for 15 min at room temperature in the dark. After incubation, cells were washed twice with 1×PBS and RBCs were then isolated using negative sorting by flow cytometry (FACS). RBCs and WB were pelleted by centrifugation (2000 g, 10 minutes) and were resuspended to 250,000 cells/50 µL. Cells were frozen at −80° C., and samples were subjected to 3 freeze/thaw cycles to lyse all the cells. Samples were then analysed on a Hu MIF ELISA. For fingertip and venous blood, whole blood was collected from either the capillary bed (fingertip collection) or from a vein. Blood was anti-coagulated (1:1) with EDTA (30 mg/mL) solution, washed twice with PBS+FBS (2%) and cells were stained with CD45-FITC (5 µL) for 15 min at room temperature in the dark. After incubation, cells were washed twice with 1×PBS and RBCs isolated using negative sorting on FACS. RBCs and WB were pelleted by centrifugation (2000 g, 10 minutes) and were resuspended to 250,000 cells/50 µL). Cells were frozen at −80° C., and samples were subjected to 3 freeze/thaw cycles to lyse all the cells. Samples were analysed on a Hu MIF ELISA As shown in FIG. 7, MIF was identified at high concentrations in FACS isolated RBCs. However, levels were approximately 10 times lower than that measured in whole blood. As shown in FIG. 8, there was a difference in MIF concentration in RBCs collected from the fingertip versus venous collection. Concentration of MIF in whole blood was too high to be analysed by ELISA (data not shown). The results demonstrated that MIF is present in RBCs, but that measurable MIF concentration differs depending on the collection site (fingertip or vein) and chosen anticoagulant (EDTA or heparin).

Example 4. Optimization of RBC Isolation 4.1 Dextran Sedimentation Versus Flow Cytometry Whole blood was collected by venous collection into EDTA and heparin VACUTAINERS. RBCs were isolated using either FACS, dextran sedimentation, or RBC lysis buffer. For FACS isolation, blood was washed twice with FACS wash buffer (PBS+2% FBS) by centrifugation (1000 g for 5 minutes). The resulting cell pellet was resuspended in 50 µL of FACs wash buffer, stained with CD45-FITC (5 µL, FITC-mouse anti-human CD45, H130, eBioscience 11-0459-42), and incubated for 15 min at room temperature in the dark. After incubation, the cells were washed twice with FACS wash buffer (1000 g for 5 minutes) and RBCs resuspended in the buffer were then isolated using negative sorting on FACS (FACSAria III flow cytometer, 4 lasers). RBCs and WBCs were gated from platelets according to size by forward scatter and side scatter. RBCs were then gated from WBCs by the WBCs lack of CD45 staining. For dextran sedimentation, anti-coagulated WB was added to high molecular weight dextran (6% w/v in 0.15 M sodium chloride, 1:1 blood:dextran), the solution was gently mixed and left to sit for up to 60 minutes at room temperature (~23° C.) for the RBCs to sediment and, after sedimentation, RBCs were isolated and washed twice in 1×PBS. RBCs and WB were pelleted by centrifugation (2000 g, 10 minutes) and were resuspended to 250,000 cells/50 µL). RBCs were then lysed: 250 million cells were added to 6 mL ice cold MILLI-Q water and were left to incubate for 30 seconds; after incubation, 2 mL of ice cold 0.6 M KCl was added to restore isotonicity; the solution was diluted up to 50 mL with ice cold PBS; and contaminating cells were pelleted and lysate was collected (equal to 250,000 cells/50 µL); finally samples were frozen at −80° C., and subjected to 3 freeze/thaw cycles to lyse all the cells.

Concentrations of MIF in the lysed cells were measured using a MIF ELISA (R&D Systems, USA) and the absorbance data for the MIF ELISA collected with a Synergy 2 plate reader (BioTeck, USA) at 450 nm (absorbence correction at 570 nm). The calibration curve was analysed using a log/log curve fit (GraphPad Prism software (ver. 6, USA).

To determine the purity of isolated RBCs, whole blood was collected into an EDTA VACUTAINER and RBCs isolated using dextran sedimentation as described above. RBCs were washed twice in PBS+FBS (2%), 500 g, 5 minutes and finally resuspended to 1 mL of solution. Five uL of solution was added to each respective tube and cells were stained with 5 µL or 20 µL of each antibody (anti-CD45, and an IgG control) and 50 of PBS+FBS (2%). Cell solutions were incubated in the dark at room temperature for 15 minutes and, after incubation, cells were washed three times in 1×PBS (500 g, 5 minutes). Cells were resuspended in 200 uL of PBS and analysed by flow cytometry using quadrant statistics and overlay histograms (Coulter AcT Diff, Beckman Coulter).

Figure 9:
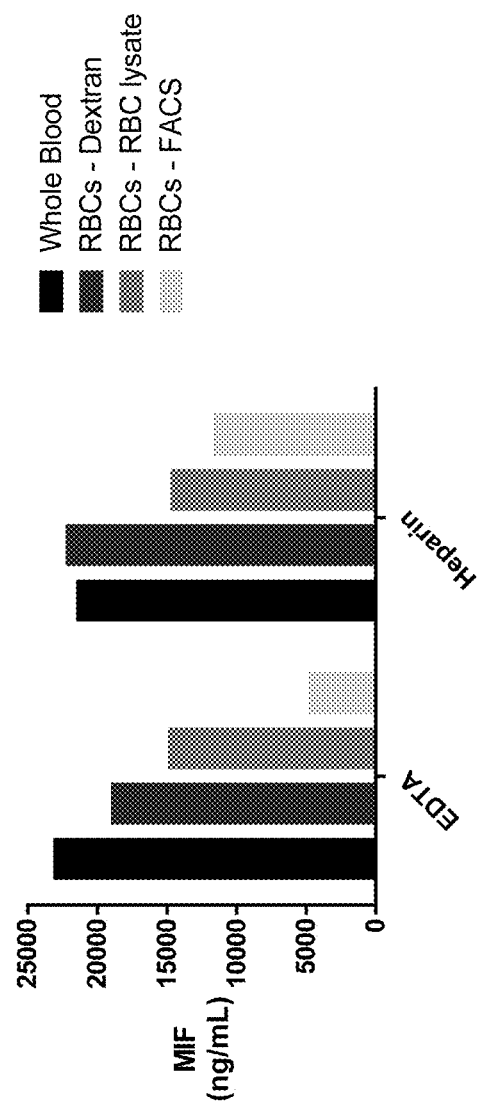
FIG. 9 is a graph showing RBCs isolated using FACS, dextran sedimentation and RBC lysis buffer, with blood collected from venipuncture (n=1).
Figure 10:
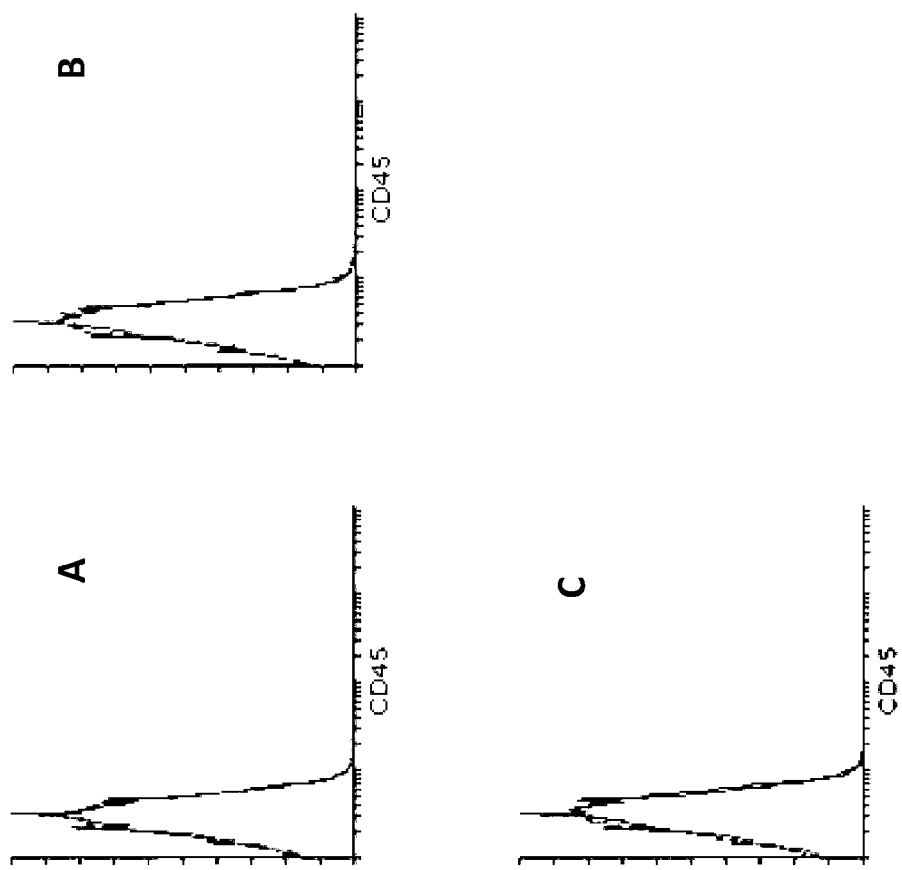
FIG. 10A-10C shows the results of tests for WBC contamination in isolated RBCs using immunophenotyping for CD45 against IgG. Cells (filled grey histogram) were largely negative for CD45 (n=3).
Figure 11:
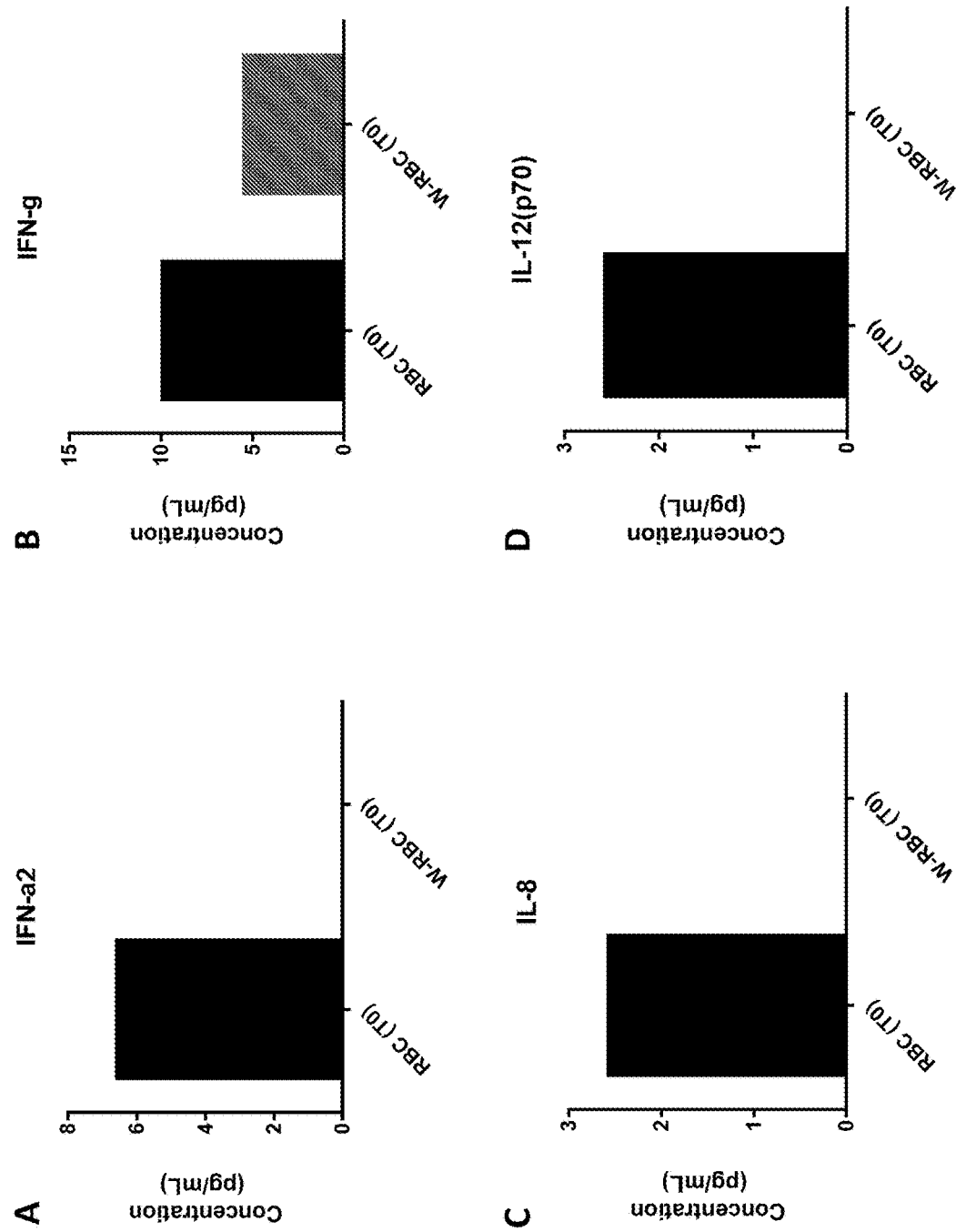
FIG. 11A-11GG is a series of graphs showing the levels of various proteins in RBCs that have been processed by washing compared to RBCs that have not been processed by washing.
Figure 11:
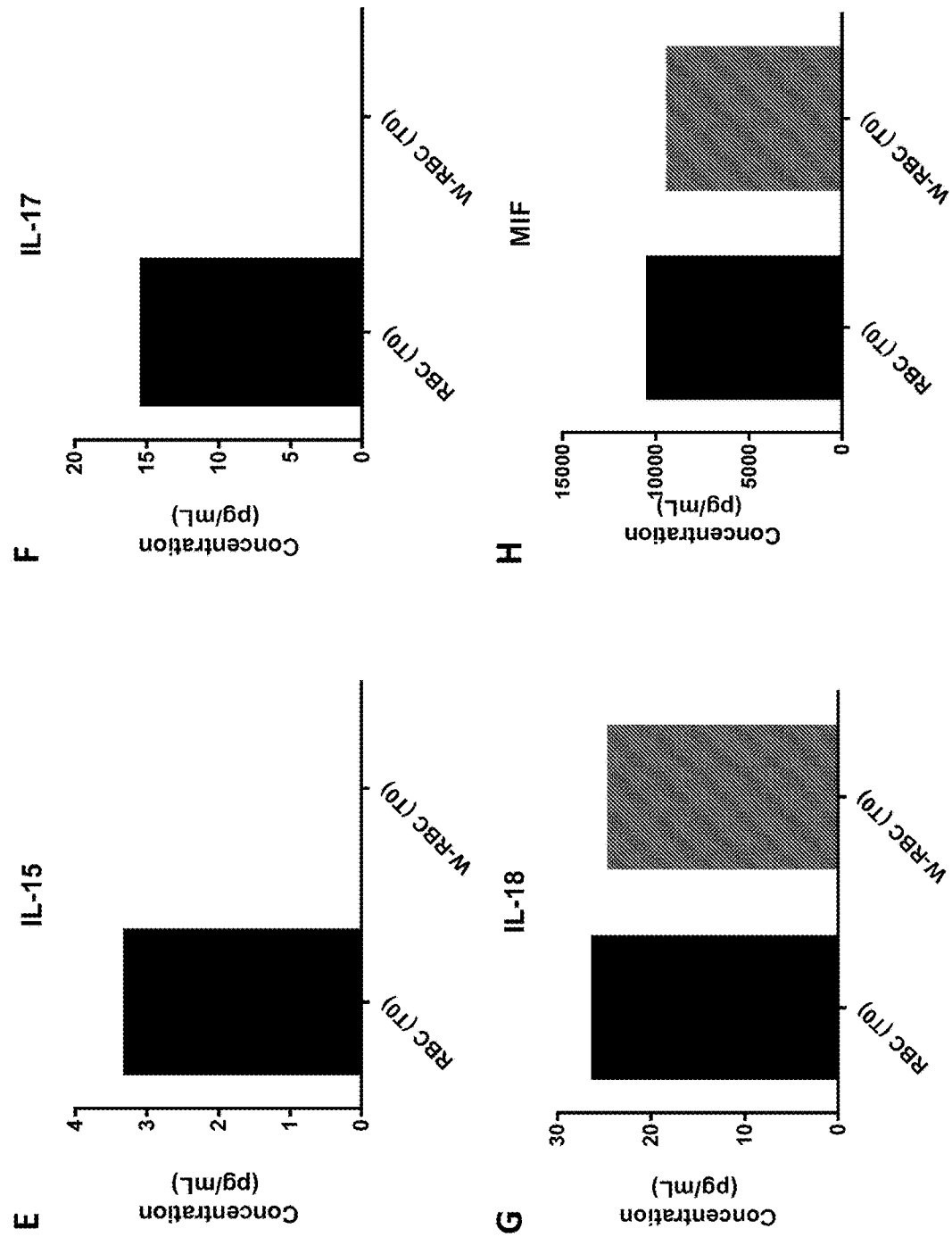
Figure 11:
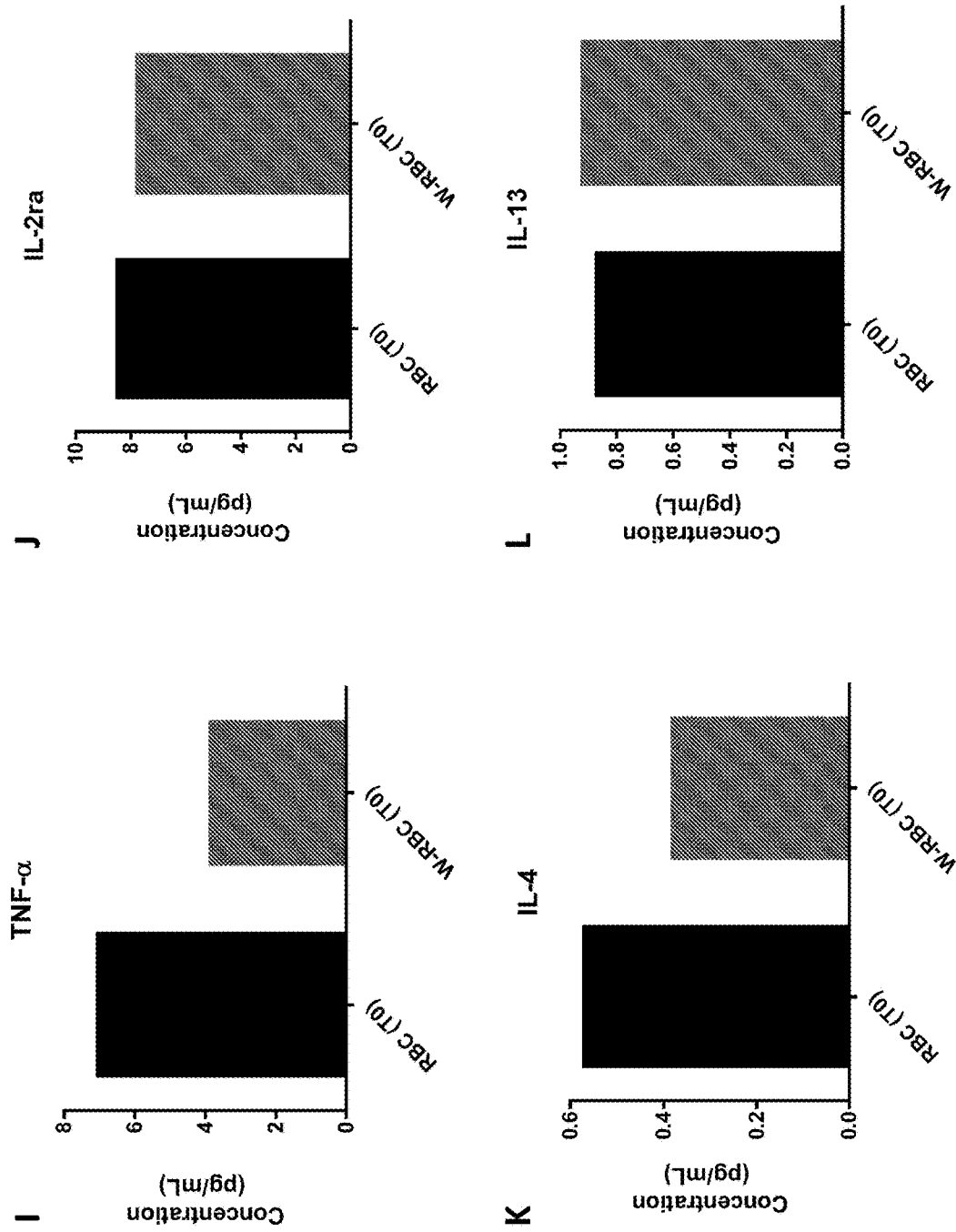
Figure 11:
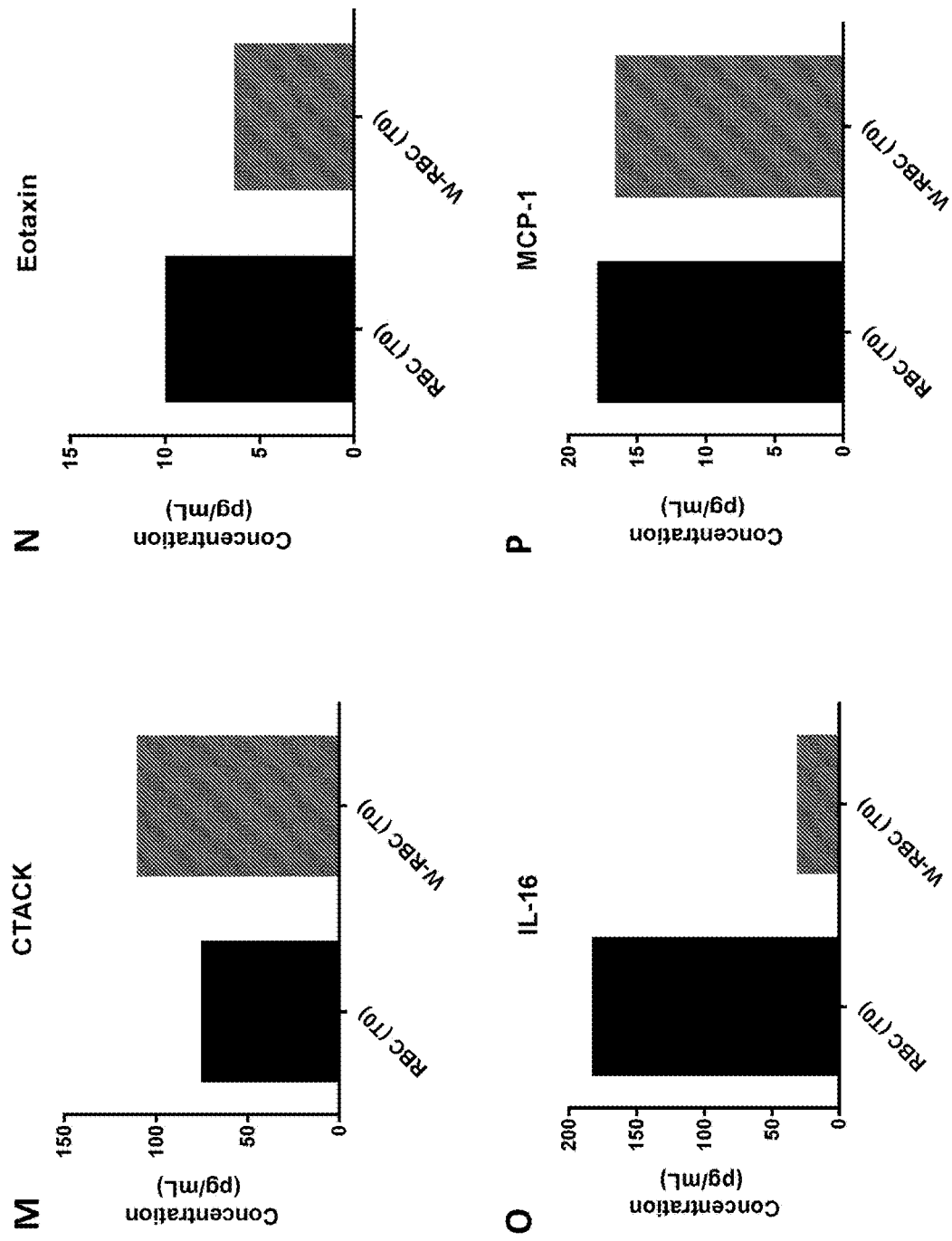
Figure 11:
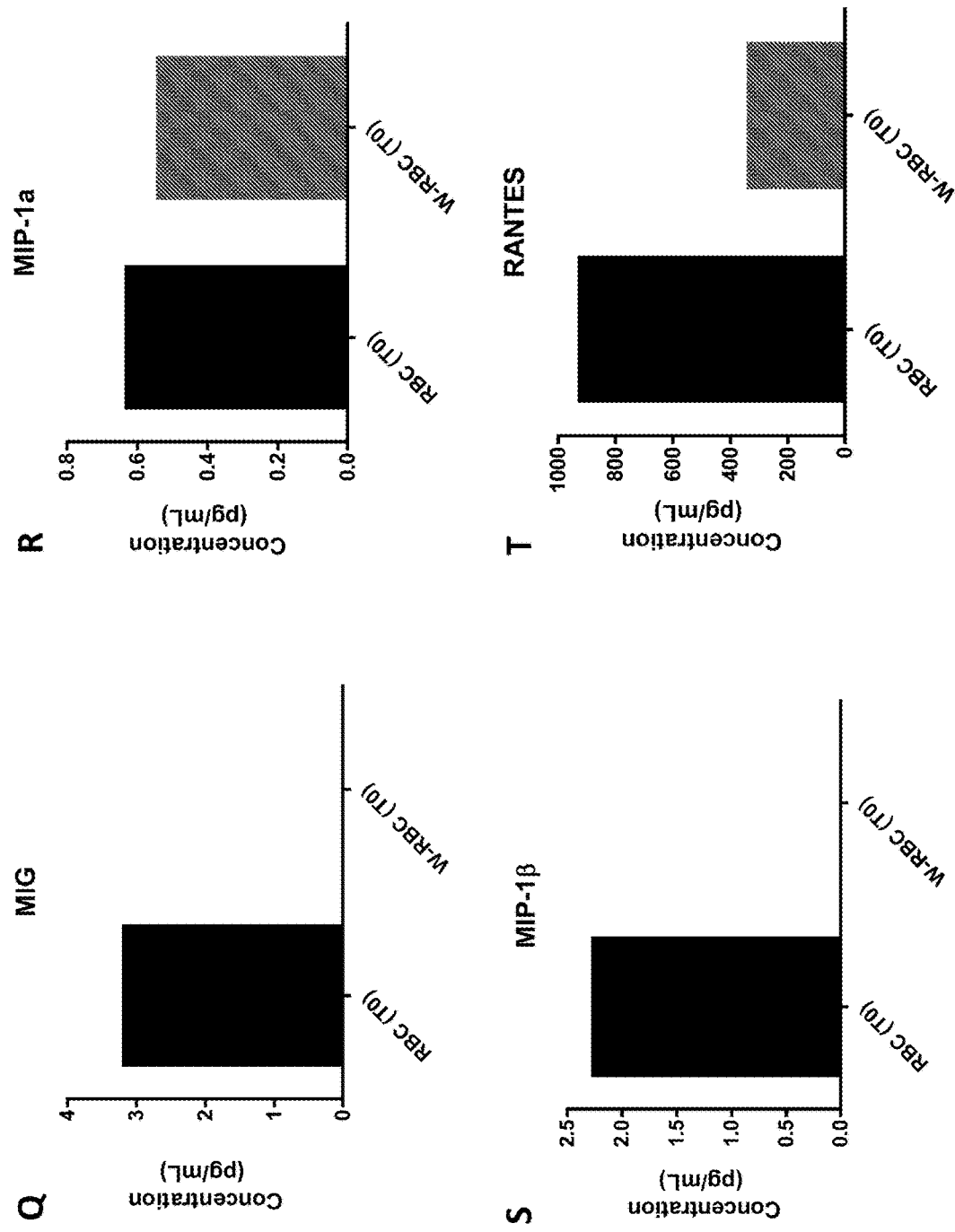
Figure 11:
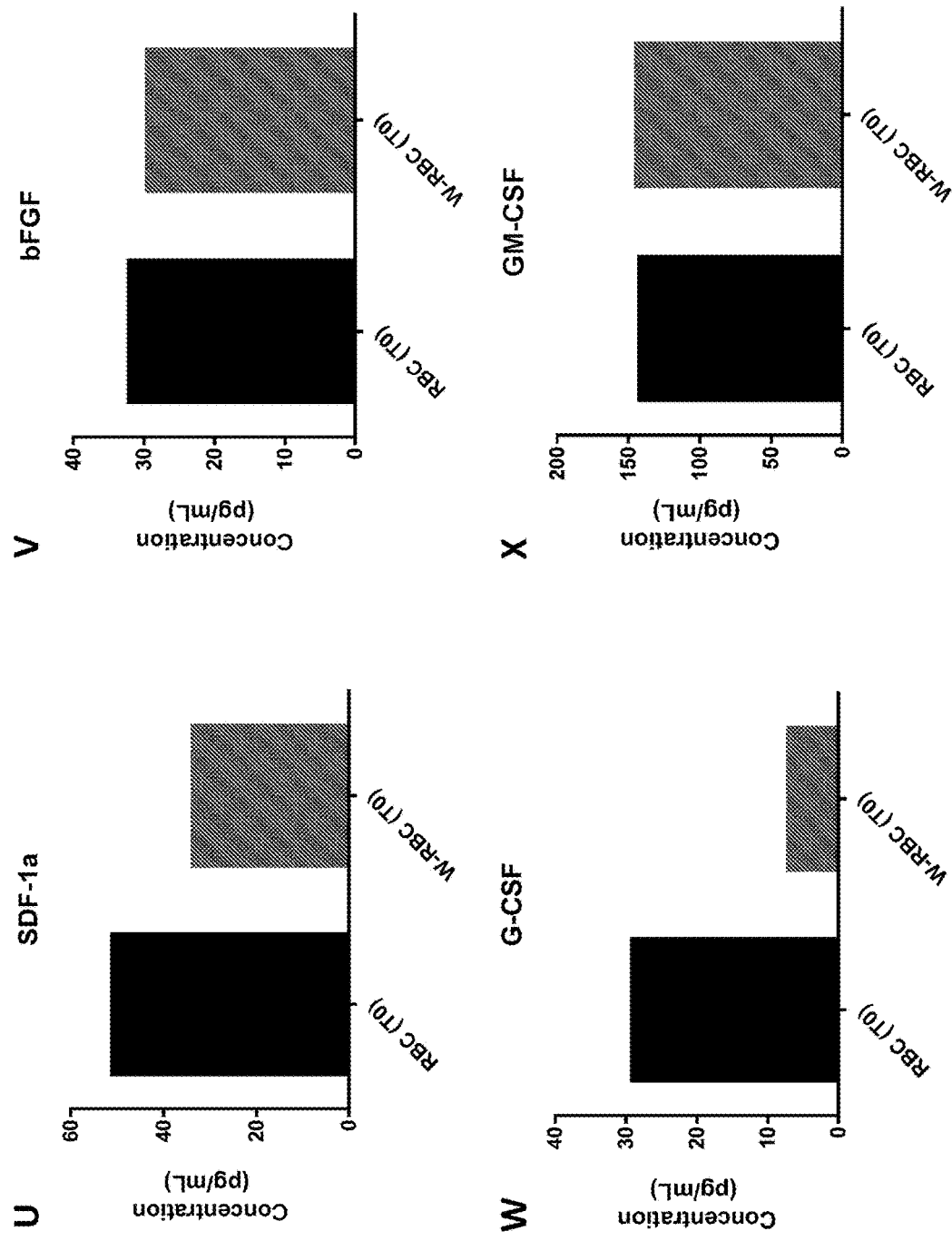
Figure 11:
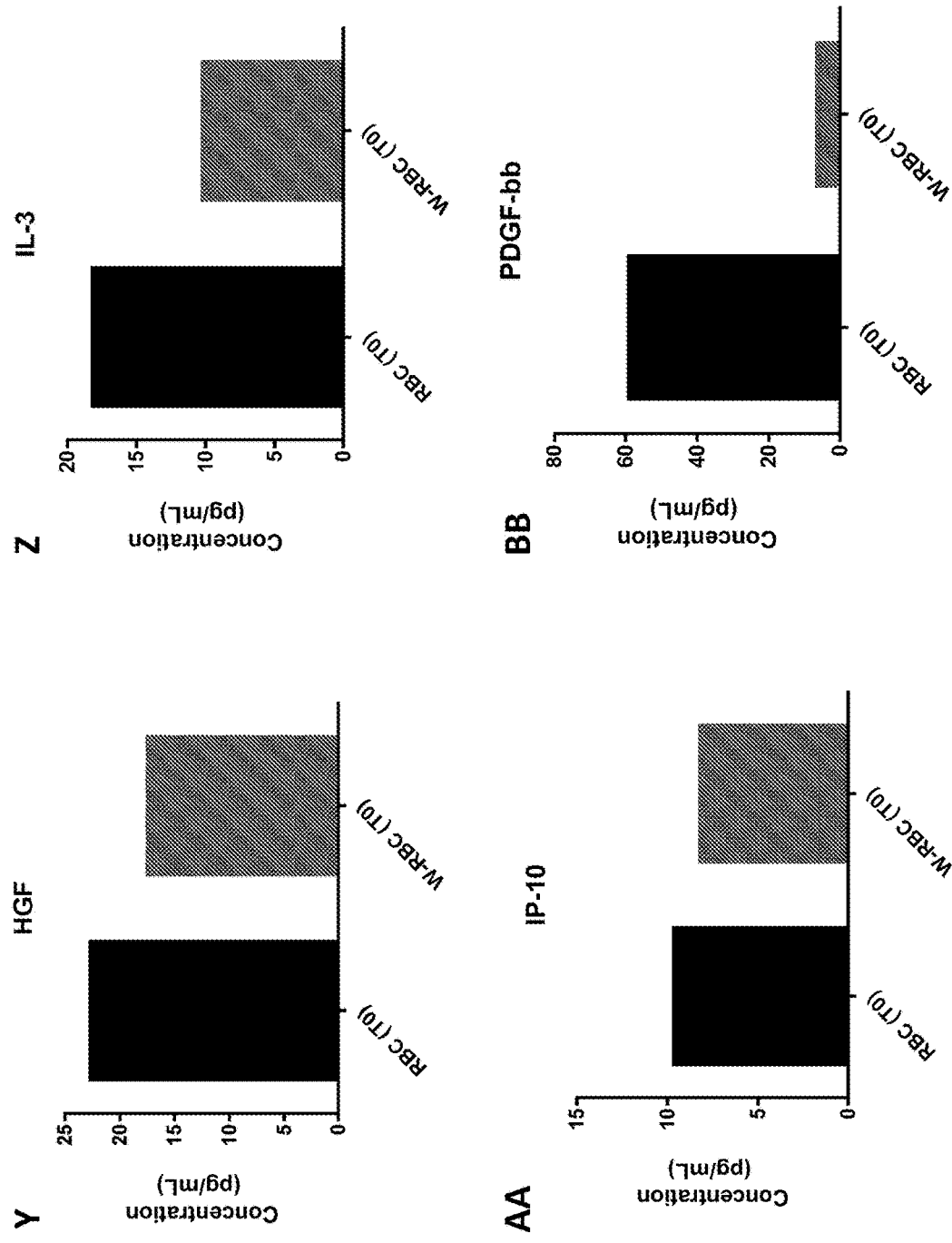
Figure 11:
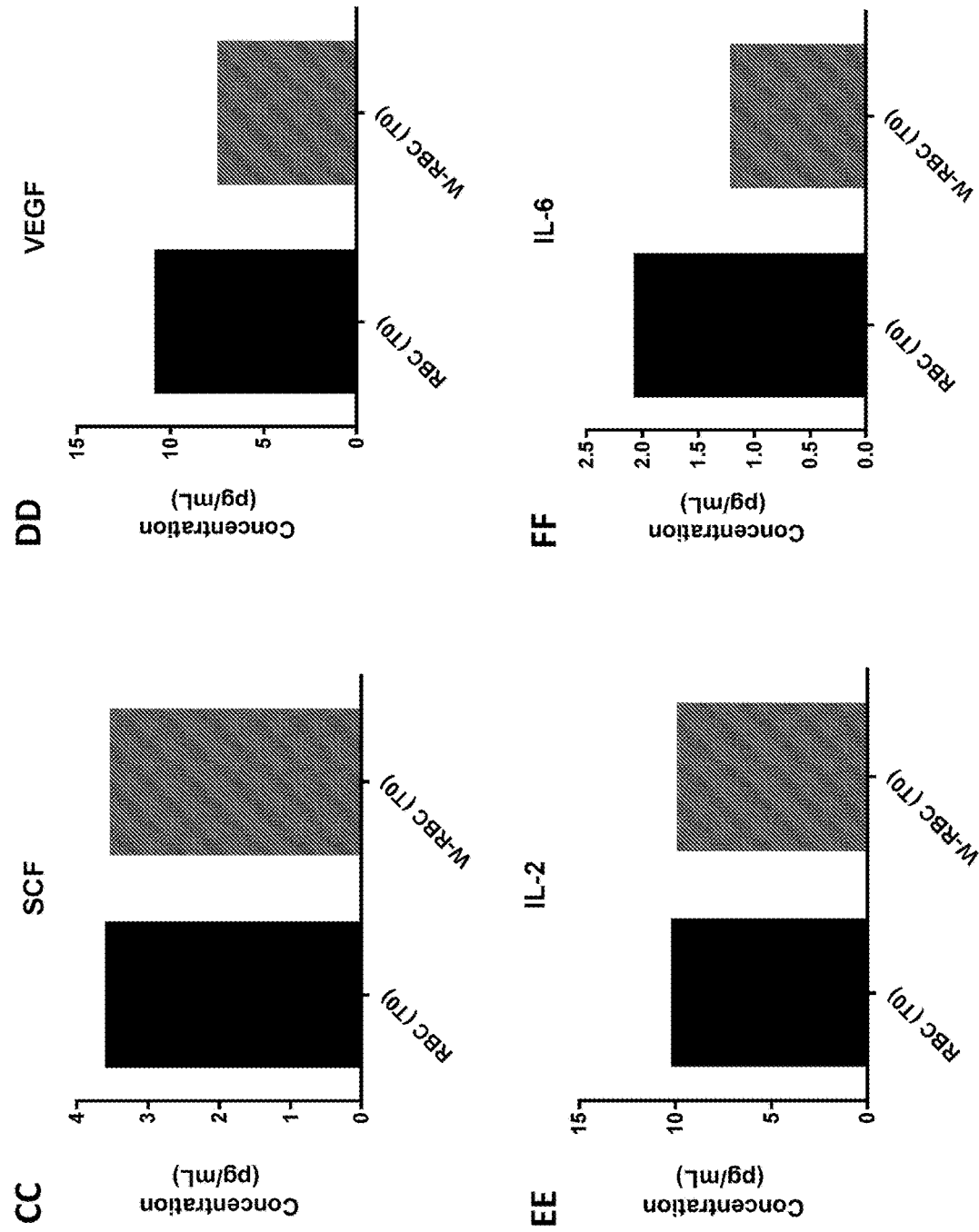
Figure 11:
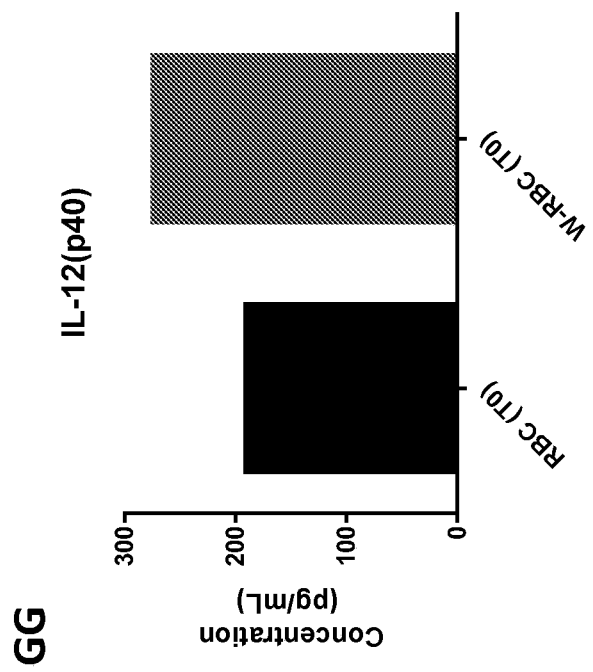
Figure 12:
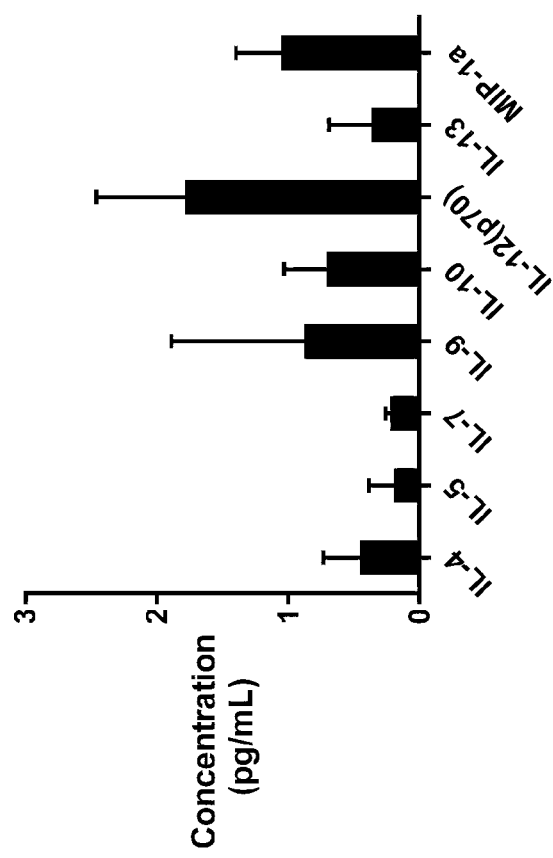
FIG. 12 is a graph summarizing the proteins secreted or released from RBCs into PBS over 24 hours at 37° C. as measured by BIOPLEX and reported as pg/mL (20 million RBCs in 100 uL PBS). Data presented as mean±SD.
Figure 13:
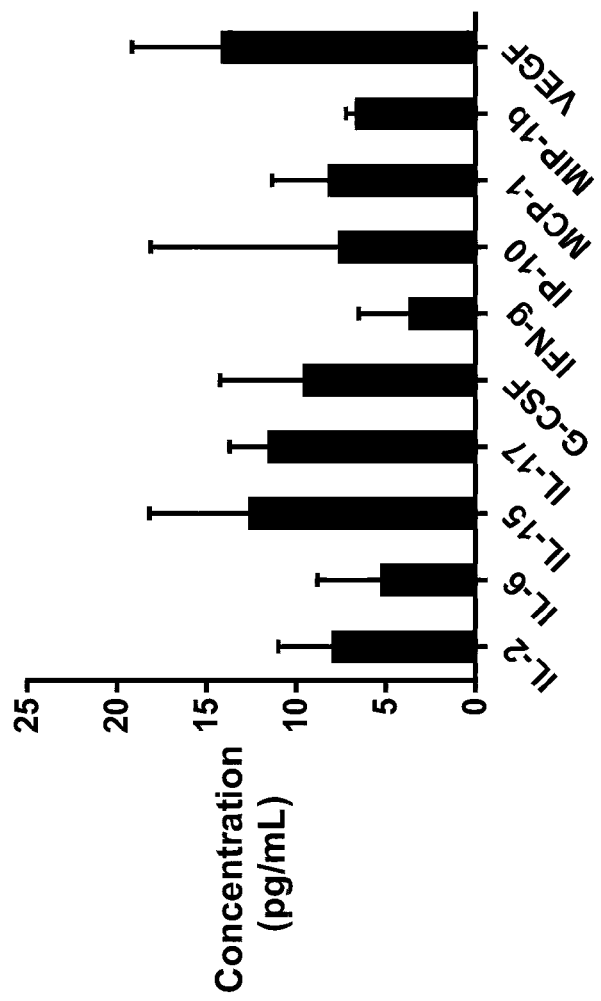
FIG. 13 is a graph summarizing the proteins secreted or released from RBCs into PBS over 24 hours at 37° C. as measured by BIOPLEX and reported as pg/mL (20 million RBCs in 100 uL PBS). Data presented as mean±SD.
Figure 14:
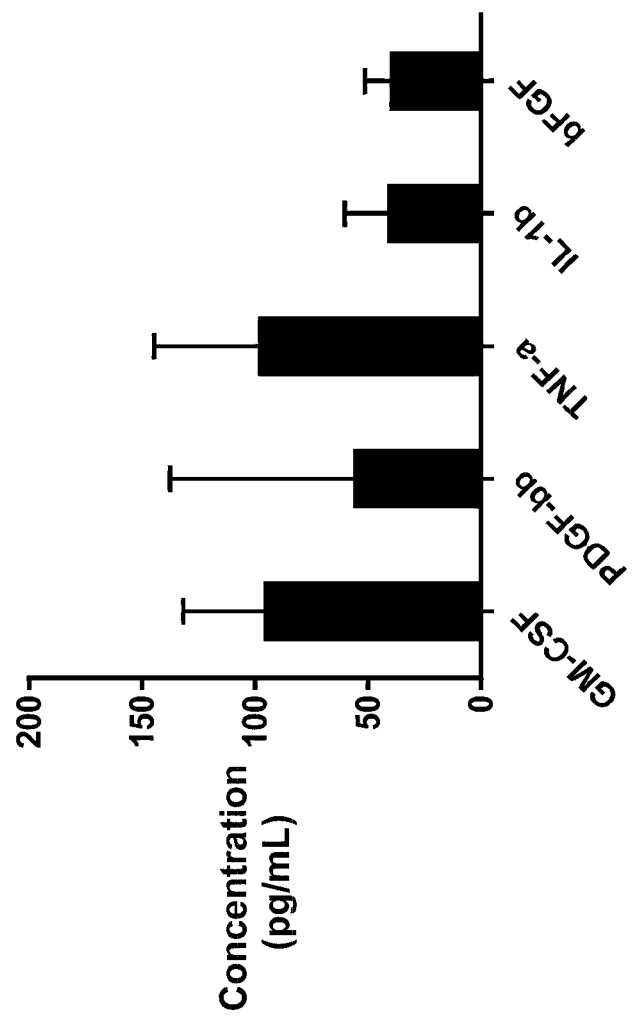
FIG. 14 is a graph summarizing the proteins secreted or released from RBCs into PBS over 24 hours at 37° C. as measured by BIOPLEX and reported as pg/mL (20 million RBCs in 100 uL PBS). Data presented as mean±SD.
Figure 15:
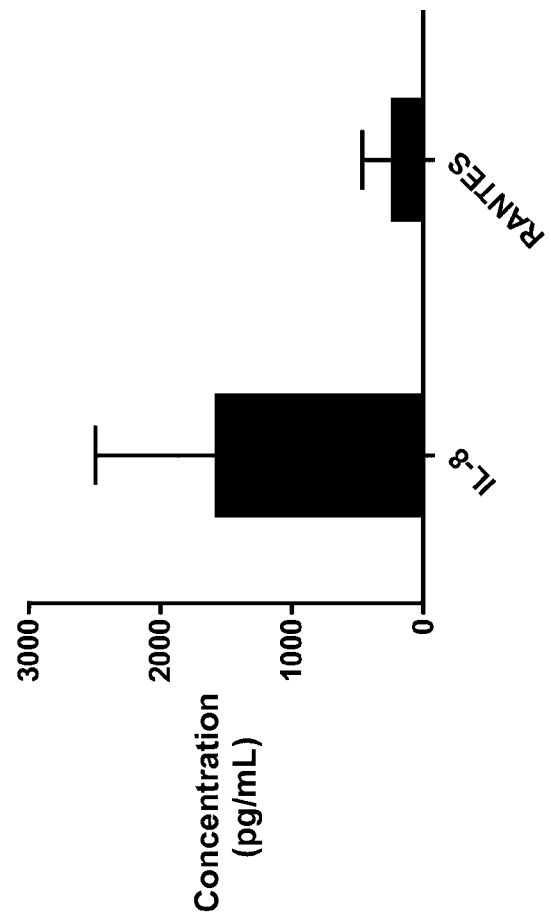
FIG. 15 is a graph summarizing the proteins secreted or released from RBCs into PBS over 24 hours at 37° C. as measured by BIOPLEX and reported as pg/mL (20 million RBCs in 100 uL PBS). Data presented as mean±SD.

As shown in FIG. 9, dextran sedimentation of RBCs resulted in a higher measured concentration of MIF than using RBC lysis buffer or FACS isolation (concentration normalized to relative contribution to 1 mL of whole blood). The presence of dextran itself did not alter the level of MIF measured (data not shown). In addition, RBCs isolated using dextran sedimentation were stained for the presence of contaminating CD45+ cells (WBCs). The RBCs were approximately 0.0025% pure (FIG. 10A-10C).

The results demonstrated that the amount of MIF measured in a RBC population is dependent on the method of RBC isolation. Dextran sedimentation was the optimal RBC isolation technique, yielding the highest number of RBCs with a high level of purity. The results indicated dextran sedimentation was as effective, or even more effective than other commonly used RBC isolation techniques. In addition, dextran sedimentation resulted in detection of much higher levels of MIF, indicating the method could be much more accurate than other methods for the measurement of protein levels.

4.2 RBC Processing: Dextran Sedimentation Versus Other Methods

Whole blood was collected from healthy volunteers by venipuncture (n=1) directly into EDTA VACUTAINERS ($k_2$EDTA VACUTAINERS, BD Biosciences). All fractions of blood were collected and processed at room temperature within 4 hours of collection. For multiplex analysis (BIOPLEX analysis) all samples were stored at −80° C. and were subjected to 3 freeze-thaw cycles at −80° C. to ensure complete cellular lysis prior to analysis.

Red blood cells were isolated using dextran sedimentation as follows. Whole blood was centrifuged (1500 g, 10 minutes) and the upper plasma layer was discarded. The remaining cell pellet was resuspended in an equal volume of sodium chloride (0.15 M). Dextran (6% w/v in 0.15 M sodium chloride) was then added to the cellular suspension at a 1:4 ratio (dextran:cell suspension). This solution was left at room temperature for 30 minutes for red blood cell sedimentation to the bottom of the tube. After this time the upper white blood cell rich layer was discarded and the lower red blood cell fraction was collected. The lower red blood cell fraction was either washed once in phosphate buffered saline (PBS, 500 g, 5 minutes) or washed thoroughly with inversion three times in PBS. The resulting red blood cells were either used fresh or were frozen (−80° C.).

An aliquot of red blood cells were diluted to 400 million cells/mL in PBS and were incubated at 37° C. and 5% $CO_2$ for 24 hrs. Following incubation, the red blood cells and the resulting conditioned PBS was separated and frozen (−80° C.).

The red blood cells were subjected to 3 freeze-thaw cycles to ensure complete cellular lysis. Following lysis, the red blood cell lysates were diluted in PBS to the equivalent of 400 million cells/mL. These lysates were then analysed on the multiplex cytokine assays. Two multiplex assays were utilised. The first was the 27-plex human cytokine panel that assays for FGF basic, Eotaxin, G-CSF, GM-CSF, IFN-γ, IL-1β, IL-1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1β, PDGF-BB, RANTES, TNF-α, and VEGF, and the second was the 21-plex human cytokine panel that assays for IL-1α, IL-2Ra, IL-3, IL-12, IL-16, IL-18, CTACK, GRO-α, HGF, IFN-α2, LIF, MCP-3, M-CSF, MIF, MIG, β-NGF, SCF, SCGF-β, SDF-1α, TNF-β, TRAIL (BIOPLEX Pro 27-plex and 21-plex, Bio-Rad). The assays were performed according to manufacturer's instructions using an automated magnetic wash station (BIOPLEX Pro II, Bio-Rad) for the washing steps. The assays were run on the LUMINEX® 200™ system (Bio-Rad) and fluorescent values were collected. The calibration curve for each cytokine was analysed with 5 parametric logistic curve regression using BIOPLEX manager software (ver. 5.0, Bio-Rad, USA).

The data once again showed that isolation of red blood cells by dextran sedimentation resulted in average white blood cell and platelet depletion of greater than 95% (Table 3).

TABLE 3

The percentage depletion of white blood cells and platelets from enriched red blood cell fractions produced using dextran sedimentation.

| White blood cell depletion (%) | Platelet depletion (%) | Red blood cell purity (%) |
|---|---|---|
| 95.5 ± 5.0 | 96.1 ± 5.5 | 99.992 ± 0.004 |

To evaluate the effect of washing steps typically used in RBC isolation methods. The addition of a thorough washing step following dextran sedimentation isolation of red blood cells resulted in an altered cytokine profile when compared to cells that did not undergo this washing step. There was an overall reduction in measurable cytokines in washed cells (FIG. 11A-11GG).

The concentration of most proteins in the washed red blood cells was notably lower than what was observed in unwashed red blood cells, as seen for, instance, in IFN-γ (2-fold less), G-CSF (4-fold less), and PDGF-bb (6-fold less). Further to that point, the levels of a collection of proteins were below the level of detection unlike the unwashed control. Where IFN-α2 and IL-17 were detectable in the unwashed red blood cells, they were entirely absent in the washed cells. These results demonstrate that excessive washing of red blood cells can alter their cytokine profile. This washing is a critical step in most red blood cell isolation techniques.

Because RBCs lysis is incomplete, the data suggest that dextran sedimentation gave the most accurate answer with respect to MIF levels. The primary difference between the RBC isolation techniques is how extensively each was processed. The dextran sedimentation method is relatively gentle and involves minimal washing steps, while the FACs method necessitates that the cells undergo numerous washing steps and high speed flow through a cytometer for cell sorting.

Example 5. Distribution of MIF Across Blood Components

To determine whether RBCs were the primary reservoir for MIF, RBCs were analyzed for the presence of MIF. Whole blood was collected by venous collection into EDTA VACUTAINER. Plasma was collected after centrifugation and cells were isolated using either FACS or dextran sedimentation. For FACS isolation, blood was washed twice with PBS+FBS (2%), cells were stained with CD45-FITC (5 µL) for 15 min at room temperature in the dark, and then washed twice with 1×PBS. RBCs were then isolated using negative sorting on FACS; WBCs were isolated using positive staining for CD45; and platelets were isolated according to size. Dextran sedimentation was performed as described above, after which WBCs and platelets were isolated from the supernatant with centrifugation. Cells and WB were pelleted by centrifugation (2000 g, 10 minutes) and were resuspended to set concentrations. Samples were frozen at −80° C., and samples were subjected to 3× freeze/thaw cycles to lyse all the cells. Samples were then analysed on a Hu MIF ELISA.

MIF distribution when cells were isolated by FACS or dextran sedimentation is shown in Tables 4 and 5. Whilst MIF was present in all components of blood, RBCs contributed the largest proportion of the total MIF. WBCs contained the highest concentration of MIF per cell; however, there were 1000 times more RBCs in blood.

TABLE 4

The distribution of MIF between blood components as compared to whole blood after isolation using dextran sedimentation (n = 1)

| Blood Fraction | Percentage of MIF contribution (%) | Total MIF contribution to 1 mL whole blood (ng/mL) | Measured MIF/cell (fg/cell) | Previously reported MIF/cell (fg/cell) |
|---|---|---|---|---|
| Whole blood | 100 | 21,179 | n/a | n/a |
| RBCs | 82.6 | 17,500 | 2.97 | n/a |
| WBCs | 2.0 | 416 | 70.6 | 3.9-100 |
| Platelets | 1.2 | 258 | 1.49 | 0.3 |
| Plasma | 0.05 | 11.53 | n/a | n/a |

TABLE 5

The distribution of MIF between blood components as compared to whole blood after isolation using FACS (n = 1)

| Blood Fraction | Percentage of MIF contribution (%) | Total MIF contribution to 1 mL whole blood (ng/mL) | Measured MIF/cell (fg/cell) | Previously reported MIF/cell (fg/cell) |
|---|---|---|---|---|
| Whole blood | 100 | 21,179 | n/a | n/a |
| RBCs | 11.4 | 2,420 | 0.41 | n/a |
| WBCs | 0.7 | 157 | 2.67 | 3.9-100 |
| Platelets | 0.3 | 72 | 0.42 | 0.3 |
| Plasma | 0.05 | 11.53 | n/a | n/a |

TABLE 6

The distribution of MIF between blood components as compared to whole blood after isolation using dextran sedimentation, data presented as mean ± standard deviation (n = 3)

| Blood Fraction | Percentage of MIF contribution (%) | Total MIF contribution to 1 mL whole blood (ng/mL) | Measured MIF/cell (fg/cell) | Previously reported MIF/cell (fg/cell) |
|---|---|---|---|---|
| Whole blood | 100 | 17,297 ± 3,682 | n/a | n/a |
| RBCs | 43.9 | 7,591 ± 1,223 | 1.4 ± 0.2 | n/a |
| WBCs | 0.13 | 23.1 ± 13.6 | 4.0 ± 3.3 | 3.9-100 |
| Platelets | 0.04 | 7.1 ± 0.5 | 0.02 ± 0.02 | 0.3 |
| Plasma | 0.10 | 16.8 ± 1.3 | n/a | n/a |

Example 6. Identification of Proteins Present in RBCs

To investigate whether RBCs are a reservoir for proteins other than MIF, the levels of other proteins in RBCs were assessed. Whole blood was collected by venous collection into EDTA VACUTAINERS. Plasma was collected after centrifugation and cells were isolated using either FACS or dextran sedimentation as described above. Isolated cells and WB were pelleted by centrifugation (2000 g, 10 minutes) and were resuspended to set concentrations. Samples were frozen at −80° C., and subjected to 3 times freeze/thaw cycles to lyse all the cells. Samples were analysed on a Hu 27-plex BIOPLEX. In addition, proteins released or secreted by RBCs were analyzed. Whole blood was collected by venous collection into EDTA VACUTAINERS and RBCs isolated by dextran sedimentation as described previously. Isolated RBCs were aliquoted to 20 million cells in 100 uL of PBS or PBS+protease inhibitors (lx) and cells were incubated at 37° C. with 5% CO2 for 24 hours. After incubation, supernatant and cells were separated by centrifugation, samples were frozen at −80° C., and subjected to 3 times freeze/thaw cycles to lyse all the cells. The samples were analysed on Hu 27-plex BIOPLEX.

A number of proteins were identified as being present in RBCs as well as other blood components after samples were run on the BIOPLEX. The analysis reports the respective concentrations of the 16 proteins (out of a total 27) that were present in both whole blood and RBCs in substantial quantities (Tables 7-11). Total yield is reported as the total yield of protein from each blood component as compared back to the measured protein in whole blood (Tables 7-11).

TABLE 7

Summary of pro-inflammatory cytokines in whole blood and blood components as measured by BioPlex and reported as pg/mL of whole blood, total yield is reported according to protein concentration in whole blood (n = 1). Underlined values have been extrapolated off the bottom of the standard curve.

| Blood components | IFN-g | IL-1b | IL-5 | IL-8 | IL-9 | IL-12 (p70) | IL-15 | IL-17 | TNF-a |
|---|---|---|---|---|---|---|---|---|---|
| Whole blood | 2,401 | 71 | 38 | 242 | 728 | 484 | 2,546 | 5,044 | 1687 |
| RBCs | 805 | 50 | 18 | 242 | 321 | 165 | 2,366 | 4,883 | 401 |
| WBCs | 324 | 20 | 4 | 159 | 48 | 59 | 83 | 323 | 323 |
| Platelets | 380 | 28 | 7 | 114 | 238 | 195 | 890 | 2,188 | 419 |
| Plasma | 36 | 0.71 | 1 | 6 | 5 | 7 | 5 | 12 | 21 |
| Total yield (%) | 64.3 | 139 | 79 | 215 | 84.1 | 88 | 131.3 | 146.8 | 69 |

TABLE 8

Summary of anti-inflammatoty cytokines in whole blood and blood components as measured by BioPlex and reported as pg/mL of whole blood, total yield is reported according to protein concentration in whole blood (n = 1). Underlined values have been extrapolated off the bottom of the standard curve.

| Blood components | IL-1ra | IL-4 | IL-10 | IL-13 |
|---|---|---|---|---|
| Whole blood | — | 106 | 991 | 124 |
| RBCs | — | — | 760 | 53 |
| WBCs | 684 | 17 | 46 | 54 |
| Platelets | — | 39 | 391 | 39 |
| Plasma | 76 | 0.98 | 3.55 | 31 |
| Total yield (%) | — | 54 | 121 | 143 |

TABLE 9

Summary of growth factors in whole blood and blood components as measured by BioPlex and reported as pg/mL of whole blood, total yield is reported according to protein concentration in whole blood (n = 1). Underlined values have been extrapolated off the bottom of the standard curve.

| Blood components | bFGF | G-CSF | GM-CSF | PDGF | VEGF | IL-7 |
|---|---|---|---|---|---|---|
| Whole blood | 5,381 | 6,340 | 109,454 | 28,586 | 2,950 | — |
| RBCs | 2,717 | 2,844 | 107,721 | 2,287 | 2,254 | — |
| WBCs | 368 | 773 | 3,355 | 18,349 | 92 | 4.3 |
| Platelets | 2,027 | 921 | 41,436 | 1007 | 800 | — |
| Plasma | 2.3 | 36 | — | 50 | 11 | 3 |
| Total yield (%) | 95.4 | 72.1 | 139.3 | 75.9 | 107.0 | — |

TABLE 10

Summary of chemokines in whole blood and blood components as measured by BioPlex and reported as pg/mL of whole blood, total yield is reported according to protein concentration in whole blood (n = 1). Underlined values have been extrapolated off the bottom of the standard curve.

| Blood components | Eotaxin | IP-10 | MCP-1 | MCP-1a | MIP-1b | RANTES |
|---|---|---|---|---|---|---|
| Whole blood | 1617 | 3,233 | 2,738 | 133 | 732 | 432,325 |
| RBCs | 486 | 1,494 | 1,636 | 77 | 610 | 37,197 |
| WBCs | 91 | 273 | 84 | 38 | 347 | 26,163 |
| Platelets | 167 | 618 | 748 | 28 | 89 | 50,907 |
| Plasma | 14 | 81 | 7 | 1 | 7 | 741 |
| Total yield (%) | 47 | 76.3 | 90.4 | 108.3 | 144 | 26.6 |

TABLE 11

Summary of cytokines with multiple functions in whole blood and blood components as measured by BioPlex and reported as pg/mL of whole blood, total yield is reported according to protein concentration in whole blood (n = 1). Underlined values have been extrapolated off the bottom of the standard curve.

| Blood components | IL-2 | IL-6 |
|---|---|---|
| Whole blood | 1,345 | 540 |
| RBCs | 834 | 218 |
| WBCs | 72 | 59 |
| Platelets | 441 | 154 |
| Plasma | 5 | 7 |
| Total yield (%) | 100.5 | 81.1 |

A number of proteins were released or secreted after RBCs were cultured in PBS for 24 hours at 37° C. See Tables 7-11 for protein classification as anti-inflammatory, pro-inflammatory, chemokine, or growth factors. FIGS. 12-15 show a summary of analytes released or secreted from RBCs into PBS over 24 hours at 37° C. as measured by BIOPLEX and reported as pg/mL (20 million RBCs in 100 uL PBS). Figures are separated according to average detected concentration of each protein. The addition of protease inhibitors during RBCs culture altered protein release or secretion (24 hours at 37° C.).

Culture conditions were as follows:
1. RBCs+PBS (20 million RBCs in 100 uL PBS)
2. RBCs+PBS+protease inhibitors (PI) (20 million RBCs in 100 uL PBS+PI)

Figure 16:
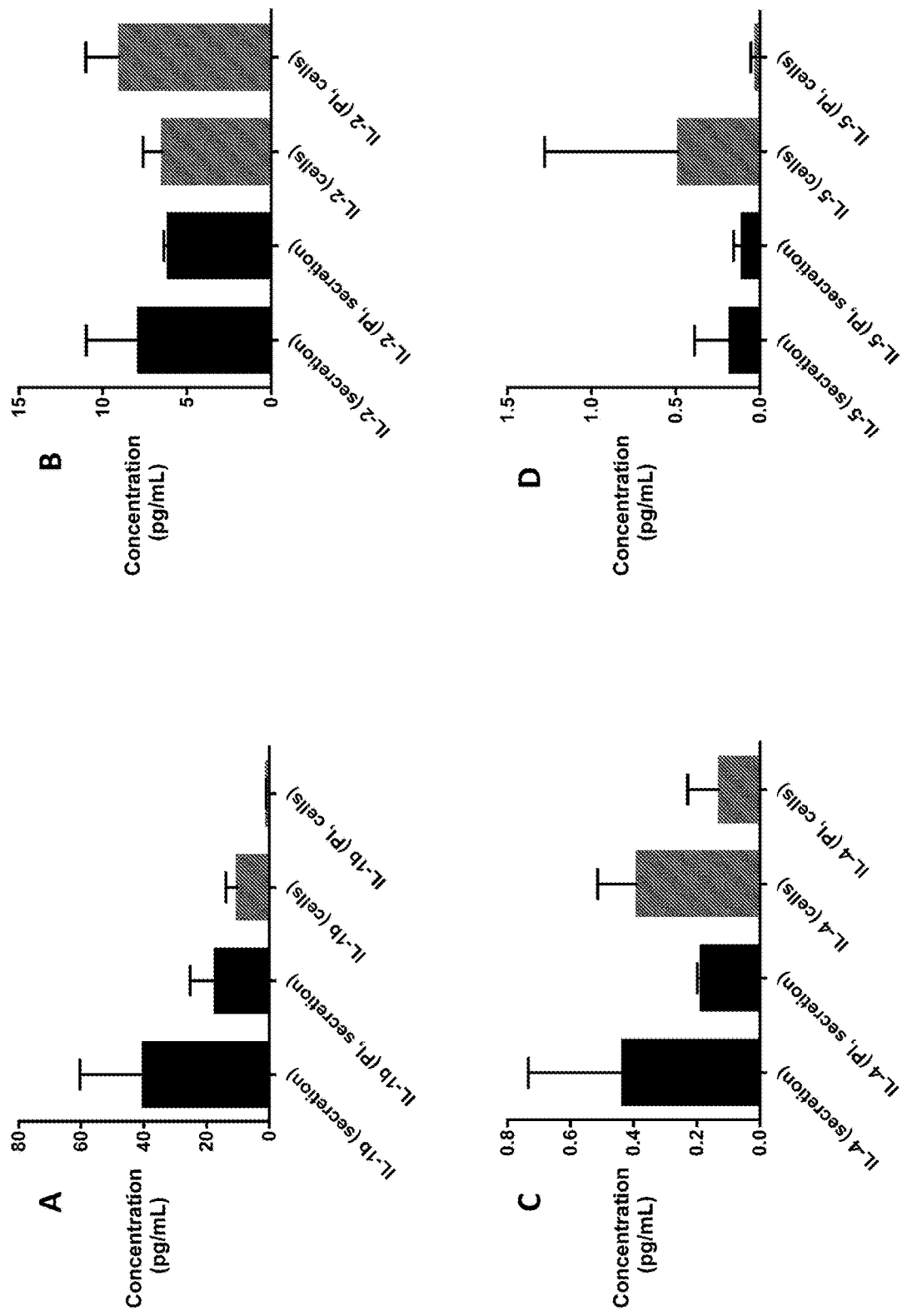
FIG. 16A-16Z is a series of graphs showing the effect of protease inhibitors (PI) on the concentration of proteins secreted from RBCs (black columns) and the concentration of proteins remaining in the cells after incubation (grey columns).
Figure 16:
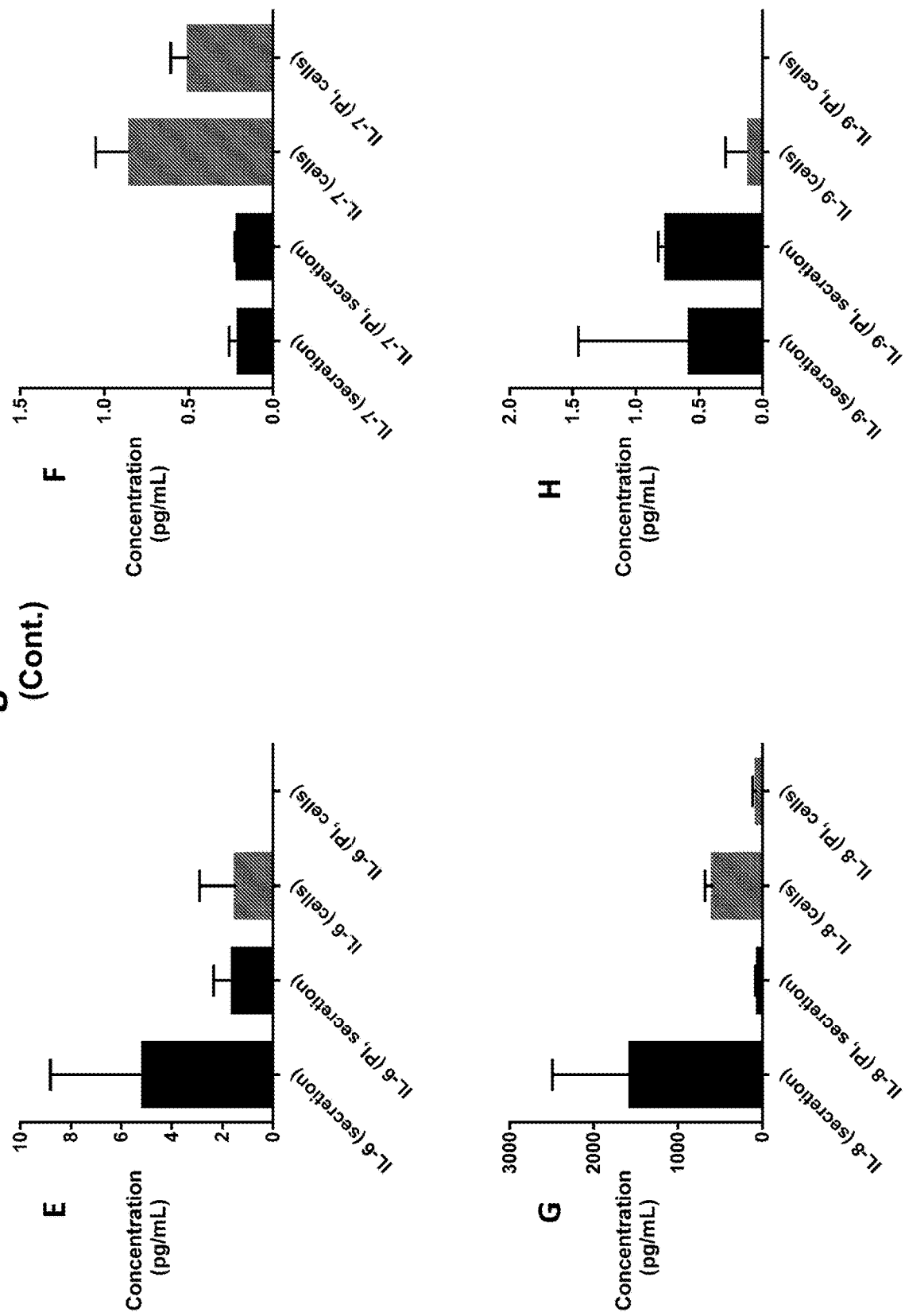
Figure 16:
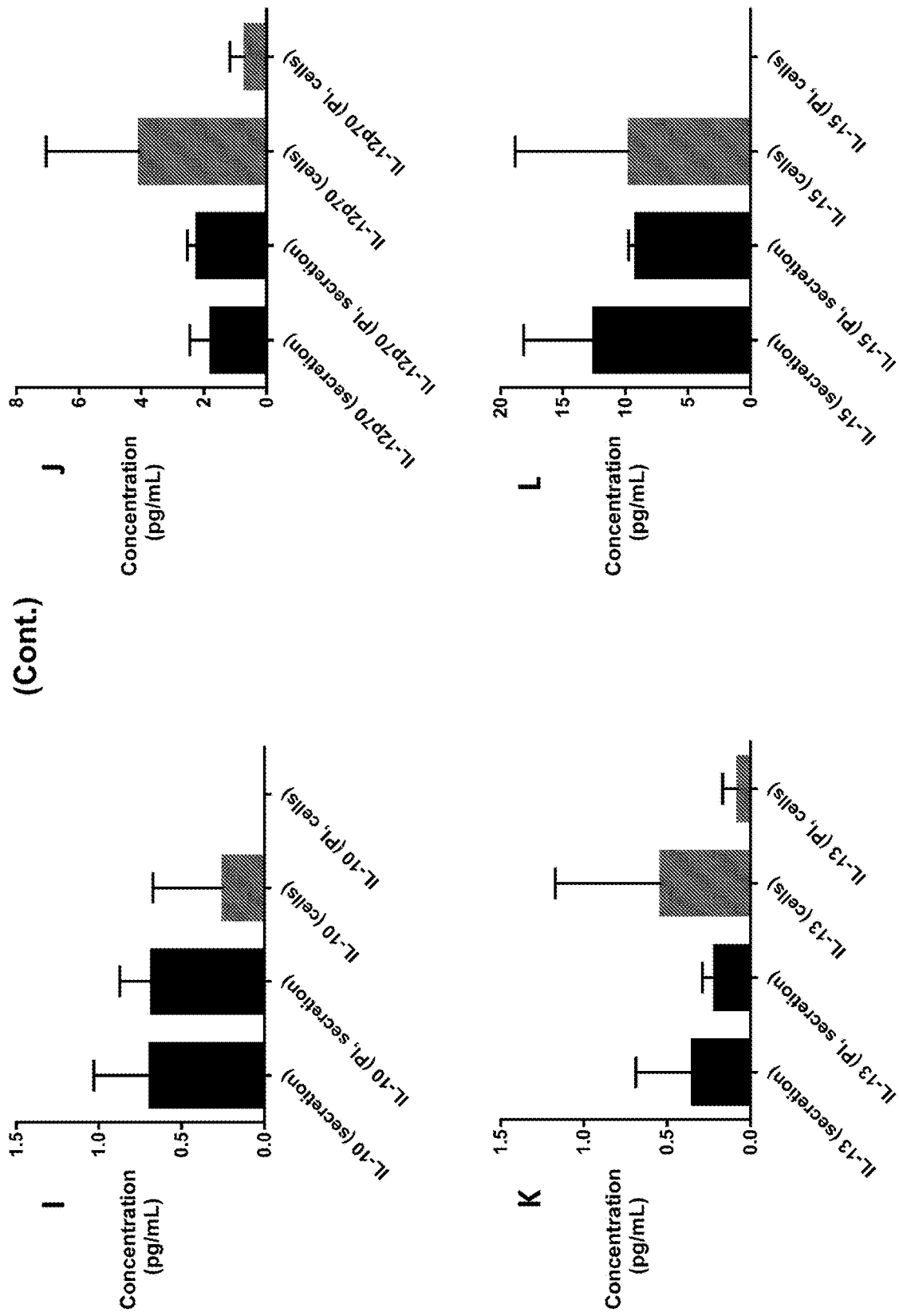
Figure 16:
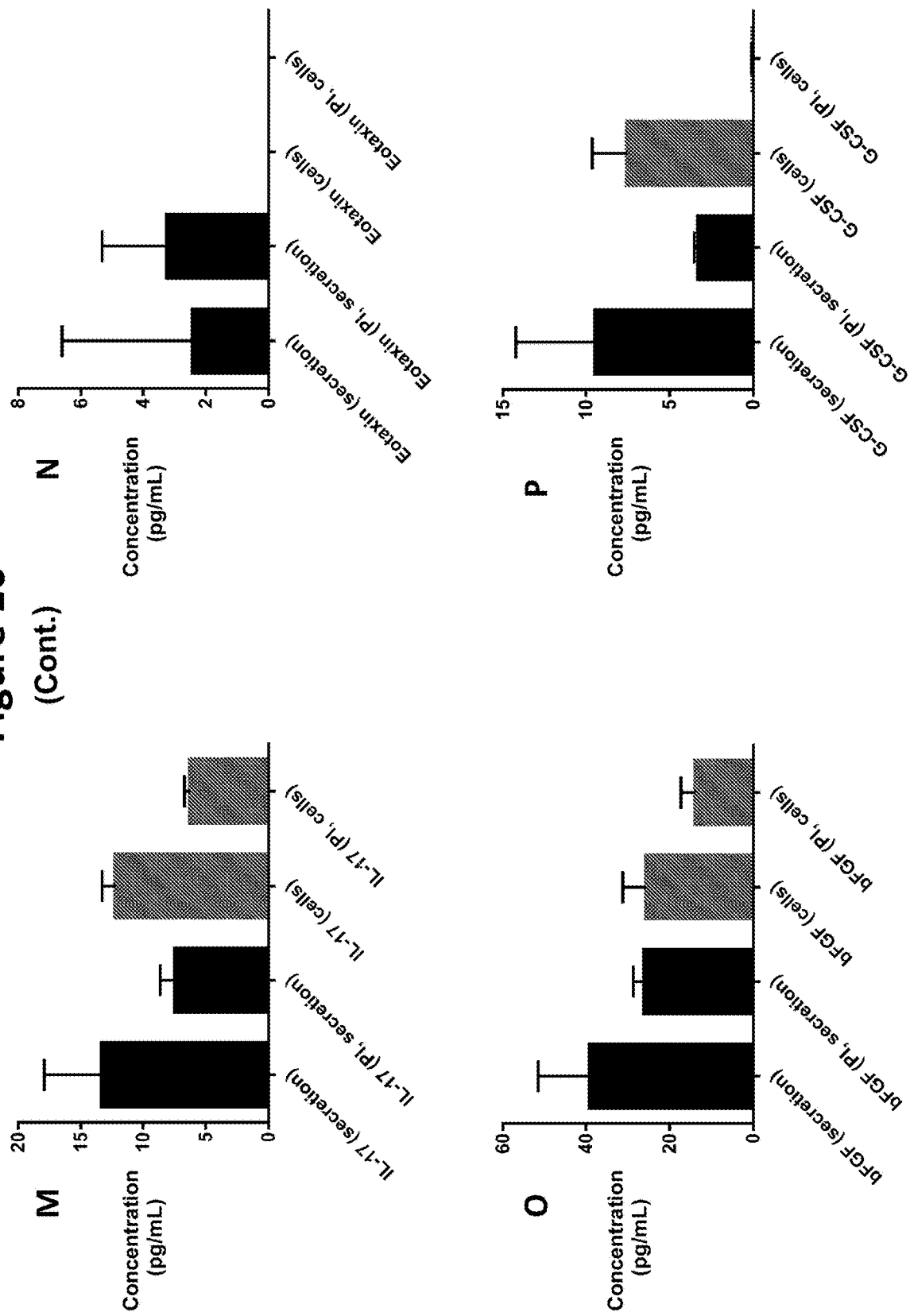
Figure 16:
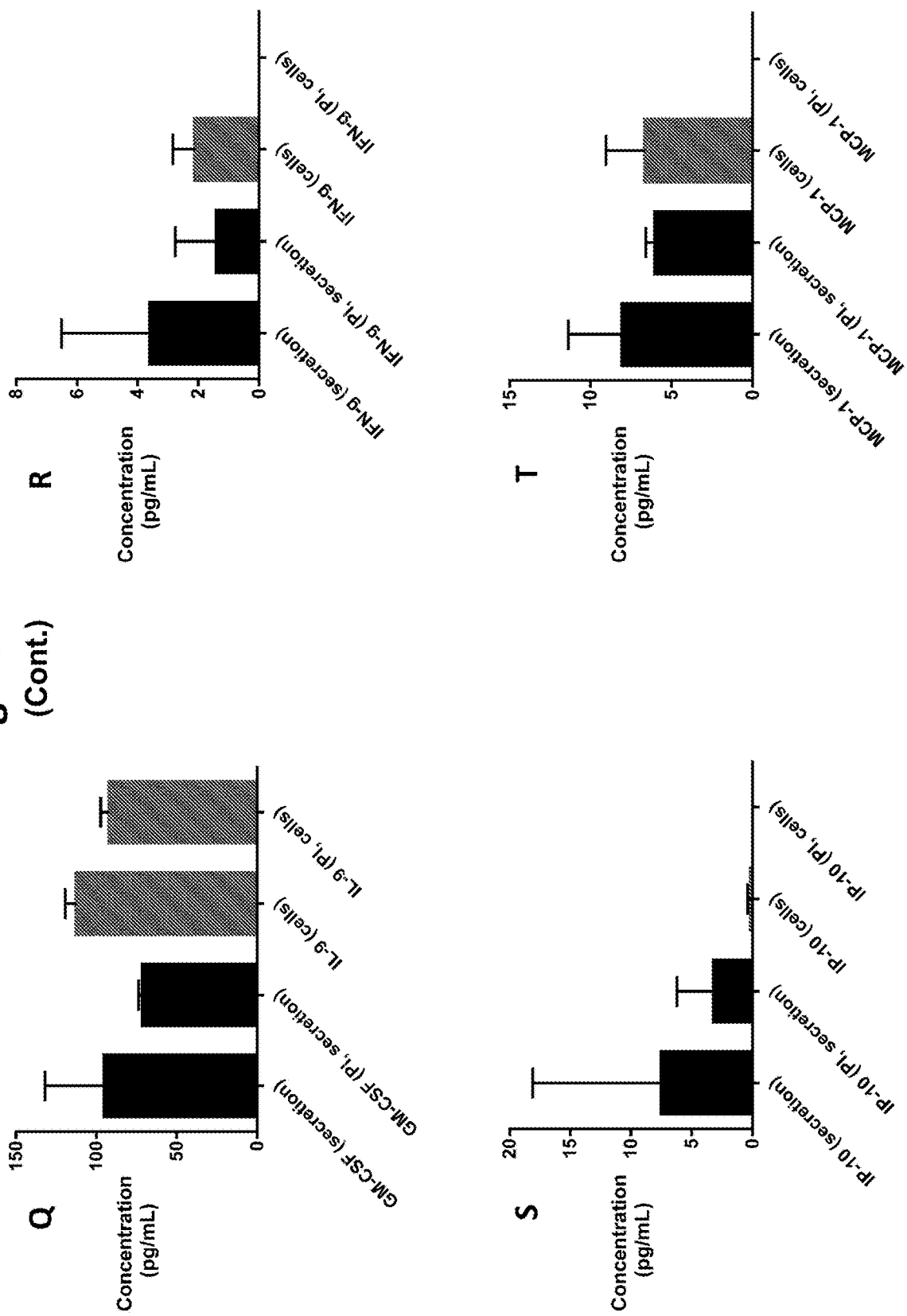
Figure 16:
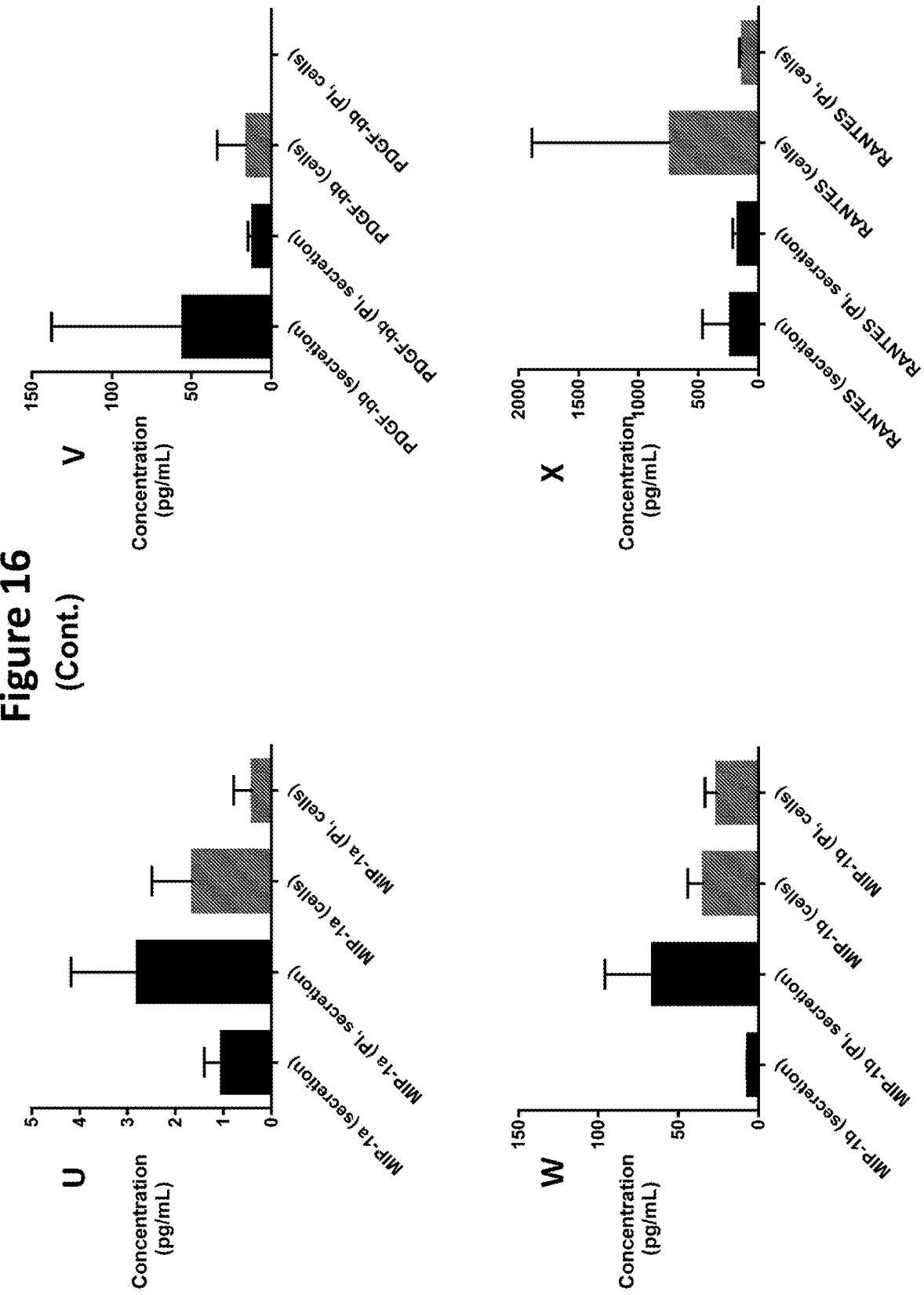
Figure 16:
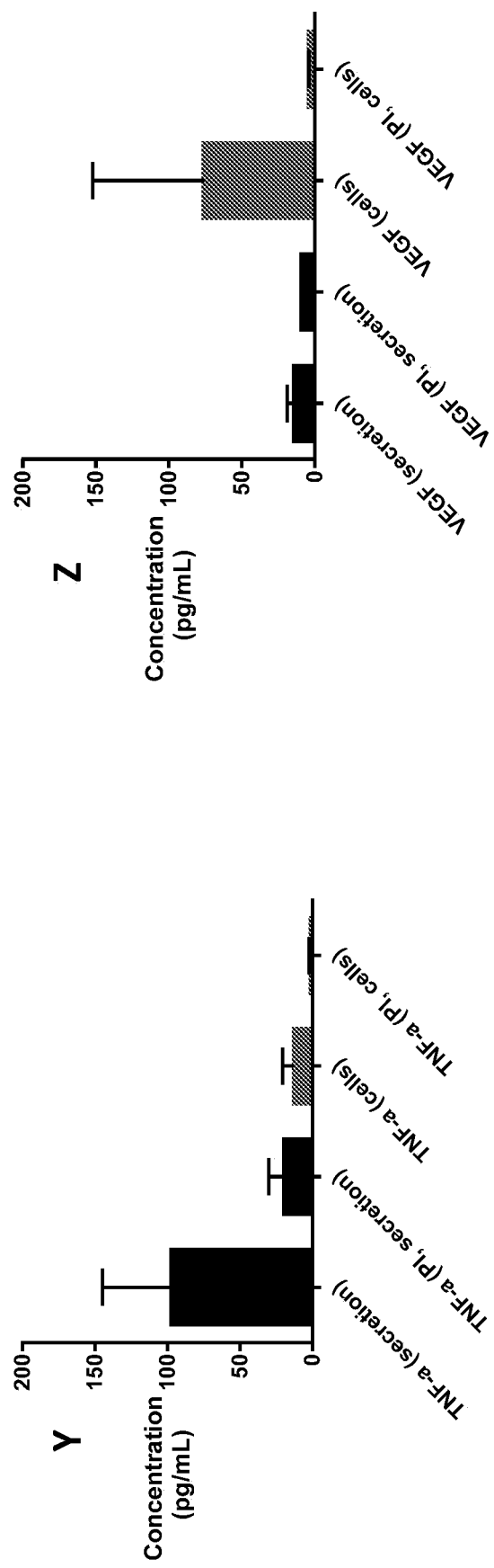

The series of graphs shown in FIG. 16A-16Z depict the effect of protease inhibitors (PI) on the concentration of proteins released or secreted from RBCs (black columns) and the concentration of proteins remaining in the cells after secretion (grey columns). Inclusion of protease inhibitors in the culture solution typically resulted in a lower detectable concentration for both release or secretion and cell lysate, although there were some exceptions (i.e., MIP-1b). Data presented as mean±standard deviation (SD).

The data demonstrated that many cytokines are present in RBCs. Because cytokine levels in whole blood are much different compared to in plasma, they give a very different picture of the cytokine profile of peripheral blood, and this has implications for biomarker analysis.

Example 7. Presence of CRP in or on RBCs

To investigate whether the CRP inflammatory marker is associated with RBCs, WB was collected by finger prick using lancets. The blood was analysed for CRP levels using the ICHROMA instrument on either fresh blood (which detects plasma levels) or after three freeze-thaw cycles to lyse all of the cells (for whole blood levels). Purified RBCs (after dextran sedimentation) were collected and lysed using 3 freeze-thaw cycles, were run on the ICHROMA instrument, and protein levels compared to those in stored plasma samples.

Figure 17:
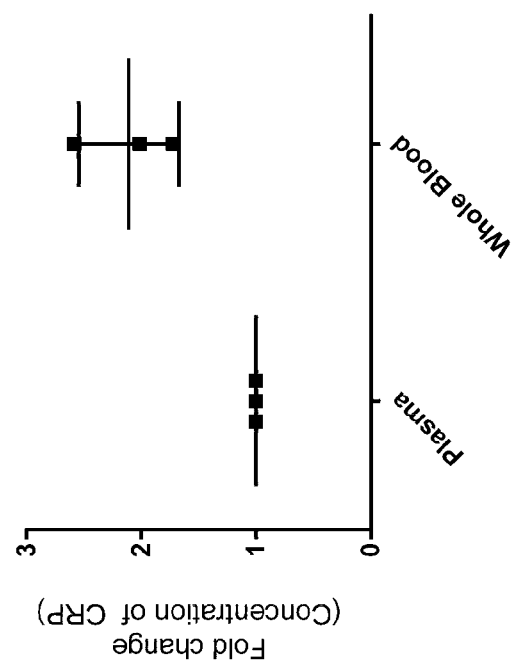
FIG. 17 is a graph showing fold change of CRP in lysed whole blood when normalized to plasma levels.
Figure 18:
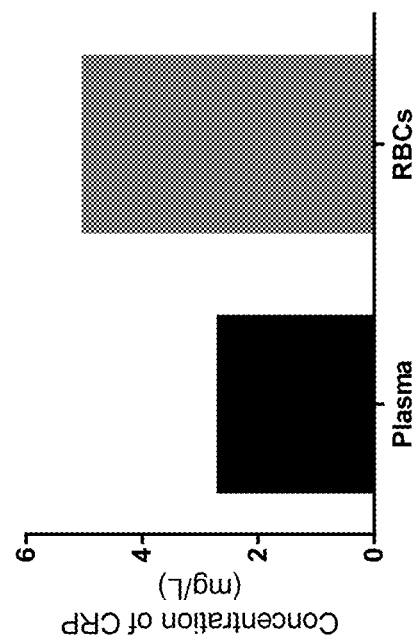
FIG. 18 is a graph showing the concentration of CRP in plasma and in purified, lysed RBCs.

As shown in FIG. 17, CRP was detectable in higher levels in lysed whole blood than in the plasma component. CRP was also detectable in a similar ratio in RBCs lysate when compared to corresponding plasma concentrations (FIG. 18). The results suggested that CRP is associated with RBCs, and the RBCs are responsible for approximately 50% of the total CRP detectable in whole blood.

Example 8. Measurement of Protein Levels in a Small Blood Volume

The discovery of a high level of various proteins in red blood cells as compared to their levels in an equivalent volume in plasma, for example, suggested that a small volume of whole blood and/or RBCs could be used to identify protein markers. The levels of numerous proteins were analyzed in a small volume of whole blood and RBCs.

Whole blood was collected from healthy volunteers by finger prick (n=1) directly into EDTA solution (3 mg/mL). For multiplex analysis (BIOPLEX analysis) all samples were stored at −80° C. and were subjected to 3 freeze-thaw cycles at −80° C. to ensure complete cellular lysis prior to analysis. The red blood cells were subjected to 3 freeze-thaw cycles to ensure complete cellular lysis. Following lysis, the whole blood was analysed on the multiplex cytokine assay at 5 µL whole blood (in 45 µL PBS), 10 whole blood (in 40 µL PBS), 15 µL whole blood (in 35 µL PBS), 20 µL whole blood (in 30 µL PBS), or 25 µL whole blood (in 25 µL PBS). Two multiplex assays were utilised. The first was the 27-plex human cytokine panel that assays for FGF basic, Eotaxin, G-CSF, GM-CSF, IFN-γ, IL-1β, IL-1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1β, PDGF-BB, RANTES, TNF-α, and VEGF, and the second was the 21-plex human cytokine panel that assays for IL-1α, IL-2Ra, IL-3, IL-12, IL-16, IL-18, CTACK, GRO-α, HGF, IFN-α2, LIF, MCP-3, M-CSF, MIF, MIG, β-NGF, SCF, SCGF-β, SDF-1α, TNF-β, TRAIL (BIOPLEX Pro 27-plex and 21-plex, Bio-Rad). The assays were performed according to manufacturer's instructions using an automated magnetic wash station (BIOPLEX Pro II, Bio-Rad) for the washing steps. The assays were run on the LUMINEX® 200™ system (Bio-Rad) and fluorescent values were collected. The calibration curve for each cytokine was analysed with 5 parametric logistic curve regression using BIOPLEX manager software (ver. 5.0, Bio-Rad, USA).

Figure 19:
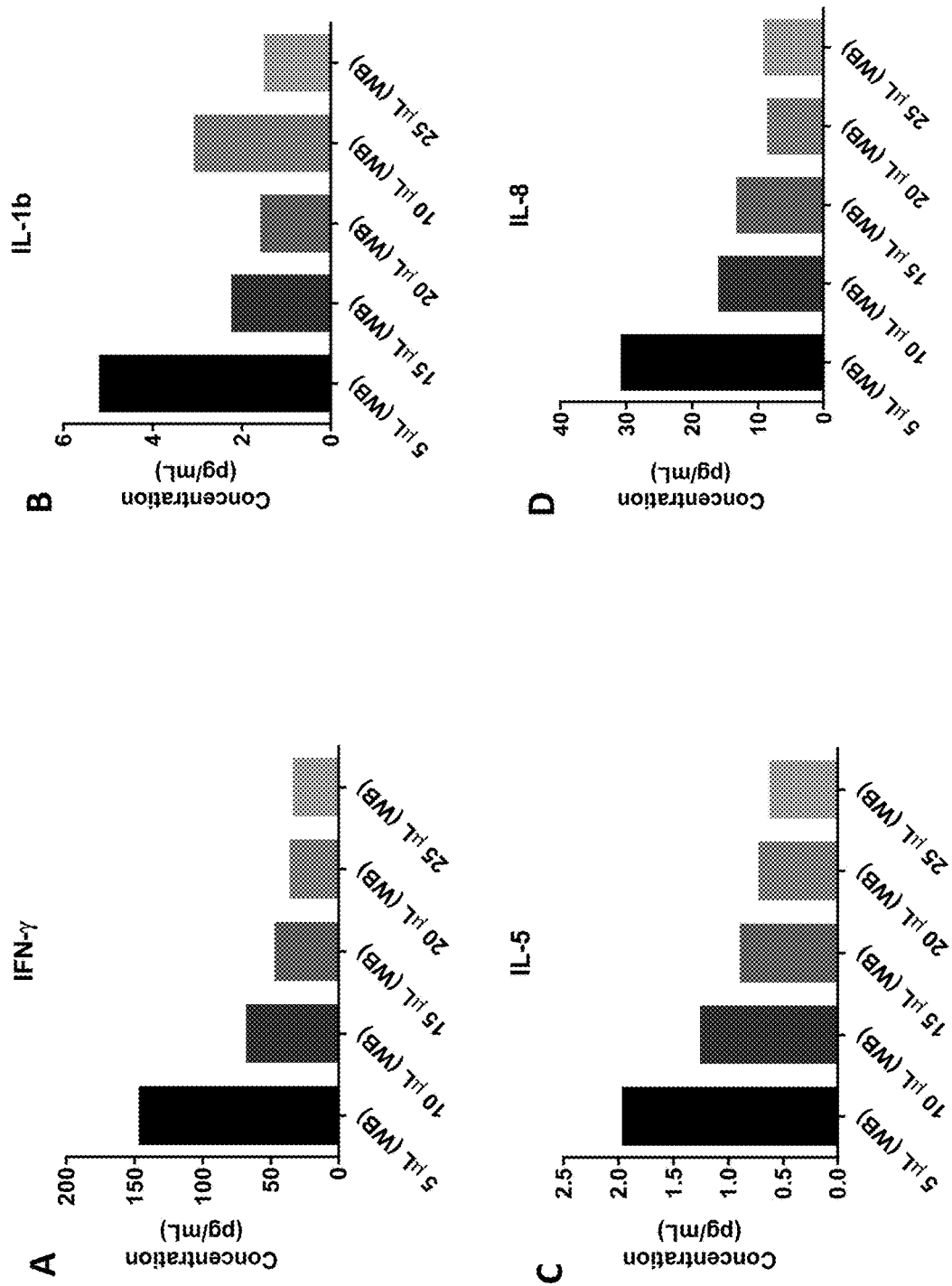
FIG. 19A-19TT is a series of graphs showing the levels of various proteins in small volumes of whole blood.
Figure 19:
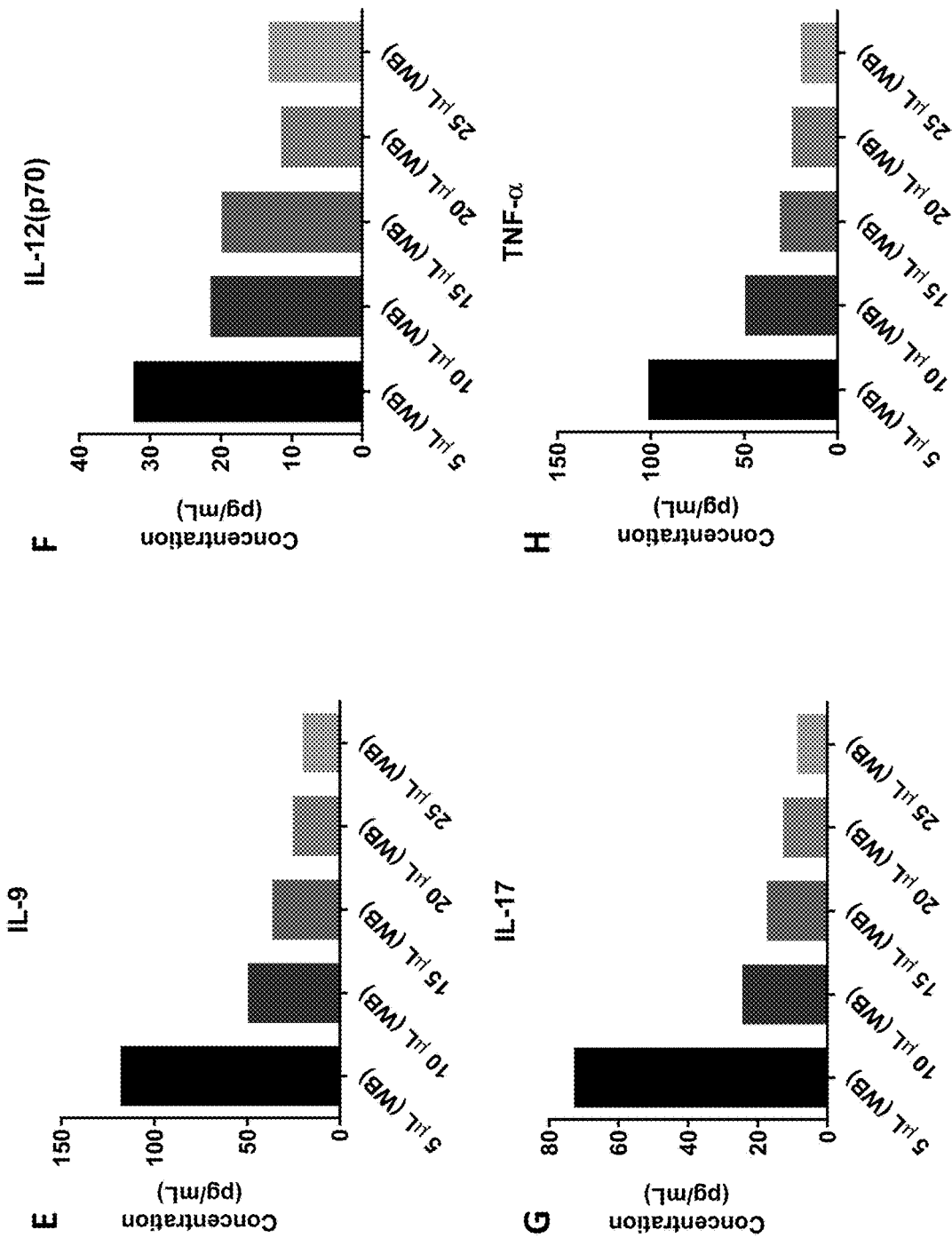
Figure 19:
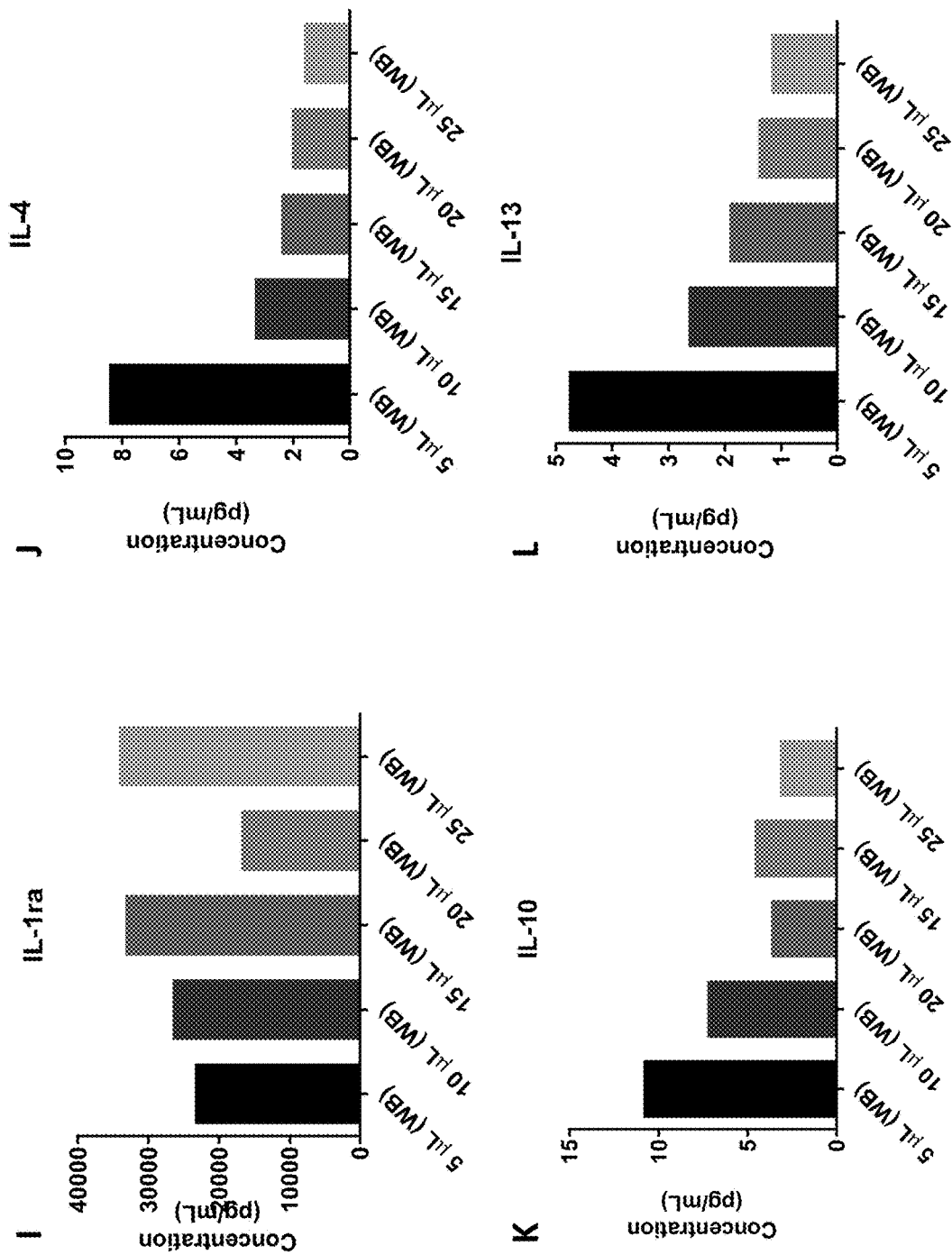
Figure 19:
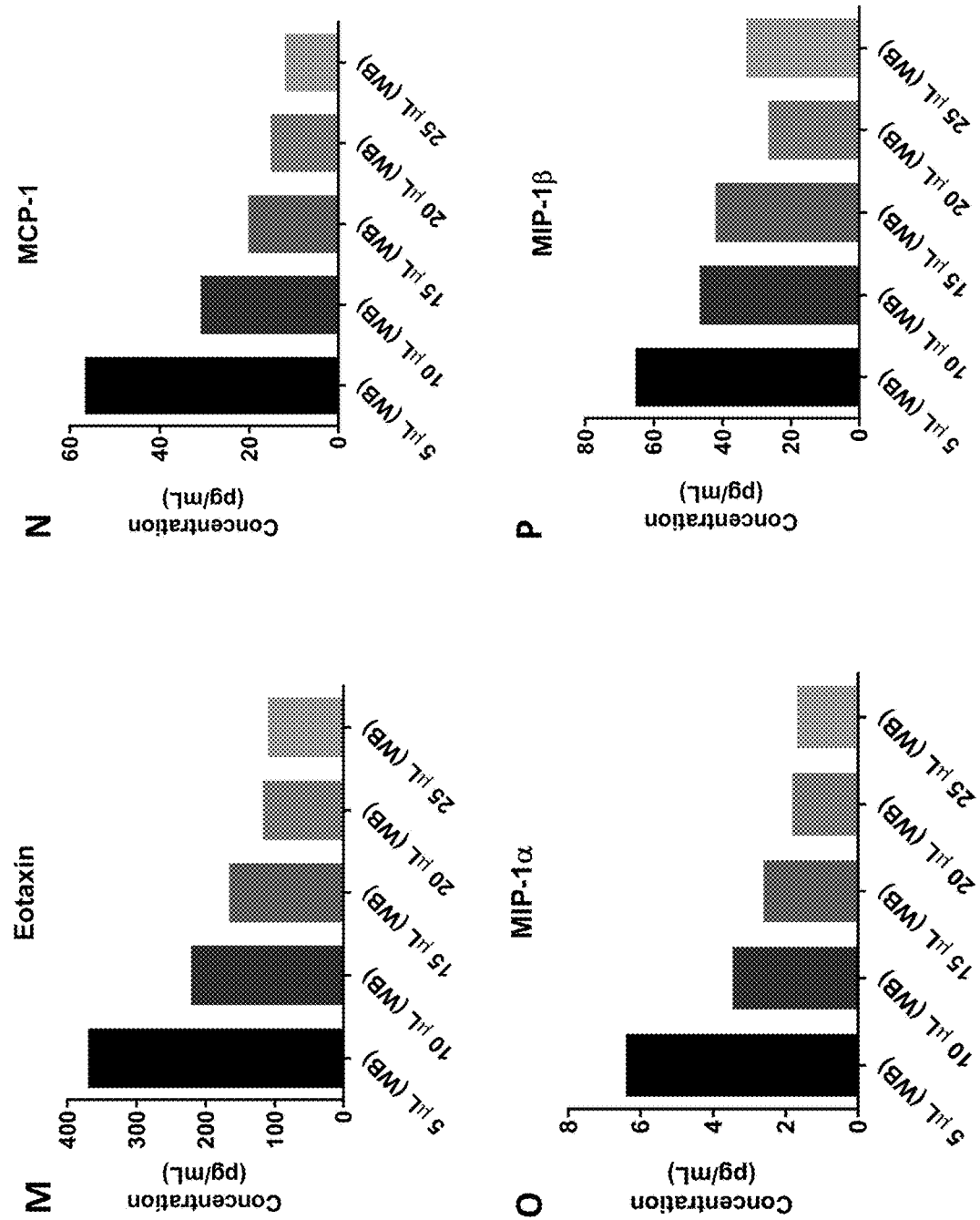
Figure 19:
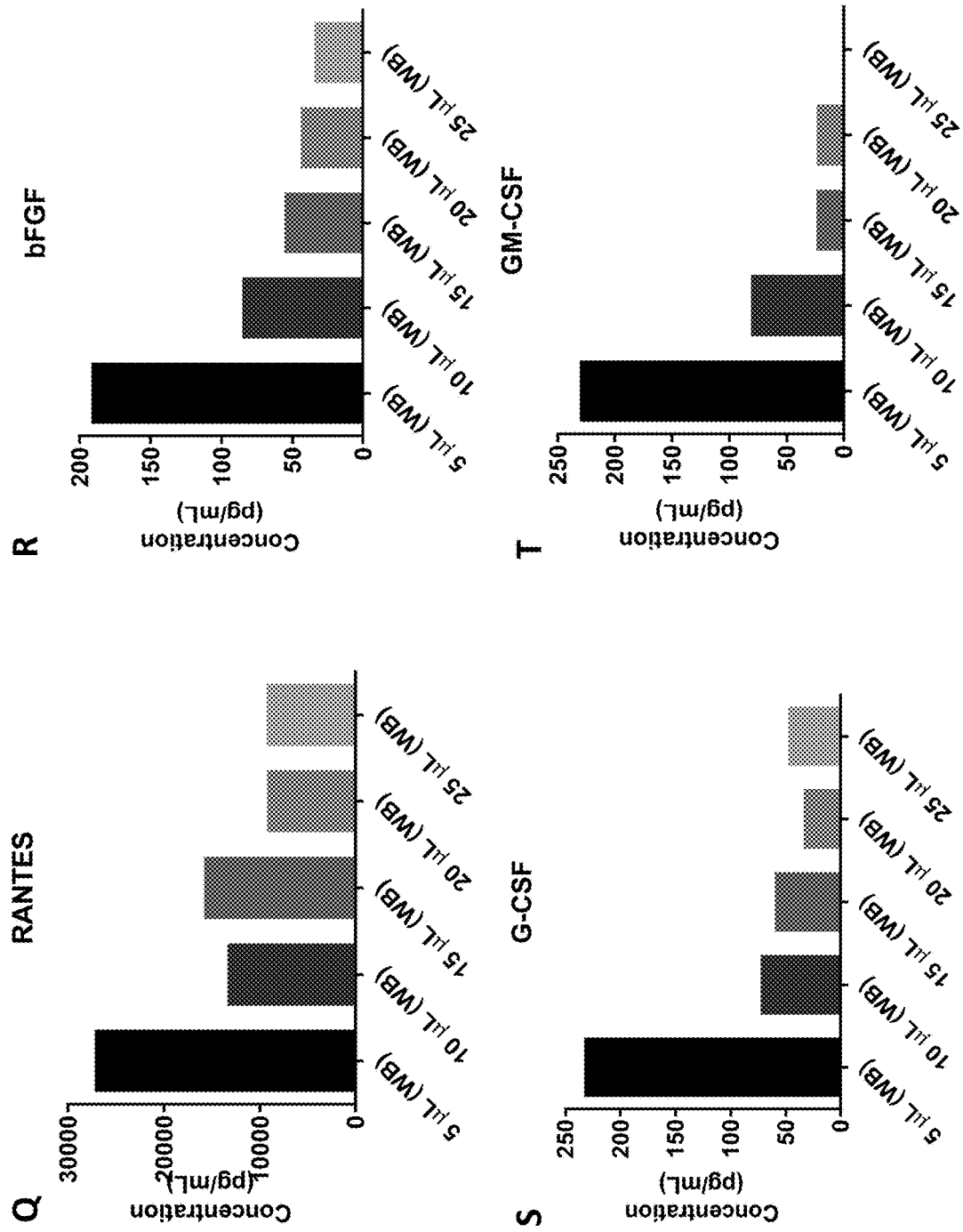
Figure 19:
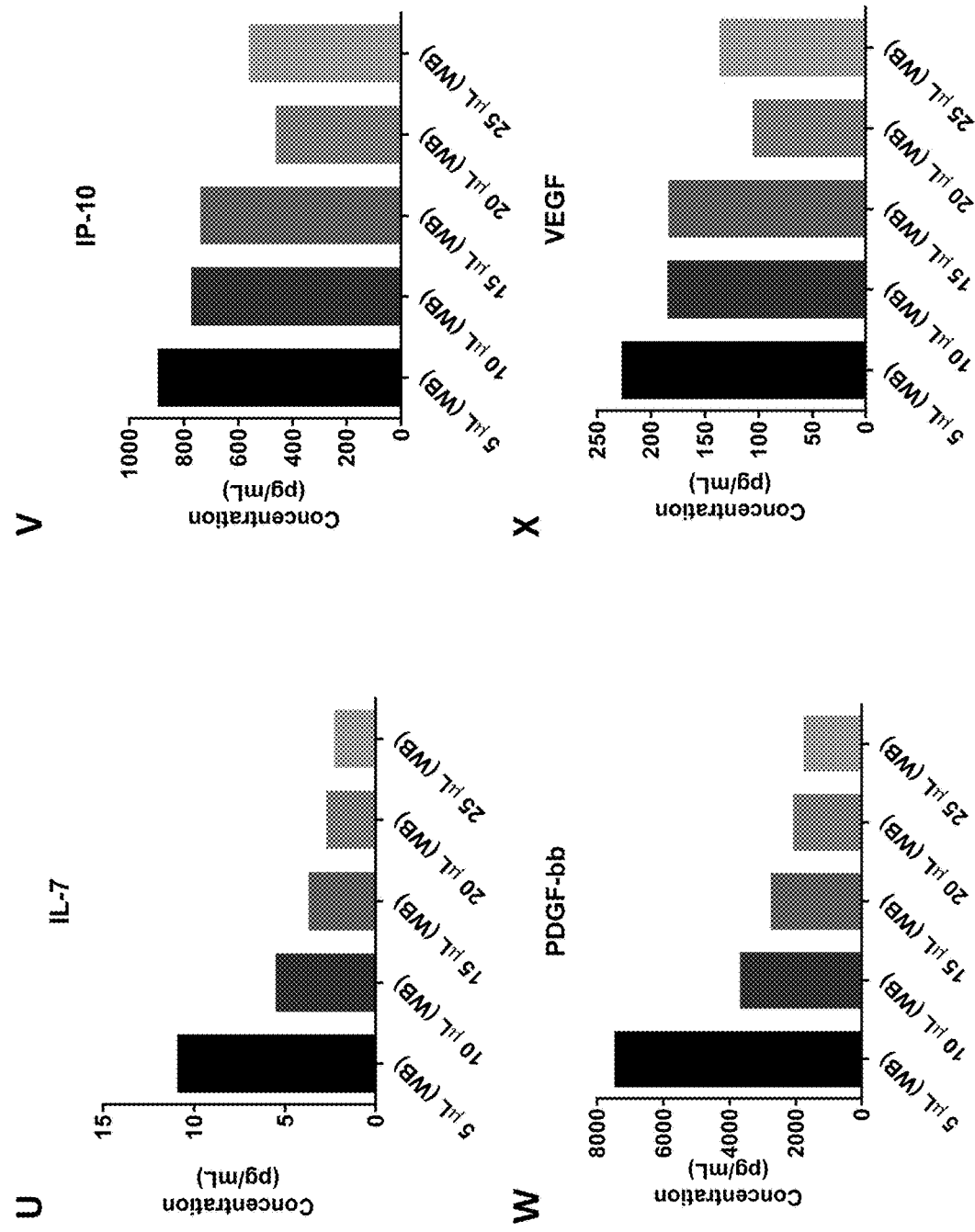
Figure 19:
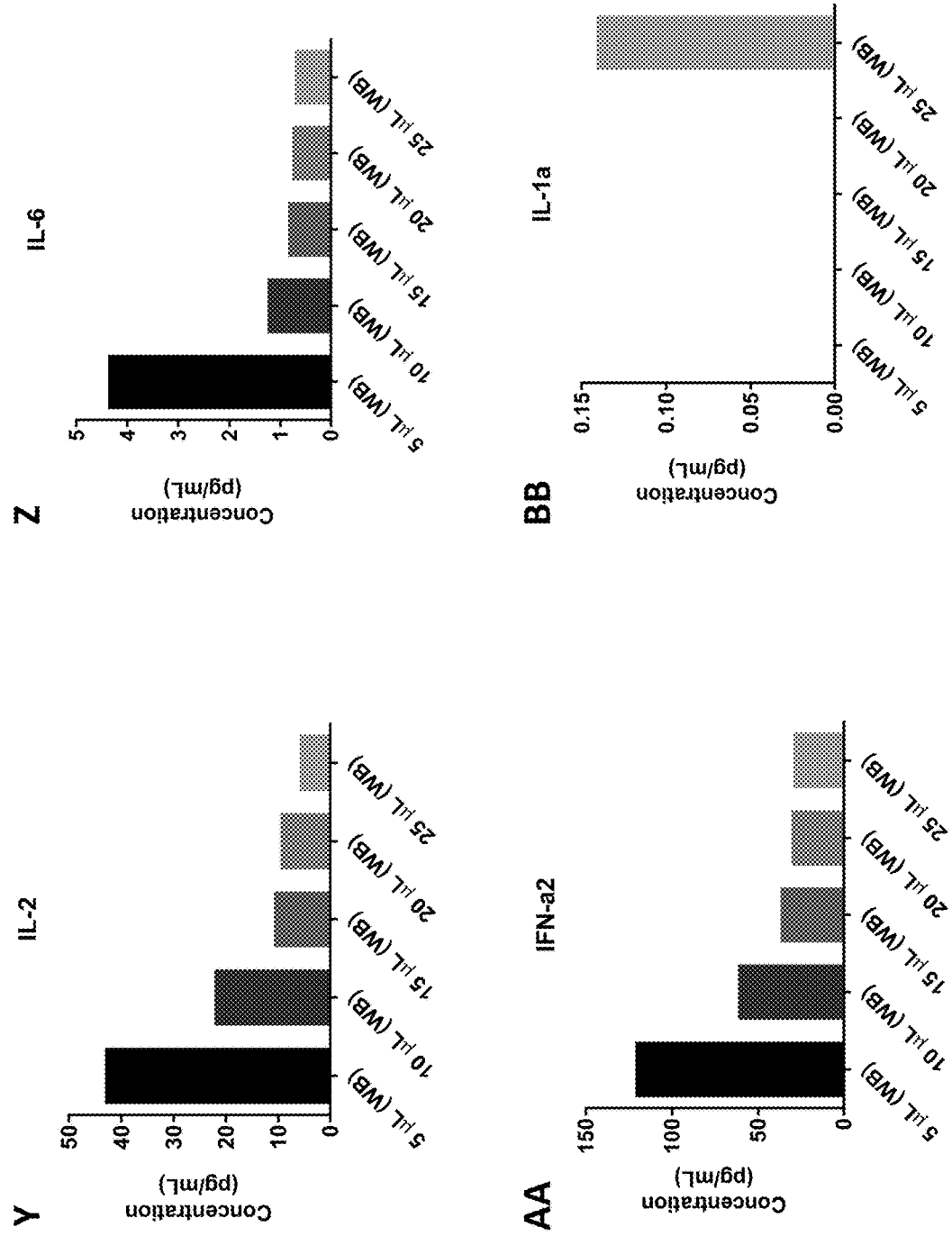
Figure 19:
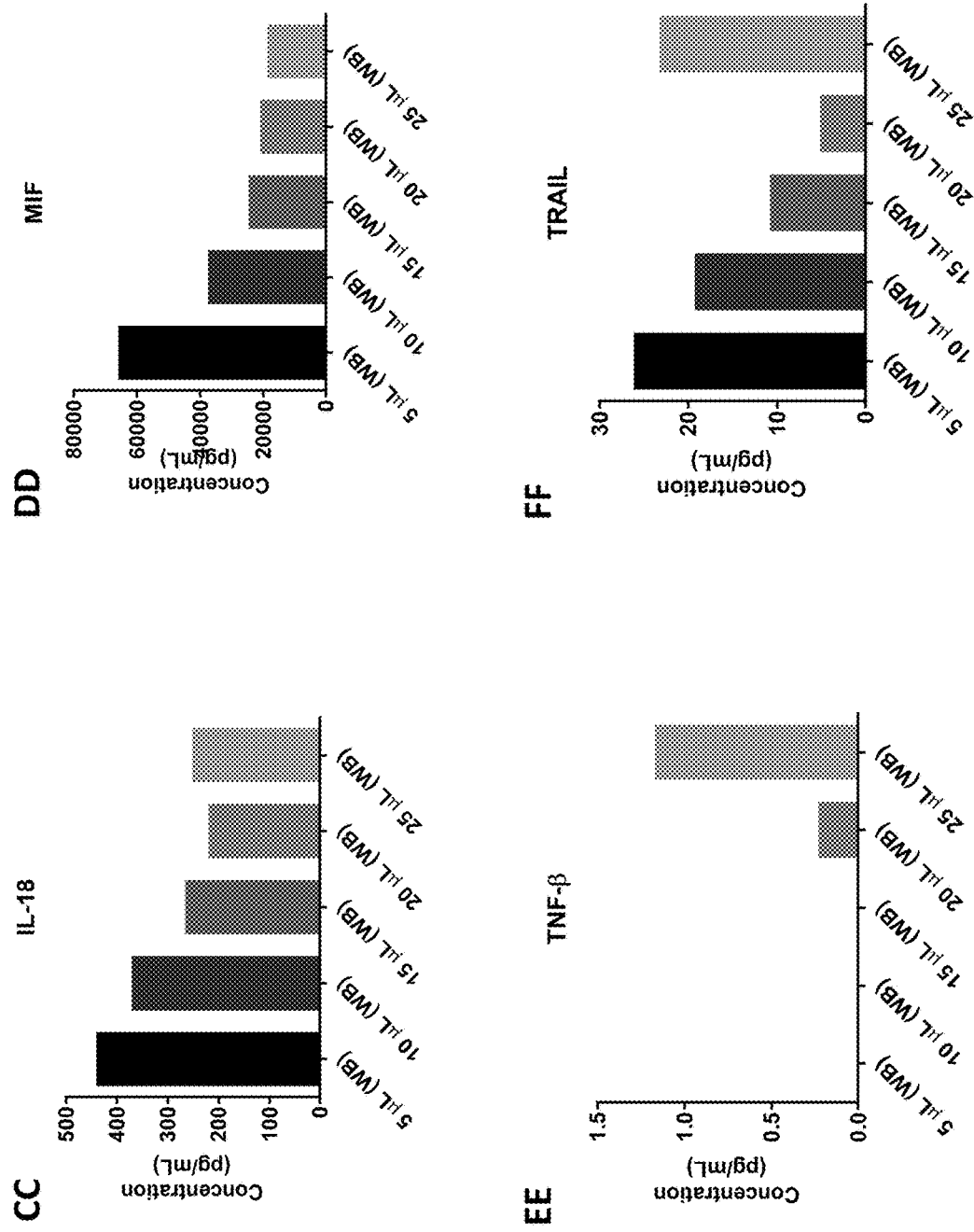
Figure 19:
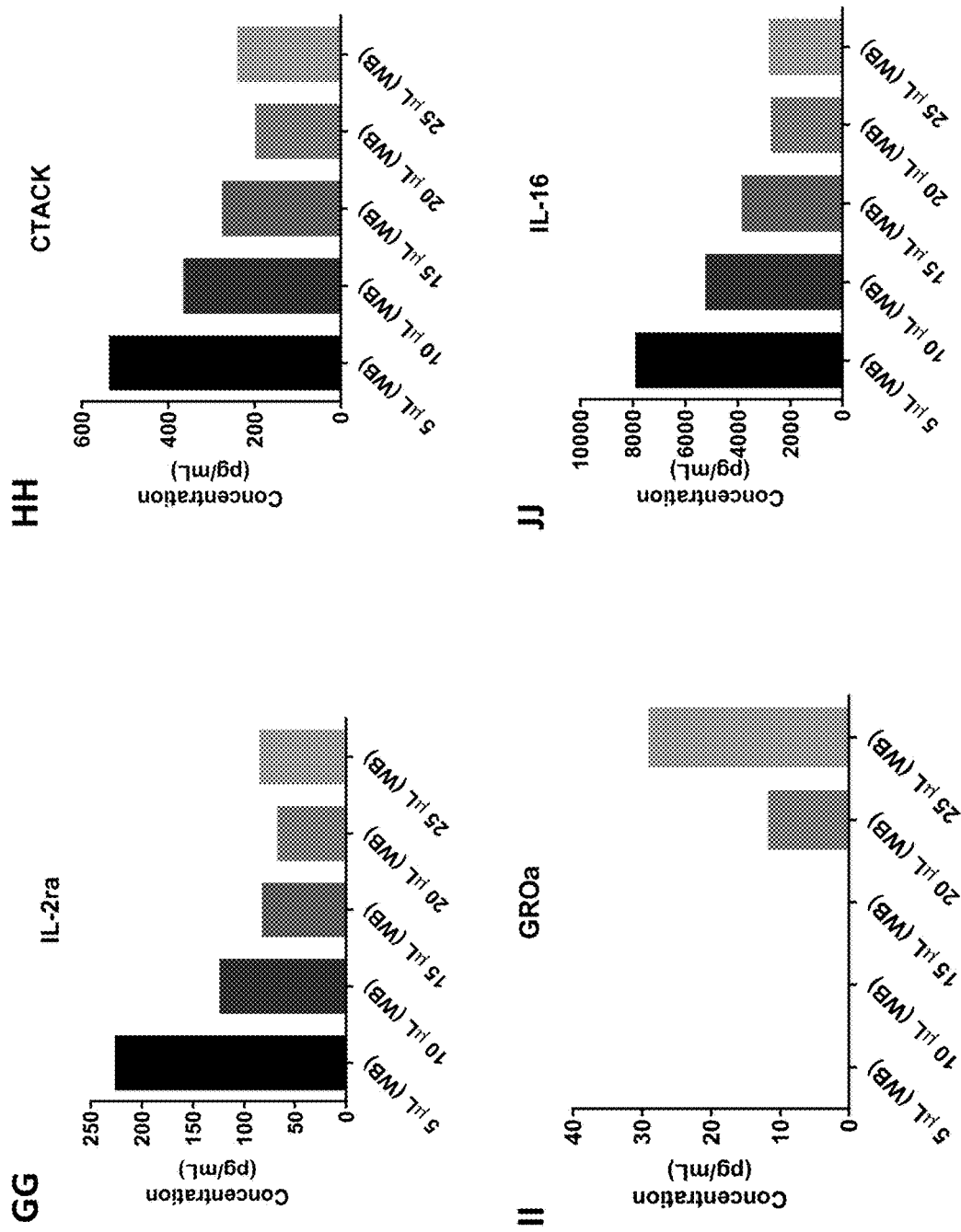
Figure 19:
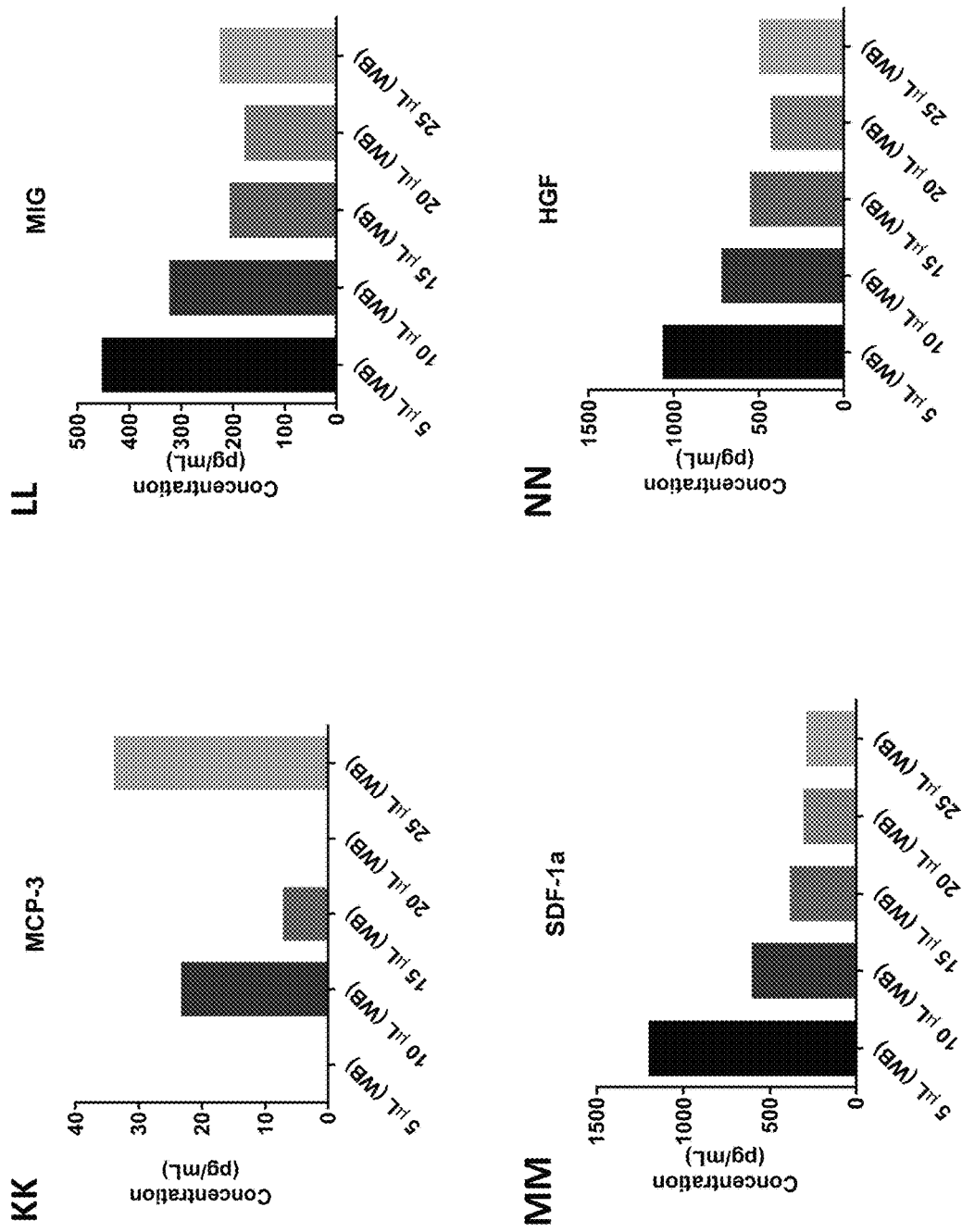
Figure 19:
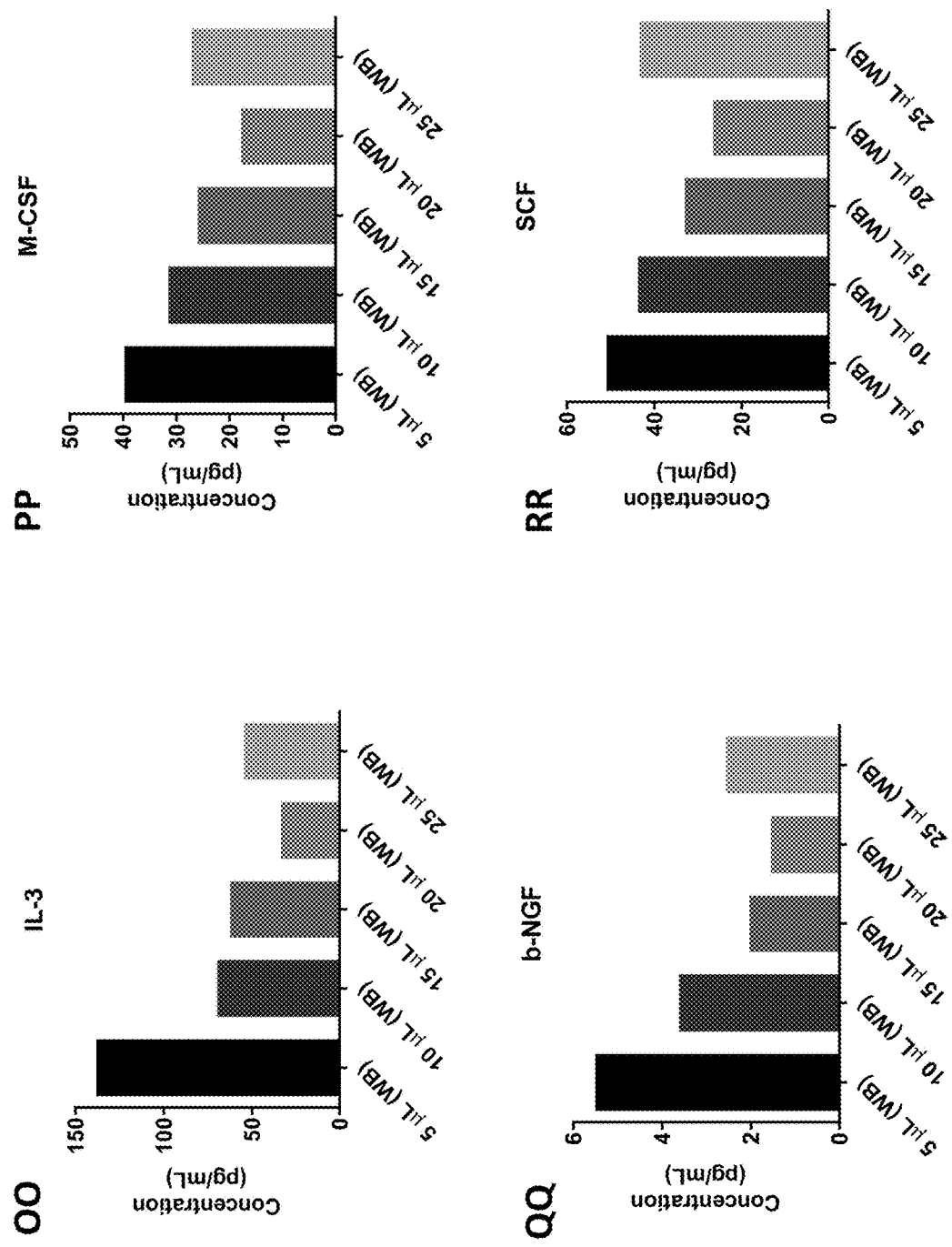
Figure 19:
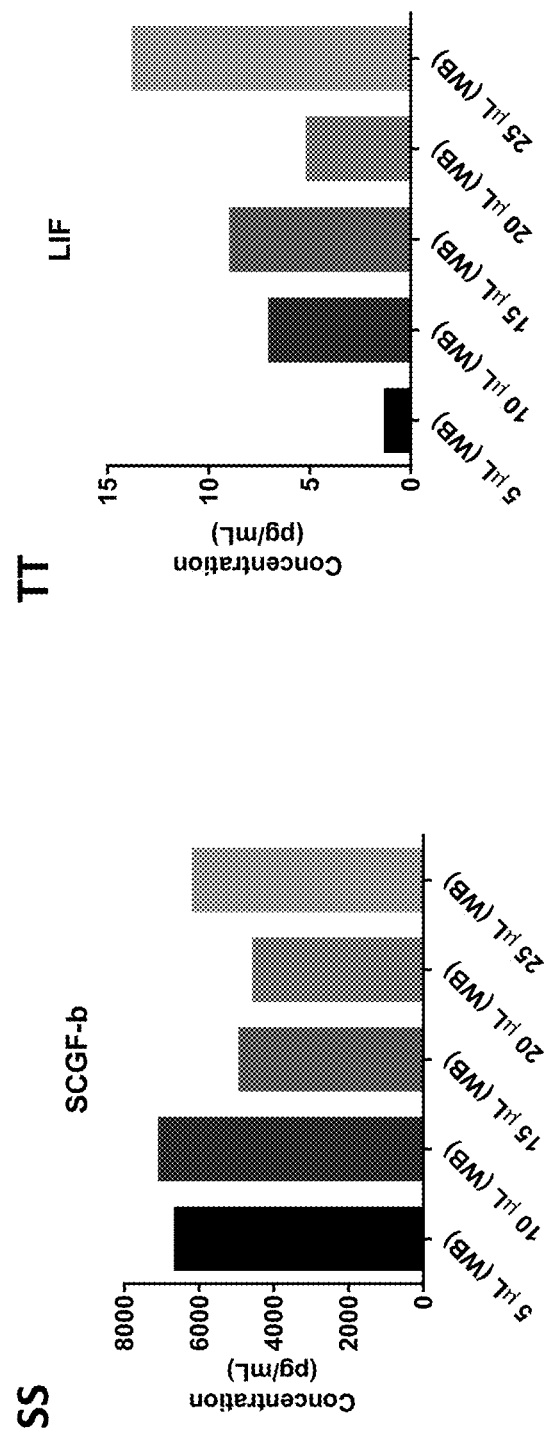

The concentration of the indicated proteins in whole blood at various dilutions (1:10, 1:5, 1:3.3, 1:2.5, 1:2) are shown in FIG. 19A-19TT (calculated back to the undiluted concentration). Analysis of whole blood revealed the presence of a number of proteins and these proteins were also present at a range of dilutions. However, there was no dilution linearity for many of the analysed proteins, which is not unique to whole blood; it is also observed in the analysis of plasma on LUMINEX platforms such as BIOPLEX (more protein is typically detected with dilution). The results indicate that proteins can be monitored in small volumes of whole blood (down to 5 µL). The ease of detection of numerous proteins in whole blood demonstrates that very small blood volumes (obtained from e.g., the fingertip) could be collected and used for analysis of protein levels.

Example 9. Presence of Proteins in Fingertip Versus Venous Blood Samples

To further explore the detection of proteins in small blood volumes, the levels of numerous proteins in a finger prick was compared to their levels in venous blood collected by known methods.

Whole blood was collected from healthy volunteers by venipuncture or by finger prick (n>12) directly into EDTA VACUTAINERS (k₂EDTA VACUTAINERS, BD Biosciences) or EDTA solution (3 mg/mL). All fractions of blood were collected and processed at room temperature within 4 hours of collection. For multiplex analysis (BIOPLEX analysis) all samples were stored at −80° C. and were subjected to 3 freeze-thaw cycles at −80° C. to ensure complete cellular lysis prior to analysis. The plasma and red blood cells were isolated using dextran sedimentation as follows. Whole blood was centrifuged (1500 g, 10 minutes) and the upper plasma layer was collected. The remaining cell pellet was resuspended in an equal volume of sodium chloride (0.15 M). Dextran (6% w/v in 0.15 M sodium chloride) was then added to this cellular suspension at a 1:4 ratio (dextran:cell suspension). This solution was left at room temperature for 30 minutes for red blood cell sedimentation to the bottom of the tube. After this time the upper white blood cell rich layer was discarded and the lower red blood cell fraction was isolated. The red blood cell fraction was washed twice in phosphate buffered saline (PBS, 500 g, 5 minutes) and the remaining red blood cell pellet was counted (Coulter Act Diff, Beckman Coulter) and then frozen (−80° C.) until analysis.

The red blood cells were subjected to 3 freeze-thaw cycles to ensure complete cellular lysis. Following lysis, the red blood cell lysates were diluted in PBS to the equivalent of 400 million cells/mL. These lysates were then analysed on the multiplex cytokine assay. One multiplex assay was utilised. It was the 27-plex human cytokine panel that assays for FGF basic, Eotaxin, G-CSF, GM-CSF, IFN-γ, IL-1β, IL-1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1β, PDGF-BB, RANTES, TNF-α, and VEGF (BIOPLEX Pro 27-plex, Bio-Rad). The assay were performed according to manufacturer's instructions using an automated magnetic wash station (BIOPLEX Pro II, Bio-Rad) for the washing steps. The assays were run on the LUMINEX® 200™ system (Bio-Rad) and fluorescent values were collected. The calibration curve for each cytokine was analysed with 5 parametric logistic curve regression using BIOPLEX manager software (ver. 5.0, Bio-Rad, USA).

Figure 20:
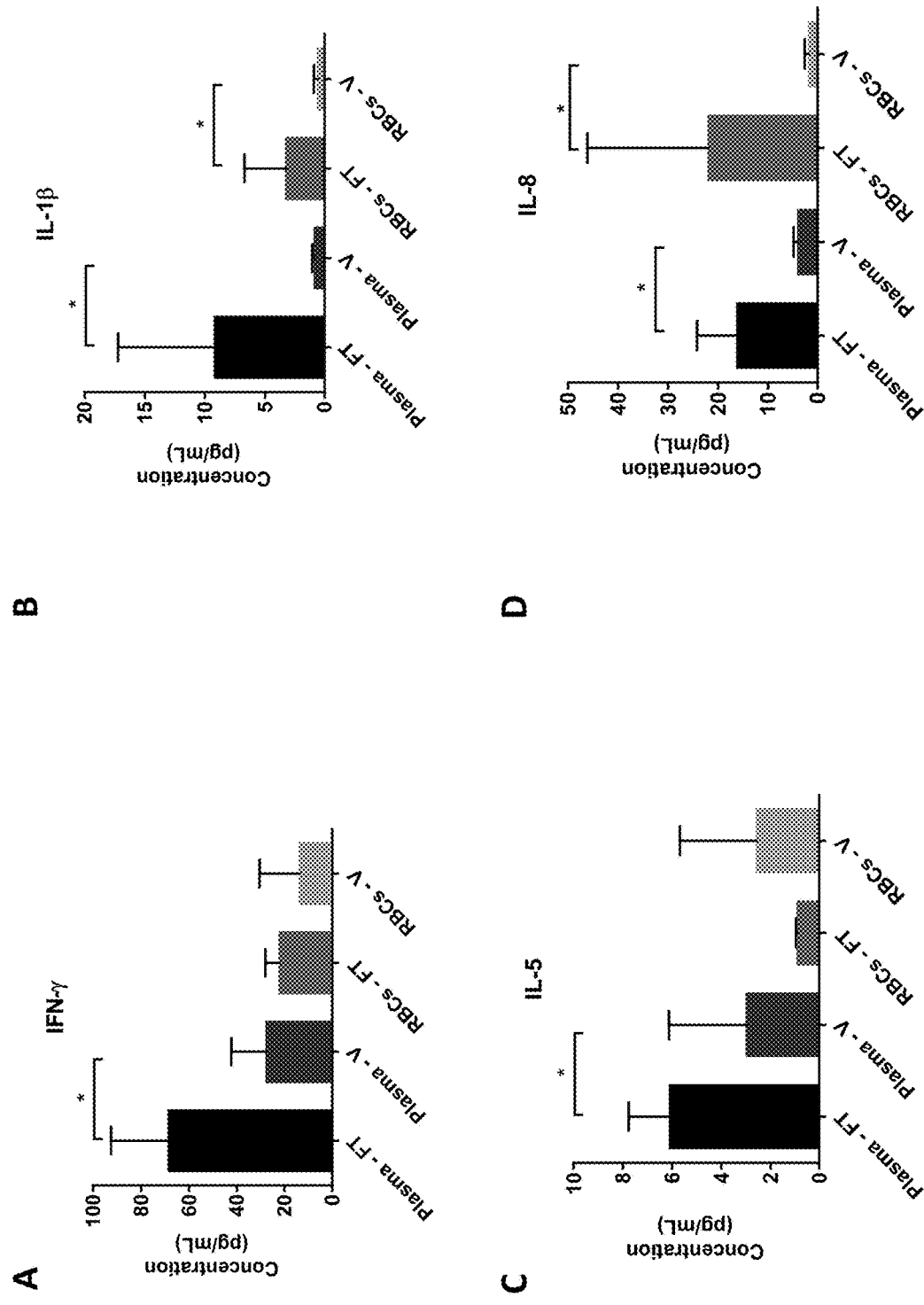
FIG. 20A-20AA is a series of graphs showing the levels of various proteins in red blood cells isolated from whole blood samples obtained from healthy subjects by finger prick (FT) or venipuncture (V).
Figure 20:
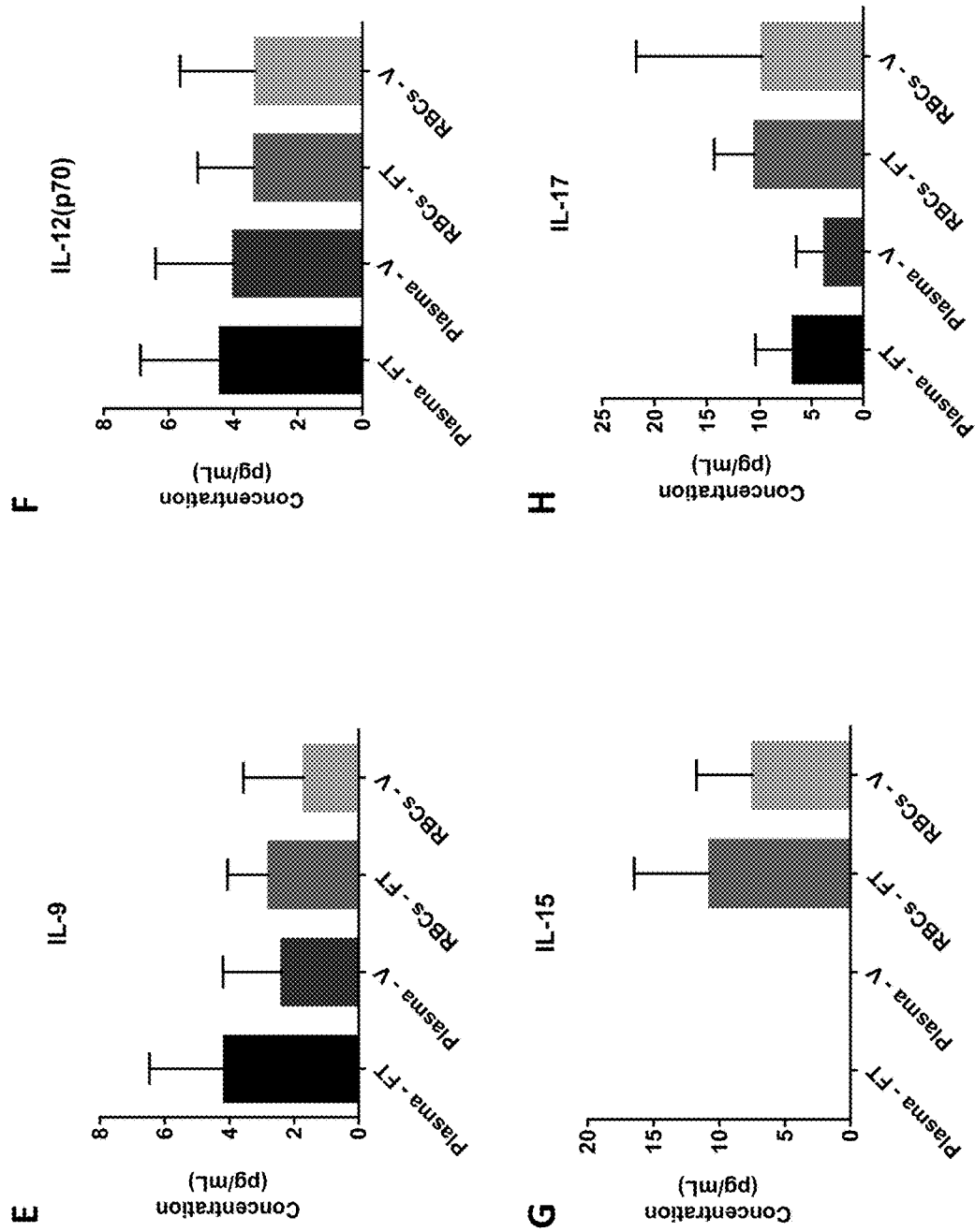
Figure 20:
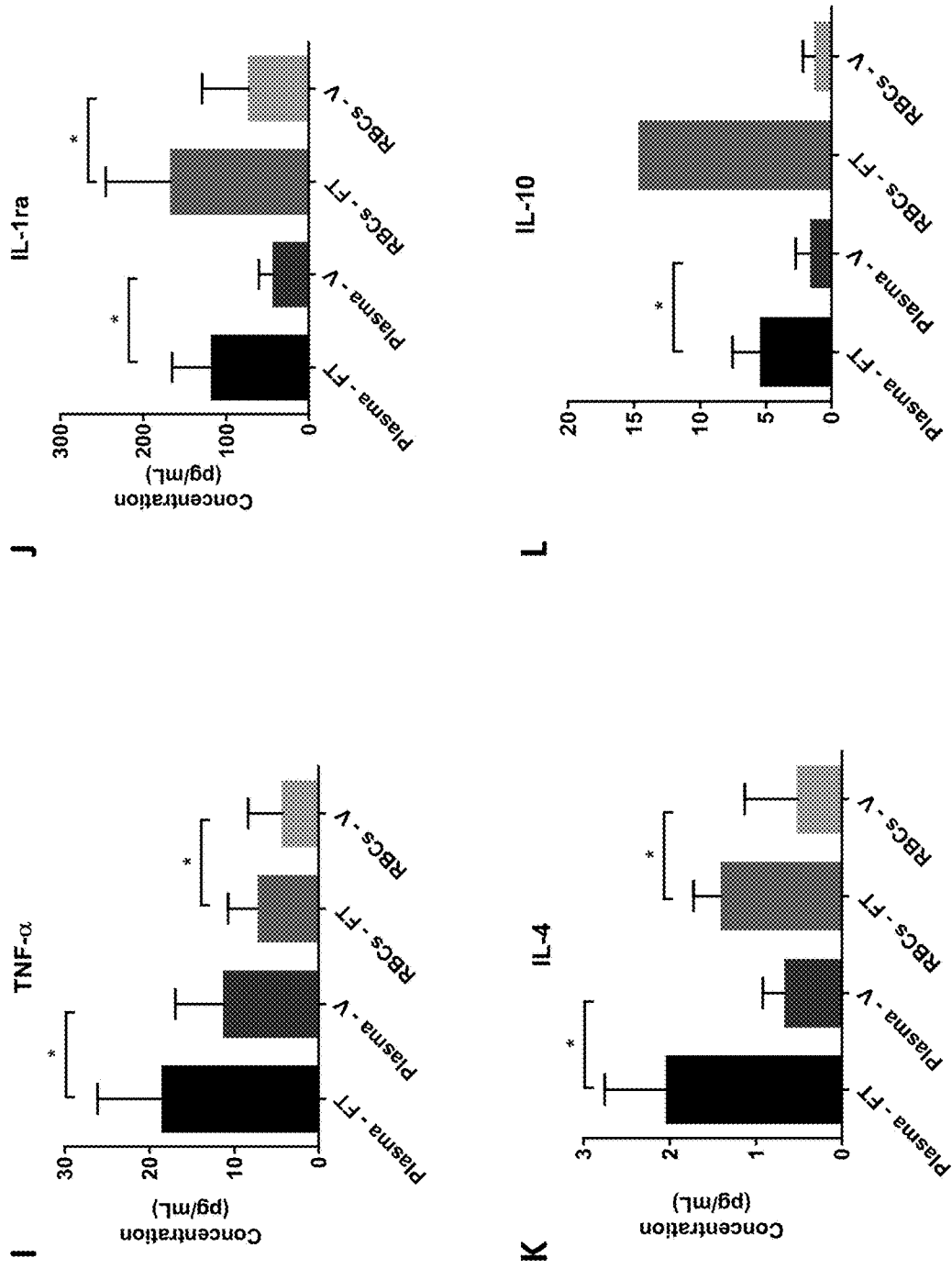
Figure 20:
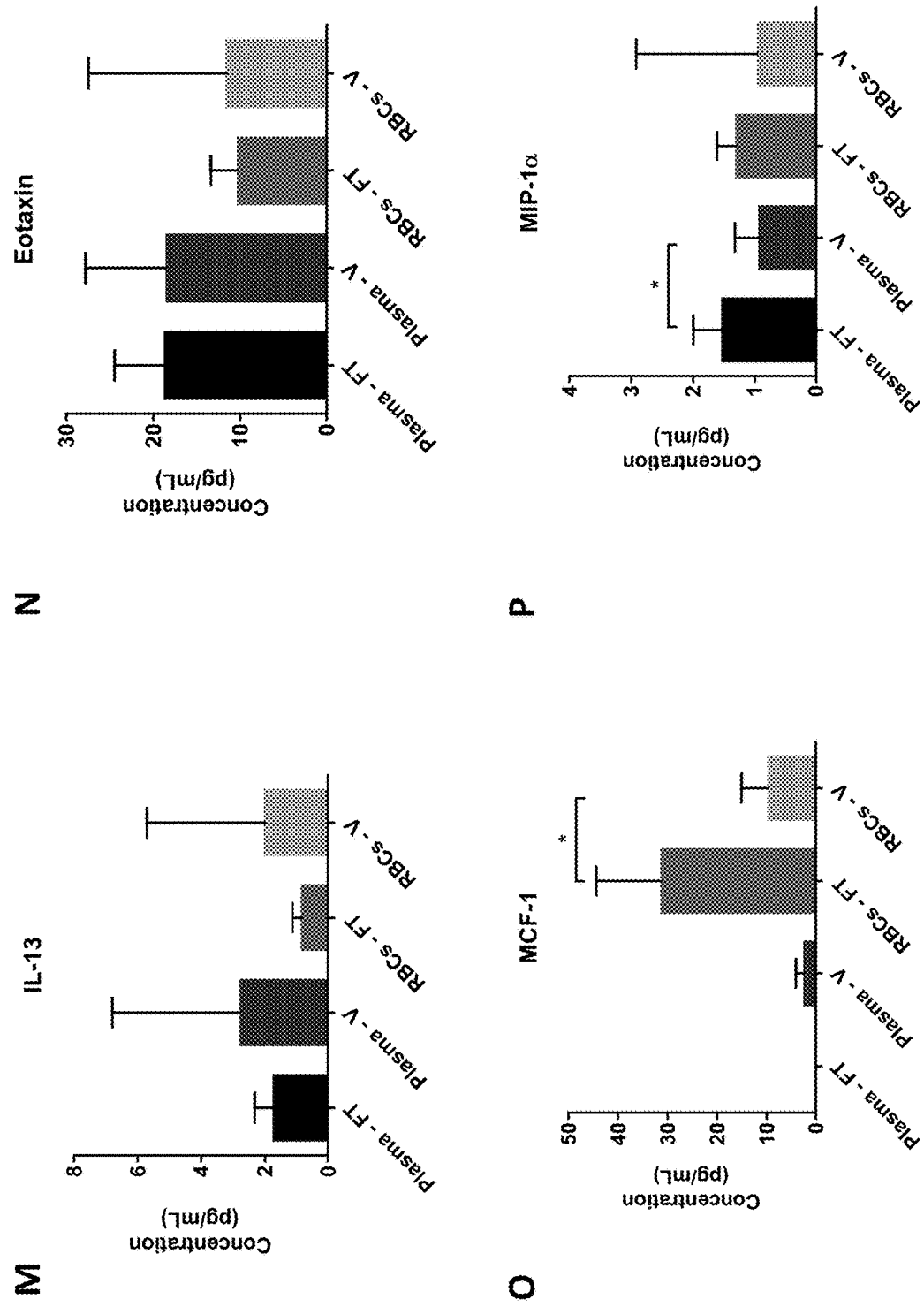
Figure 20:
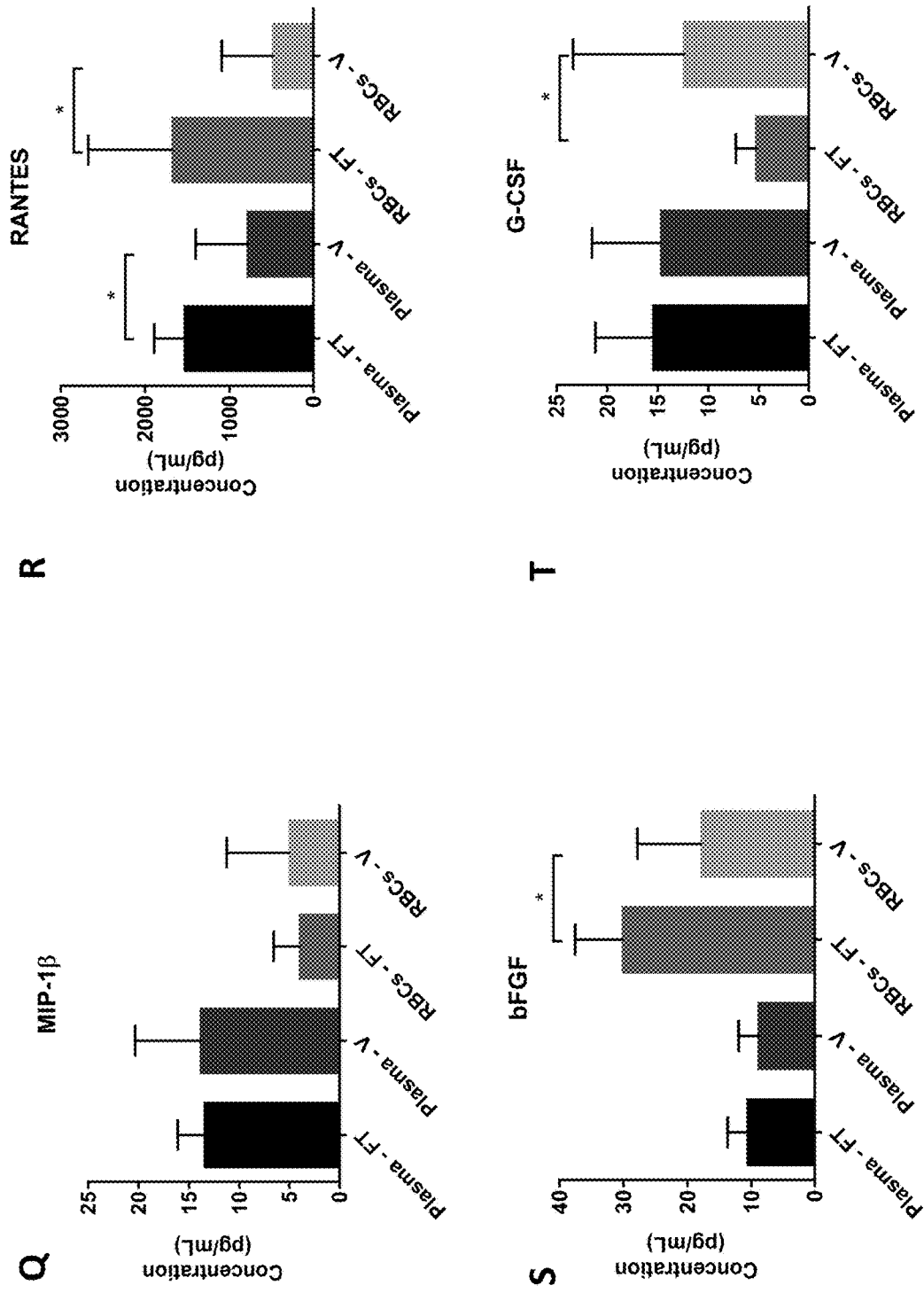
Figure 20:
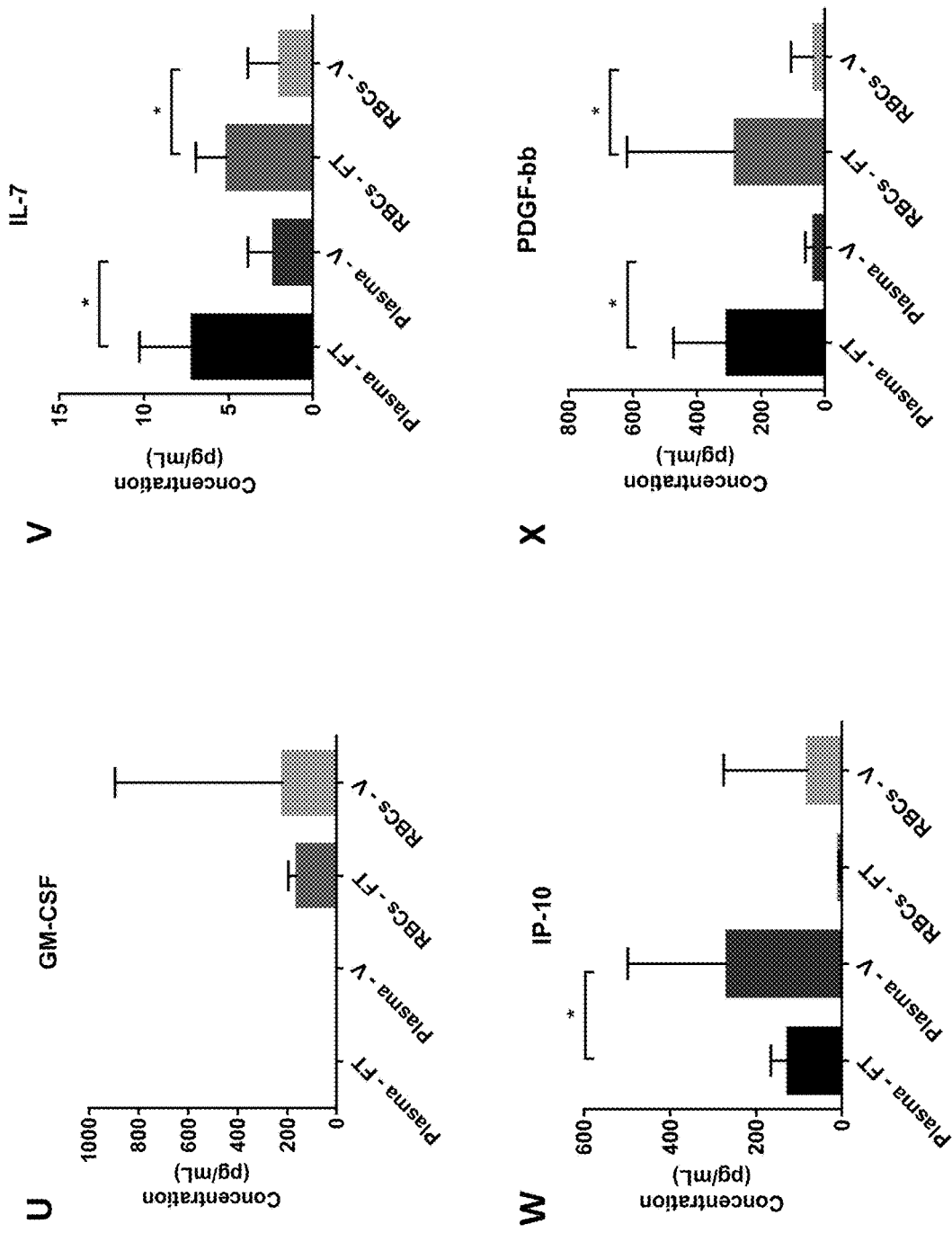
Figure 20:
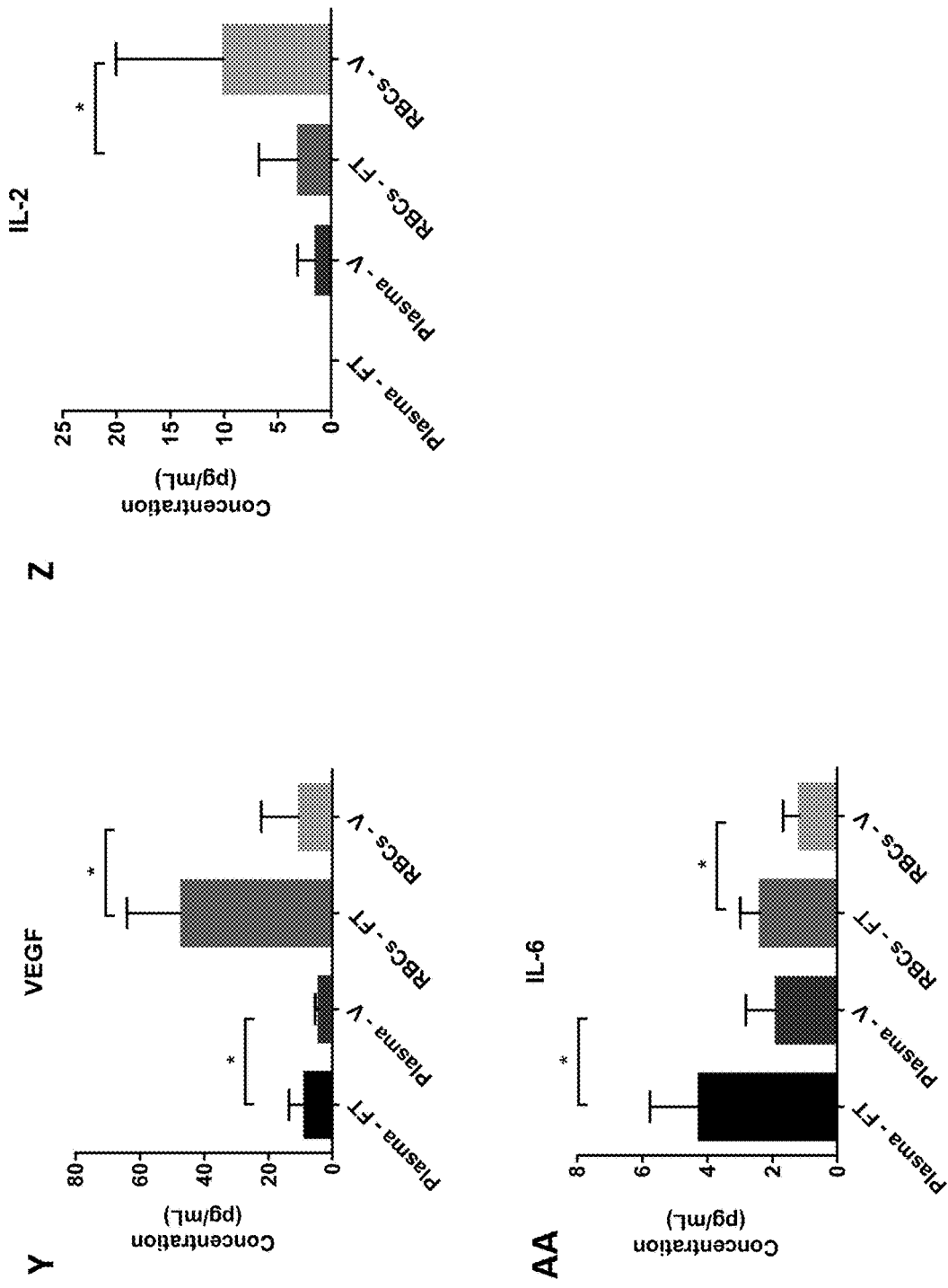

The concentration of the indicated proteins in the plasma isolated from venous blood and fingertip blood, or the lysate of red blood cells isolated from venous blood and fingertip blood are depicted in FIG. 20A-20AA. Significant differences ($p<0.05$) were determined using Student T-tests. There were consistent trends between levels of proteins in the plasma and the red blood cells when fingertip blood and venous blood were compared. For example, the concentration of IL-6 was at a significantly higher concentration in the plasma isolated from the fingertip as opposed to that in venous plasma. This same trend was observed with the red blood cells, with significantly higher levels of proteins observed in the cells isolated from fingertip blood. This trend was observed for a number of proteins including, for example, IL-2, RANTES, and IP-10. For a number of proteins, higher concentrations were observed in the plasma and red blood cells isolated from fingertip blood, including, for instance, IL-1β, IL-8, and TNF-α.

For the red blood cells, the biological variation (standard deviation) was lower in the fingertip samples than the venous samples (e.g., MIP-1β, G-CSF). This suggested that analysis of the red blood cells collected from the fingertip would be more reproducible than analysis of venous blood. The opposite was observed for a number of proteins in plasma, where venous plasma was less variable than the fingertip blood (e.g., IL-7, PDGF-bb). These results supported the case for isolating and analysing red blood cells from the fingertip, where frequent blood collection could be used.

Example 10. Profile of Proteins in RBCs Versus Plasma

Given the relatively high level of proteins in red blood cells, protein levels in the red blood cells lysates were compared to that in plasma. Whole blood was collected from healthy volunteers by venipuncture (n=6) directly into EDTA VACUTAINERS ($k_2$EDTA VACUTAINERS, BD Biosciences). All fractions of blood were collected and processed at room temperature within 4 hours of collection. For multiplex analysis (BIOPLEX analysis) all samples were stored at −80° C. and were subjected to 3 freeze-thaw cycles at −80° C. to ensure complete cellular lysis prior to analysis.

The plasma, red blood cells, and white blood cells were isolated using dextran sedimentation as follows. Whole blood was centrifuged (1500 g, 10 minutes) and the upper plasma layer was discarded. The remaining cell pellet was resuspended in an equal volume of sodium chloride (0.15 M). Dextran (6% w/v in 0.15 M sodium chloride) was then added to this cellular suspension at a 1:4 ratio (dextran:cell suspension). This solution was left at room temperature for 30 minutes for red blood cell sedimentation to the bottom of the tube. After this time the upper white blood cell rich layer and the lower red blood cell fraction were separated and added into individual tubes. The lower red blood cell fraction was washed twice in phosphate buffered saline (PBS, 500 g, 5 minutes) and the remaining red blood cell pellet was frozen (−80° C.). The upper, white blood cell rich layer was washed twice in PBS (1000 g, 10 minutes). The supernatant was discarded, and any contaminating red blood cells were lysed by hypotonic shock by resuspending the cell pellet in 3 mL MILLI-Q water for 30 seconds. After this time, isotonicity was restored by adding 1 mL potassium chloride (0.65 M) and the solution was diluted up to 15 mL with PBS. The remaining cells were pelleted and washed twice in PBS (1000 g, 5 minutes). The remaining cell pellet was resuspended in PBS and frozen immediately at −80° C.

The red blood cells and white blood cells were subjected to 3 freeze-thaw cycles to ensure complete cellular lysis. Following lysis, the red blood cell lysates were diluted in PBS to the equivalent of 400 million cells/mL, and the white blood cell lysates were diluted to 20,000 cells/mL. These lysates were then analysed on the multiplex cytokine assays. Two multiplex assays were utilised. The first was the 27-plex human cytokine panel that assays for FGF basic, Eotaxin, G-CSF, GM-CSF, IFN-γ, IL-1β, IL-1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1β, PDGF-BB, RANTES, TNF-α, and VEGF, and the second was the 21-plex human cytokine panel that assays for IL-1α, IL-2Ra, IL-3, IL-12, IL-16, IL-18, CTACK, GRO-α, HGF, IFN-α2, LIF, MCP-3, M-CSF, MIF, MIG, β-NGF, SCF, SCGF-β, SDF-1α, TNF-β, TRAIL (BIOPLEX Pro 27-plex and 21-plex, Bio-Rad). The assays were performed according to manufacturer's instructions using an automated magnetic wash station (BIOPLEX Pro II, Bio-Rad) for the washing steps. The assays were run on the LUMINEX® 200™ system (Bio-Rad) and fluorescent values were collected. The calibration curve for each cytokine was analysed with 5 parametric logistic curve regression using BIOPLEX manager software (ver. 5.0, Bio-Rad, USA).

A chart indicating the concentration of the indicated proteins in plasma and in the lysate of red blood cells (400 million cells/mL) is shown in FIG. 21A-21B. The protein concentration was calculated back to the relative concentration per mL of whole blood (approximately 5 billion cells/mL) and corrected for white blood cell contamination. The fold difference between the corrected red blood cell protein concentration and plasma protein concentration was also determined (FIG. 21A-21B). Across the 48 proteins (e.g., cytokines, chemokines) analyzed there were 31 proteins that had a substantially higher concentration in RBCs than in plasma. The range of fold change increase in protein concentration in RBCs versus that in plasma (the RBC:plasma ratio) was 3.6 to 3970. The median RBC:plasma ratio was 11.3. These results suggested that a small volume of blood (e.g., $\frac{1}{10}^{th}$ of the volume of whole blood or RBCs isolated from a small volume of blood could be used detect proteins of interest (including the proteins identified in the experiment). In addition, the ability to sample a small volume of blood (through, e.g., a finger prick) would allow for frequent, minimally-invasive sampling.

Example 11. Protein Profile in RBCs Using Cationic Salts

Red blood cells were isolated using dextran sedimentation as follows. Whole blood was centrifuged (1500 g, 10 minutes) and the upper plasma layer was discarded. The remaining cell pellet was resuspended in an equal volume of sodium chloride (0.15 M). Dextran (6 w/v in 0.15 M sodium chloride) was then added to this cellular suspension at a 1:4 ratio (dextran:cell suspension). This solution was left at room temperature for 30 minutes for red blood cell sedimentation to the bottom of the tube. After this time the upper white blood cell rich layer and the lower red blood cell fraction were separated and the white blood cells discarded. The lower red blood cell fraction was washed twice in phosphate buffered saline (PBS, 500 g, 5 minutes). The supernatant was discarded, and the red blood cell pellet resuspended in either PBS or PBS containing 100 mM LiCl.

The red blood cells were subjected to 3 freeze-thaw cycles to ensure complete cellular lysis. Following lysis, the red blood cell lysates were diluted in PBS to the equivalent of 400 million cells/mL. The red blood cell lysates were analysed on a 21-plex human cytokine panel that assays for IL-1α, IL-2Ra, IL-3, IL-12, IL-16, IL-18, CTACK, GRO-α, HGF, IFN-α2, LIF, MCP-3, M-CSF, MIF, MIG, β-NGF, SCF, SCGF-β, SDF-1α, TNF-β, TRAIL (BIOPLEX Pro 27-plex and 21-plex, Bio-Rad). The assays were performed according to manufacturer's instructions using an automated magnetic wash station (BIOPLEX Pro II, Bio-Rad) for the washing steps. The assays were run on the LUMINEX® 200™ system (Bio-Rad) and fluorescent values were collected. The calibration curve for each cytokine was analysed with 5 parametric logistic curve regression using BIOPLEX manager software (ver. 5.0, Bio-Rad, USA).

Figure 22:
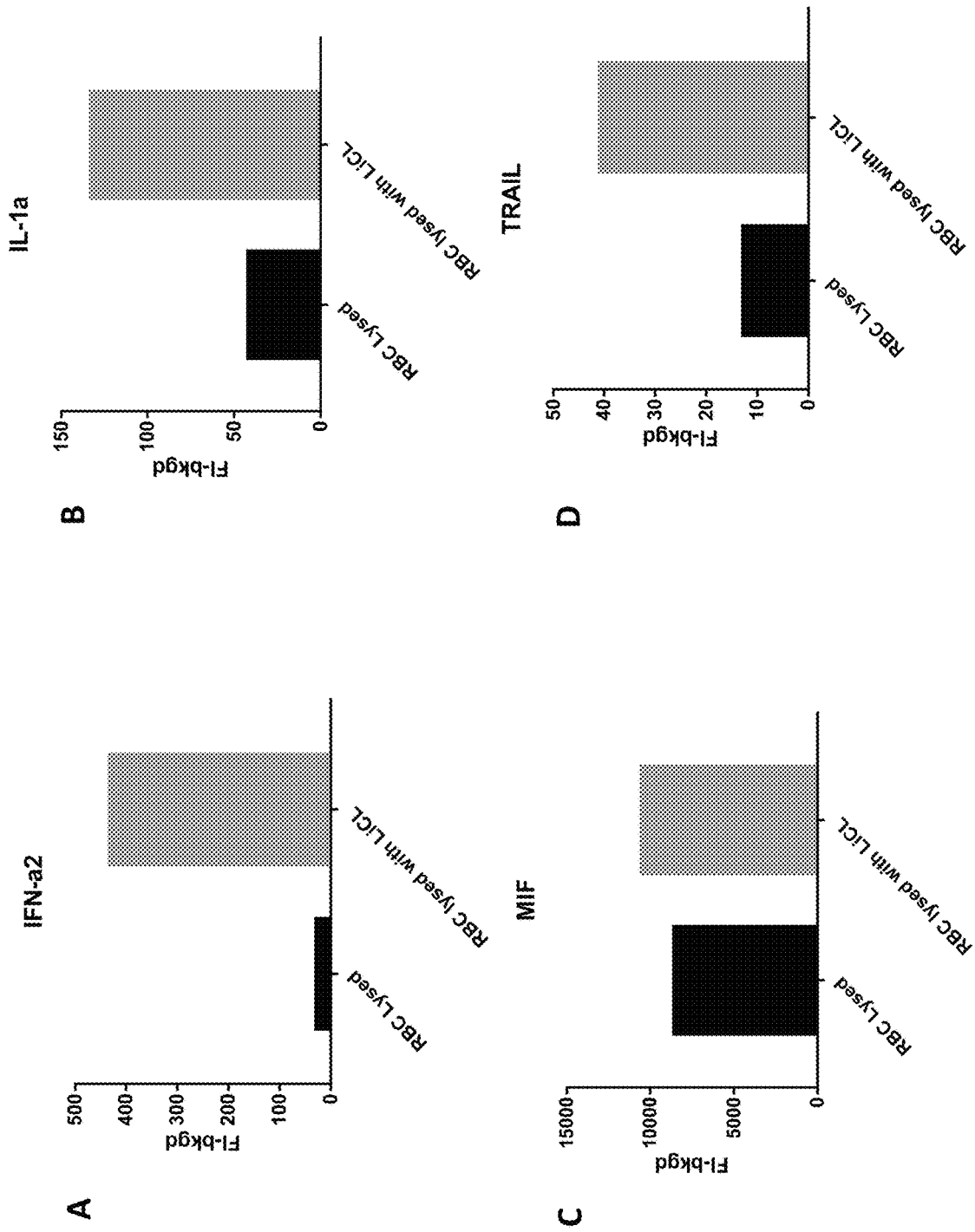
FIG. 22A-22G is a series of graphs showing the levels of various proteins in red blood cells contacted with lithium chloride.
Figure 22:
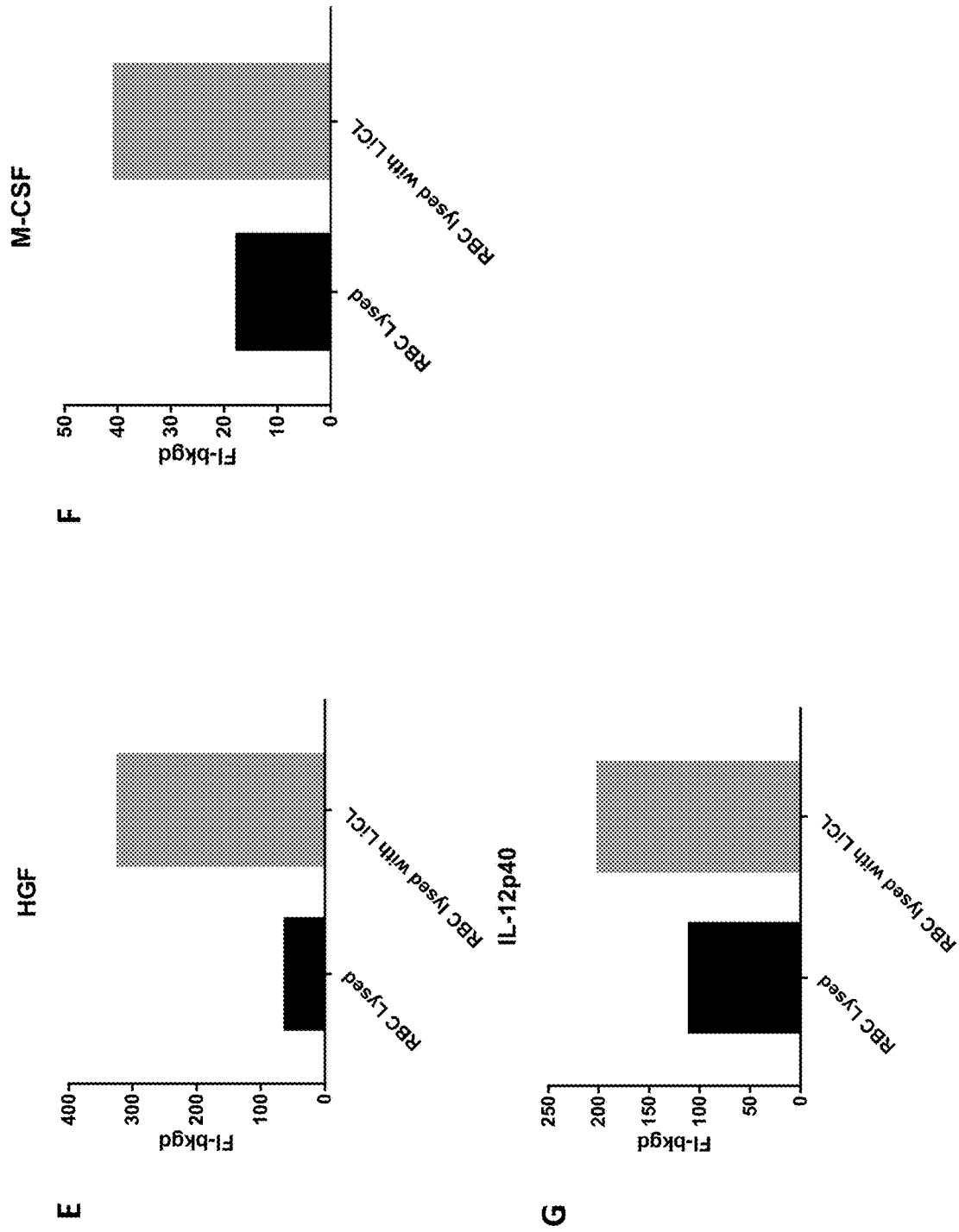

As seen in FIG. 22, lithium chloride increased and/or enhanced the level of several of the proteins in the assay.

Example 12. Protein Profile in RBCs from Healthy Individuals Versus Individuals Having Preeclampsia or Cancer The difference in the levels of proteins in the blood of healthy individuals compared to those with a disease or disorder was measured. Whole blood was collected from four groups of people including: 1) healthy volunteers, 2) healthy, pregnant women, 3) pregnant women with preeclampsia, and 4) oncology patients (see Table 12). The healthy, pregnant controls were matched with the preeclampsia samples according to gestation. Blood was collected from each volunteer by venipuncture (n≥3) directly into EDTA VACUTAINERS (k$_2$EDTA VACUTAINERS, BD Biosciences).

TABLE 12

Participant summary.

| Subject | Condition | Relevant information |
|---|---|---|
| OBS-101 | Lymphoma | Chemotherapy and radiation therapy |
| OBS-102 | Lymphoma | Chemotherapy |
| OBS-103 | Cancer (specific type unknown) | Chemotherapy |
| PE-001 | Preeclampsia | 3$^{rd}$ trimester |
| PE-002 | Preeclampsia | 3$^{rd}$ trimester |
| PE-003 | Preeclampsia | 3$^{rd}$ trimester |

All fractions of blood were collected and processed at room temperature within 4 hours of collection. For multiplex analysis (BIOPLEX analysis) all samples were stored at −80° C. and were subjected to 3 freeze-thaw cycles at −80° C. to ensure complete cellular lysis prior to analysis.

The plasma and red blood cells were isolated using dextran sedimentation as follows. Whole blood was centrifuged (1500 g, 10 minutes) and the upper plasma layer was collected. The remaining cell pellet was resuspended in an equal volume of sodium chloride (0.15 M). Dextran (6% w/v in 0.15 M sodium chloride) was then added to this cellular suspension at a 1:4 ratio (dextran:cell suspension). This solution was left at room temperature for 30 minutes for red blood cell sedimentation to the bottom of the tube. After this time the upper white blood cell rich layer was discarded and the lower red blood cell fraction was isolated. The red blood cell fraction was washed twice in phosphate buffered saline (PBS, 500 g, 5 minutes) and the remaining red blood cell pellet was counted (Coulter Act Diff, Beckman Coulter) and then frozen (−80° C.) until analysis.

The red blood cells were subjected to 3 freeze-thaw cycles to ensure complete cellular lysis. Following lysis, the red blood cell lysates were diluted in PBS to the equivalent of 400 million cells/mL. These lysates and the plasma samples (undiluted) were then analysed on the multiplex cytokine assays. Two multiplex assays were utilised. The first was the 27-plex human cytokine panel that assays for FGF basic, Eotaxin, G-CSF, GM-CSF, IFN-γ, IL-1β, IL-1ra, IL-2, IL-4, IL-5, IL-6, IL-7, IL-8, IL-9, IL-10, IL-12(p70), IL-13, IL-15, IL-17, IP-10, MCP-1, MIP-1α, MIP-1β, PDGF-BB, RANTES, TNF-α, and VEGF, and the second was the 21-plex human cytokine panel that assays for IL-1α, IL-2Ra, IL-3, IL-12, IL-16, IL-18, CTACK, GRO-α, HGF, IFN-α2, LIF, MCP-3, M-CSF, MIF, MIG, β-NGF, SCF, SCGF-β, SDF-1α, TNF-β, TRAIL (BIOPLEX Pro 27-plex and 21-plex, Bio-Rad). The assays were performed according to manufacturer's instructions using an automated magnetic wash station (BIOPLEX Pro II, Bio-Rad) for the washing steps. The assays were run on the LUMINEX® 200™ system (Bio-Rad) and fluorescent values were collected. The calibration curve for each cytokine was analysed with 5 parametric logistic curve regression using BIOPLEX manager software (ver. 5.0, Bio-Rad, USA).

Figure 23:
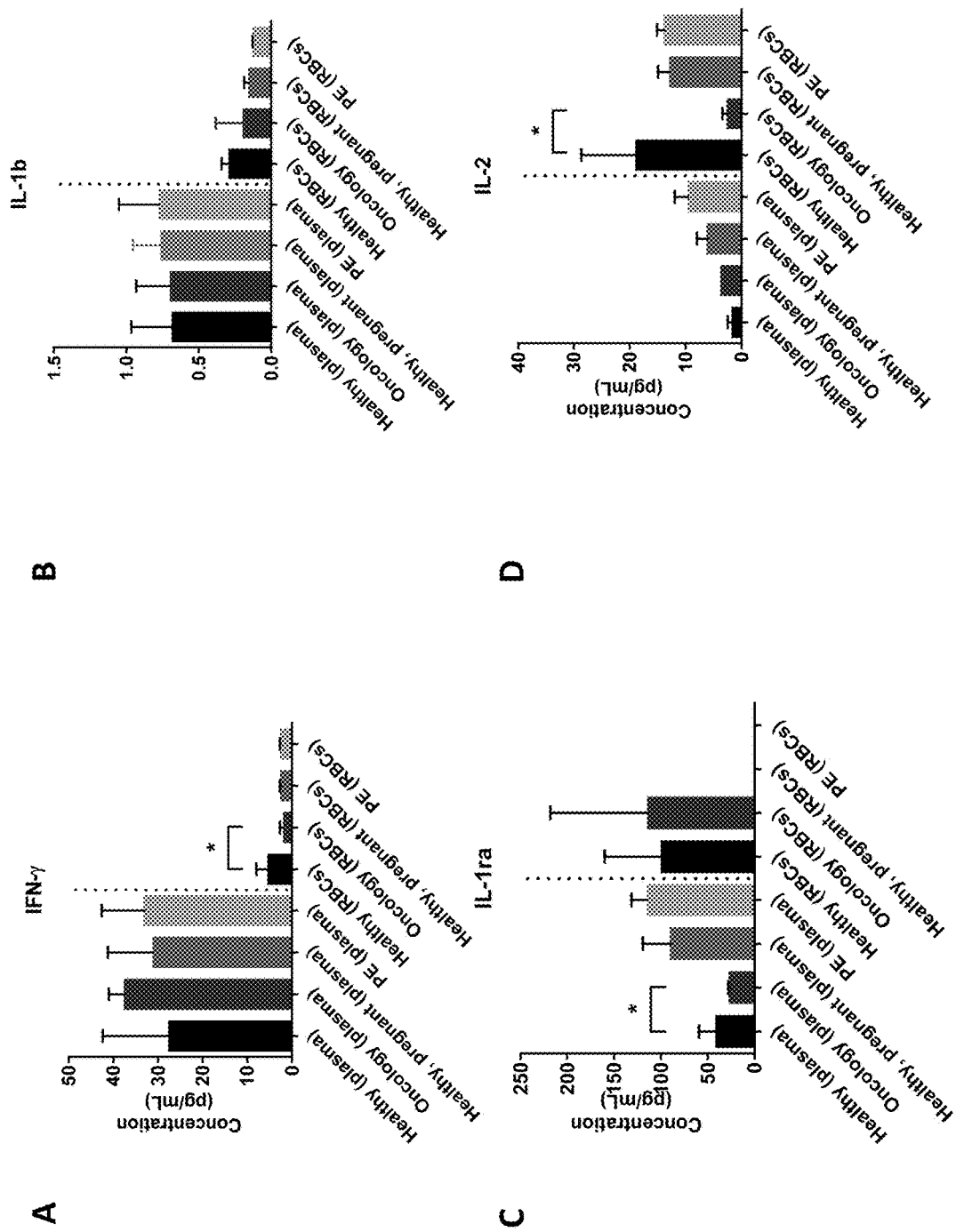
FIG. 23A-23VV is a series of graphs showing the difference in the level of various proteins in red blood cells isolated from healthy individuals, healthy pregnant women, pregnant women with preeclampsia, and oncology patients.
Figure 23:
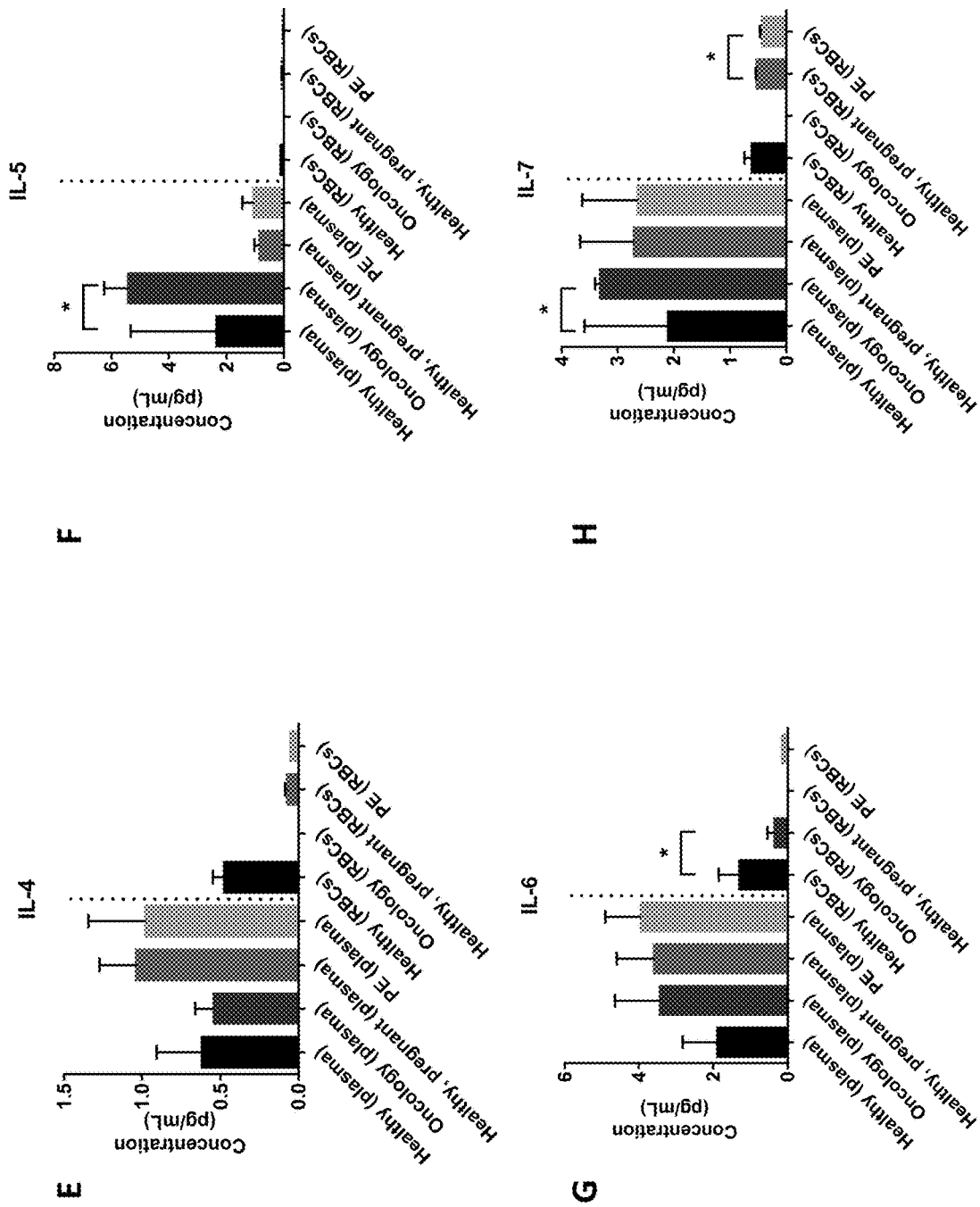
Figure 23:
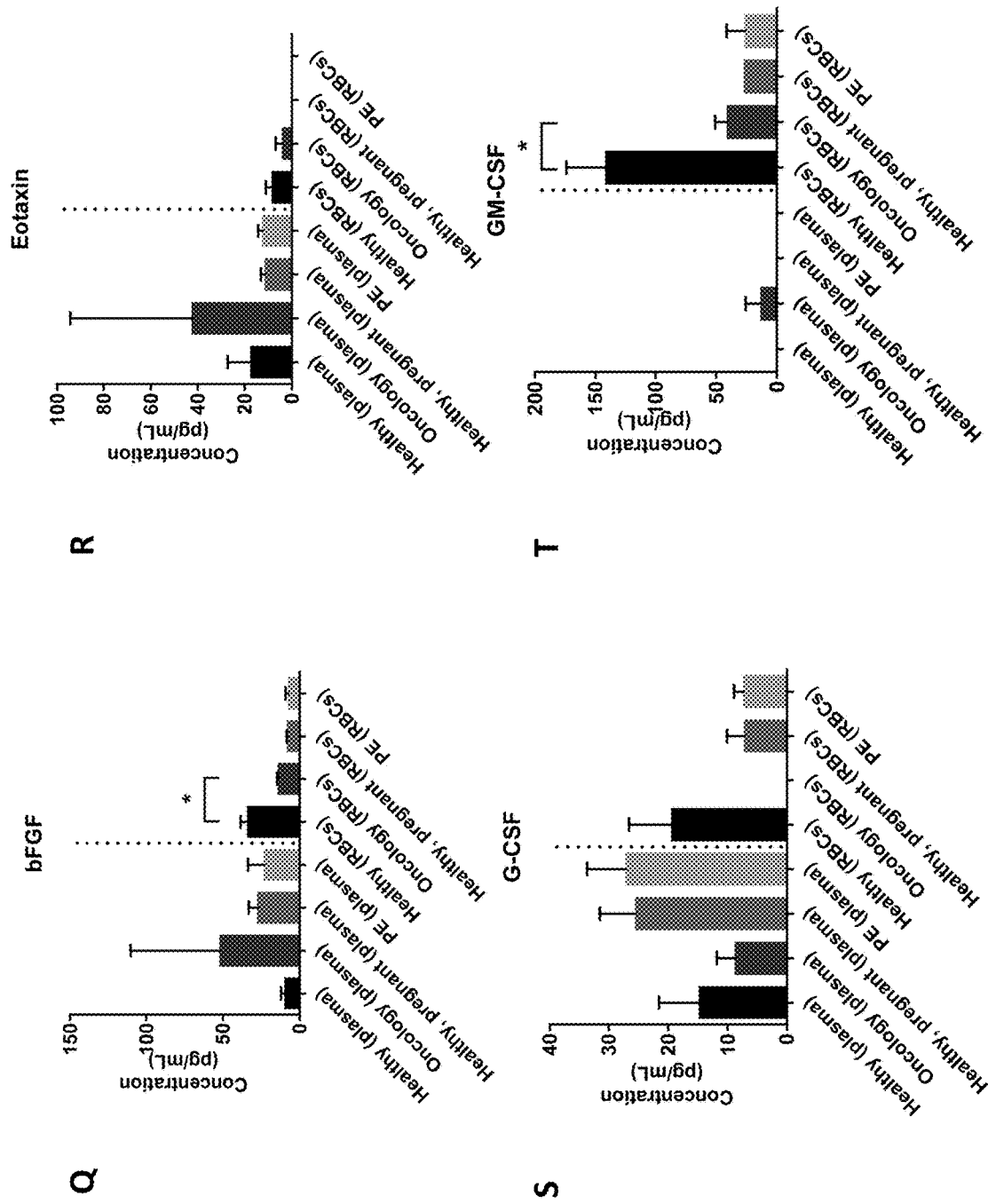
Figure 23:
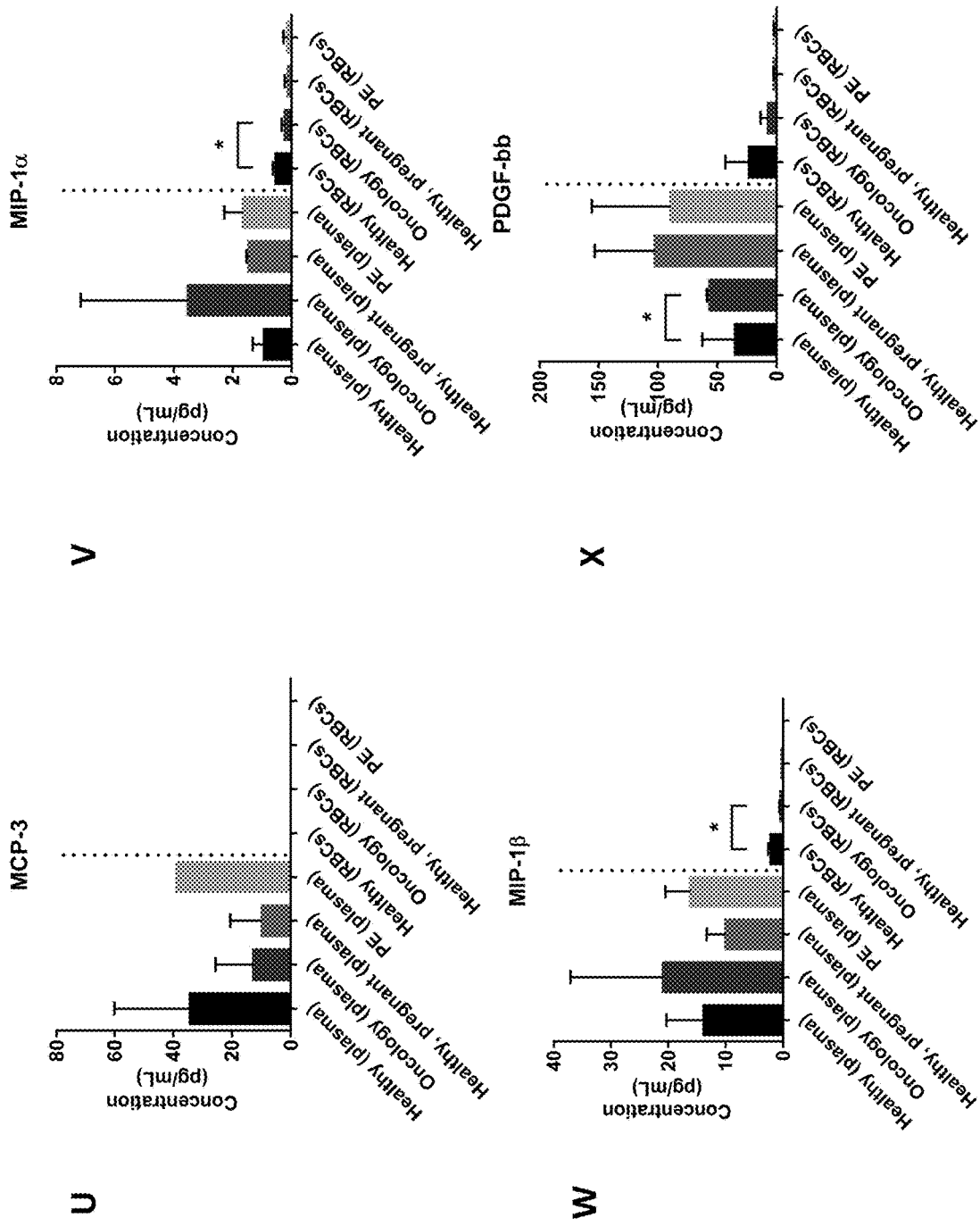
Figure 23:
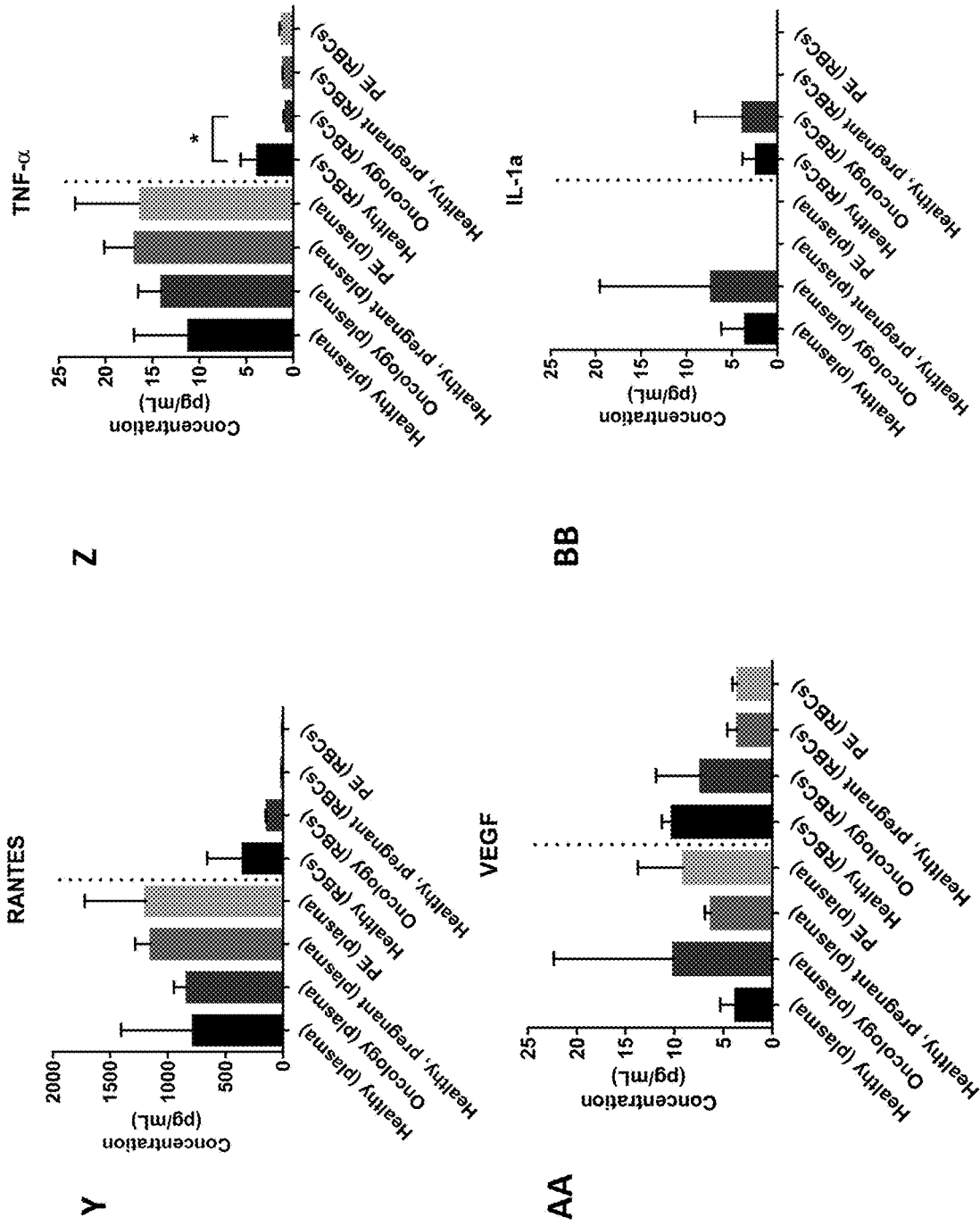
Figure 23:
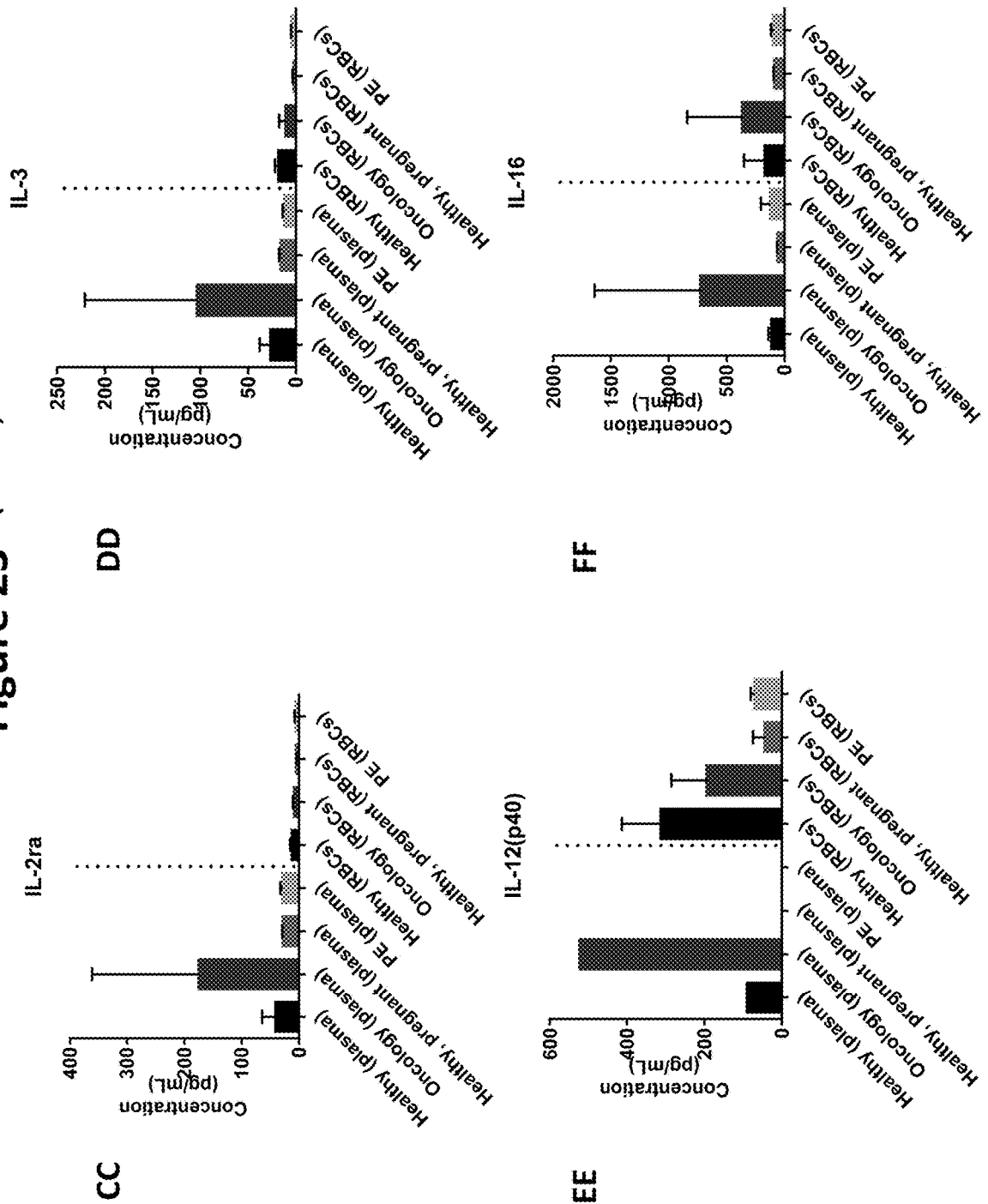
Figure 23:
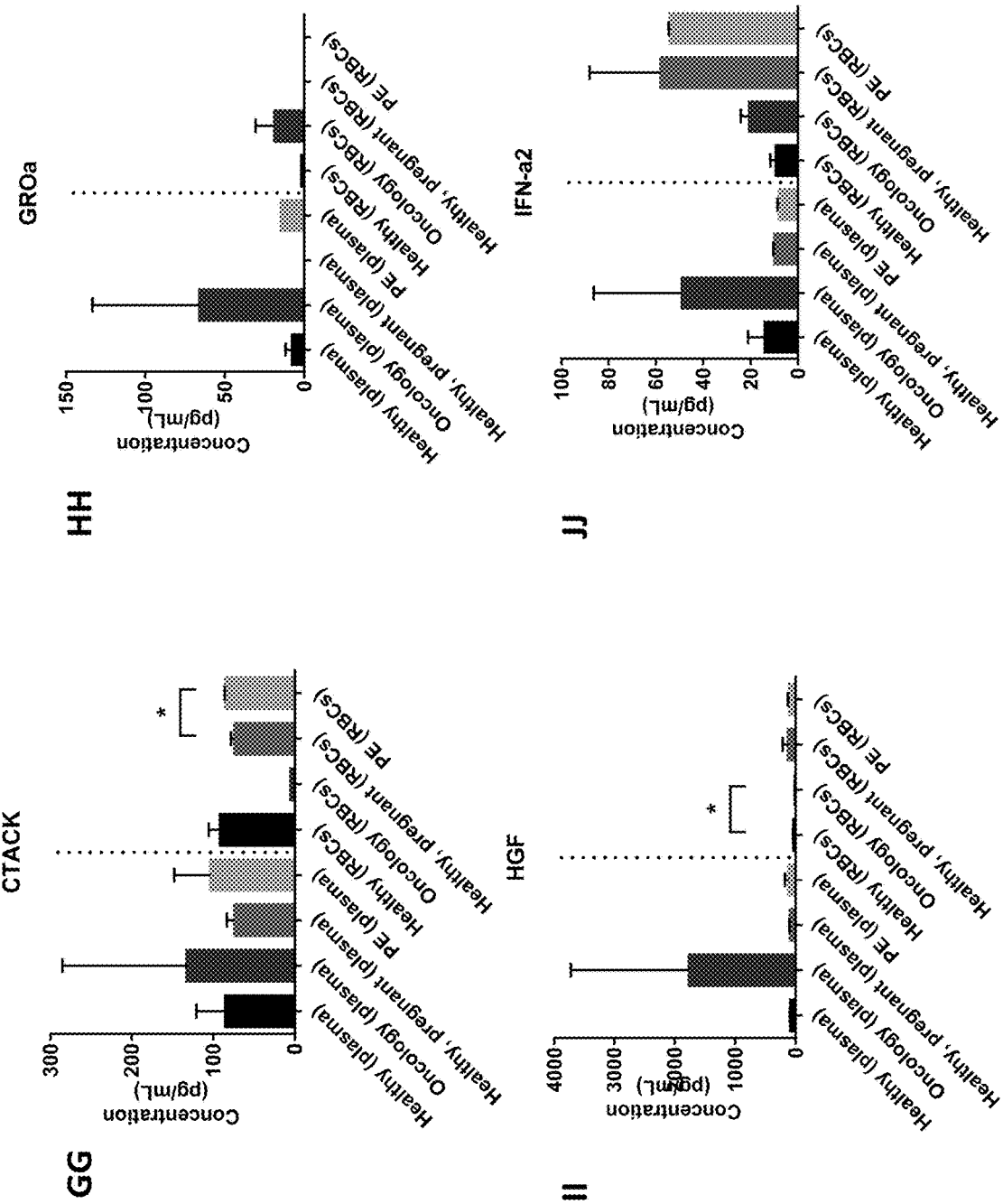
Figure 23:
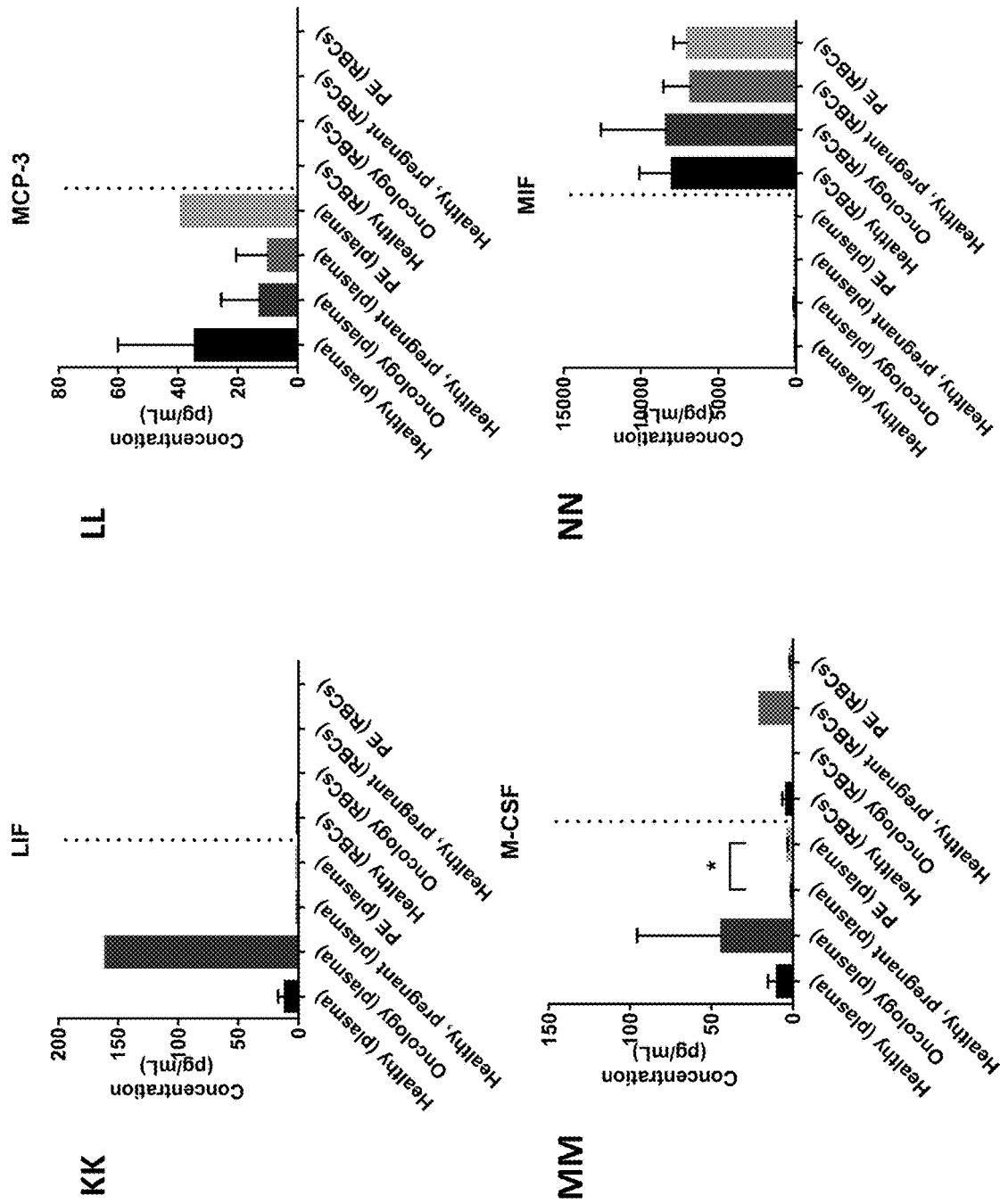
Figure 23:
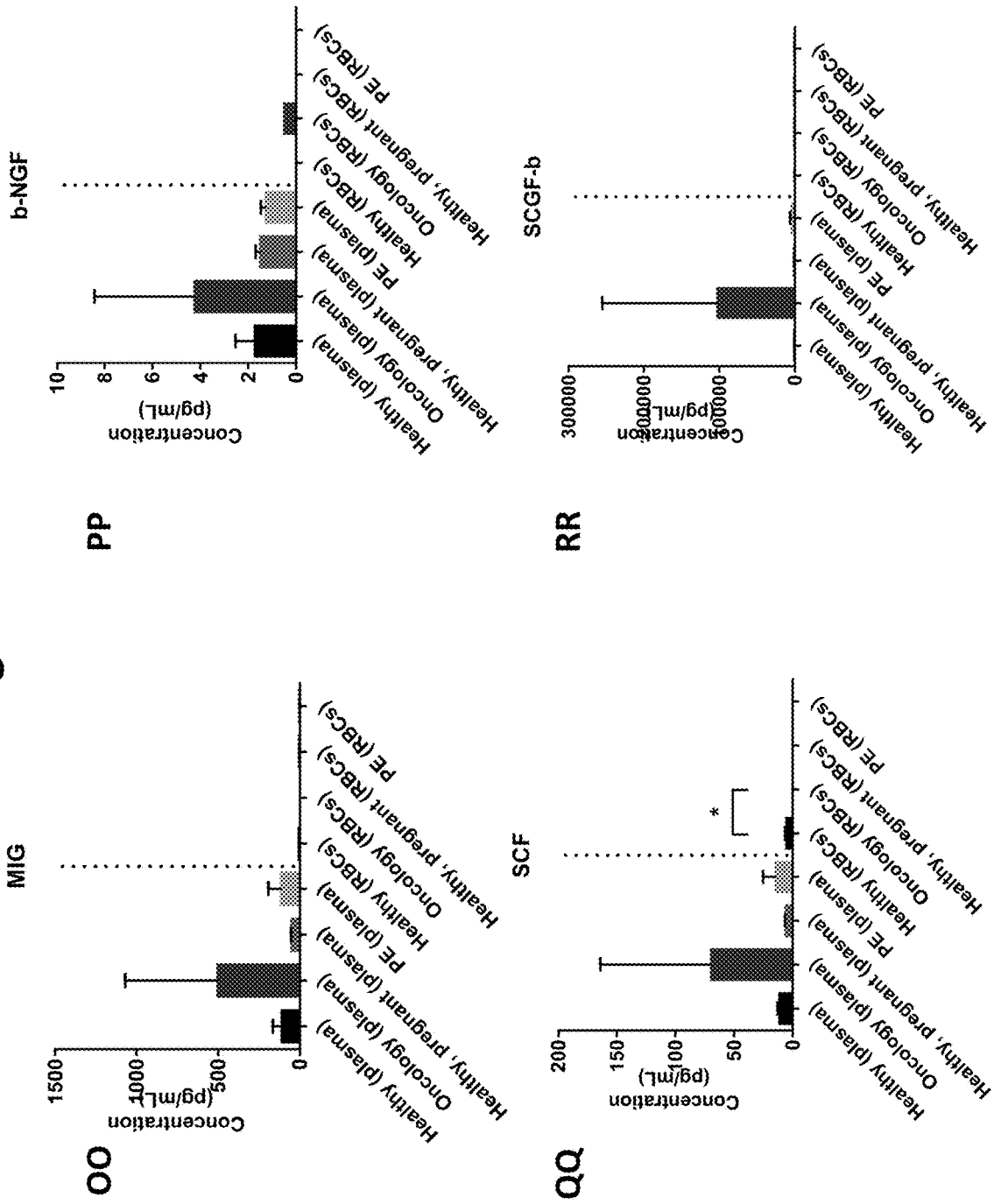
Figure 23:
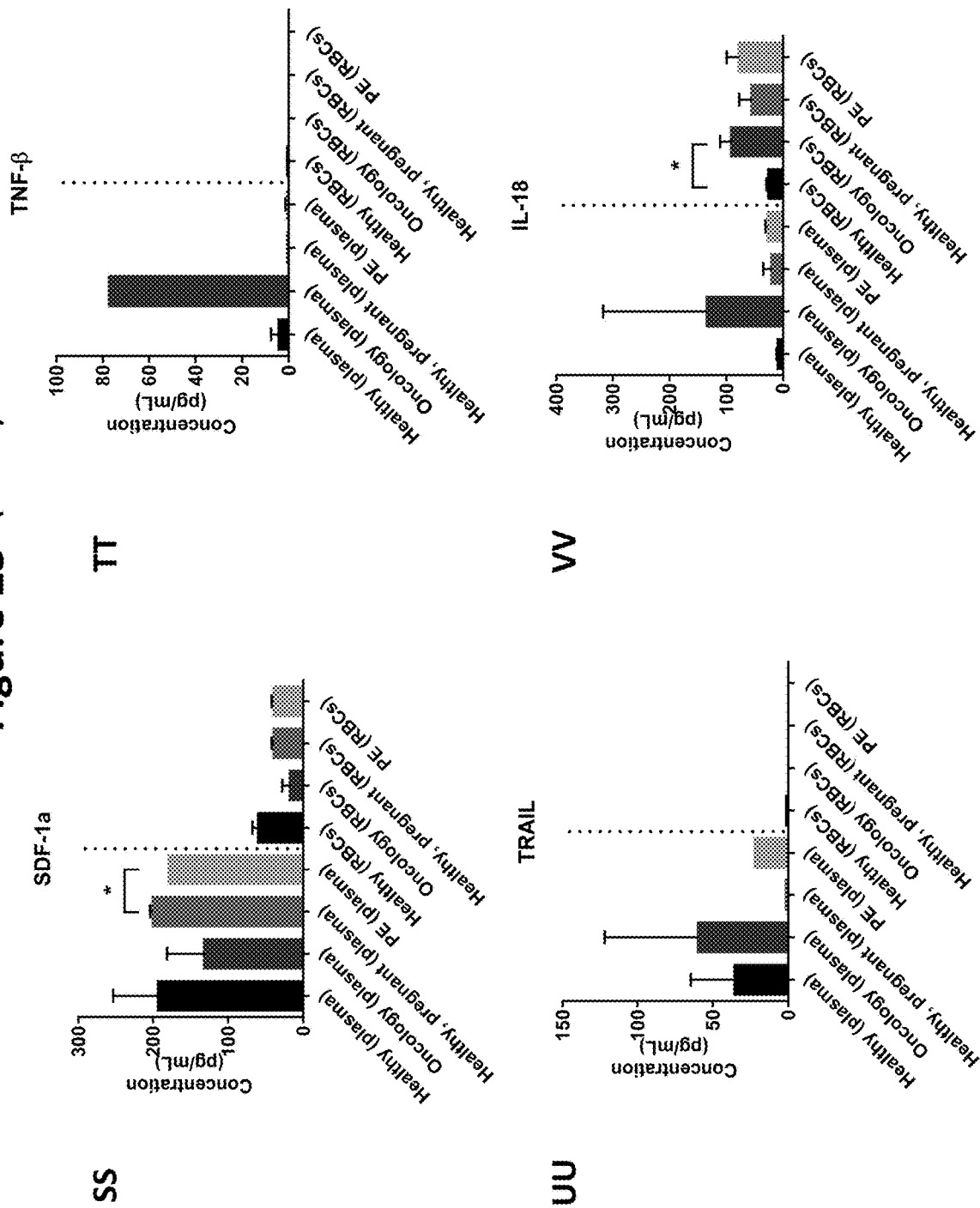

FIG. 23A-23VV shows the concentration of the indicated proteins in the plasma and the lysate of red blood cells (400 million cells/mL) from participant groups calculated back to the relative concentration per mL of whole blood (approximately 5×10$^9$ cells/mL). Significant differences (p<0.05) were determined using Student T-tests. The protein levels in the blood of healthy (non-pregnant) individuals were compared to the oncology patients and that of healthy, pregnant individuals was compared to that of pregnant individuals with preeclampsia. FIG. 24A-24C shows the fold difference between the concentration of the proteins in red blood cell as opposed to plasma.

There were significant differences between the protein levels in healthy control individuals and that in the individuals with a disease or disorder in a collection of proteins. For example, IL-2 was significantly lower (approximately 10-fold lower) in the red blood cells collected from the oncology group than in the healthy group and the chemokine CTACK was significantly higher in the red blood cells collected from the preeclampsia group than the healthy, pregnant group. In addition, twenty-eight of the 48 cytokines had a level of protein in RBCs that substantially exceeded the plasma level (greater than 2:1), with the fold change ranging from 2:1 to ~280:1 (RBC:plasma ratio). The median RBC-plasma ratio was 5.9:1. The results of the study demonstrated that red blood cells may be a useful tool for identifying biomarkers in disease. Moreover, analysis of red blood cells in conjunction with plasma could provide more information about the disease state that is currently unachievable, especially in instances in which there are no clear differences in protein levels in plasma alone, but identifiable differences in red blood cells (e.g., bFGF) or between red blood cells and plasma.

Example 13. Protein Profile in RBCs and RBC Protein Release from Healthy Individuals Versus Individuals Having Preeclampsia or Cancer The levels of proteins released by red blood cells was evaluated in healthy individuals and those with a disease or disorder. Whole blood was collected from four groups of people including: 1) healthy volunteers, 2) healthy, pregnant women, 3) pregnant women with pre-eclampsia, and 4) oncology patients (Table 13).

TABLE 13

Participant summary

| Subject | Condition | Relevant information |
|---------|-----------|----------------------|
| OBS-101 | Lymphoma | Chemotherapy and radiation therapy |
| OBS-102 | Lymphoma | Chemotherapy |
| OBS-103 | Cancer (specific type unknown) | Chemotherapy |
| PE-001 | Preeclampsia | $3^{rd}$ trimester |
| PE-002 | Preeclampsia | $3^{rd}$ trimester |
| PE-003 | Preeclampsia | $3^{rd}$ trimester |

The healthy, pregnant control samples were matched with the preeclampsia samples according to gestation. Blood was collected from each volunteer by venipuncture (n≥3) directly into EDTA VACUTAINERS ($k_2$EDTA VACUTAINERS, BD Biosciences). All fractions of blood were collected and processed at room temperature within 4 hours of collection. For multiplex analysis (BIOPLEX analysis) all samples were stored at −80° C. and were subjected to 3 freeze-thaw cycles at −80° C. to ensure complete cellular lysis prior to analysis.

The red blood cells were isolated using dextran sedimentation as follows. Whole blood was centrifuged (1500 g, 10 minutes) and the upper plasma layer was discarded. The remaining cell pellet was resuspended in an equal volume of sodium chloride (0.15 M). Dextran (6 w/v in 0.15 M sodium chloride) was then added to this cellular suspension at a 1:4 ratio (dextran:cell suspension). This solution was left at room temperature for 30 minutes for red blood cell sedimentation to the bottom of the tube. After this time the upper white blood cell rich layer was discarded and the lower red blood cell fraction was isolated. The red blood cell fraction was washed twice in phosphate buffered saline (PBS, 500 g, 5 minutes) and the remaining red blood cell pellet was counted (Coulter Act Diff, Beckman Coulter). The red blood cells were then diluted to 400 million cells/mL in PBS and were incubated at 37° C. and 5% $CO_2$ for 24 hrs. After incubation, the resulting conditioned PBS was isolated by centrifugation (500 g, 5 minutes). All samples were stored at −80° C., and underwent 3 freeze/thaw cycles before analysis. The conditioned PBS samples were then analysed on the multiplex cytokine assays. Two multiplex assays were utilised. The first was the 27-plex human cytokine panel that assays for FGF basic, Eotaxin, G-CSF, GM-CSF, IL-1ra, IL-4, IL-5, IL-6, IL-7, IL-8, IL-9, IL-10, IL-12(p70), IL-13, IL-15, IL-17, IP-10, MCP-1, MIP-1a, MIP-1β, PDGF-BB, RANTES, TNF-α, and VEGF, and the second was the 21-plex human cytokine panel that assays for IL-1α, IL-2Ra, IL-3, IL-12, IL-16, IL-18, CTACK, GRO-α, HGF, LIF, MCP-3, M-CSF, MIF, MIG, β-NGF, SCF, SCGF-β, SDF-1α, TNF-β, TRAIL (BIOPLEX Pro 27-plex and 21-plex, Bio-Rad). The assays were performed according to the manufacturer's instructions using an automated magnetic wash station (BIOPLEX Pro II, Bio-Rad) for the washing steps. The assays were run on the LUMINEX® 200™ system (Bio-Rad) and fluorescent values were collected. The calibration curve for each cytokine was analysed with 5 parametric logistic curve regression using BIOPLEX manager software (ver. 5.0, Bio-Rad, USA).

Figure 25:
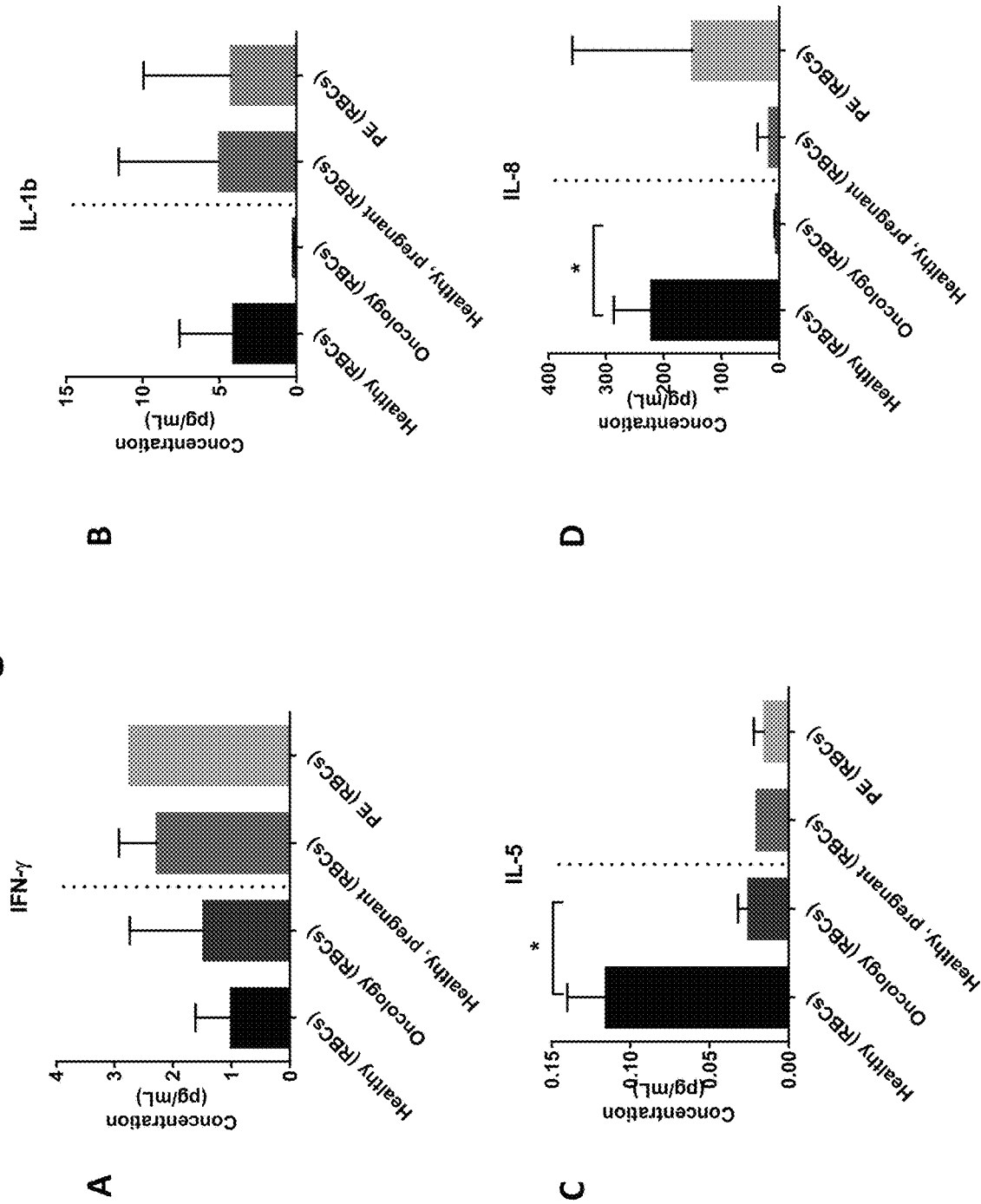
FIG. 25A-25RR is graphs is a series of graphs showing the levels of various proteins secreted or released from red blood cells isolated from healthy individuals, healthy pregnant women, pregnant women with preeclampsia, and oncology patients.
Figure 25:
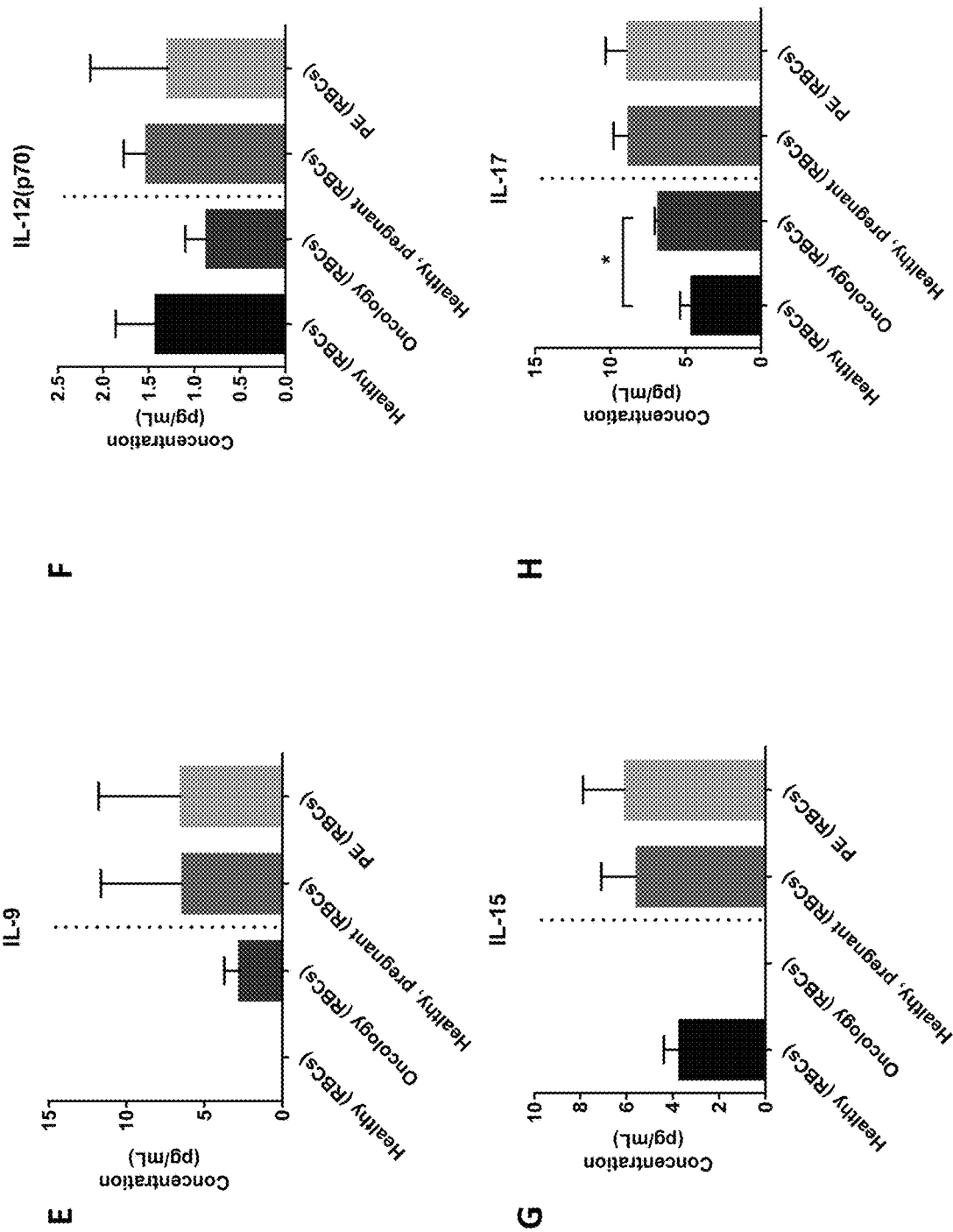
Figure 25:
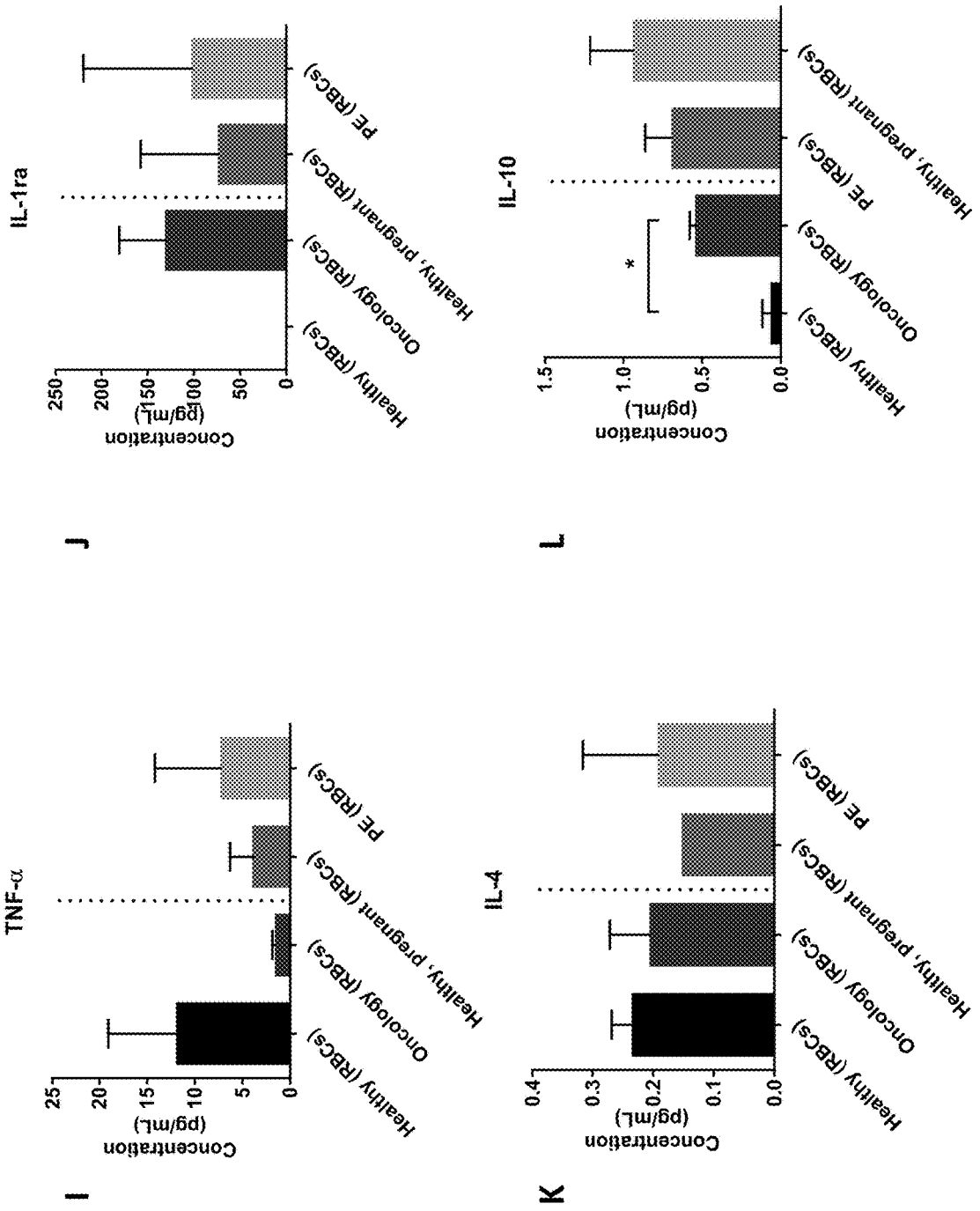
Figure 25:
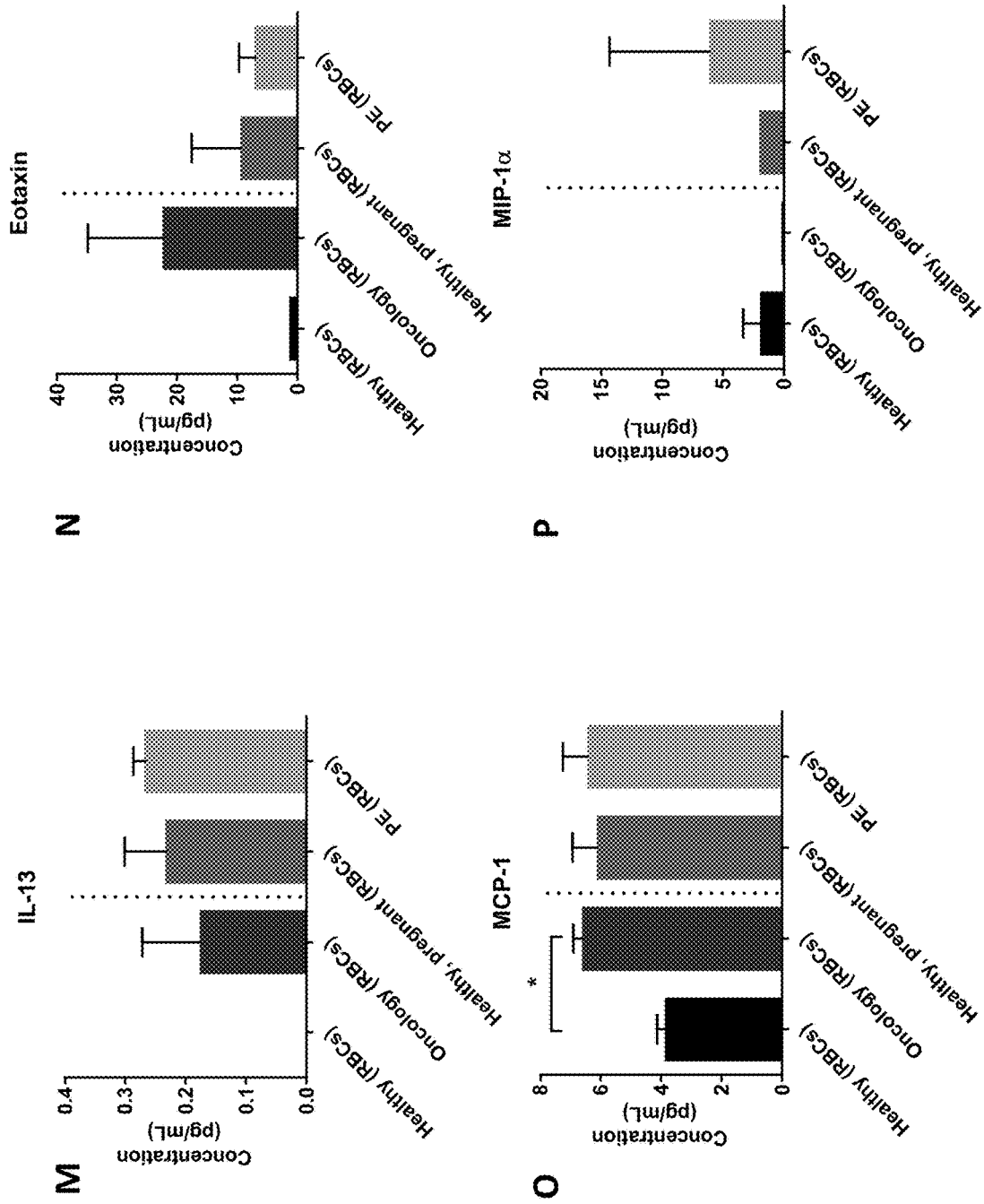
Figure 25:
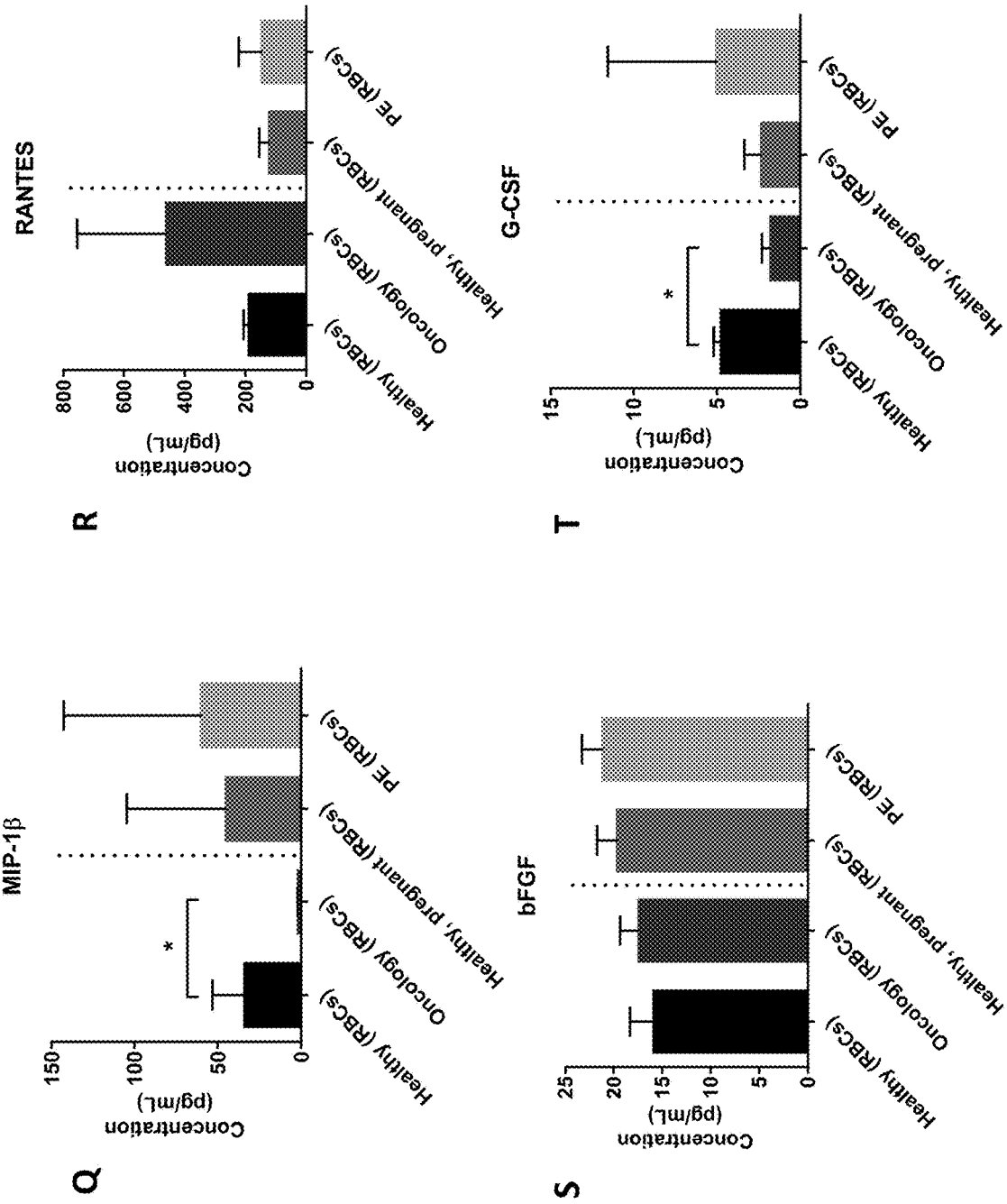
Figure 25:
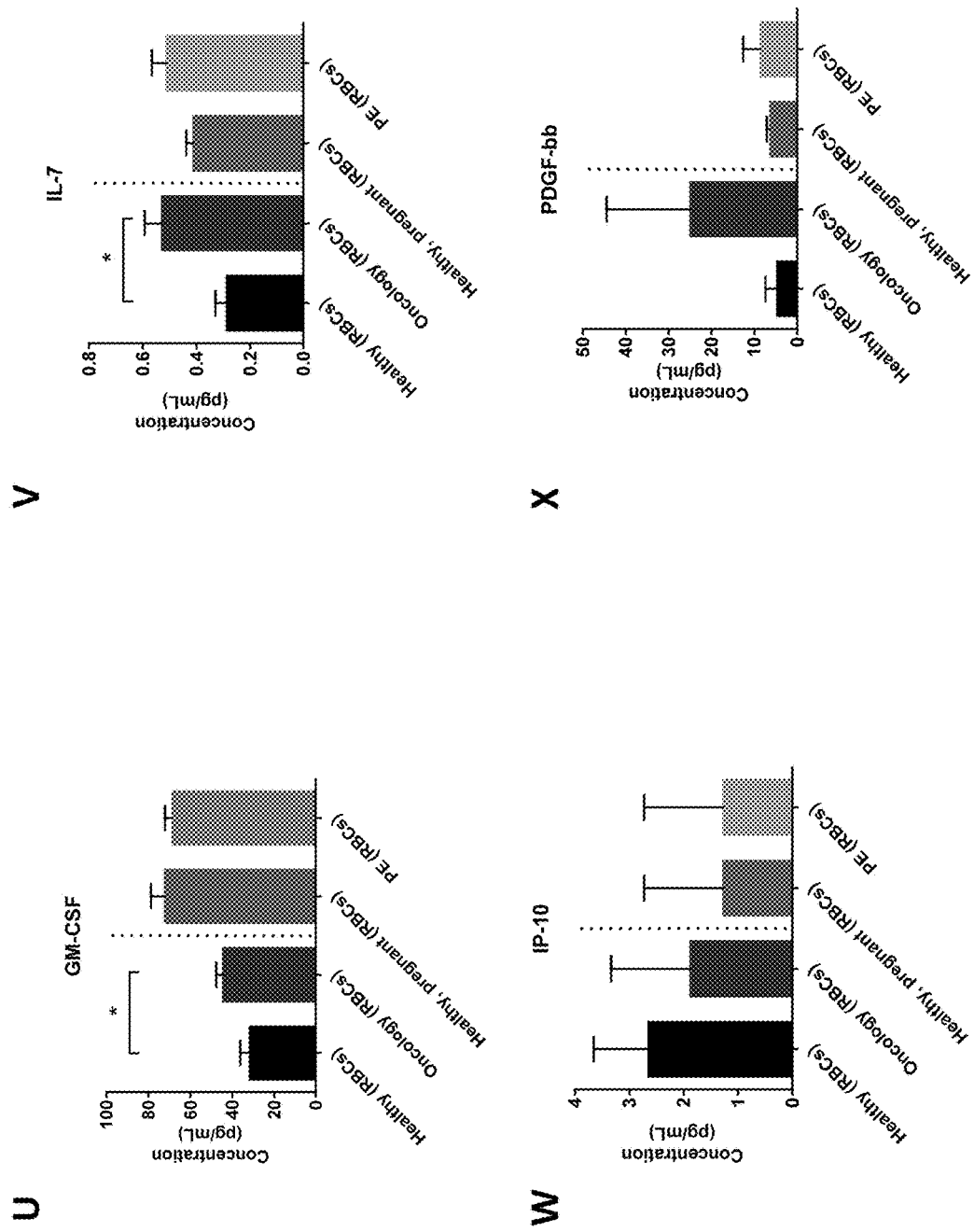
Figure 25:
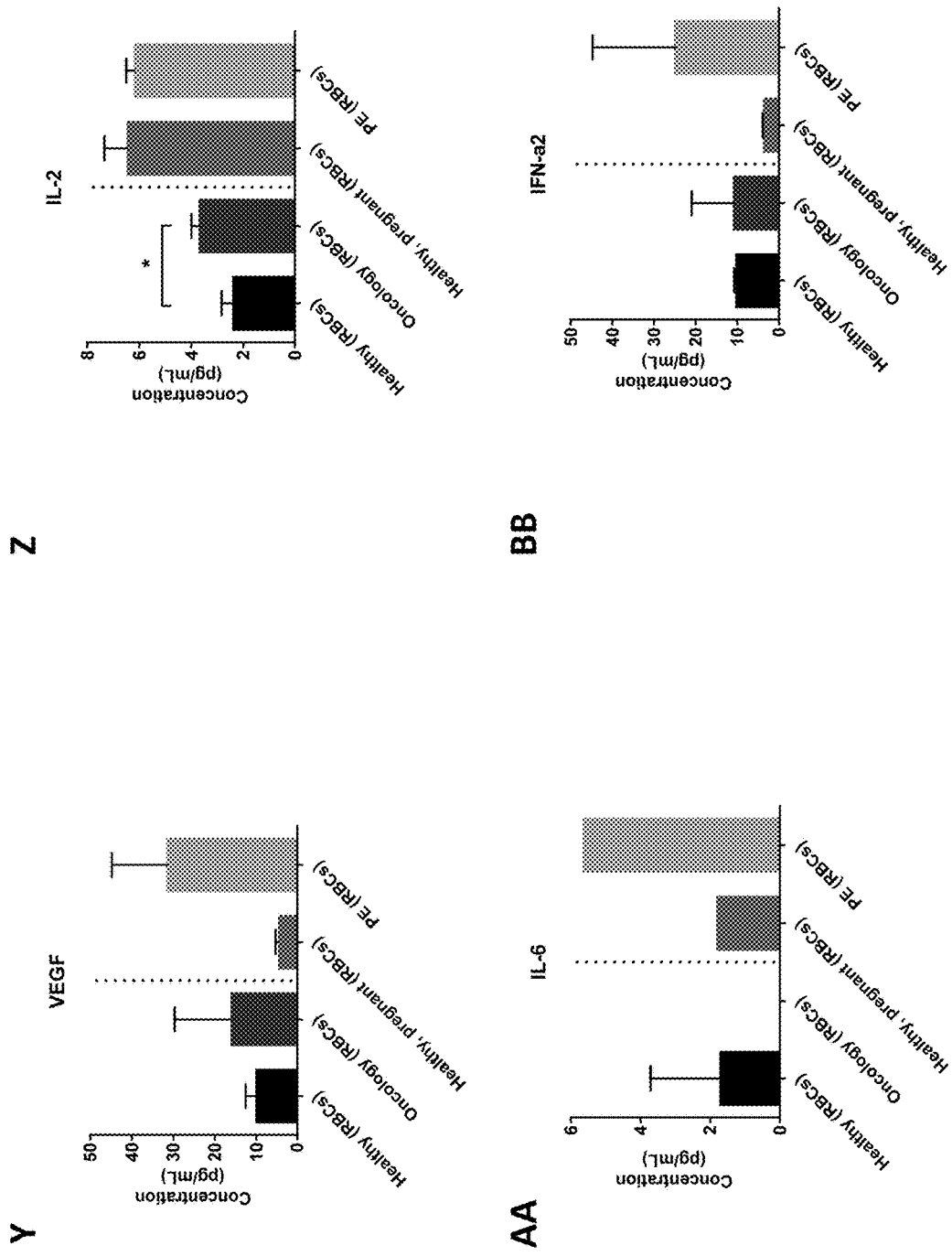
Figure 25:
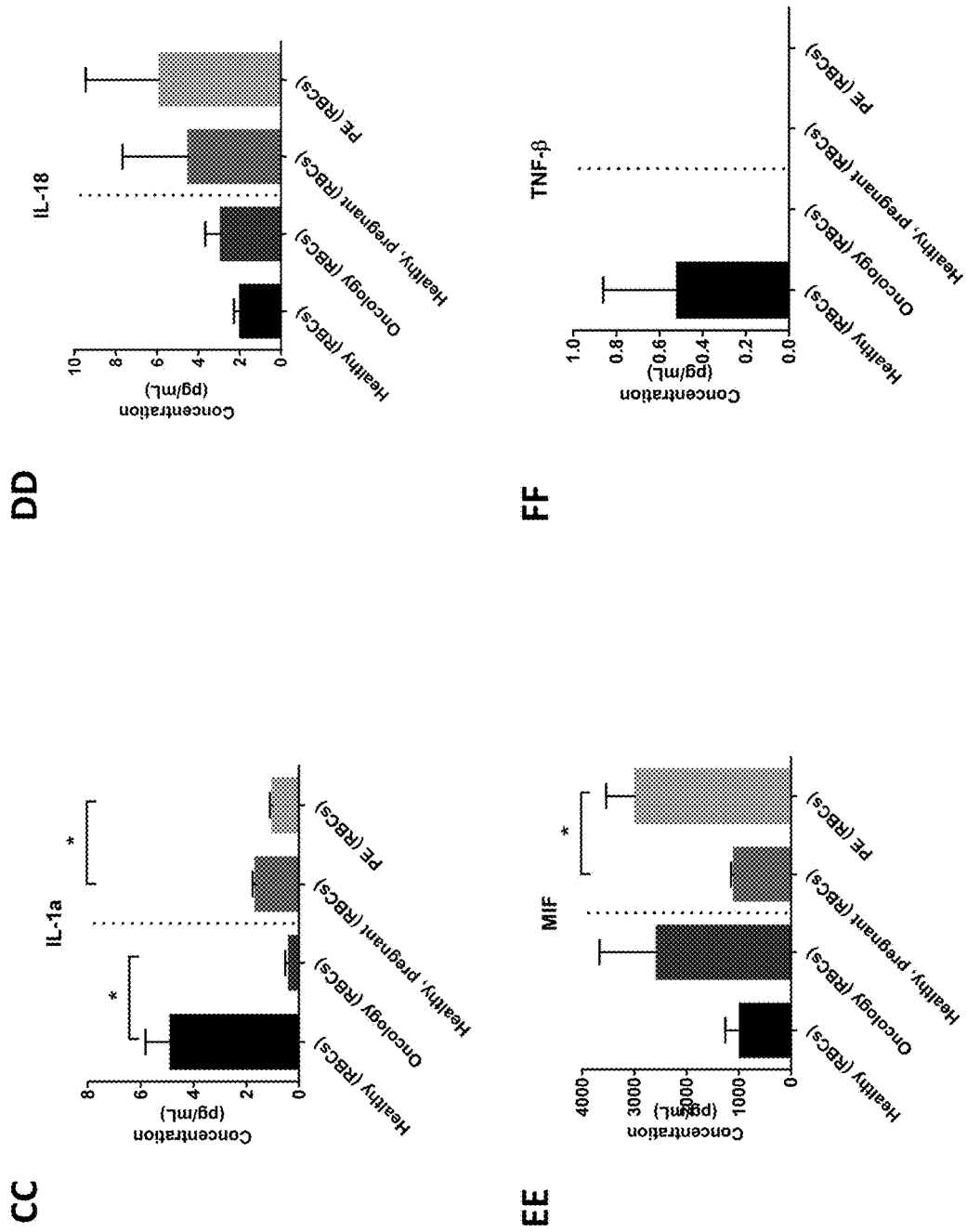
Figure 25:
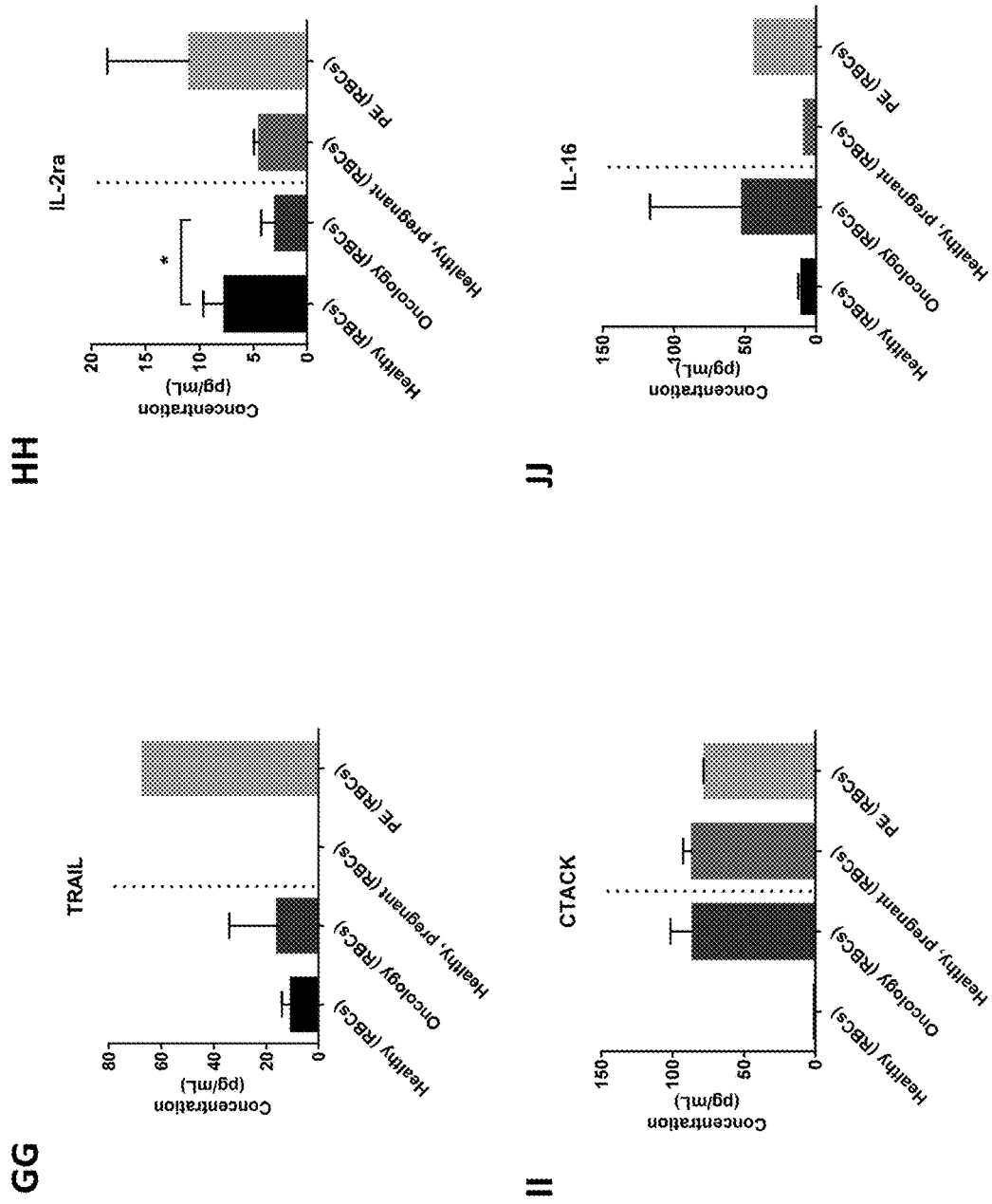
Figure 25:
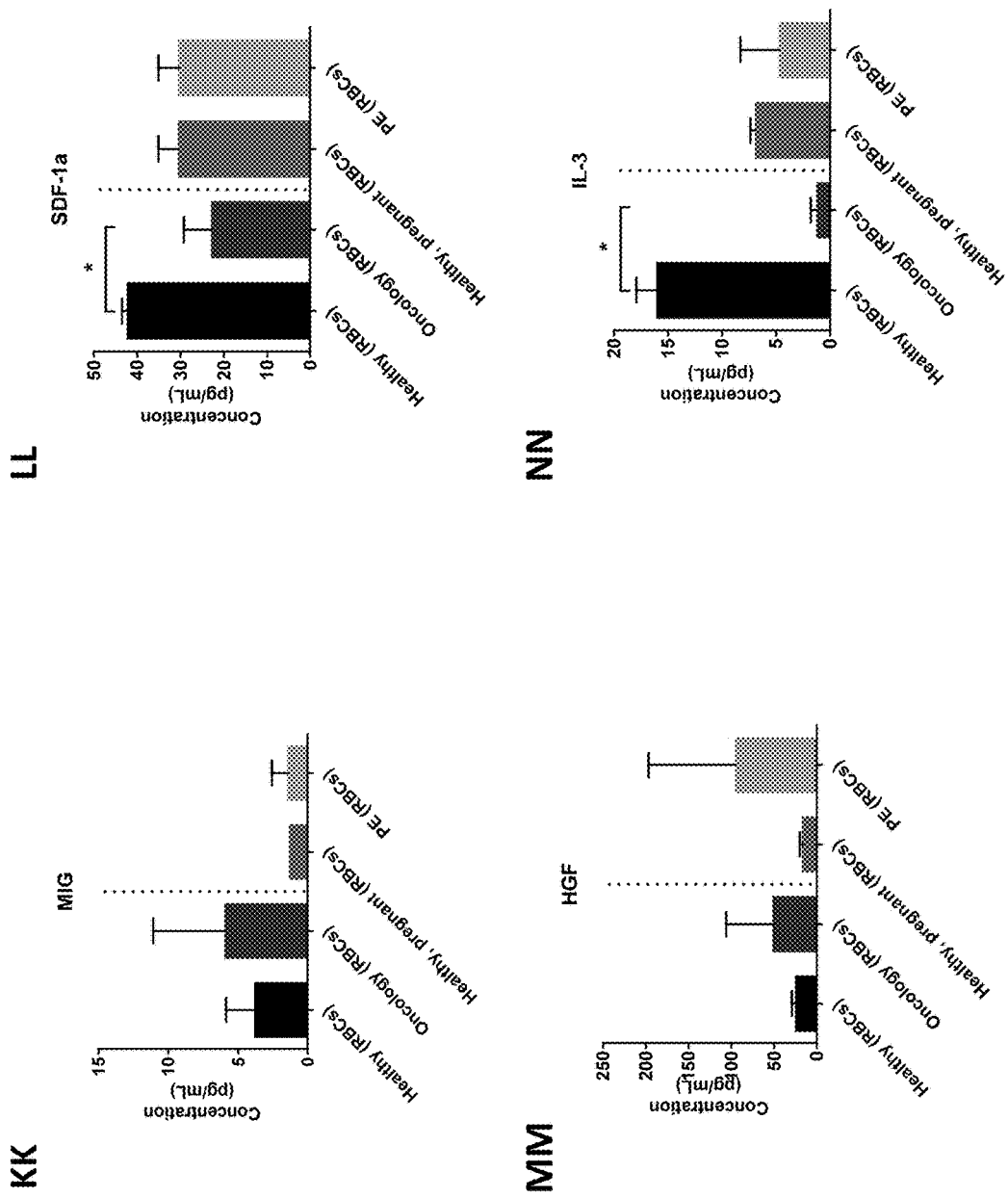
Figure 25:
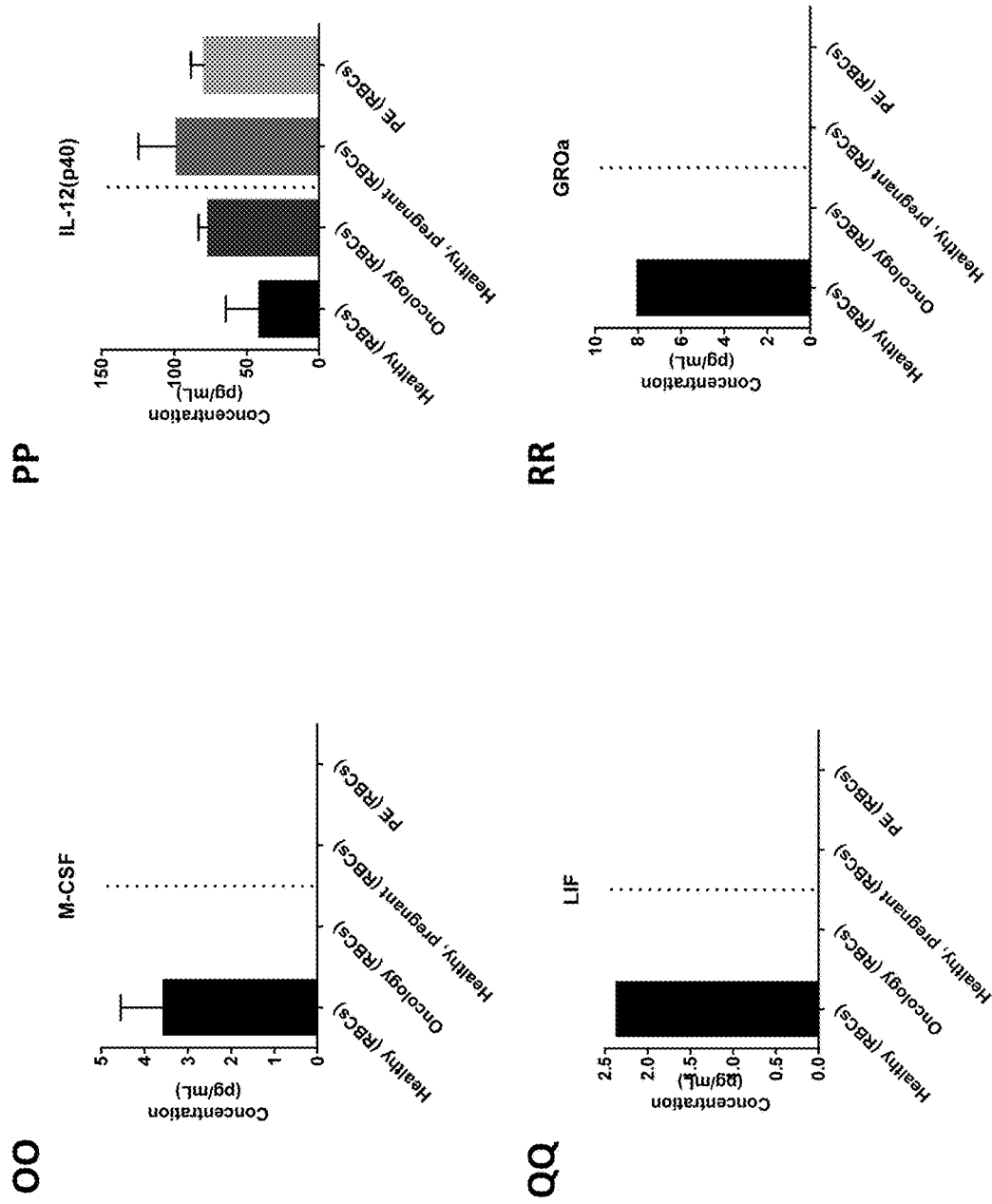

FIG. 25A-25RR shows the concentration of the indicated proteins in the red blood cell conditioned PBS from the participant groups. The conditioned PBS was produced following red blood cell incubation for 24 hrs at 37° C. Significant differences ($p<0.05$) were determined using Student T-tests. There were significant differences in protein levels between the healthy control individuals and individuals in the disease groups. For example, significantly less IL-1α and GCS-F was released from red blood cells isolated from people with cancer when compared to the healthy controls, and significantly more IL-12(p40) and Eotaxin was released from the red blood cells isolated from cancer patients than healthy individuals. Similarly, a few cytokines were significantly different between the healthy pregnant group and the group with preeclampsia, such as MIF The results suggested that analysis of the secretome of red blood cells could be a useful diagnostic tool for identifying and tracking biomarkers in disease. Analysis of the secretion of red blood cells (red blood cell protein release) could provide additional information regarding disease state.

Example 14. Other Exemplary Non-Limiting Embodiments

Further advantages of the claimed subject matter will become apparent from the following examples describing certain embodiments of the claimed subject matter.

1. A method of producing a protein profile comprising:
a.) obtaining a blood sample;
b.) leukodepleting at least a portion of the blood sample to produce a red blood cell-enriched sample; and
c.) detecting the presence of one or more proteins in a small volume of the red blood cell-enriched sample, wherein the small volume is 5 μL to 100 μL,
wherein the protein profile produced comprises one or more proteins detected in the red blood cell-enriched sample;
wherein the method further comprises measuring the level of the one or more proteins detected in the red blood cell-enriched sample, wherein the protein profile produced comprises one or more proteins measured in the red blood cell-enriched sample;
wherein the method further comprises contacting the red blood cell-enriched sample with at least one cationic salt prior to detecting the presence or measuring the level of the one or more proteins, wherein the cationic salt increases the detectable level of one or more proteins in the red blood cell-enriched sample.

2. A method of producing a protein profile comprising:
a.) obtaining a blood sample;
b.) leukodepleting at least a portion of the blood sample to produce a red blood cell-enriched sample;
c.) contacting the red blood cell-enriched sample with at least one cationic salt, wherein the cationic salt increases the detectable level of one or more proteins in the red blood cell-enriched sample; and
d.) detecting the presence of one or more proteins in a small volume of the red blood cell-enriched sample, wherein the small volume is 5 μL to 100 μL,
wherein the protein profile produced comprises one or more proteins detected in the red blood cell-enriched sample;
wherein a cation of the at least one cationic salt is a metal ion or an ammonium ion;

wherein the at least one cationic salt is selected from the group consisting of a sodium salt, a potassium salt, a magnesium salt, a lithium salt, a rubidium salt, a cesium salt, an iron salt, a francium salt, a pyridinium salt, and combinations thereof;
wherein the at least one cationic salt is a chloride salt selected from the group consisting of sodium chloride, potassium chloride, rubidium chloride, cesium chloride, lithium chloride, and combinations thereof;
wherein the at least one cationic salt is a carbonate salt selected from the group consisting of sodium carbonate, potassium carbonate, rubidium carbonate, cesium carbonate, lithium carbonate, and combinations thereof;
wherein the at least one cationic salt is an ammonium salt;
wherein the ammonium salt is selected from the group consisting of ammonium carbonate, ammonium chloride, ammonium nitrate, and combinations thereof.

3. A method of producing a protein profile comprising:
a.) obtaining a blood sample;
b.) leukodepleting at least a portion of the blood sample to produce a red blood cell-enriched sample;
c.) isolating red blood cells and plasma in the red blood cell-enriched sample;
d.) measuring the level of one or more proteins in the red blood cells and the level of the one or more proteins in the plasma; and
e.) calculating a protein ratio comprising the level of the one or more proteins in the red blood cells to the level of the one or more proteins in the plasma,
wherein the protein profile produced comprises one or more proteins that have a protein ratio of at least 2:1;
wherein the level of the one or more proteins in the red blood cells and the plasma is measured in a small volume from the red blood cell-enriched sample;
wherein the protein ratio is selected from the group consisting of at least 10:1, at least 20:1, at least 30:1, at least 40:1, at least 50:1, at least 60:1, at least 70:1, at least 80:1, at least 90:1, at least 100:1, at least 110:1, at least 120:1, at least 130:1, at least 140:1, at least 150:1, at least 160:1, at least 170:1, at least 180:1, at least 190:1, and at least 200:1,
wherein the protein ratio is selected from the group consisting of at least 2:1, at least 3:1, at least 4:1, at least 5:1, at least 6:1, at least 7:1, at least 8:1, at least 9:1, and at least 10:1.

4. A method of producing a protein profile comprising:
a.) obtaining a blood sample;
b.) leukodepleting at least a portion of the blood sample to produce a red blood cell-enriched sample;
c.) isolating red blood cells and plasma in the red blood cell-enriched sample;
d.) contacting the red blood cells with a cationic salt, wherein the at least one cationic salt increases the detectable level of one or more proteins in the red blood cells;
e.) measuring in a small volume of the red blood cell-enriched sample the level of one or more proteins in the red blood cells and the level of the one or more proteins in the plasma; and
f.) calculating a protein ratio comprising the level of the one or more proteins in the red blood cells to the level of the one or more proteins in the plasma,
wherein the protein profile produced comprises one or more proteins that have a protein ratio of at least 2:1;
wherein the protein ratio is selected from the group consisting of at least 10:1, at least 20:1, at least 30:1, at least 40:1, at least 50:1, at least 60:1, at least 70:1, at least 80:1, at least 90:1, at least 100:1, at least 110:1, at least 120:1, at least 130:1, at least 140:1, at least 150:1, at least 160:1, at least 170:1, at least 180:1, at least 190:1, and at least 200:1,
wherein the protein ratio is selected from the group consisting of at least 2:1, at least 3:1, at least 4:1, at least 5:1, at least 6:1, at least 7:1, at least 8:1, at least 9:1, and at least 10:1.

5. A method of producing a protein profile comprising:
a.) obtaining a blood sample;
b.) leukodepleting at least a portion of the blood sample to produce a red blood cell-enriched sample;
c.) incubating red blood cells in the red blood cell-enriched sample in a medium; and
d.) detecting one or more proteins in the medium,
wherein the protein profile produced comprises one or more proteins detected in the medium;
wherein the method further comprises measuring the level of the one or more proteins detected in the medium, wherein the protein profile produced comprises one or more proteins measured in the red blood cell-enriched sample;
wherein the medium is one or more selected from the group consisting of isotonic salt solution, balanced salt solution, saline, phosphate buffered saline (PBS), hank's balanced salt solution (HBSS), and/or Earles' balanced salt solution (EBSS), Roswell Park Memorial Institute medium (RPMI), minimum essential medium (MEM), Improved Minimum Essential Medium (IMEM), Eagle's minimal essential medium (EMEM), Dubelco's modified Eagle's medium (DMEM), and/or Iscove's Modified Dulbecco's Media (IMDM).

6. A method of producing a protein profile comprising:
a.) obtaining a blood sample;
b.) leukodepleting at least a portion of the blood sample to produce a red blood cell-enriched sample;
c.) incubating red blood cells in the red blood cell-enriched sample in a medium, wherein the medium contains a cationic salt that increases the detectable level of one or more proteins in the red blood cell-enriched sample; and
d.) detecting one or more proteins in the medium,
wherein the protein profile produced comprises one or more proteins detected in the medium;
wherein the method further comprises measuring the level of the one or more proteins detected in the medium, wherein the protein profile produced comprises one or more proteins measured in the red blood cell-enriched sample;
wherein the medium is one or more selected from the group consisting of isotonic salt solution, balanced salt solution, saline, phosphate buffered saline (PBS), hank's balanced salt solution (HBSS), and/or Earles' balanced salt solution (EBSS), Roswell Park Memorial Institute medium (RPMI), minimum essential medium (MEM), Improved Minimum Essential Medium (IMEM), Eagle's minimal essential medium (EMEM), Dubelco's modified Eagle's medium (DMEM), and/or Iscove's Modified Dulbecco's Media (IMDM).

7. A method of producing a protein profile comprising:
a.) obtaining a small volume blood sample;
b.) leukodepleting at least a portion of the small volume blood sample to produce a red blood cell-enriched sample; and
c.) detecting one or more proteins in the red blood cell-enriched sample,
wherein the protein profile produced comprises one or more proteins detected in the red blood cell-enriched sample;
wherein the method further comprising measuring the level of the one or more proteins detected in the red blood cell-enriched sample, wherein the protein profile produced comprises one or more proteins measured in the red blood cell-enriched sample;
wherein the small volume blood sample is 5 μL to 100 μL;
wherein the small volume blood sample is 5 μL to 20 μL;

wherein the blood sample is obtained from a subject;
wherein the subject is a human or a non-human animal;
wherein the small volume blood sample is obtained from a finger, heel, ear, or tail;
wherein the small volume blood sample is obtained by finger prick, heel prick, or ear prick;
wherein the subject is a human;
wherein the small volume blood sample is obtained from a finger, heel, or ear;
wherein the small volume blood sample is obtained by finger prick, heel prick, ear prick, or tail prick;
wherein the subject is a non-human animal selected from the group consisting of a mouse, rat, hamster, ferret, gerbil, rabbit, monkey, chimpanzee, horse, pony, donkey, sheep, pig, chicken, goat, cat, and dog;
wherein the small volume blood sample is obtained by a tail prick or an ear prick;
wherein the small volume blood sample is obtained a number of times selected from the group consisting of one or more times per day, two or more times per day, three or more times per day, four or more times per day, and five or more times per day;
wherein the small volume blood sample is obtained a number of times selected from the group consisting of one or more times per week, two or more times per week, three or more times per week, four or more times per week, five or more times per week, six or more times per week, and seven or more times per week;
wherein the small volume blood sample is obtained daily;
wherein the small volume blood sample is obtained a number of times selected from the group consisting of once a week, once every two weeks, once every three weeks, and once every four weeks;
wherein the small volume blood sample is obtained once a month.

8. A method of producing a disease protein profile comprising:
a.) obtaining at least one protein profile produced according to one or more of one or more of the above examples from:
(i) a subject having a disease or disorder, and
(ii) at least one subject not having the disease or disorder; and
b.) comparing the protein profile of the subject having the disease or disorder to the protein profile of the at least one subject not having the disease or disorder,
wherein the disease protein profile produced comprises one or more proteins that have a different presence or level in the protein profile from the subject having the disease or disorder compared to the protein profile of the at least one subject not having the disease or disorder;
wherein the disease or disorder is cancer;
wherein the disease protein profile is a cancer protein profile comprising one or more proteins selected from the group consisting of IL-1, IL-2, IL-4, IL-5, IL-6, IL-8, IL-10, IL-12, IL-15, IL-17, TNF-α, TGF-β, and IFN-γ;
wherein the disease or disorder is preeclampsia;
wherein the disease profile is a preeclampsia protein profile comprising one or more proteins selected from the group consisting of TNF-α, IFN-γ, IL-4, IL-5, IL-10, IL-1β, IL-6, IL-8, and IL-12;
wherein the preeclampsia protein profile comprises one or more proteins selected from the group consisting of IL-6, IL-8, and IFN-γ.

9. A method for determining whether a subject has a disease or disorder comprising:
a.) obtaining a protein profile of the subject produced according to one or more of the above examples; and
b.) comparing the protein profile of the subject to a disease protein profile,
wherein similarities in the presence or level of one or more proteins in the protein profile of the subject compared to the presence or level of the one or more proteins in the disease protein profile indicate the subject has the disease or disorder;
wherein the disease or disorder is selected from the group consisting of cancer, preeclampsia, autoimmune disease, cardiovascular disease, neurodegenerative disease, diabetes, metabolic disorders, musculoskeletal disease, infectious disease, genetic disorders, renal disorders, and gastrointestinal disorders.

10. A method of monitoring treatment in a subject comprising:
a.) obtaining a protein profile produced according to one or more of the above examples from a subject before treatment and after treatment; and
b.) comparing the protein profile of the subject before treatment to the protein profile of the subject after treatment,
wherein a difference in the presence or level of one or more proteins in the protein profile of the subject before treatment compared to the protein profile of the subject after treatment indicates an effect of the treatment on the subject;
wherein the protein profile of a subject who has received no treatment is compared to the protein profile of the subject after receiving treatment;
wherein at least one protein profile of a subject after treatment at one point in time is compared to at least one protein profile of the subject after treatment at a different point in time;
wherein the subject has received the same treatment;
wherein the subject has received a different treatment;
wherein the blood sample is a small volume blood sample;
wherein the subject is monitored a number of times selected from the group consisting of one or more times per day, two or more times per day, three or more times per day, four or more times per day, and five or more times per day;
wherein the subject is monitored a number of times selected from the group consisting of one or more times per week, two or more times per week, three or more times per week, four or more times per week, five or more times per week, six or more times per week, and seven or more times per week;
wherein the subject is monitored daily;
wherein the subject is monitored a number of times selected from the group consisting of once a week, once every two weeks, once every three weeks, and once every four weeks;
wherein the subject is monitored once a month.

11. A method of determining the effectiveness of a treatment comprising:
a.) obtaining at least one protein profile produced according to one or more of the above examples from:
(i) a subject that has undergone the treatment, and
(ii) a subject that has not undergone the treatment; and
b.) comparing the protein profile of the subject who has undergone the treatment to the protein profile of the subject who has not undergone the treatment,
wherein similarities in the presence or level of one or more proteins in the protein profile of the subject that has undergone the treatment compared to the protein profile of the subject that has not undergone the treatment indicate the effectiveness of the treatment.

12. The method of one or more of the above examples, wherein the blood sample is obtained from a subject.

13. The method one or more of the above examples, wherein the blood sample is obtained from a capillary of the subject or a vein of the subject.

14. The method of one or more of the above examples, wherein the subject is a human or a non-human animal.

15. The method of one or more of the above examples, wherein the subject is a human.

16. The method of one or more of the above examples, wherein the small volume of the red blood cell-enriched sample is 5 µL to 20 µL.

17. The method of one or more of the above examples, wherein the small volume of the red blood cell-enriched sample is 5 µL.

18. The method of one or more of the above examples, wherein the presence of the one or more proteins is detected or the level of the one or more proteins is measured using one or more antibodies.

19. The method of one or more of the above examples, wherein the presence of three or more proteins is detected or the level of three or more proteins is measured in the red blood cell-enriched sample.

20. The method of one or more of the above examples, wherein the presence of five or more proteins is detected or the level of five or more proteins is measured in the red blood cell-enriched sample.

21. The method of one or more of the above examples, wherein the presence of ten or more proteins is detected or the level of ten or more proteins is measured in the red blood cell-enriched sample.

22. The method of one or more of the above examples, wherein the presence of twenty or more proteins is detected or the level of twenty or more proteins is measured in the red blood cell-enriched sample.

23. The method of one or more of the above examples, wherein the presence of thirty or more proteins is detected or the level of thirty or more proteins is measured in the red blood cell-enriched sample.

24. The method of one or more of the above examples, wherein the one or more proteins are selected from the group consisting of chemokines, cytokines, growth factors, receptors, intracellular signal transmitters, hormones, nuclear transcription factors, neurotransmitters, and extracellular matrix components, and enzymes.

25. The method of one or more of the above examples, wherein the one or more proteins are selected from the group consisting of the proteins listed in Table 1 or a combination of proteins listed in Table 2.

26. The method of one or more of one or more of the above examples, wherein the one or more proteins are selected from the group consisting of basic FGF, CTACK, Eotaxin, G-CSF, GM-CSF, HGF, IFN-α2, IFN-γ, IL-10, IL-12p70, IL-13, IL-12p40, IL-15, IL-16, IL-17A, IL-18, IL-1α, IL-1β, IL-2, IL-2ra, IL-3, IL-4, IL-5, IL-6, IL-7, IL-9, IP-10, LIF, M-CSF, MIG, MIP-1α, MIP-1β, PDGF-BB, SDF-1α, TNF-α, TNF-β, TRAIL, VEGF, CRP, and DDT.

27. The method of one or more of the above examples, wherein the blood sample is leukodepleted by one or more methods selected from the group consisting of flow cytometry, magnetic bead separation, centrifugation, cellulose column, and dextran sedimentation.

28. The method of one or more of the above examples, wherein the red blood cells are leukodepleted by dextran sedimentation.

29. The method of one or more of the above examples, wherein the one or more proteins are detected or measured from one or more places selected from the group consisting of the surface of the red blood cells, the interior of red blood cells, the lysate of red blood cells, the supernatant of the red blood cells, medium containing the red blood cells, and medium that previously contained the red blood cells.

30. The method of one or more of the above examples, wherein the subject has a disease or disorder.

31. A method for increasing the accuracy of the detection or measurement of one or more proteins in a blood sample comprising:
a.) contacting the blood sample with dextran;
b.) allowing the blood sample to form a leukocyte-containing layer and a red blood cell dense layer;
c.) isolating red blood cells in the red blood cell dense layer to create a red blood cell-enriched blood sample; and
d.) detecting the presence or measuring the level of one or more proteins in the red blood cell-enriched blood sample,
wherein the blood sample is a small volume blood sample;
wherein the small volume blood sample is between 5 µL and 100 µL.
wherein the ratio of blood to dextran in the blood sample is selected from the group consisting of 1:1, 2:1, 3:1, 4:1, 5:1, 6:1, 7:1, 8:1, 9:1, and 10:1;
wherein the average depletion of white blood cells and platelets from the blood sample is 85% to 95%.

32. A kit for measuring the protein profile of a blood sample comprising:
a.) at least one reagent to leukodeplete a blood sample and produce a red blood cell-enriched sample; and
b.) at least one reagent to detect the presence or measure the level of one or more proteins in a small volume red blood cell-enriched sample,
wherein the cationic salt increases the detectable level of one or more proteins in the blood sample;
wherein the method further comprises at least one reagent to obtain a blood sample from a subject;
wherein the reagent to detect the presence or measure the level of one or more proteins is one or more antibodies;
wherein the reagent to detect the presence or measure the level of one or more proteins is an enzyme-linked immunosorbent assay (ELISA) apparatus.

33. A method for generating a protein profile from a blood sample obtained from a subject or a component of the blood sample, the method comprising:
a.) determining levels of one or more proteins in the blood sample or the blood sample component,
b.) wherein the blood sample and the blood sample component each comprise red blood cells (RBCs),
wherein the protein profile is generated from the blood sample component;
wherein the RBCs constitute more than 0.5%, 1%, 5%, 10%, 20%, 30%, 40%, 50%, 60%, 70%, 80%, 90%, 95%, 97.5%, 98%, 99%, 99.5%, 99.75%, 99.9%, or 99.95% of total number of blood cells present in the blood sample component;
wherein the blood sample component is an RBC-enriched fraction produced by leukodepletion of the blood sample;
wherein the leukodepletion removes more than 90%, 92.5%, 95%, 97.5%, 99%, 99.5%, 99.75%, 99.9%, or 99.95% of the number of leukocytes from the blood sample or portion thereof;
wherein the leukodepletion provides an RBC-enriched fraction in which more than 99%, 99.5%, 99.75%, 99.9%, or 99.95% of the number of blood cells in the fraction are RBCs;
wherein the blood sample or portion thereof is subjected to platelet depletion;

wherein the platelet depletion removes more than: 90%, 92.5%, 95%, 97.5%, 99%, 99.5%, 99.75%, 99.9%, or 99.95% of the number of platelets from the blood sample or portion thereof;
wherein the one or more proteins is/are selected from the group consisting of basic FGF, CTACK, Eotaxin, G-CSF, GM-CSF, HGF, IFN-α2, IFN-γ, IL-10, IL-12p70, IL-13, IL-12p40, IL-15, IL-16, IL-17A, IL-18, IL-1α, IL-1β, IL-2, IL-2ra, IL-3, IL-4, IL-5, IL-6, IL-7, IL-9, IP-10, LIF, M-CSF, MIG, MIP-1α, MIP-1β, PDGF-BB, SDF-1α, TNF-α, TNF-β, TRAIL, VEGF, CRP, DDT, and any combination thereof;
wherein the one or more proteins comprise or consist of:
a.) a protein listed in Table 1; or
b.) a combination of proteins listed in Table 2.

34. A method according to one or more of the above examples, comprising one or more of:
a.) determining the levels of one or more proteins on the surface of the RBCs;
b.) determining the levels of one or more proteins within the RBCs;
c.) determining the levels of one or more proteins released by the RBCs,
wherein the blood sample is a dried blood spot sample (DBS).

35. A method according to one or more of the above examples, wherein generating the protein profile comprises:
a.) producing a cell lysate, a cell wash, or a cell supernatant from a cell population comprising the RBCs; and
b.) determining levels of one or more proteins in the cell lysate, the cell wash, or the cell supernatant,
wherein the determining levels of one or more proteins is conducted using the cell lysate.

36. The method of one or more of the above examples, comprising:
a.) snap freezing the RBCs;
b.) thawing the RBCs to produce the cell lysate; and
c.) determining levels of the one or more proteins in the cell lysate,
wherein the determining levels of one or more proteins is conducted using the cell wash;
wherein the cell wash is produced by combining two or more cell washes;
wherein the cell wash is produced using wash liquid comprising one or more of isotonic salt solution, balanced salt solution, saline, phosphate buffered saline (PBS), hank's balanced salt solution (HBSS), and/or Earles' balanced salt solution (EBSS);
wherein the determining levels of one or more proteins is conducted using the cell supernatant;
wherein the cell supernatant is produced by culturing cells used to produce the cell supernatant in cell culture media comprising any one or more of Roswell Park Memorial Institute medium (RPMI), minimum essential medium (MEM), Improved Minimum Essential Medium (IMEM), Eagle's minimal essential medium (EMEM), Dubelco's modified Eagle's medium (DMEM), and/or Iscove's Modified Dulbecco's Media (IDMM);
wherein the step of determining levels of one or more proteins is conducted using multiple samples of the cell supernatant;
wherein the samples of the cell supernatant are extracted at different time points from a culture of the cells used to produce the cell supernatant.

37. A method of one or more of the above examples, comprising:
a.) contacting the blood sample with an anticoagulant;
b.) determining levels of one or more proteins in leukocytes separated from the RBCs;
wherein the method further comprises:
i.) snap freezing the leukocytes;
ii.) thawing the leukocytes to produce a leukocyte lysate; and
iii.) determining levels of one or more proteins in the thawed leukocytes,
wherein the method further comprises, determining levels of one or more proteins in a cell wash and/or a cell supernatant generated by washing and/or culturing the leukocytes.

38. The method of one or more of the above examples, comprising:
a.) contacting the blood sample with an anticoagulant; and
b.) determining levels of one or more proteins in platelets separated from the RBCs,
wherein the method further comprises:
i.) snap freezing the platelets;
ii.) thawing the platelets to produce a platelet lysate; and
iii.) determining levels of one or more proteins in the thawed platelets;
wherein the method further comprises determining levels of one or more proteins in a cell wash and/or a cell supernatant generated by washing and/or culturing the platelets.

39. The method of one or more of the above examples, comprising:
a.) contacting the blood sample with an anticoagulant;
b.) determining levels of one or more proteins in plasma separated from the RBCs, wherein the snap freezing is at a temperature of below or at −10° C., −20° C., −30° C., −40° C., −50° C., −60° C., −70° C., −75° C., −80° C., 100° C., −120° C., −140° C., −160° C., −180° C., −190° C., −195° C., or −196° C.

40. The method of one or more of the above examples, wherein the snap freezing and thawing comprises multiple freeze-thaw cycles.

41. The method of one or more of the above examples, wherein leukocytes are separated from the RBCs by flow cytometry and/or dextran sedimentation.

42. The method of one or more of the above examples, wherein platelets are separated from the RBCs by centrifugation.

43. The method of one or more of the above examples, wherein the blood sample has been mixed with a blood stabilising agent during collection.

44. The method of one or more of the above examples, further comprising contacting the blood sample obtained from the subject with a blood stabilising agent prior to the determining levels of one or more proteins,
wherein the blood stabilising agent is one or more selected from the group consisting of a protease inhibitor, a protein denaturation agent, an RNA stabiliser, an anticoagulant, and an anticoagulant in combination with another stabilising agent that is not an anticoagulant;
wherein the blood stabilising agent is not an anticoagulant;
wherein the blood stabilising agent is a protease inhibitor selected from the group consisting of aprotinin, leupeptin, α2-macroglobulin, antipain dihydrochloride, calpain inhibitor I, calpain inhibitor II, chymostatin, TLCK (CAS 131918-97-3), trypsin-inhibitor, Pefabloc SC (Roche), PMSF (C6H5CH2S2F—Thermo Fisher Scientific), complete protease inhibitor cocktail (Roche), and any combination thereof;
wherein the blood stabilizing agent is an anticoagulant is selected from the group consisting of: heparin, citrate, acid citrate dextrose, EDTA, and any combination thereof;

wherein the step of contacting with the blood stabilising agent is performed within 5 seconds, 10 seconds, 20 seconds, 30 seconds, 1 minute, 2 minutes, 3 minutes, 4 minutes, 5 minutes, 10 minutes, 15 minutes, 30 minutes, 45 minutes, 1 hour, 2 hours, 3 hours, 4 hours, 5 hours, 7.5 hours or 10 hours of conducting the step of the blood sample being obtained from the subject;

45. The method of one or more of the above examples, wherein the blood sample is obtained from a capillary of the subject.

46. The method of one or more of the above examples, wherein the blood sample is obtained from a vein of the subject.

47. The method of one or more of the above examples, wherein the step of determining levels of one or more proteins is conducted within 2 minutes, 5 minutes, 10 minutes, 15 minutes, 20 minutes, 25 minutes, 30 minutes, 40 minutes, 50 minutes, 1 hour, 1.5 hours, 2 hours, 3 hours, 4 hours, 5 hours, 6 hours, 7 hours, 8 hours, 9 hours, 10 hours, 11 hours, 12 hours, 18, hours, 24 hours, 36 hours, or 48 hours of when the blood sample is obtained.

48. The method of one or more of the above examples, further comprising a first step of obtaining the blood sample from the subject.

It will be appreciated by persons of ordinary skill in the art that numerous variations and/or modifications may be made to the present embodiments as disclosed in the specific embodiments without departing from the spirit or scope of the present disclosure as broadly described. The present embodiments are, therefore, to be considered in all respects as illustrative and not restrictive.

What is claimed:

1. A method of producing a protein profile, comprising:
   a) obtaining a blood sample;
   b) separating plasma from the blood sample to produce a cell pellet;
   c) leukodepleting the cell pellet to produce a red blood cell-enriched sample;
   d) incubating a small volume of the red blood cell-enriched sample in a medium; and
   e) detecting one or more proteins secreted or released from the red blood cell-enriched sample into the incubated medium, said one or more proteins selected from the group consisting of: basic fibroblast growth factor (FGF), cutaneous T cell-attracting chemokine (CTACK), granulocyte-colony stimulating factor (G-CSF), granulocyte-macrophage colony-stimulating factor (GM-CSF), hepatocyte growth factor (HGF), interferon alpha subtype α2 (IFN-α2), interferon gamma (IFN-γ), interleukin (IL) 12 p35 and p40 heterodimer (IL-12p70), IL-13, interleukin 12 p40 subunit (IL-12p40), IL-15, IL-16, IL-17A, IL-18, IL-1α, IL-1β, IL-2, interleukin 2 receptor alpha chain (IL-2ra), IL-3, IL-4, IL-5, IL-6, IL-7, IL-9, interferon gamma-induced protein 10 (IP-10), leukemia inhibitory factor (LIF), macrophage colony-stimulating factor (M-CSF), monokine induced by IFNγ (MIG), macrophage inflammatory protein-1 beta (MIP-1β), platelet-derived growth factor B chain homodimer (PDGF-BB), stromal cell-derived factor 1 (SDF-1α), tumor necrosis factor alpha (TNF-α), TNF-β, TNF-related apoptosis-inducing ligand (TRAIL), and vascular endothelial growth factor (VEGF);
   wherein the protein profile produced comprises the detected one or more proteins in the incubated medium.

2. The method of claim 1, wherein the detected one or more proteins in the incubated medium are secreted or released from a surface or an interior of a red blood cell in said red blood cell-enriched sample.

3. The method of claim 1, wherein the method further comprises measuring the level of the one or more detected proteins in the incubated medium.

4. The method of claim 1, wherein the method further comprises separating the red blood cell-enriched sample in step d) from the incubated medium in step d).

5. The method of claim 4, wherein the method further comprises lysing the separated red blood cell-enriched sample.

6. The method of claim 5, wherein the method further comprises detecting the level of one or more proteins in the lysed red blood cell-enriched sample.

7. The method of claim 6, wherein the method further comprises measuring the level of the one or more detected proteins in the lysed red blood cell-enriched sample.

8. The method of claim 1, wherein the leukodepleting of the cell pellet is by dextran sedimentation.

9. The method of claim 1, wherein the small volume in step d) is between 5 μL and 100 μL.

10. The method of claim 1, wherein the detected one or more proteins in the incubated medium is a cytokine.

11. The method of claim 1, wherein the detected one or more proteins in the incubated medium is two or more proteins selected from the group consisting of: basic FGF, CTACK, G-CSF, GM-CSF, HGF, IFN-α2, IFN-γ, IL-12p70, IL-13, IL-12p40, IL-15, IL-16, IL-17A, IL-18, IL-1α, IL-1β, IL-2, IL-2ra, IL-3, IL-4, IL-5, IL-6, IL-9, IP-10, LIF, M-CSF, MIG, MIP-1β, PDGF-BB, SDF-1α, TNF-α, TNF-β, TRAIL and VEGF.

12. The method of claim 1, wherein the detected one or more proteins in the incubated medium is three or more proteins selected from the group consisting of basic FGF, CTACK, G-CSF, GM-CSF, HGF, IFN-α2, IFN-γ, IL-12p70, IL-13, IL-12p40, IL-15, IL-16, IL-17A, IL-18, IL-1α, IL-1β, IL-2, IL-2ra, IL-3, IL-4, IL-5, IL-6, IL-7, IL-9, IP-10, LIF, M-CSF, MIG, MIP-1β, PDGF-BB, SDF-1α, TNF-α, TNF-β, TRAIL and VEGF.

13. The method of claim 1, wherein the protein profile produced further comprises one or more proteins selected from the group consisting of: D-dopachrome tautomerase (DDT), Eotaxin, growth-regulated oncogene alpha (GRO-α), IL-8, IL-10, monocyte chemoattractant protein-1 (MCP-1), macrophage migration inhibitory factor (MIF), macrophage inflammatory protein-1 alpha (MIP-Iα), and regulated on activation, normal T cell expressed and secreted (RANTES).

14. A method of producing a protein profile, comprising:
   a) obtaining a blood sample;
   b) separating plasma from the blood sample to produce a cell pellet;
   c) leukodepletion the cell pellet to produce a red blood cell-enriched sample;
   d) measuring the level of one or more proteins in the red blood cell-enriched sample from step c) and the level in the separated plasma from step b); and
   e) calculating a protein ratio of the measured level of the one or more proteins in the red blood cell-enriched sample relative to the measured level in the separated plasma;
   wherein the produced protein profile comprises the calculated ratio having a value of at least 2:1; and
   wherein the one or more proteins is selected from the group consisting of: FGF, CTACK, G-CSF, GM-CSF, HGF, IFN-α2, IFN-γ, IL-12p70, IL-13, IL-12p40, IL-15, IL-16, IL-17A, IL-18, IL-1α, IL-1β, IL-2, IL-2ra, IL-3, IL-4, IL-5, IL-6, IL-7, IL-9, IP-10, LIF, M-CSF, MIG, MIP-1β, PDGF-BB, SDF-Iα, TNF-α, TNF-β, TRAIL and VEGF.

15. The method of claim 14, wherein the one or more proteins measured in the red blood cell-enriched sample from step c) is from a surface or an interior of a red blood cell in said red blood cell-enriched sample.

16. The method of claim 14, Therein the method further comprises lysing the red blood cell-enriched sample.

17. The method of claim 16, wherein the one or more proteins measured in the lysed red blood cell-enriched sample is from a surface of a red blood cell, an interior of a red blood cell, or a lysate of a red blood cell, in said red blood cell-enriched sample.

18. The method of claim 14, wherein the one or more proteins is a cytokine.

\* \* \* \* \*